(12) United States Patent
Ruthstein et al.

(10) Patent No.: US 12,156,922 B2
(45) Date of Patent: Dec. 3, 2024

(54) COPPER-CONTAINING COMPLEX AND USES THEREOF

(71) Applicant: Bar-Ilan University, Ramat-Gan (IL)

(72) Inventors: Sharon Ruthstein, Mazor (IL); Yulia Shenberger, Netanya (IL)

(73) Assignee: Bar-Ilan University, Ramat-Gan (IL)

( * ) Notice: Subject to any disclaimer, the term of this patent is extended or adjusted under 35 U.S.C. 154(b) by 0 days.

(21) Appl. No.: 16/868,618

(22) Filed: May 7, 2020

(65) Prior Publication Data

US 2020/0297878 A1    Sep. 24, 2020

Related U.S. Application Data

(63) Continuation of application No. PCT/IL2018/051211, filed on Nov. 9, 2018.

(60) Provisional application No. 62/583,630, filed on Nov. 9, 2017.

(51) Int. Cl.
| | | |
|---|---|---|
| *A61K 9/00* | (2006.01) | |
| *A61K 51/04* | (2006.01) | |
| *A61K 51/08* | (2006.01) | |

(52) U.S. Cl.
CPC ........ *A61K 51/088* (2013.01); *A61K 51/0402* (2013.01); *A61K 51/0455* (2013.01)

(58) Field of Classification Search
CPC .... A61K 49/0004; A61K 51/00; A61K 51/08; A61K 51/088; A61K 51/04; A61K 51/0402; A61K 51/0455; A61K 51/0497; A61K 2121/00; A61K 2123/00; C07K 14/705; C07C 337/04; C07D 403/08; C07D 471/04
USPC .... 424/1.11, 1.65, 9.1, 9.2; 514/1, 1.1, 19.2, 514/19.3, 19.4, 19.5, 19.6, 21.2, 21.3, 514/21.4, 21.5, 21.6, 21.7, 21.8, 21.9, 514/21.91; 534/7, 10–16; 530/300
See application file for complete search history.

(56) References Cited

U.S. PATENT DOCUMENTS 6,051,206 A * 4/2000 Dean .................... A61K 51/088
424/9.1

FOREIGN PATENT DOCUMENTS

| WO | WO 2011/119114 | 9/2011 |
| WO | WO 2012/155124 | 11/2012 |
| WO | WO 2019/092721 | 5/2019 |

OTHER PUBLICATIONS

Kumar et al., Advances in Molecular Imaging, vol. 1, pp. 1-11. (Year: 2011).*
International Preliminary Report on Patentability Dated May 22, 2020 From the International Bureau of WIPO Re. Application No. PCT/IL2018/051211. (9 Pages).

(Continued)

*Primary Examiner* — Paul W Dickinson

(57) ABSTRACT

Complexes comprising a coordinated Cu(II) ion are described herein, which are capable of binding to an extracellular portion of Ctr1 such that the complex with the Cu(II) ion is transported through the Ctr1. The complexes may comprise a Cu(II) ion coordinated to a ligand and to a peptide, wherein the peptide is released upon contact of the complex with an extracellular portion of Ctr1, thereby forming a second complex comprising the ligand, the copper ion and the extracellular portion of Ctr1. Further described herein are uses and methods utilizing the complex, in imaging, in radiation therapy, and for determining a redox state of cells.

8 Claims, 66 Drawing Sheets
(55 of 66 Drawing Sheet(s) Filed in Color)
Specification includes a Sequence Listing.

(56) References Cited

OTHER PUBLICATIONS

International Search Report and the Written Opinion Dated Jan. 28, 2019 From the International Searching Authority Re. Application No. PCT/IL2018/051211. (13 Pages).
Adonai et al. "Ex Vivo Cell Labeling With 64Cu-Pyruvaldehyde-Bis(N4-Methylthiosemicarbazone) for Imaging Cell Trafficking in Mice With Positron-Emission Tomography", Proc. Natl. Acad. Sci. USA, PNAS, 99(5): 3030-3035, Mar. 5, 2002.
Aller et al. "Projection Structure of the Human Copper Transporter CTR1 at 6-Å Resolution Reveals a Compact Trimer With a Novel Channel-Like Architecture", Proc. Natl. Acad. Sci. USA, PNAS, 103(10): 3627-3632, Mar. 7, 2006.
Anderson et al. "Copper-64 Radiopharmaceuticals for PET Imaging of Cancer: Advances in Preclinical and Clinical Research", Cancer Biotherapy and Radiopharmaceuticals, 24(4): 379-393, Aug. 2009.
Aronoff-Spencer et al. "Identification of the Cu2+ Binding Sites in the N-Terminal Domain of the Prion Protein by EPR and CD Spectroscopy", Biochemistry, 39(45): 13760-13771, Nov. 14, 2000.
Asabella et al. "The Copper Radioisotopes: A systemic Review With Special Interest to 64Cu", BioMed Research International, 2014(Art. ID 786463): 1-9, May 7, 2014.
Burkhead et al. "Copper Homeostasis", New Phytologist, 182(4): 799-816, Jun. 2009.
Colombie et al. "Focus on the Controversial Aspects of 64Cu-ATSM in tumoral Hypxia Mapping by PET Imaging", Frontiers in Medicine, 2(Art.58): 1-7, Aug. 24, 2015.
Cunha et al. "The Role of Molecular Imaging in Modern Drug Development", Drug Discovery Today, 19(7): 936-948, Jul. 2014.
Dalah et al. "Simulation of Tissue Activity Curves of 64Cu-ATSM for Sub-Target Volume Delineation in Radiotherapy", Physics in Medicine and Biology, 55(3): 681-694, Published Online Jan. 13, 2010.
De Bruycker et al. "Baseline [18F]FMISO μPET as a Predictive Biomarker for Response to HIF-1Alpha Inhibition Combined With 5-FU Chemotherapy in a Human Colorectal Cancer Xenograft Model", Molecular Imaging and Biology, 18(4): 606-616, Published Online Jan. 4, 2016.
De Feo et al. "Three-Dimensional Structure of the Human Copper Transporter hCTR1", Proc. Natl. Acad. Sci. USA, PNAS, 106(11): 4237-4242, Mar. 17, 2009.
Dearling et al. "On the Destiny of (Copper) Species", The Journal of Nuclear Medicine, Invited Perspective, 55: 7-8, Published Online Dec. 12, 2013.
Du et al. "Comparison Between Copper and Cisplatin Transport Mediated by Human Copper Transporter 1 (hCTR1)", Metallomics, 4(7): 679-685, Published Online May 3, 2012.
Du et al. "Kinetics and Thermodynamics of Metal Binding to the N-Terminus of a Human Copper Transporter, hCTR1", Chemical Communications, 49(80): 9134-9136, Published Online Aug. 21, 2013.
Ebenhan et al. "Antimicrobial Peptides: Their Role as Infection-Selective Tracers for Molecular Imaging", Bio Med Research Internationl, 2014(Art.ID 867381): 1-15, Aug. 27, 2014.
Eisses et al. "Molecular Characterization of hCTR1, the Human Copper Uptake Protein", The Journal of Biological Chemistry, 277(32): 29162-29171, Published Online May 28, 2002.
Eisses et al. "The Mechanism of Copper Uptake Mediated by Human CTR1. A Mutational Analysis", The Journal of Biological Chemistry, 280(44): 37159-37168, Published Online Aug. 31, 2005.
Evangelista et al. "New Issues for Copper-64: From Precursor to Innovative Pet Tracers in Clinical Oncology", Current Radiopharmaceuticals, 6(3): 117-123, Sep. 2013.
Fabisiak et al. "Redox Regulation of Copper-Metallothionein", Archives of Biochemistry and Biophysics, 363(1): 171-181, Mar. 1, 1999.
Gaggelli et al. "Copper Homeostasis and Neurodegenerative Disorders (Alzheimer's, Prion, and Parkinson's Diseases and Amyotrophic Lateral Sclerosis)", Chemical Reviews, 106(6): 1995-2044, Published on Web Jun. 1, 2006.
Godt et al. "EPR Probes With Well-Defined, Long Distances Between Two or Three Unpaired Electrons", The Journal of Organic Chemistry, 65(22): 7575-7582, Published on Web Oct. 12, 2000.
Haas et al. "Model Peptides Provide New Insights Into the Role of Histidine Residues as Potential Ligands in Human Cellular Copper Acquisition via Ctr1", Journal of the American Chemical Society, JACS, 133(12): 4427-4437, Published Online Mar. 4, 2011.
Hansen et al. "64Cu-ATSM and 18FDG PET Uptake and 64Cu-ATSM Autoradiography in Spontaneous Canine Tumors: Comparison With Pimonidazole Hypoxia Immunohistochemistry", Radiation Oncology, 7(89): 1-8, Jun. 15, 2012.
Harris "Cellular Copper Transport and Metabolism", Annual Review of Nutrition, 20(1): 291-310, Jul. 2000.
Höckel et al. "Association Between Tumor Hypoxia and Malignant Progression in Advanced Cancer of the Uterine Cervix", Cancer Research, 56(19): 4509-4515, Oct. 1, 1996.
Holland et al. "Copper-64 Radiopharmaceuticals for Oncologic Imaging", PET Clinics, 4(1): 49-67, Jan. 2009.
Hueting et al. "A Comparison of the Behavior of 64Cu-Acetate and 64Cu-ATSM In Vitro and In Vivo", The Journal of Nuclear Medicine, 55(1): 128-134, Jan. 2014.
Jalilian et al. "The Current Status and Future of Theranostic Copper-64 Radiopharmaceuticals", Iranian Journal of Nuclear Medicine, 25(1): 1-10, Jan. 2017.
Jiang et al. "A Mets Motif Peptide Found in Copper Transport Proteins Selectively Binds Cu(I) With Methionine-Only Coordination", Inorganic Chemistry, 44(26): 9787-9794, Published on Web Nov. 22, 2005.
Kidane et al. "Uptake of Copper From Plasma Proteins in Cells Where Expression of CTR1 Has Been Modulated", Biometals, 25(4): 697-709, Published Online Feb. 22, 2012.
Kizaka-Kondoh et al. "Significance of Nitroimidazole Compounds and Hypoxia-Inducible Factor-1 for Imaging Tumor Hypoxia", Cancer Science, 100(8): 1366-1373, Published Online May 15, 2009.
Koay et al. "CopC Protein From Pseudomonas Syringae: Intermolecular Transfer of Copper From Both the Copper(I) and Copper(II) Sites", Inorganic Chemistry, 44(15): 5203-5205, Published on Web Jun. 22, 2005.
Kondo et al. "Hypoxia-Induced Enrichment and Mutagenesis of Cells That Have Lost DNA Mismatch Repair", Cancer Research, 61(20): 7603-7607, Oct. 15, 2001.
Kuo et al. "Galectin-1 Links Tumor Hypoxia and Radiotherapy", Glycobiology, 24(10): 921-925, Published Online Jun. 27, 2014.
Laforest et al. "Dosimetry of 60/61/62/64Cu-ATSM: A Hypoxia Imaging Agent for PET", European Journal of Nuclear Medicine and Molecular Imaging, 32(7): 764-770, Published Online Mar. 23, 2005.
Lehtiö et al. "Imaging of Blood Flow and Hypoxia in Head and Neck Cancer: Initial Evaluation With [15O]H2O and [18F]Fluoroerythronitroimidazole PET", Journal of Nuclear Medicine, 42(11): 1643-1652, Nov. 2001.
Levy et al. "CTR1 Intracellular Loop Is Involved in the Copper Transfer Mechanism to the Atox1 Metallochaperone", the Journal of Physical Chemistry B, 120(48):12334-12345. Nov. 10, 2016.
Levy et al. "Probing the Structural Flexibility of the Human Copper Metallochaperone Atox1 Dimer and Its Interaction With the CTR1 C-Terminal Domain", The Journal of Physical Chemistry B, 118(22): 5832-5842, May 16, 2014.
Li et al. "A Near-Infrared Fluorescent Probe for Detecting Copper(II) With High Selectivity and Sensitivity and Its Biological Imaging Applications", Chemical Communicaitons, 47(27): 7755-7757, Published Online May 27, 2011.
Linder et al. "Copper Transport", The American Journal of Clinical Nutrition, 67(Suppl.): 965S-971S, May 1998.
Liu et al. "Biodistribution, Pharmacokinetics and PET Imaging of [18F]FMISO, [18F]FDG and [18F]FAc in a Sarcoma- and Inflammation-Bearing Mouse Model", Nuclear Medicine and Biology, 36(3): 305-312, Apr. 30, 2009.
Liu et al. "Four Cu(II) Complexes Based on Antitumor Chelators: Synthesis, Structure, DNA Binding/Damage, HSA Interaction and Enhanced Cytotoxicity", Dalton Transactions, 45(19): 8036-8049, Mar. 30, 2016.

(56) References Cited

OTHER PUBLICATIONS

Lutsenko "Human Copper Homeostasis: A Network of Interconnected Pathways", Current Opinion in Chemical Biology, 14(2): 211-217, Available Online Feb. 1, 2010.
Maryon et al. "Rate and Regulation of Copper Transport by Human Copper Transporter 1 (hCTR1)", The Journal of Biological Chemistry, 288(25): 18035-18046, Jun. 21, 2013.
Mathias et al. "Species-Dependent Binding of Copper(II) Bis(Thiosemicarbazone) Radiopharmaceuticals to Serum Albumin", Journal of Nuclear Medicine, 36(8): 1451-1455, Aug. 1, 1995.
Matsuura et al. "Adsorption Spectral Analysis of Zn2+ or Cu2+ Coordination With Human Serum Albumin Using Zincon", Journal of Analytical & Bioanalytical Techniques, 5(5): 1000209-1-100209-4, Published Online Sep. 30, 2014.
McConathy et al. "Imaging Biomarkers Associated With Cognitive Decline: A Review", Biological Psychiatry, 77(8): 685-692, Apr. 15, 2015.
Mees et al. "Molecular Imaging of Hypoxia With Radiolabelled Agents", European Journal of Nuclear Medicine and Molecular Imaging, 36(10): 1674-1686, Published Online Jun. 30, 2009.
Meir et al. "EPR Spectroscopy Identifies Met and Lys Residues That Are Essential for the Interaction Between the CusB N-Terminal Domain and Metallochaperone CusF", Metallomics, 7(7): 1163-1172, Published Online May 5, 2015.
Migliorini et al. "Copper-Induced Structural Propensities of the Amyloidogenic Region of Human Prion Protein", Journal of Biological Inorganic Chemistry, JBIC, 19(4-5): 635-645, Published Online Apr. 16, 2014.
Millar et al. "FDG-Positron Emission Tomography (PET) Has a Role to Play in the Diagnosis and Therapy of Infective Endocarditis and Cardiac Device Infection", International Journal of Cardiology, 167(5): 1724-1736, Available Online Jan. 11, 2013.
Nomura et al. "PET Imaging Analysis With 64Cu in Disulfiram Treatment for Aberrant Copper Biodistribution in Menkes Disease Mouse Model", Journal of Nuclear Medicine, 55(5): 845-851, Published Online Mar. 13, 2014.
Palmer et al. "Introduction to 'Cellular Metal Homeostasis and Trafficking'", Chemical Reviews, 109(10): 4533-4535, Published on Web Sep. 24, 2009.
Park et al. "64Cu-ATSM Hypoxia Positron Emission Tomography for Detection of Conduit Ischemia in an Experimental Rat Esophagectomy Model", PLOS ONE, 10(6): e0131083-1-e0131083-11, Jun. 22, 2015.
Peisach et al. "Structural Implications Derived From the Analysis of Electron Paramagnetic Resonance Spectra of Natural and Artificial Copper Proteins", Archives of Biochemistry and Biophysics, 165(2): 691-708, Dec. 1974.
Prohaska "Role of Copper Transporters in Copper Homeostasis", American Journal of Clinical Nutrition, 88(3): 826S-829S, Sep. 2009.
Pushie et al. "Model Peptide Studies Reveal a Mixed Histidine-Methionine Cu(1) Binding Site at the N-Terminus of Human Copper Transporter 1", Inorganic Chemistry, 54(17): 8544-8551, Aug. 10, 2015.
Rahmim et al. "PET Versus SPECT: Strengths, Limitations and Challenges", Nuclear Medicine Communications, 29(3): 193-207, Mar. 2008.
Rajendran et al. "Tumor Hypoxia Imaging With [F-18] Fluoromisonidazole Positron Emission Tomography in Head and Neck Cancer", Clinical Cancer Research, 12(18): 5435-5441, Sep. 15, 2006.
Raz et al. "The Neuropathology and Cerebrovascular Mechanisms of Dementia", Journal of Cerebral Blood Flow & Metabolism, 36(1): 172-186, Jan. 2016.
Rubino et al. "Methionine Motifs of Copper Transport Proteins Provide General and Flexible Thioether-Only Binding Sites for Cu(I) and Ag(I)", Journal of Biological Inorganic Chemistry, JBIC, 15(7): 1033-1049, Published Online May 1, 2010.
Schushan et al. "A Structural Model of the Copper ATPase ATP7B to Facilitate Analysis of Wilson Disease-Causing Mutations and Studies of the Transport Mechanism", Metallomics, 4(7): 669-678, Published Online Jun. 13, 2012.
Schushan et al. "C[Alpha]-Trace Model of the Transmembrane Domain of Human Copper Transporter 1, Motion and Functional Implications", Proc. Natl. Acad. Sci. USA, PNAS, 107(24): 10908-10913, Jun. 15, 2010.
Schwab et al. "Sequence Proximity Between Cu(II) and Cu(I) Binding Sites of Human Copper Transporter 1 Model Peptides Defines Reactivity With Ascorbate and O2", Journal of Inorganic Biochemistry, 158: 70-76, Published Online Dec. 30, 2015.
Semenza "Hypoxia, Clonal Selection, and the Role of HIF-1 in Tumor Progression", Critical Reviews in Biochemistry and Molecular Biology, 35(2): 71-103, Jan. 2000.
Sharma et al. "Development of Radiotracers for Oncology—The Interface With Pharmacology", British Journal of Pharmacology, 163(8): 1565-1585, Aug. 2011.
Shenberger et al. "EPR and NMR Spectroscopies Provide Input on the Coordination of Cu(I) and Ag(I) to a Siordered Methionine Segment", Journal of Biological Inorganic Chemistry, JBIC, 20(4): 719-727, Published Online Mar. 31, 2015.
Shenberger et al. "EPR Spectroscopy Shows That the Blood Carrier Protein, Human Serum Albumin, Closely Interacts With the N-Terminal Domain of the Copper Transporter, Ctr1", The Journal of Physical Chemistry B, 119(14): 4824-4830, Mar. 20, 2015.
Shenberger et al. "Exploring the Interaction Between the Human Copper Transporter, CTR1, C-Terminal Domain and a Methionine Motif in the Presence of Cu(I) and Ag(I) Ions, Using EPR Spectroscopy", Molecular Physics, 111(18-19): 2980-2991, Oct. 2013.
Shenberger et al. "Insights Into the N-Terminal Cu(II) and Cu(I) Binding Sites of the Human Copper Transporter CTR1", Journal of Coordination Chemistry, 71(11-13): 1985-2002, Published Online Sep. 12, 2018.
Shokeen et al. "Molecular Imaging of Cancer With Copper-64 Radiopharmaceuticals and Positron Emission Tomography (PET)", Accounts of Chemical Research, 42(7): 832-841, Jul. 21, 2009.
Soon et al. "Diacetylbis(N(4)-Methylthiosemicarbazonato) Copper (II) (CuII(ATSM)) Protects Against Peroxynitrite-Induced Nitrosative Damage and Prolongs Survival in Amyotrophic Lateral Sclerosis Mouse Model", The Journal of Biological Chemistry, 286(51): 44035-44044, Published Online Oct. 27, 2011.
Sun et al. "Tumor Hypoxia Imaging", Molecular Imaging and Biology, 13(3): 399-410, Published Online Sep. 14, 2010.
Syme et al. "Copper Binding to the Amyloid-Beta (ABeta) Peptide Associated With Alzheimer's Disease. Folding Coordination Geometry, pH Dependence Stoichiometry, and Affinity of ABeta-(1-28): Insights From A Range of Complementary Sepctroscopic Techniques", The Journal of Biological Chemistry, 279(18): 18169-18177, Published Online Feb. 20, 2004.
Szymanski et al. "Development of Copper Based Drugs, Radiopharmaceuticals and Medical Materials", Biometals, 25(6): 1089-1112, Published Online Aug. 23, 2012.
Szyszko et al. "The Role of New PET Tracers for Lung Cancer", Lung Cancer, 94: 7-14, Apr. 30, 2016.
Tümer et al. "Mutation Spectrum of ATP7A, the Gene Defective in Menkes Disease", Advances in Experimental Medicine and Biology, 448(Chap.7): 83-95, 1999.
Uriu-Adams et al. "Copper, Oxidative Stress, and Human Health", Molecular Aspects of Medicine, 26(4): 268-298, Oct. 31, 2005.
Vaupel et al. "hypoxia in Cancer: Significance and Impact on Clinical Outcome", Cancer Metastasis Review, 26: 225-239, Published Online Apr. 18, 2007.
Vavere et al. "Cu-ATSM: A Radiopharmaceutical for the PET Imaging of Hypoxia", Dalton Transactions, 2007: 4893-4902, Published Online Sep. 25, 2007.
Wachsmann et al. "Molecular Imaging and Therapy Targeting Copper Metabolism in Hepatocellular Carcinoma", World Journal of Gastroenterology, 22(1): 221-231, Published Online Jan. 7, 2016.
Wadas et al. "Coordinating Radiometals of Copper, Gallium, Indium, Yttrium and Zirconium for PET and SPECT Imaging of Disease", Chemical Reviews, 110(5): 2858-2902, May 12, 2010.

(56) References Cited

OTHER PUBLICATIONS

Wang et al. "Interaction Between Platinum Complexes and the C-Terminal Motif of Human Copper Transporter 1", Inorganic Chemistry, 52(10): 6153-6159, May 3, 2013.

Wang et al. "Radiosensitizing Effect of Irisquinone on Glioma Through the Downregulation of HIF-1 [Alpha] Evaluated by 18F-FDG and 18F-FMISO PET/CT", Nuclear Medicine Communications, 37(7): 705-714, Jul. 2016.

Wei et al. "A Comparative Study of Noninvasive Hypoxia Imaging With 18F-Fluoroerythronitroimidazole and 18F-Fluoromisonidazole PET/CT in Patients With Lung Cancer", PLOS ONE, 11(6): e0157606-1-e0157606-9, Jun. 20, 2016.

Wernimont et al. "Structural Basis for Copper Transfer by the Metallochaperone for the Menkes/Wilson Disease Proteins", Nature Structural Biology, 7(9): 766-771, Sep. 2000.

Wilson et al. "Targeting Hypoxia in Cancer Therapy", Nature Reviews Cancer, 11(6): 393-410, Jun. 2011.

Xiao et al. "C-Terminal Domain of the Membrane Copper Transporter Ctrl From *Saccharomyces cerevisiae* Binds Four Cu(I) Ions as a Cuprous-Thiolate Polynuclear Cluster: Sub-Femtomolar Cu(I) Affinity of Three Proteins Involved in Copper Trafficking", Journal of the American Chemical Society, JACS, 126(10): 308103090, Mar. 17, 2004.

Xie et al. "Exploiting Copper Redox for 19F Magnetic Resonance-Based Detection of Cellular Hypoxia", Journal of the American Chemical Society, JACS, 138(9): 2937-2940, Feb. 23, 2016.

Yang et al. "Hypoxia Induces DNA Overreplication and Enhances Metastatic Potential of Murine Tumor Cells", Proc. Natl. Acad. Sci. USA, 85(24): 9533-9537, Dec. 1988.

Zeglis et al. "Underscoring the Influence of Inorganic Chemistry on Nuclear Imaging With Radiometals", Inorganic Chemistry, 53(4): 1880-1899, Feb. 17, 2014.

Zhang et al. "Synthesis and Evaluation of 18F-Labeled 4-Nitrobenzyl Derivatives for Imaging Tumor Hypoxia With Positron Emission Tomography: Comparison of 2-[18F]Fluoroethyl Carbonate and 2-[18F]Fluoroethyl Carbamate", Bioorganic & Medicinal Chemistry Letters, 26(2): 584-588, Available Online Nov. 19, 2015.

Zheng et al. "Synthesis of [18F]FMISO in a Flow-Through Microfluidic Reactor: Development and Clinical Application", Nuclear Medicine and Biology, 42(6): 578-584, Jun. 30, 2015.

Chen et al. "Coordination of Two High-Affinity Hexamer Peptides to Copper(II) and Palladium(II) Models of the Peptide-Metal Chelation Site on IMAC Resins", Inorganic Chemistry, 39(6):1180-1186, Mar. 2, 2000.

Kruppa et al. "A Luminescent Receptor with Affinity for NTerminal Histidine in Peptides in Aqueous Solution", Journal of the American Chemical Society, 127(10):3362-3365, Feb. 18, 2005.

Pireu et al. "Mixed Ligand Complexes of Copper(II) Iminodiacetate with Di- and Tripeptides in Solution", Journal of Coordination Chemistry, 69(22):3424-3435,Sep. 14, 2016.

Timari et al. "Characterization of CuZnSOD Model Complexes from a Redox Point of View:", Journal of Inorganic Biochemistry, 105(8): 1009-1017, Aug. 2011.

Xiao et al. "Transfer of Copper between Bis(thiosemicarbazone) Ligands and Intracellular Copper-Binding Proteins. Insights into Mechanisms of Copper Uptake and Hypoxia Selectivity", Inorganic Chemistry, 47(10):4338-4347, Apr. 16, 2008.

Office Action Dated May 17, 2022 From the Israel Patent Office Re. Application No. 274525. (7 Pages).

Supplementary European Search Report and the European Search Opinion Dated Aug. 5, 2021 From the European Patent Office Re. Application No. 18875859.3. (19 Pages).

Chen et al. "MicroPET and Autoradiographic Imaging of Breast Cancer AlphaV-Integrin Expression Using 18F- and 64Cu-Labeled RGD Peptide", Bioconjugate Chemistry, 15(1): 41-49, Jan. 21, 2004.

\* cited by examiner

Cu-ATSM

| Position | | NH | | α | | β | | γ | | δ | |
|---|---|---|---|---|---|---|---|---|---|---|---|
| | | H | + Cu(I) | H | + Cu(I) | H | + Cu(I) | H | + Cu(I) | H | + Cu(I) |
| 1 | M | 8.55 | d | 4.10 | 4.05 | 2.06, 2.13 | | 2.46 | | 2.063[b] | |
| 2 | D | 8.76 | 8.70 | 4.64 | >4.6 | 2.72 | | | | | |
| 3 | H | 8.80 | 8.70 | 4.75 | >4.6 | 3.14, 3.37 | 3.12, 3.35 | 7.33 (δ) | 7.27 | 8.64 (ζ) | 8.51[c] |
| 4 | S | 8.42 | 8.38 | 4.33 | 4.29 | 3.80 | 3.79 | | | | |
| 5 | H | 8.49 | 8.49 | 4.67 | >4.6 | 3.11, 3.25 | 3.12, 3.24 | 7.27 (δ) | 7.24 | 8.59 (ζ) | 8.53[c] |
| 6 | H | 8.56 | d | 4.65 | >4.6 | 3.13, 3.22 | 3.12, 3.24 | 7.26 (δ) | 7.24 | 8.59 (ζ) | 8.53[c] |
| 7 | M | 8.54 | d | 4.47 | 4.54 | 1.98, 2.07 | | 2.49, 2.56 | | 2.061[b] | |
| 8 | G | 8.51 | 8.48 | 3.94, 4.01 | 3.92, 3.99 | | | | | | |
| 9 | M | 8.25 | 7.88 | 4.49 | 4.53 | 1.95, 2.03 | 1.95,d | 2.49, 2.53 | | 2.067 | |
| 10 | S | 8.37 | 8.44 | 4.41 | 4.44 | 3.79 | 3.79 | | | | |
| 11 | Y | 8.16 | 8.14 | 4.53 | 4.50 | 2.95, 3.02 | 2.81, 3.01 | 7.08 (δ) | 7.08 | 6.79 (ε) | 8.82 |
| 12 | M | 8.11 | 7.88 | 4.37 | 4.38 | 1.90, 2.02 | | 2.38, 2.44 | | 2.055 | |
| 13 | D | 8.29 | 8.22 | 4.68 | >4.6 | 2.78, 2.89 | d,2.81 | | | | |
| 14[a] | S | 8.20 | 8.11 | 4.38 | 4.38 | 3.83, 3.90 | 3.82, 3.89 | | | | |

FIG. 16

Cu-Imino diacetic acid (IDA)

2-((*E*)-2-((*E*)-3-(2-((*E*)-3,3-dimethyl-1-propylindolin-2-ylidene)ethylidene)-2-(*N*-(3-(dimethylamino)propyl)acetamido)cyclohex-1-en-1-yl)vinyl)-3,3-dimethyl-1-propyl-3*H*-indol-1-ium (CyNa-427)

SEQUENCE LISTING

```
<160> NUMBER OF SEQ ID NOS: 51

<210> SEQ ID NO 1
<211> LENGTH: 14
<212> TYPE: PRT
<213> ORGANISM: Artificial sequence
<220> FEATURE:
<223> OTHER INFORMATION: Pep1 peptide amino acid sequence

<400> SEQUENCE: 1

Met Asp His Ser His His Met Gly Met Ser Tyr Met Asp Ser
1               5                   10

<210> SEQ ID NO 2
<211> LENGTH: 14
<212> TYPE: PRT
<213> ORGANISM: Artificial sequence
<220> FEATURE:
```

```
<223> OTHER INFORMATION: Pep2 peptide amino acid sequence

<400> SEQUENCE: 2

Met Asp His Ser His His Met Ala Met Ser Tyr Met Asp Ser
1               5                   10

<210> SEQ ID NO 3
<211> LENGTH: 14
<212> TYPE: PRT
<213> ORGANISM: Artificial sequence
<220> FEATURE:
<223> OTHER INFORMATION: Pep3 peptide amino acid sequence

<400> SEQUENCE: 3

Met Asp Ala Ser His His Met Gly Met Ser Tyr Met Asp Ser
1               5                   10

<210> SEQ ID NO 4
<211> LENGTH: 14
<212> TYPE: PRT
<213> ORGANISM: Artificial sequence
<220> FEATURE:
<223> OTHER INFORMATION: Pep4 peptide amino acid sequence

<400> SEQUENCE: 4

Met Asp His Ser Ala His Met Gly Met Ser Tyr Met Asp Ser
1               5                   10

<210> SEQ ID NO 5
<211> LENGTH: 14
<212> TYPE: PRT
<213> ORGANISM: Artificial sequence
<220> FEATURE:
<223> OTHER INFORMATION: Pep5 peptide amino acid sequence

<400> SEQUENCE: 5

Met Asp His Ser His Ala Met Gly Met Ser Tyr Met Asp Ser
1               5                   10

<210> SEQ ID NO 6
<211> LENGTH: 16
<212> TYPE: PRT
<213> ORGANISM: Artificial sequence
<220> FEATURE:
<223> OTHER INFORMATION: Peptide sequence
<220> FEATURE:
<221> NAME/KEY: MISC_FEATURE
<222> LOCATION: (1)..(1)
<223> OTHER INFORMATION: MTSSL
      (S-(1-oxyl-2,2,5,5-tetramethyl-2,5-dihydro-1H-pyrrol-3-yl)methyl
      methanesulfonothioate) conjugate
<220> FEATURE:
<221> NAME/KEY: MISC_FEATURE
<222> LOCATION: (16)..(16)
<223> OTHER INFORMATION: MTSSL
      (S-(1-oxyl-2,2,5,5-tetramethyl-2,5-dihydro-1H-pyrrol-3-yl)methyl
      methanesulfonothioate) conjugate

<400> SEQUENCE: 6

Cys Met Asp His Ser His His Met Gly Met Ser Tyr Met Asp Ser Cys
1               5                   10                  15

<210> SEQ ID NO 7
<211> LENGTH: 16
<212> TYPE: PRT
<213> ORGANISM: Artificial sequence
<220> FEATURE:
<223> OTHER INFORMATION: Peptide sequence
<220> FEATURE:
```

```
<221> NAME/KEY: MISC_FEATURE
<222> LOCATION: (1)..(1)
<223> OTHER INFORMATION: MTSSL
      (S-(1-oxyl-2,2,5,5-tetramethyl-2,5-dihydro-1H-pyrrol-3-yl)methyl
      methanesulfonothioate) conjugate
<220> FEATURE:
<221> NAME/KEY: MISC_FEATURE
<222> LOCATION: (16)..(16)
<223> OTHER INFORMATION: MTSSL
      (S-(1-oxyl-2,2,5,5-tetramethyl-2,5-dihydro-1H-pyrrol-3-yl)methyl
      methanesulfonothioate) conjugate

<400> SEQUENCE: 7

Cys Ala Asp His Ser His His Met Gly Met Ser Tyr Met Asp Ser Cys
1               5                   10                  15

<210> SEQ ID NO 8
<211> LENGTH: 16
<212> TYPE: PRT
<213> ORGANISM: Artificial sequence
<220> FEATURE:
<223> OTHER INFORMATION: Peptide sequence
<220> FEATURE:
<221> NAME/KEY: MISC_FEATURE
<222> LOCATION: (1)..(1)
<223> OTHER INFORMATION: MTSSL
      (S-(1-oxyl-2,2,5,5-tetramethyl-2,5-dihydro-1H-pyrrol-3-yl)methyl
      methanesulfonothioate) conjugate
<220> FEATURE:
<221> NAME/KEY: MISC_FEATURE
<222> LOCATION: (16)..(16)
<223> OTHER INFORMATION: MTSSL
      (S-(1-oxyl-2,2,5,5-tetramethyl-2,5-dihydro-1H-pyrrol-3-yl)methyl
      methanesulfonothioate) conjugate

<400> SEQUENCE: 8

Cys Met Asp His Ser His His Ala Gly Met Ser Tyr Met Asp Ser Cys
1               5                   10                  15

<210> SEQ ID NO 9
<211> LENGTH: 16
<212> TYPE: PRT
<213> ORGANISM: Artificial sequence
<220> FEATURE:
<223> OTHER INFORMATION: Peptide sequence
<220> FEATURE:
<221> NAME/KEY: MISC_FEATURE
<222> LOCATION: (1)..(1)
<223> OTHER INFORMATION: MTSSL
      (S-(1-oxyl-2,2,5,5-tetramethyl-2,5-dihydro-1H-pyrrol-3-yl)methyl
      methanesulfonothioate) conjugate
<220> FEATURE:
<221> NAME/KEY: MISC_FEATURE
<222> LOCATION: (16)..(16)
<223> OTHER INFORMATION: MTSSL
      (S-(1-oxyl-2,2,5,5-tetramethyl-2,5-dihydro-1H-pyrrol-3-yl)methyl
      methanesulfonothioate) conjugate

<400> SEQUENCE: 9

Cys Met Asp His Ser His His Met Gly Ala Ser Tyr Met Asp Ser Cys
1               5                   10                  15

<210> SEQ ID NO 10
<211> LENGTH: 16
<212> TYPE: PRT
<213> ORGANISM: Artificial sequence
<220> FEATURE:
<223> OTHER INFORMATION: Peptide sequence
<220> FEATURE:
<221> NAME/KEY: MISC_FEATURE
<222> LOCATION: (1)..(1)
<223> OTHER INFORMATION: MTSSL
      (S-(1-oxyl-2,2,5,5-tetramethyl-2,5-dihydro-1H-pyrrol-3-yl)methyl
```

```
          methanesulfonothioate) conjugate
<220> FEATURE:
<221> NAME/KEY: MISC_FEATURE
<222> LOCATION: (16)..(16)
<223> OTHER INFORMATION: MTSSL
      (S-(1-oxyl-2,2,5,5-tetramethyl-2,5-dihydro-1H-pyrrol-3-yl)methyl
      methanesulfonothioate) conjugate

<400> SEQUENCE: 10

Cys Met Asp His Ser His His Met Gly Met Ser Tyr Ala Asp Ser Cys
1               5                   10                  15

<210> SEQ ID NO 11
<211> LENGTH: 4
<212> TYPE: PRT
<213> ORGANISM: Artificial sequence
<220> FEATURE:
<223> OTHER INFORMATION: Exemplary tetrapeptides amino acid sequence

<400> SEQUENCE: 11

His Ala Ala His
1

<210> SEQ ID NO 12
<211> LENGTH: 4
<212> TYPE: PRT
<213> ORGANISM: Artificial sequence
<220> FEATURE:
<223> OTHER INFORMATION: Exemplary tetrapeptides amino acid sequence

<400> SEQUENCE: 12

His Ala Ala Met
1

<210> SEQ ID NO 13
<211> LENGTH: 4
<212> TYPE: PRT
<213> ORGANISM: Artificial sequence
<220> FEATURE:
<223> OTHER INFORMATION: Exemplary tetrapeptides amino acid sequence

<400> SEQUENCE: 13

His Ala Ala Gly
1

<210> SEQ ID NO 14
<211> LENGTH: 8
<212> TYPE: PRT
<213> ORGANISM: Artificial sequence
<220> FEATURE:
<223> OTHER INFORMATION: Met 1 peptide sequence

<400> SEQUENCE: 14

Met Tyr Gly Met Lys Gly Met Ser
1               5

<210> SEQ ID NO 15
<211> LENGTH: 5
<212> TYPE: PRT
<213> ORGANISM: Artificial sequence
<220> FEATURE:
<223> OTHER INFORMATION: Met2  peptide sequence

<400> SEQUENCE: 15

Met Tyr Gly Met Lys
1               5
```

```
<210> SEQ ID NO 16
<211> LENGTH: 8
<212> TYPE: PRT
<213> ORGANISM: Artificial sequence
<220> FEATURE:
<223> OTHER INFORMATION: Cys1 peptide sequence

<400> SEQUENCE: 16

Lys Ser Met Ala Ala Cys Ala Met
1               5

<210> SEQ ID NO 17
<211> LENGTH: 8
<212> TYPE: PRT
<213> ORGANISM: Artificial sequence
<220> FEATURE:
<223> OTHER INFORMATION: Cys2 peptide sequence

<400> SEQUENCE: 17

Ala Ser Cys Gly Gly Cys Ala Met
1               5

<210> SEQ ID NO 18
<211> LENGTH: 5
<212> TYPE: PRT
<213> ORGANISM: Artificial sequence
<220> FEATURE:
<223> OTHER INFORMATION: Cys3 peptide sequence

<400> SEQUENCE: 18

His Thr Gly Cys Lys
1               5

<210> SEQ ID NO 19
<211> LENGTH: 7
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 19

Cys Xaa Xaa Met Xaa Xaa Met
1               5

<210> SEQ ID NO 20
<211> LENGTH: 7
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 20

Cys Xaa Xaa His Xaa Xaa His
1               5
```

```
<210> SEQ ID NO 21
<211> LENGTH: 7
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 21

Met Xaa Xaa His Xaa Xaa His
1               5

<210> SEQ ID NO 22
<211> LENGTH: 6
<212> TYPE: PRT
<213> ORGANISM: Artificial sequence
<220> FEATURE:
<223> OTHER INFORMATION: Mets motif amino acid sequence
<220> FEATURE:
<221> NAME/KEY: misc_feature
<222> LOCATION: (2)..(5)
<223> OTHER INFORMATION: Xaa can be any naturally occurring amino acid

<400> SEQUENCE: 22

Met Xaa Xaa Xaa Xaa Met
1               5

<210> SEQ ID NO 23
<211> LENGTH: 5
<212> TYPE: PRT
<213> ORGANISM: Artificial sequence
<220> FEATURE:
<223> OTHER INFORMATION: Mets motif amino acid sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 23

Met Xaa Xaa Xaa Met
1               5

<210> SEQ ID NO 24
<211> LENGTH: 5
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 24

Met Xaa Xaa Xaa Cys
1               5

<210> SEQ ID NO 25
<211> LENGTH: 5
<212> TYPE: PRT
<213> ORGANISM: Artificial sequence
<220> FEATURE:
```

```
<223> OTHER INFORMATION: Peptide sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 25

Met Xaa Xaa Xaa His
1               5

<210> SEQ ID NO 26
<211> LENGTH: 5
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 26

Cys Xaa Xaa Xaa Met
1               5

<210> SEQ ID NO 27
<211> LENGTH: 5
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 27

Cys Xaa Xaa Xaa Cys
1               5

<210> SEQ ID NO 28
<211> LENGTH: 5
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 28

Cys Xaa Xaa Xaa His
1               5

<210> SEQ ID NO 29
<211> LENGTH: 5
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 29

His Xaa Xaa Xaa Met
1               5
```

```
<210> SEQ ID NO 30
<211> LENGTH: 5
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 30

His Xaa Xaa Xaa Cys
1               5

<210> SEQ ID NO 31
<211> LENGTH: 4
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 31

Met Xaa Xaa Met
1

<210> SEQ ID NO 32
<211> LENGTH: 4
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 32

Met Xaa Xaa Cys
1

<210> SEQ ID NO 33
<211> LENGTH: 4
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 33

Met Xaa Xaa His
1

<210> SEQ ID NO 34
<211> LENGTH: 4
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(3)
<223> OTHER INFORMATION: Xaa can be any naturally occurring amino acid
```

```
<400> SEQUENCE: 34

Cys Xaa Xaa Met
1

<210> SEQ ID NO 35
<211> LENGTH: 4
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 35

Cys Xaa Xaa Cys
1

<210> SEQ ID NO 36
<211> LENGTH: 4
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 36

Cys Xaa Xaa His
1

<210> SEQ ID NO 37
<211> LENGTH: 4
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 37

His Xaa Xaa Met
1

<210> SEQ ID NO 38
<211> LENGTH: 4
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 38

His Xaa Xaa Cys
1

<210> SEQ ID NO 39
<211> LENGTH: 5
<212> TYPE: PRT
<213> ORGANISM: Artificial sequence
```

```
<220> FEATURE:
<223> OTHER INFORMATION: Peptide sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 39

His Xaa Xaa Xaa His
1               5

<210> SEQ ID NO 40
<211> LENGTH: 4
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 40

His Xaa Xaa His
1

<210> SEQ ID NO 41
<211> LENGTH: 7
<212> TYPE: PRT
<213> ORGANISM: Artificial sequence
<220> FEATURE:
<223> OTHER INFORMATION: Peptide sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 41

Met Xaa Xaa Met Xaa Xaa Met
1               5

<210> SEQ ID NO 42
<211> LENGTH: 189
<212> TYPE: PRT
<213> ORGANISM: Artificial sequence
<220> FEATURE:
<223> OTHER INFORMATION: Ctr1 amino acid sequence

<400> SEQUENCE: 42

Met Asp His Ser His His Met Gly Met Ser Tyr Met Asp Ser Asn Ser
1               5                   10                  15

Thr Met Gln Pro Ser His His His Pro Thr Thr Ser Ala Ser His Ser
            20                  25                  30

His Gly Gly Gly Asp Ser Ser Met Met Met Pro Met Thr Phe Tyr
        35                  40                  45

Phe Gly Phe Lys Asn Val Glu Leu Leu Phe Ser Gly Leu Val Ile Asn
    50                  55                  60

Thr Ala Gly Glu Met Ala Gly Ala Phe Val Ala Val Phe Leu Leu Ala
65                  70                  75                  80

Met Phe Tyr Glu Gly Leu Lys Ile Ala Arg Glu Ser Leu Leu Arg Lys
                85                  90                  95

Ser Gln Val Ser Ile Arg Tyr Asn Ser Met Pro Val Pro Gly Pro Asn
```

```
                    100                 105                 110
Gly Thr Ile Leu Met Glu Thr His Thr Val Gly Gln Gln Met Leu Ser
            115                 120                 125

Phe Pro His Leu Leu Gln Thr Val Leu His Ile Ile Gln Val Val Ile
        130                 135                 140

Ser Tyr Phe Leu Met Leu Ile Phe Met Thr Tyr Asn Gly Tyr Leu Cys
145                 150                 155                 160

Ile Ala Val Ala Ala Gly Ala Gly Thr Gly Tyr Phe Leu Phe Ser Trp
                165                 170                 175

Lys Lys Ala Val Val Val Asp Ile Thr Glu His Cys His
            180                 185
```

<210> SEQ ID NO 43
<211> LENGTH: 192
<212> TYPE: PRT
<213> ORGANISM: Artificial Sequence
<220> FEATURE:
<223> OTHER INFORMATION: native Ctr1 amino acid sequence with a 3
      additional amino acids at the N-terminus

<400> SEQUENCE: 43

```
Gly Thr Thr Met Asp His Ser His His Met Gly Met Ser Tyr Met Asp
1               5                   10                  15

Ser Asn Ser Thr Met Gln Pro Ser His His His Pro Thr Thr Ser Ala
            20                  25                  30

Ser His Ser His Gly Gly Gly Asp Ser Ser Met Met Met Met Pro Met
        35                  40                  45

Thr Phe Tyr Phe Gly Phe Lys Asn Val Glu Leu Leu Phe Ser Gly Leu
50                  55                  60

Val Ile Asn Thr Ala Gly Glu Met Ala Gly Ala Phe Val Ala Val Phe
65                  70                  75                  80

Leu Leu Ala Met Phe Tyr Glu Gly Leu Lys Ile Ala Arg Glu Ser Leu
                85                  90                  95

Leu Arg Lys Ser Gln Val Ser Ile Arg Tyr Asn Ser Met Pro Val Pro
            100                 105                 110

Gly Pro Asn Gly Thr Ile Leu Met Glu Thr His Thr Val Gly Gln Gln
        115                 120                 125

Met Leu Ser Phe Pro His Leu Leu Gln Thr Val Leu His Ile Ile Gln
130                 135                 140

Val Val Ile Ser Tyr Phe Leu Met Leu Ile Phe Met Thr Tyr Asn Gly
145                 150                 155                 160

Tyr Leu Cys Ile Ala Val Ala Ala Gly Ala Gly Thr Gly Tyr Phe Leu
                165                 170                 175

Phe Ser Trp Lys Lys Ala Val Val Val Asp Ile Thr Glu His Cys His
            180                 185                 190
```

<210> SEQ ID NO 44
<211> LENGTH: 5
<212> TYPE: PRT
<213> ORGANISM: Artificial Sequence
<220> FEATURE:
<223> OTHER INFORMATION: Peptide sequence
<220> FEATURE:
<221> NAME/KEY: MISC_FEATURE
<222> LOCATION: (1)..(1)
<223> OTHER INFORMATION: X is a His residue, a Met residue or a Gly
      residue
<220> FEATURE:
<221> NAME/KEY: MISC_FEATURE
<222> LOCATION: (2)..(4)

```
<223> OTHER INFORMATION: X is Ala residue or Gly residue
<220> FEATURE:
<221> NAME/KEY: MISC_FEATURE
<222> LOCATION: (5)..(5)
<223> OTHER INFORMATION: X is a His residue, a Met residue or a Gly
      residue

<400> SEQUENCE: 44

Xaa Xaa Xaa Xaa Xaa
1               5

<210> SEQ ID NO 45
<211> LENGTH: 4
<212> TYPE: PRT
<213> ORGANISM: Artificial Sequence
<220> FEATURE:
<223> OTHER INFORMATION: Peptide sequence
<220> FEATURE:
<221> NAME/KEY: MISC_FEATURE
<222> LOCATION: (1)..(1)
<223> OTHER INFORMATION: X is His residue, a Met residue or a Gly
      residue
<220> FEATURE:
<221> NAME/KEY: MISC_FEATURE
<222> LOCATION: (2)..(3)
<223> OTHER INFORMATION: X is Ala residue or a Gly residue
<220> FEATURE:
<221> NAME/KEY: MISC_FEATURE
<222> LOCATION: (4)..(4)
<223> OTHER INFORMATION: X is His residue, a Met residue or a Gly
      residue

<400> SEQUENCE: 45

Xaa Xaa Xaa Xaa
1

<210> SEQ ID NO 46
<211> LENGTH: 4
<212> TYPE: PRT
<213> ORGANISM: Artificial Sequence
<220> FEATURE:
<223> OTHER INFORMATION: Peptide sequence
<220> FEATURE:
<221> NAME/KEY: MISC_FEATURE
<222> LOCATION: (1)..(1)
<223> OTHER INFORMATION: X is a His, Met or Cys residue
<220> FEATURE:
<221> NAME/KEY: MISC_FEATURE
<222> LOCATION: (2)..(3)
<223> OTHER INFORMATION: X is a Ala, Arg, Asp, Glu, Gly, Lys, Ser, Thr
      or Tyr residue
<220> FEATURE:
<221> NAME/KEY: MISC_FEATURE
<222> LOCATION: (4)..(4)
<223> OTHER INFORMATION: X is a His, Met or Cys residue

<400> SEQUENCE: 46

Xaa Xaa Xaa Xaa
1

<210> SEQ ID NO 47
<211> LENGTH: 5
<212> TYPE: PRT
<213> ORGANISM: Artificial sequence
<220> FEATURE:
<223> OTHER INFORMATION: Peptide sequence

<400> SEQUENCE: 47

His Ala Gly Ala His
1               5
```

```
<210> SEQ ID NO 48
<211> LENGTH: 4
<212> TYPE: PRT
<213> ORGANISM: Artificial sequence
<220> FEATURE:
<223> OTHER INFORMATION: Peptide sequence

<400> SEQUENCE: 48

His Gly Gly His
1

<210> SEQ ID NO 49
<211> LENGTH: 5
<212> TYPE: PRT
<213> ORGANISM: Artificial sequence
<220> FEATURE:
<223> OTHER INFORMATION: Peptide sequence

<400> SEQUENCE: 49

His Thr Gly Met Lys
1               5

<210> SEQ ID NO 50
<211> LENGTH: 9
<212> TYPE: PRT
<213> ORGANISM: Artificial sequence
<220> FEATURE:
<223> OTHER INFORMATION: Peptide sequence

<400> SEQUENCE: 50

Met Tyr Gly Met Lys Gly Met Ser Tyr
1               5

<210> SEQ ID NO 51
<211> LENGTH: 9
<212> TYPE: PRT
<213> ORGANISM: Artificial sequence
<220> FEATURE:
<223> OTHER INFORMATION: Peptide sequence

<400> SEQUENCE: 51

Lys Ser Met Ala Ala Cys Ala Met Tyr
1               5
```

COPPER-CONTAINING COMPLEX AND USES THEREOF

RELATED APPLICATIONS

This application is a US Continuation of PCT Patent Application No. PCT/IL2018/051211 having International filing date of Nov. 9, 2018, which claims the benefit of priority under 35 USC § 119(e) of U.S. Provisional Patent Application No. 62/583,630 filed on Nov. 9, 2017. The contents of the above applications are all incorporated by reference as if fully set forth herein in their entirety.

SEQUENCE LISTING STATEMENT

The ASCII file, entitled 81842SequenceListing.txt, created on May 7, 2020, comprising 18,127 bytes, submitted concurrently with the filing of this application is incorporated herein by reference.

FIELD AND BACKGROUND OF THE INVENTION

The present invention, in some embodiments thereof, relates to copper-containing complexes, and more particularly, but not exclusively, to novel copper-containing complexes which are usable in introducing copper into cells and to uses thereof in imaging and in radiation therapy, and for determining a redox state of cells.

Imaging of hypoxia is important in many disease states in fields such as, for example, oncology, cardiology, and neurology. Hypoxia is associated with a low oxygen level and it is a characteristic feature of malignant tumors that should be evaluated before the onset of therapy. Tumor hypoxia results in an aggressive phenotype, such that the survival of cancer patients is significantly affected by the natural behavior of the hypoxic tumor cells [Wilson & Hay, *Nat Rev Cancer* 2011, 11:393-410; Kondo et al., *Cancer Res* 2001, 61:7603-7607; Semenza, *Crit Rev Biochem Mol Biol* 2000, 35:71-103]. Up to 50-60% of locally advanced solid tumors exhibit hypoxic tissue areas [Mees et al., *Eur J Nucl Med Mol Imaging* 2009, 36:1674-1686; Sun et al., *Mol Imaging Biol* 2011, 13:399-410; Wilson & Hay, *Nat Rev Cancer* 2011, 11:393-410; Wei et al., *PloS One* 2016, 11:e0157606]. Hypoxia leads to angiogenesis and promotes the invasiveness and metastasis of neoplastic cells, make the tumor cells more aggressive and less responsive to chemotherapy and radiation treatment [Hockel et al., *Cancer Res* 1996, 56:4509-4515; Young et al., *Proc Nat Acad Sci USA* 1988, 85:9533-9537].

Molecular imaging techniques, particularly X-ray computed tomography (CT) and magnetic resonance imaging (MRI), have long been the standard tools for the accurate localization of organs and lesions in radiation oncology. However, the effectiveness of structural imaging techniques in determining metabolic or functional tissue information is limited.

PET, SPECT, PET/CT, and PET/MRI are considered to be much more powerful techniques and are able to image an increasing variety of physiological phenomena [Szyszko et al., *Lung Cancer* 2016, 94:7-14; Rahmim & Zaidi, *Nucl Med Comm* 2008, 29:193-207; Wernick, *Emission Tomography: The Fundamentals of PET and SPECT*; Elsevier Academic Press, 2004].

Radiolabeled agents contain radionuclides which emit ionizing radiation, and are used in the nuclear imaging field to diagnose and treat diseases. Radiolabeled agents for diagnostic applications include single photon emission computed tomography (SPECT) and positron emission tomography (PET) imaging modalities [Anderson & Ferdani, *Cancer Biother Radiopharm* 2009, 24:379-393; Millar et al., *Int J Cardiology* 2013, 167:1724-1736; Szyszko et al., *Lung Cancer* 2016, 94:7-14].

This versatility arises from the ability to select a radiolabeled agent that specifically targets a particular mechanism. With the growth in cancer incidence, the market continuously demands development of new and novel radiolabeled agents for early cancer diagnosis and chemotherapy targets. Nowadays, radiolabeled agents exist for mostly the imaging of glucose metabolism, where some radiolabeled agents also exist for ligand/receptor interactions [Cunha et al., *Drug Discov Today* 2014, 19:936-948], gene expression [Sharma & Aboagye, *Br J Pharm* 2011, 163:1565-1585], peptide/membrane interactions [Ebenhan et al., *BioMed Res Int* 2014, 2014:867381], and hypoxia [Xie et al., *J Am Chem Soc* 2016, 138:2937-2940; McConathy & Sheline, *Biol Psychiatry* 2015, 77:685-692].

$^{18}$F-2-Fluoro-2-deoxy-glucose ($^{18}$F-FDG) is the most common radiolabeled agent used for PET applications, and plays an important role in oncology [Millar et al., *Int J Cardiology* 2013, 167:1724-1736; Hansen et al., *Radiat Oncol* 2012, 7:89; Liu et al., *Nucl Med Biol* 2009, 36:305-312]. Increased glucose consumption is a typical characteristic of most cancers. The primary drawback of FDG-PET for oncologic imaging is that glucose uptake is not specific to cancer. Moreover, some tumors (such as carcinoid, prostate, head and neck tumors) do not consume glucose [Vavere & Lewis, *Dalton Trans* 2007, 43:4893-4902; Shokeen & Anderson, *Acc Chem Res* 2009, 42:832-841]. Additionally, FDG cannot penetrate the necrotic centers, and thus cannot accurately evaluate the degree of risk of a specific tumor.

In the effort to develop accurate, noninvasive imaging modality techniques of tumor hypoxia, several PET radiolabeled agents have been produced, such as various nitroimidazole derivatives, e.g., $^{18}$F-fluromisonidazole (FMISO) [Liu et al., *Nucl Med Biol* 2009, 36:305-312; Zheng et al., *Nucl Med Biol* 2015, 42:578-584]. The mechanism of these biomarkers is based on reduction of the nitrogen dioxide group to an amine in a low oxygen environment. The amine complex can then easily be trapped in the cellular cycle, and the retention time of the radiolabeled tracer is increased in hypoxic tissues. However, these tracers have not been used routinely due to slow passive uptake by the cells (about 10% uptake as compared to FDG uptake). In such cases, a waiting time of 1.5 hour after injection is required to obtain a sufficient signal to background ratio, which approaches the half life time of the $^{18}$F isotope. This waiting time, results in a comparable brief imaging time (a few minutes) [Wei et al., *PloS One* 2016, 11:e0157606; Szyszko et al., *Lung Cancer* 2016, 94:7-14; Zhang et al., *Bioorg Med Chem Lett* 2016, 26:584-588; Wang et al., *Nucl Med Commun* 2016, 37:705-714; Bruycker et al., *Mol Imaging Biol* 2016, 18:606-616].

Owing to the potential of metal ions to undergo oxidation-reduction reactions, researchers have recently investigated metal-based radiolabeled agents for high sensitivity measurements of the cellular oxygen pressure.

Copper is an important trace element in humans and plays a role as a cofactor for numerous enzymes and other proteins crucial for respiration, iron transport, metabolism, cell growth, and homeostasis [Syme et al., *J Biol Chem* 2004, 279:18169-18177; Wernimont et al., *Nat Struct Biol* 2000, 7:766-771; Uriu-Adams & Keen, *Mol Aspects Med* 2005, 26:268-298].

In recent years, copper isotopes have been linked to antibodies, proteins, peptides, and nanoparticles for preclinical and clinical research of pathological conditions that influence copper metabolism [Asabella et al., *BioMed Res Int* 2014, 2014:786463; Nomura et al., *J Nucl Med* 2014, 55:845-851].

Many animal and human studies examined several radiolabeled agents for hypoxia based on the copper radioisotope $^{64}$Cu(II) [Asabella et al., *BioMed Res Int* 2014, 2014: 786463]. Recruitment of patients has begun for $^{64}$Cu(II)-based clinical trials with various cancer indications: breast, gastric, stomach, colon, bile, gall bladder, liver, lung and others; and there are ongoing clinical trials using $^{64}$Cu(II) with trastuzumab for breast cancer, or CEA protein, the most commonly used biomarker for colorectal cancer.

$^{64}$Cu(II)-labeled tracers such as $^{64}$Cu(II)-diacetyl-bis(N4-methylthiosemicarbazone) ($^{64}$Cu-ATSM) have been proposed to be one of the most promising PET agents for hypoxia imaging [Xie et al., *J Am Chem Soc* 2016, 138: 2937-2940; Vāvere & Lewis, *Dalton Trans* 2007, 43:4893-4902; Shokeen & Anderson, *Acc Chem Res* 2009, 42:832-841; Zeglis et al., *Inorg Chem* 2014, 53:1880-1899; Wadas et al., *Chem Rev* 2010, 110:2858-2902]. The structure of Cu-ATSM is depicted in Background Art FIG. 1.

$^{64}$Cu isotope labelling exhibits the following advantages: (1) the half-life time (12.8 hours), which is not too long for patient exposure, but enough time for handling the radiocompound for imaging; (2) $^{64}$Cu(II) is highly sensitive to the oxygen pressure; and (3) high uptake ratio—$^{64}$Cu-ATSM has a reported ability to rapidly identify hypoxic tissue owing to combination of its small molecular weight and high cell membrane permeability [Colombié et al., *Front Med (Lausanne)* 2015, 2:58; Xie et al., *J Am Chem Soc* 2016, 138:2937-2940; Vāvere & Lewis, *Dalton Trans* 2007, 43:4893-4902].

The effectiveness of Cu-ATSM for providing clinically relevant tumor oxygenation information has been confirmed in multiple studies and its predictive value of tumor behavior and treatment response has been demonstrated [Park et al., *PloS One* 2015, 10:e0131083; Soon et al., *J Biol Chem* 2011, 286:44035-44044; Vāvere & Lewis, *Dalton Trans* 2007, 43:4893-4902; Hansen et al., *Radiat Oncol* 2012, 7:89; Laforest et al., *Eur J Nucl Med Mol Imaging* 2005, 32:764-770].

Colombie et al. [*Front Med (Lausanne)* 2015, 2:58] reports that while FDG-PET failed to distinguish between benign and malignant disease, Cu-ATSM succeeded in distinguishing between them, indicating the specificity of this biomarker to hypoxia tissues.

$^{64}$Cu(II)-ATSM tracer is incorporated in the cellular copper cycle by 3 proteins: Ctr1, Atox1, and ATP7B, and upon reduction at low oxygen levels, it is distributed to other copper cycles in the cells, which increase its retention [Laforest et al., *Eur J Nucl Med Mol Imaging* 2005, 32:764-770; Dalah et al., *Phys Med Biol* 2010, 55:681-694; Adonai et al., *Proc Nat Acad Sci USA* 2002, 99:3030-3035; Wachsmann & Peng, *World J Gastroenterol* 2016, 22:221-231].

In general, Cu(II) is accumulated into the body and it is transferred to the main copper transporter Ctr1 by blood carrier proteins [Eisses & Kaplan, *J Biol Chem* 2002, 277:29162-29171; Maryon et al., *J Biol Chem* 2013, 288:18035-18046]. One of the blood carrier proteins, serum albumin, has been reported to exhibit high affinity to the first 15 residues of extracellular N-terminal domain of Ctr1 [Shenberger et al., *J Phys Chem B* 2015, 119:4824-4830].

Ctr1 is a trimer [De Feo et al., *Proc Nat Acad Sci* 2009, 106:4237-4242; Aller & Unger, *Proc Nat Acad Sci* 2006, 103:3627-3632] in which each monomer comprises 190 amino acids (SEQ ID NO: 42). On the extracellular domain of Ctr1, Cu(II) is reduced to Cu(I) by an unknown mechanism. The extracellular domain of Ctr1 includes three methionine-rich sequences referred to as Mets motifs, which are of the form MXXXXM (SEQ ID NO: 22) or MXXXM (SEQ ID NO: 23) (wherein X can be any amino acid), and which are capable of binding Cu(I) with micromolar affinity [Xiao et al., *J Am Chem Soc* 2004, 126:3081-3090]. The extracellular domain of Ctr1 also includes two histidine-rich sites: one involving His3, His5 and His6, and one involving His22-His24. Pushie et al. [*Inorg Chem* 2015, 54:8544-8551] have reported that His3 can coordinate one Cu(II) ion with an affinity of 10 pM at pH 7.4; and Du et al. [*Metallomics* 2012, 4:679-685] have reported that mutations at His22-His24 affect copper uptake.

On the intracellular side, Ctr1 can bind Cu(I) via residues Met85, Met96 and His99 in an intracellular loop domain, as well as via the last three residues of the C-terminal domain, His-Cys-His [Levy et al., *J Phys Chem B* 2016, 120:12334-12345].

Inside the human cell, the copper cycle for Cu(I) involves three different pathways: to cytochrome C, to SOD, and to the Golgi apparatus. Mutations in each of these proteins may lead to severe neurological disease and disorders such as Alzheimer's disease, Parkinson's disease, Menkes disease, Wilson disease, and ALS (amyotrophic lateral sclerosis) [Schushan et al., *Metallomics* 2012, 4:669-678; Tümer et al., *Adv Exp Med Biol* 1999, 448:83-95; Gaggelli et al., *Chem Rev* 2009, 106:1995-2044; Lutsenko, *Curr Opin Chem Biol* 2010, 14:211-217; Prohaska, *Am J Clin Nutr* 2008, 88:826S-829S].

International Patent Application Publication WO 2011/119114 describes amine-acetylated cyanine (CyNA) compounds, such as CyNA-414, which have a stable, intense near-infrared signal upon adsorption to metal nanoparticles. Such compounds are proposed for use as in vivo biosensors.

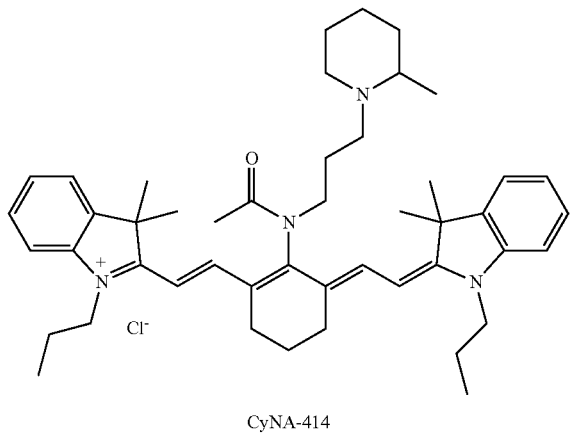

CyNA-414

Li et al. [*Chem Commun* 2011, 47:7755-7757] describe a cyanine derivative, referred to as "Cy-Cu", which can serve as a near-IR fluorescent probe for detecting Cu(II) based on increased fluorescence following selective binding to Cu(II).

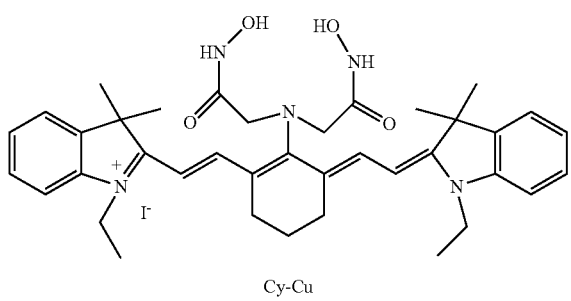

Cy-Cu

Additional background art includes Aronoff-Spencer et al. [*Biochemistry* 2000, 39:13760-13771]; Burkhead et al. [*New Phytol* 2009, 182:799-816]; Dearling & Packard [*J Nucl Med* 2014, 55:7-8]; Du et al. [*Chem Comm* 2013, 49:9134-9136]; Eisses & Kaplan [*J Biol Chem* 2005, 280:37159-37168]; Evangelista et al. [*Curr Radiopharmaceut* 2013, 6:117-123]; Fabisiak et al. [*Arch Biochem Biophys* 1999, 363:171-181]; Godt et al. [*J Org Chem* 2000, 65:7575-7582]; Haas et al. [*J Am Chem Soc* 2011, 133:4427-4437]; Harris [*Ann Rev Nutrition* 2000, 20:291-310]; Hueting et al. [*J Nucl Med* 2014, 55:128-134]; Jiang et al. [*Inorg Chem* 2005, 44:9787-9794]; Kidane et al. [*Biometals* 2012, 25:697-709]; Kizaka-Kondoh & Konse-Nagasawa [*Cancer Sci* 2009, 100:1366-1373]; Koay et al. [*Inorg Chem* 2005, 44:5203-5205]; Kuo & Le [Glycobiology 2014, 24:921-925]; Lehtio et al. [*J Nucl Med* 2001, 42:1643-1652]; Levy et al. [*J Phys Chem B* 2014, 118:5832-5842]; Linder et al. [*Am J Clin Nutr* 1998, 67:965S-971S]; Meir et al. [*Metallomics* 2015, 7:1163-1172]; Migliorini et al. [*J Biol Inorg* 2014, 19:635-645]; Palmer & Franz [*Chem Rev* 2009, 109: 4533-4535]; Peisach & Blumberg [*Arch Biochem Biophys* 1974, 165:691-708]; Rajendran et al. [*Clin Cancer Res* 2006, 12, 5435-5441]; Raz et al. [*J Cereb Blood Flow Metab* 2016, 36:172-186]; Rubino et al. [*J Biol Inorg Chem* 2010, 15:1033-1049]; Schushan et al. [*Proc Natl Acad Sci* 2010, 107:10908-10913]; Schwab et al. [*J Inorg Biochem* 2016, 158:70-76]; Shenberger et al. [*Mol Phys* 2013, 111:2980-2991]; Shenberger et al. [*J Biol Inorg Chem* 2015, 20:719-727]; Shenberger et al. [*J Coord Chem* 2018, 71:1985-2002]; Vaupel & Mayer [*Cancer Metastasis Rev* 2007, 26:225-239]; and Wang et al. [*Inorg Chem* 2013, 52:6153-6159].

SUMMARY OF THE INVENTION

According to an aspect of some embodiments of the invention, there is provided a complex comprising a coordinated Cu(II) ion, the complex being capable of binding to an extracellular portion of Ctr1 such that the complex with the Cu(II) ion is transported through the Ctr1.

According to an aspect of some embodiments of the invention, there is provided a complex comprising a copper ion coordinated to a ligand and to a peptide, the copper ion being a Cu(II) ion, wherein the peptide is released upon contact of the complex with an extracellular portion of Ctr1, thereby forming a second complex comprising the ligand, the copper ion and the extracellular portion of Ctr1.

According to an aspect of some embodiments of the invention, there is provided a method of determining a redox state of cells, the method comprising contacting the cells with a complex as described herein, and determining a level of at least one oxidation state of copper ion in the cells, thereby determining the redox state.

According to an aspect of some embodiments of the invention, there is provided a method of detecting uptake of copper by cells, the method comprising contacting the cells with a complex as described herein which comprises a radioactive copper isotope, and determining a level of radioactivity emitted by the radioactive copper isotope in the cells, thereby determining uptake of copper.

According to an aspect of some embodiments of the invention, there is provided a process of preparing a complex as described herein, the process comprising contacting the copper ion with the ligand and the peptide in solution, wherein a concentration of the copper ion in the solution is greater than a concentration of the ligand.

According to some embodiments of any of the embodiments of the invention, the second complex comprises Cu(II) ion coordinated to at least one Met residue of the extracellular portion of Ctr1, at a physiological partial pressure of oxygen.

According to some embodiments of any of the embodiments of the invention, the at least one Met residue is selected from the group consisting of Met7, Met9 and Met12 of Ctr1 (SEQ ID NO: 42).

According to some embodiments of any of the embodiments of the invention, upon formation of the second complex on a cell surface, the Cu(II) ion is transported through the Ctr1 while coordinated to the ligand.

According to some embodiments of any of the embodiments of the invention, the peptide comprises 2 or 3 atoms coordinated to the copper ion, at least one of the atoms being a sulfur atom, and wherein a total number of atoms in the ligand and the peptide coordinated to the copper ion is in a range of from 4 to 6.

According to some embodiments of any of the embodiments of the invention, 2, 3 or 4 atoms of the ligand are coordinated to the copper ion.

According to some embodiments of any of the embodiments of the invention, 2 or 3 atoms of the ligand are coordinated to the copper ion.

According to some embodiments of any of the embodiments of the invention, no more than two atoms of the ligand which are coordinated to the copper ion are sulfur atoms.

According to some embodiments of any of the embodiments of the invention, the atoms of the ligand, which are coordinated to the copper ion, are selected from the group consisting of nitrogen, oxygen and sulfur.

According to some embodiments of any of the embodiments of the invention, the atoms of the ligand which are coordinated to the copper ion are selected from the group consisting of nitrogen and oxygen.

According to some embodiments of any of the embodiments of the invention, the ligand has the general formula I or general formula II:

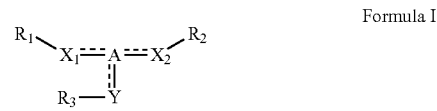

Formula I

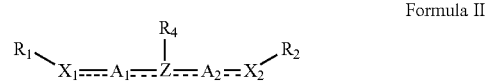

Formula II wherein:
each dashed line independently denotes a saturated or unsaturated bond;

$X_1$, $X_2$ and Z are each independently an electron-donating atom;

Y is absent or is an electron-donating atom;

A, $A_1$ and $A_2$ each independently a hydrocarbon moiety of 1 to 4 atoms in length; and $R_1$-$R_4$ are each independently absent or selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino, wherein when Y is absent, $R_3$ is also absent, or, alternatively, at least one of $R_1$-$R_4$, and at least one of A, $A_1$ and $A_2$, together form a 5- or 6-membered cyclic or heterocyclic ring.

According to some embodiments of any of the embodiments of the invention, the electron-donating atom is selected from the group consisting of nitrogen and oxygen.

According to some embodiments of any of the embodiments of the invention, $X_1$ and/or $X_2$ is an oxygen atom of a carboxylic acid ($—CO_2H$ or $—CO_2^-$) group.

According to some embodiments of any of the embodiments of the invention, Z is N, $X_2$ is O, $R_2$ is absent, and $A_2$ attached to $X_2$ is an acyl group which together with Z forms an amide group.

According to some embodiments of any of the embodiments of the invention, $R_1$, $R_3$ and/or $R_4$ comprise a fluorescent moiety.

According to some embodiments of any of the embodiments of the invention, the ligand is selected from the group consisting of:

i) imino-diacetic acid;

ii) a compound of the general formula III:

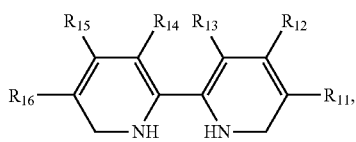

Formula III wherein $R_{11}$-$R_{16}$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino; or alternatively, $R_{13}$ and $R_{14}$ together form a 5-membered or 6-membered ring selected from the group consisting of cycloalkyl, heteroalicyclic, aryl and heteroaryl rings; and iii) a peptide having the formula $W^1$—$X^1$—$X^2$—$X^3$—$W^2$ (SEQ ID NO: 44) or $W^1$—$X^1$—$X^2$—$W^2$ (SEQ ID NO: 45), wherein:

$W^1$ and $W^2$ are each independently selected from the group consisting of a His residue, a Met residue and a Gly residue, wherein at least one of $W^1$ and $W^2$ is a His residue; and each of $X^1$, $X^2$ and $X^3$ is independently selected from the group consisting of an Ala residue and a Gly residue.

According to some embodiments of any of the embodiments of the invention, the ligand is a peptide selected from the group consisting of HAAH (SEQ ID NO: 11), HAAM (SEQ ID NO: 12) or HAAG (SEQ ID NO: 13).

According to some embodiments of any of the embodiments of the invention, the ligand is fluorescent.

According to some embodiments of any of the embodiments of the invention, the ligand is a cyanine.

According to some embodiments of any of the embodiments of the invention, a molecular weight of the ligand is no more than 1000 Da.

According to some embodiments of any of the embodiments of the invention, the peptide described herein is a water-soluble peptide.

According to some embodiments of any of the embodiments of the invention, the peptide is up to 20 amino acids in length.

According to some embodiments of any of the embodiments of the invention, the peptide comprises at least two sulfur atoms coordinated to the copper ion.

According to some embodiments of any of the embodiments of the invention, the peptide comprises a first residue and a second residue which are coordinated to the copper ion, wherein the first residue is Met or Cys, and the second residue is selected from the group consisting of Met, Cys and His.

According to some embodiments of any of the embodiments of the invention, the first residue and the second residue are separated by two other amino acid residues.

According to some embodiments of any of the embodiments of the invention, the peptide comprises 2 or 3 residues selected from the group consisting of Met and Cys.

According to some embodiments of any of the embodiments of the invention, the peptide comprises at least one Cys residue.

According to some embodiments of any of the embodiments of the invention, the peptide comprises 3 residues selected from the group consisting of Met and Cys.

According to some embodiments of any of the embodiments of the invention, the peptide is selected from the group consisting of MTGMKGMS (SEQ ID NO: 14), MTGMK (SEQ ID NO: 15), KSMAACAM (SEQ ID NO: 16), ASCGGCAM (SEQ ID NO: 17) and HTGCK (SEQ ID NO: 18).

According to some embodiments of any of the embodiments of the invention, at least 50% of the amino acid residues of the peptide are selected from the group consisting of Ala, Arg, Asp, Glu, Gly, Lys, Ser, Thr and Tyr residues.

According to some embodiments of any of the embodiments of the invention, the complex is formulated in an aqueous solution of N-ethylmorpholine having a pH in a range of from 6.5 to 8.5.

According to some embodiments of any of the embodiments of the invention, the copper comprises a radioactive copper isotope.

According to some embodiments of any of the embodiments of the invention, the radioactive copper isotope is selected from the group consisting of $^{60}Cu$, $^{61}Cu$, $^{62}Cu$, $^{64}Cu$ and $^{67}Cu$.

According to some embodiments of any of the embodiments of the invention, the radioactive copper isotope is $^{64}Cu$.

According to some embodiments of any of the embodiments of the invention, the complex described herein is for use in the manufacture of a medicament.

According to some embodiments of any of the embodiments of the invention, the complex described herein is for use in the manufacture of an imaging agent.

According to some embodiments of any of the embodiments of the invention, the complex described herein is for use in a method of in vivo imaging of a body or a portion thereof, in a subject in need thereof.

According to some embodiments of any of the embodiments of the invention, the method of in vivo imaging comprises administering the complex to a subject, and employing an imaging technique to thereby determine a level and/or distribution of radioactive copper in the subject's body or a portion thereof.

According to some embodiments of any of the embodiments of the invention, the imaging is positron emission tomography.

According to some embodiments of any of the embodiments of the invention relating to imaging, the radioactive copper isotope is selected from the group consisting of $^{60}$Cu, $^{61}$Cu, $^{62}$Cu and $^{64}$Cu.

According to some embodiments of any of the embodiments of the invention, the imaging is for monitoring or determining a level and/or distribution of hypoxic tissue within the body of the subject.

According to some embodiments of any of the embodiments of the invention, the imaging is for determining if the subject has a disease or disorder associated with hypoxic tissue.

According to some embodiments of any of the embodiments of the invention, the hypoxic tissue is associated with a tumor and/or a blood supply deficiency.

According to some embodiments of any of the embodiments of the invention, the imaging is for determining aggressiveness of the abovementioned tumor, and tumor aggressiveness is associated with increased copper concentration.

According to some embodiments of any of the embodiments of the invention, the imaging is for determining if a tissue is sensitive to cisplatin.

According to some embodiments of any of the embodiments of the invention, the complex described herein is for use in radiation therapy.

According to some embodiments of any of the embodiments of the invention rating to radiation therapy, the radioactive copper isotope is selected from the group consisting of $^{64}$Cu and $^{67}$Cu.

According to some embodiments of any of the embodiments of the invention, the radiation therapy comprises killing tumor cells.

According to some embodiments of any of the embodiments of the invention, the ligand exhibits fluorescence sensitive to an oxidation state of a copper ion coordinated thereto. According to some embodiments, the ligand is a cyanine.

According to some embodiments of any of the embodiments of the invention, determining a level of at least one oxidation state of copper ion in the cells comprises determining an amount of copper in the cells, wherein an increased level of copper is indicative of Cu(I).

According to some embodiments of any of the embodiments of the invention, the copper in the complex comprises a radioactive copper isotope, and determining an amount of copper in the cells is effected by determining a level of radioactivity emitted by the radioactive copper isotope in the cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 (Background Art) shows the structure of Cu-ATSM (Cu(II)-diacetyl-bis(N4-methylthiosemicarbazone), a state of the art copper complex.

Figure 2:
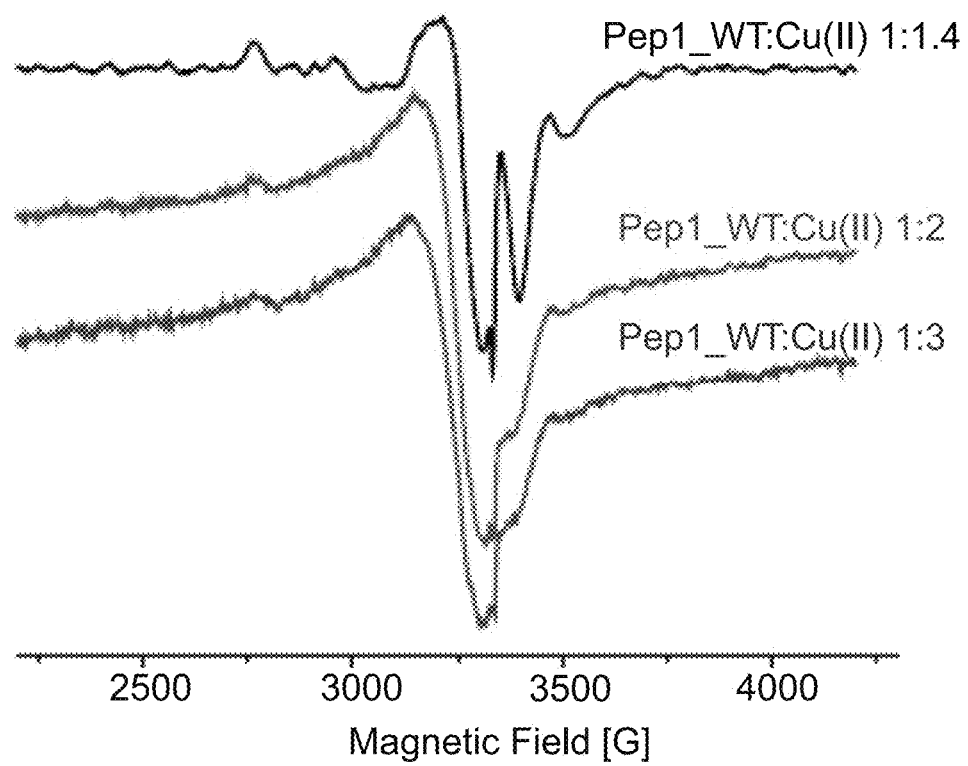

FIG. 2 presents low temperature (130±5 K) X-band CW-EPR spectra for Cu(II) in the presence of 1 mM Pep1 peptide (SEQ ID NO: 1) at molar ratios of 1:1.4, 1:2 and 1:3 (Pep1:Cu(II)) in HEPES buffer.

Figure 3:
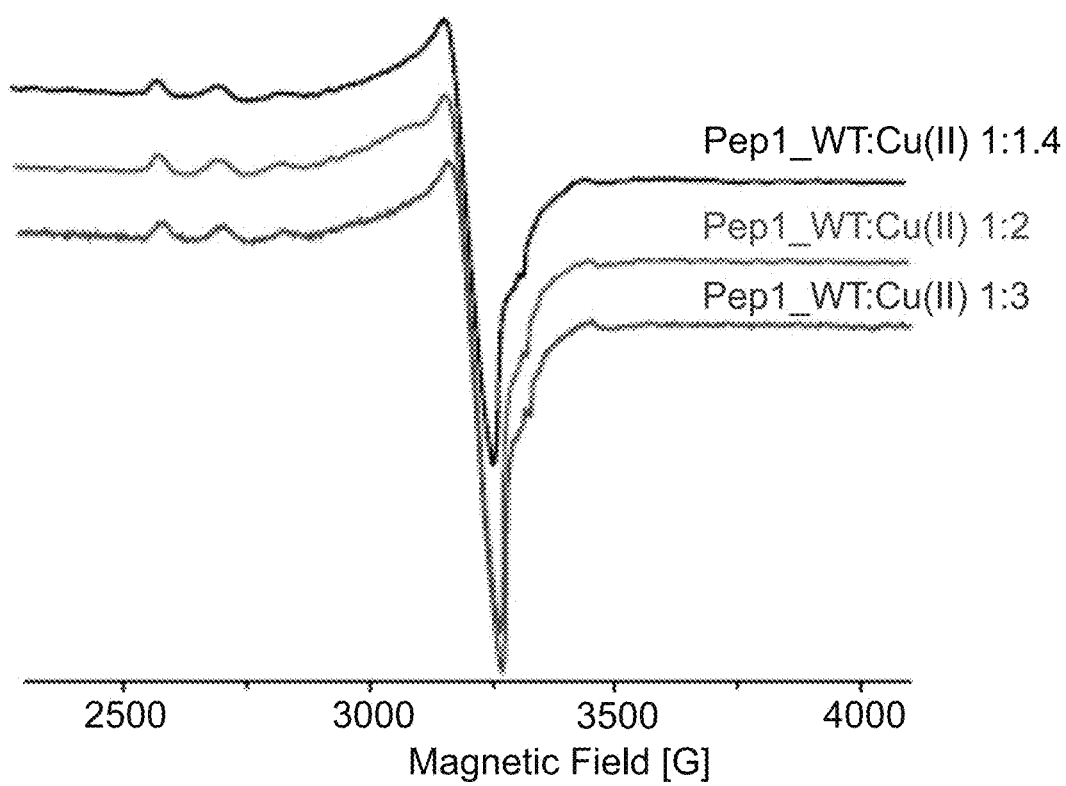

FIG. 3 presents low temperature (130±5 K) X-band CW-EPR spectra for Cu(II) in the presence of 1 mM Pep1 peptide (SEQ ID NO: 1) at molar ratios of 1:1.4, 1:2 and 1:3 (Pep1:Cu(II)) in KPi buffer.

Figure 4:
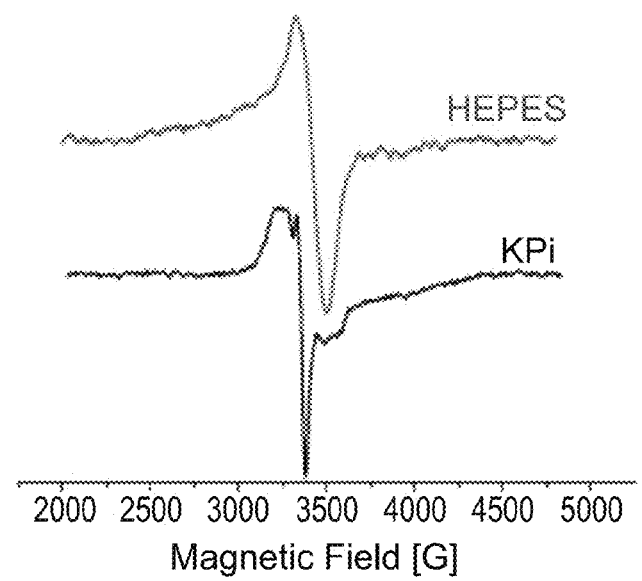

FIG. 4 presents room temperature X-band CW-EPR spectra for 2 mM Cu(II) in the presence of 1 mM Pep1 peptide (SEQ ID NO: 1) in HEPES and KPi buffers.

Figure 5:
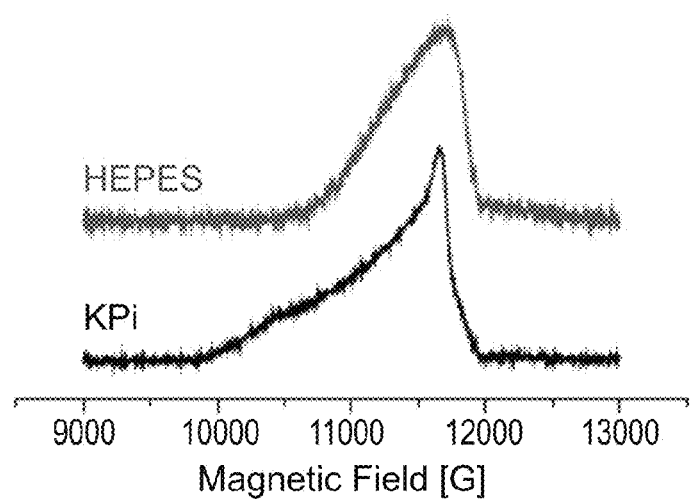

FIG. 5 presents a 2P-field sweep Q-band EPR measurement at 10 K, 33.84±0.05 GHz, for 2 mM Cu(II) in the presence of 1 mM Pep1 peptide (SEQ ID NO: 1) in HEPES and KPi buffers.

Figure 6:
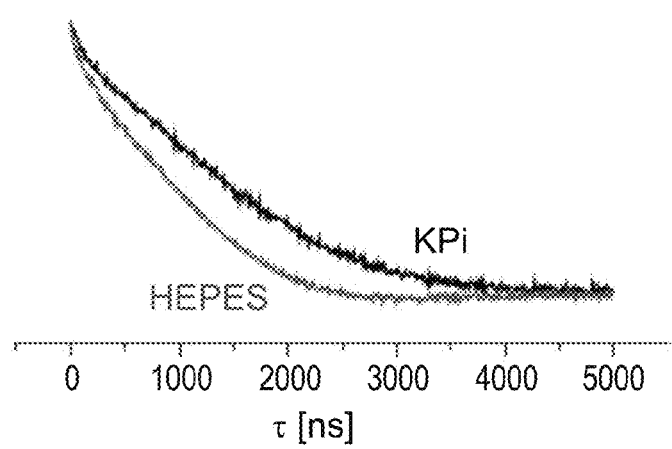

FIG. 6 presents a 2P-ESEEM echo decay Q-band EPR measurement at 10 K, 33.84±0.05 GHz, for 2 mM Cu(II) in the presence of 1 mM Pep1 peptide (SEQ ID NO: 1) in HEPES and KPi buffers.

Figure 7:
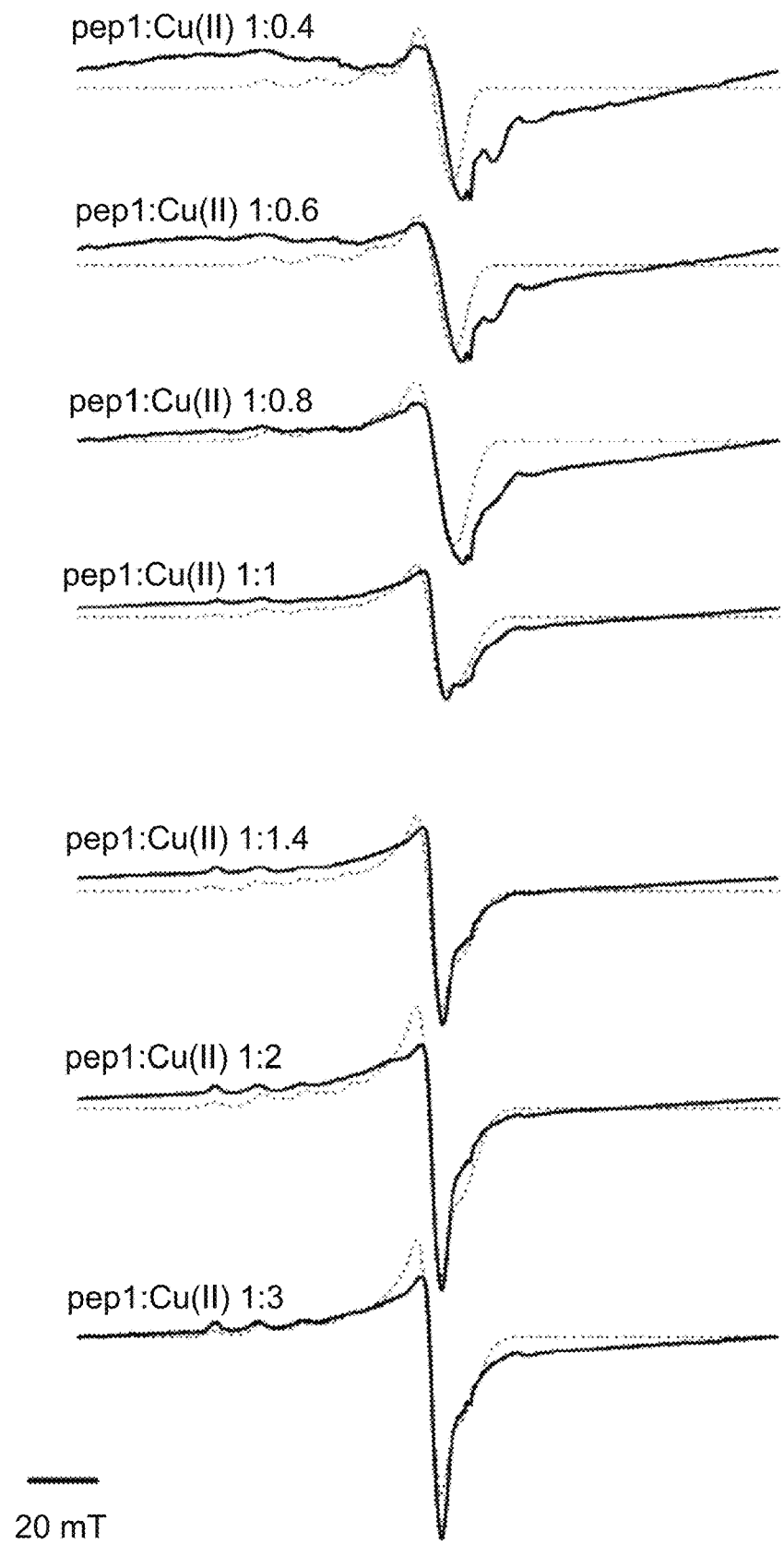

FIG. 7 presents low temperature CW-EPR spectra (solid lines) for Cu(II) in the presence of Pep1 peptide (SEQ ID NO: 1) at molar ratios of 1:0.4, 1:0.6, 1:0.8, 1:1, 1:1.4, 1:2 and 1:3 (Pep1:Cu(II)), as well as simulated data (dashed lines) using the following parameters:

for the 1:0.4 ratio—g=[2.07 2.25], line width [mT]=6.0, hyperfine [MHz]=[20 460], 2N2O/3N1O coordination;
for the 1:0.6 ratio—g=[2.07 2.24], line width [mT]=7.0, hyperfine [MHz]=[20 460], 2N2O/3N1O coordination;
for the 1:0.8 ratio—g=[2.07 2.235], line width [mT]=8.0, hyperfine [MHz]=[20 460], 3N1O coordination;
for the 1:1 ratio—a) (80%) g=[2.07 2.235], line width [mT]=9.5, hyperfine [MHz]=[20 460], 3N1O coordination; b) (20%) g=[2.05 2.38], line width [mT]=3.0, hyperfine [MHz]=[20 430], 4O coordination;

for the 1:1.4 ratio—a) (70%) g=[2.07 2.235], line width [mT]=10.5, hyperfine [MHz]=[20 460], 3N1O coordination; b) (30%) g=[2.05 2.38], line width [mT]=4.0, hyperfine [MHz]=[20 430], 4O coordination;

for the 1:2 ratio—a) (70%) g=[2.07 2.235], line width [mT]=10.5, hyperfine [MHz]=[20 460], 3N1O coordination; b) (30%) g=[2.08 2.4], line width [mT]=4.0, hyperfine [MHz]=[20 430], 4O coordination;

for the 1:3 ratio—a) (70%) g=[2.07 2.235], line width [mT]=10.5, hyperfine [MHz]=[20 460], 3N1O coordination; b) (30%) g=[2.08 2.39], line width [mT]=4.0, hyperfine [MHz]=[20 430], 4O coordination.

Figure 8:
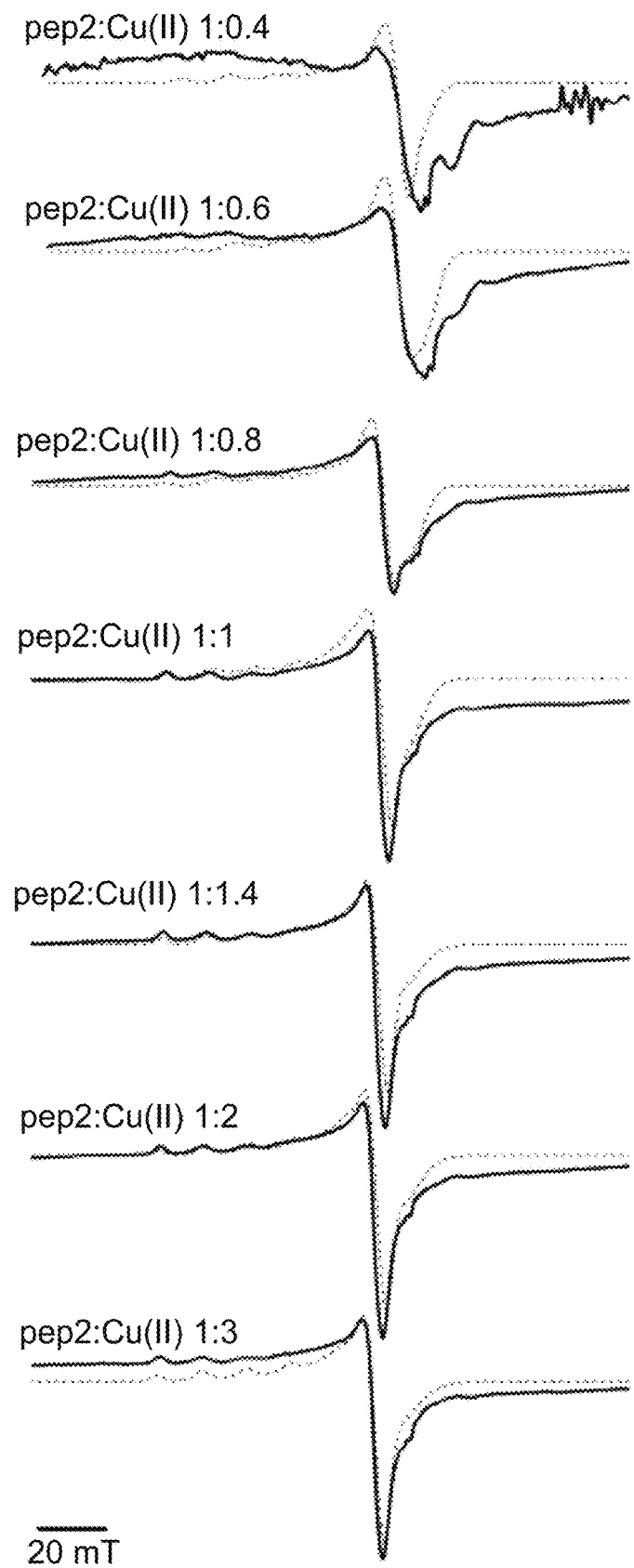

FIG. 8 presents low temperature CW-EPR spectra (solid lines) for Cu(II) in the presence of Pep2 peptide (SEQ ID NO: 2) at molar ratios of 1:0.4, 1:0.6, 1:0.8, 1:1, 1:1.4, 1:2 and 1:3 (Pep2:Cu(II)), as well as simulated data (dashed lines) using the following parameters:

for the 1:0.4 ratio—a) (60%) g=[2.07 2.24], line width [mT]=8.0, hyperfine [MHz]=[20 450], 3N1O coordination; b) (40%) g=[2.07 2.39], line width [mT]=4.0, hyperfine [MHz]=[20 430], 4O coordination;

for the 1:0.6 ratio—a) (80%) g=[2.07 2.24], line width [mT]=8.0, hyperfine [MHz]=[20 450], 3N1O coordination; b) (20%) g=[2.08 2.39], line width [mT]=4.0, hyperfine [MHz]=[20 430], 4O coordination;

for the 1:0.8 ratio—a) (85%) g=[2.06 2.235], line width [mT]=8.5, hyperfine [MHz]=[20 450], 3N1O coordination; b) (15%) g=[2.07 2.39], line width [mT]=3.0, hyperfine [MHz]=[20 430], 4O coordination;

for the 1:1 ratio—a) (70%) g=[2.07 2.235], line width [mT]=10.5, hyperfine [MHz]=[20 450], 3N1O coordination; b) (30%) g=[2.07 2.395], line width [mT]=4.0, hyperfine [MHz]=[20 420], 4O coordination;

for the 1:1.4 ratio—a) (60%) g=[2.07 2.235], line width [mT]=12.0, hyperfine [MHz]=[20 450], 3N1O coordination; b) (40%) g=[2.07 2.395], line width [mT]=3.5, hyperfine [MHz]=[20 420], 4O coordination;

for the 1:2 ratio—a) (62%) g=[2.07 2.25], line width [mT]=12.0, hyperfine [MHz]=[20 470], 3N1O/2N2O coordination; b) (38%) g=[2.07 2.395], line width [mT]=3.7, hyperfine [MHz]=[20 420], 4O coordination;

for the 1:3 ratio—a) (58%) g=[2.07 2.25], line width [mT]=13.0, hyperfine [MHz]=[20 450], 3N1O/2N2O coordination; b) (42%) g=[2.07 2.395], line width [mT]=3.7, hyperfine [MHz]=[20 420], 4O coordination.

Figure 9:
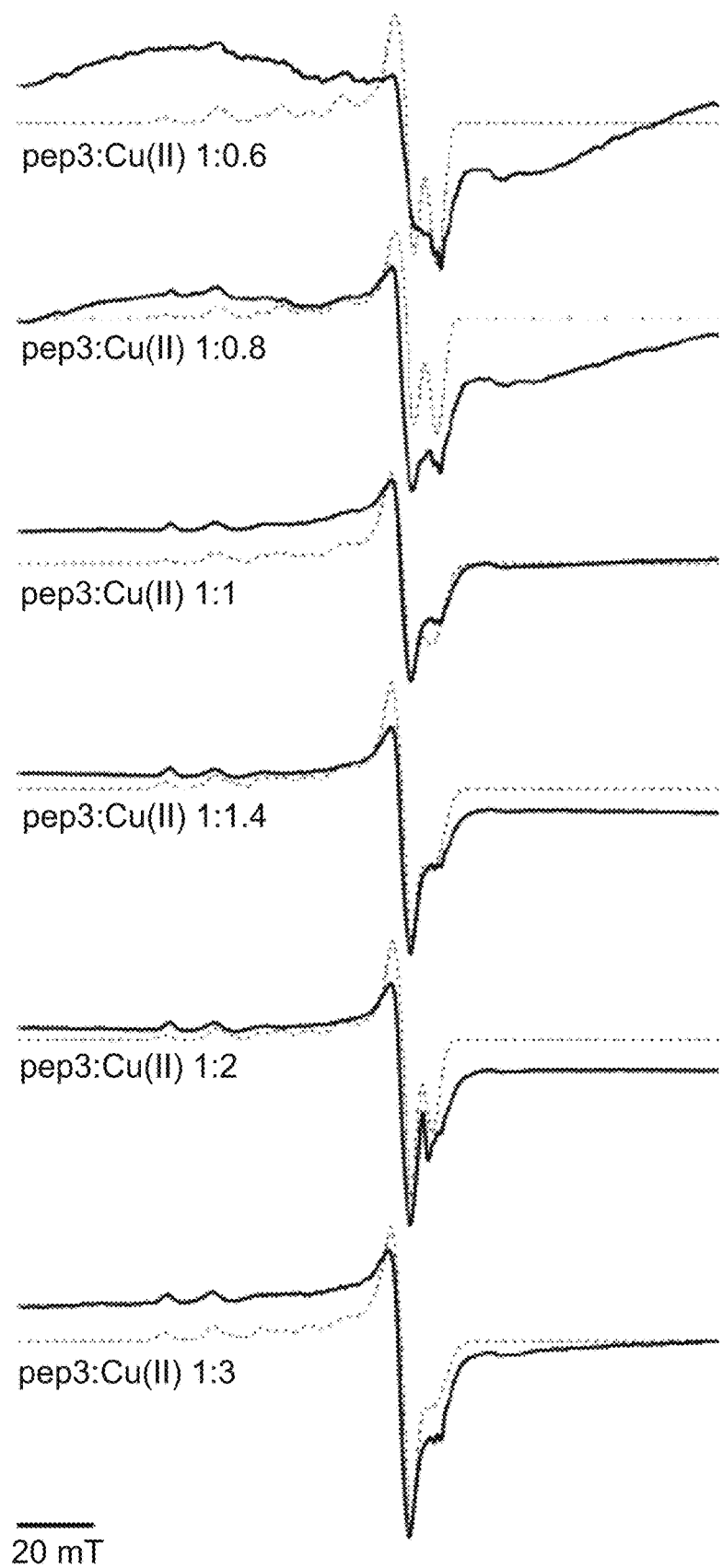

FIG. 9 presents low temperature CW-EPR spectra (solid lines) for Cu(II) in the presence of Pep3 peptide (SEQ ID NO: 3) at molar ratios of 1:0.6, 1:0.8, 1:1, 1:1.4, 1:2 and 1:3 (Pep3:Cu(II)), as well as simulated data (dashed lines) using the following parameters:

for the 1:0.6 ratio—a) (70%) g=[2.05 2.235], line width [mT]=4.0, hyperfine [MHz]=[20 490], 2N2O/3N1O coordination; b) (30%) g=[2.07 2.395], line width [mT]=3.0, hyperfine [MHz]=[20 420], 4O coordination;

for the 1:0.8 ratio—a) (70%) g=[2.05 2.235], line width [mT]=4.0, hyperfine [MHz]=[20 490], 2N2O/3N1O coordination; b) (30%) g=[2.07 2.395], line width [mT]=3.0, hyperfine [MHz]=[20 420], 4O coordination;

for the 1:1 ratio—a) (70%) g=[2.06 2.235], line width [mT]=6.0, hyperfine [MHz]=[20 490], 2N2O/3N1O coordination; b) (30%) g=[2.07 2.395], line width [mT]=3.0, hyperfine [MHz]=[20 420], 4O coordination;

for the 1:1.4 ratio—a) (63%) g=[2.06 2.235], line width [mT]=6.0, hyperfine [MHz]=[20 490], 2N2O/3N1O coordination; b) (37%) g=[2.07 2.395], line width [mT]=3.0, hyperfine [MHz]=[20 420], 4O coordination;

for the 1:2 ratio—a) (55%) g=[2.06 2.235], line width [mT]=4.0, hyperfine [MHz]=[20 490], 2N2O/3N1O coordination; b) (44%) g=[2.07 2.395], line width [mT]=3.0, hyperfine [MHz]=[20 420], 4O coordination;

for the 1:3 ratio—a) (55%) g=[2.06 2.235], line width [mT]=7.0, hyperfine [MHz]=[20 490], 2N2O/3N1O coordination; b) (45%) g=[2.07 2.395], line width [mT]=3.0, hyperfine [MHz]=[20 420], 4O coordination.

Figure 10:
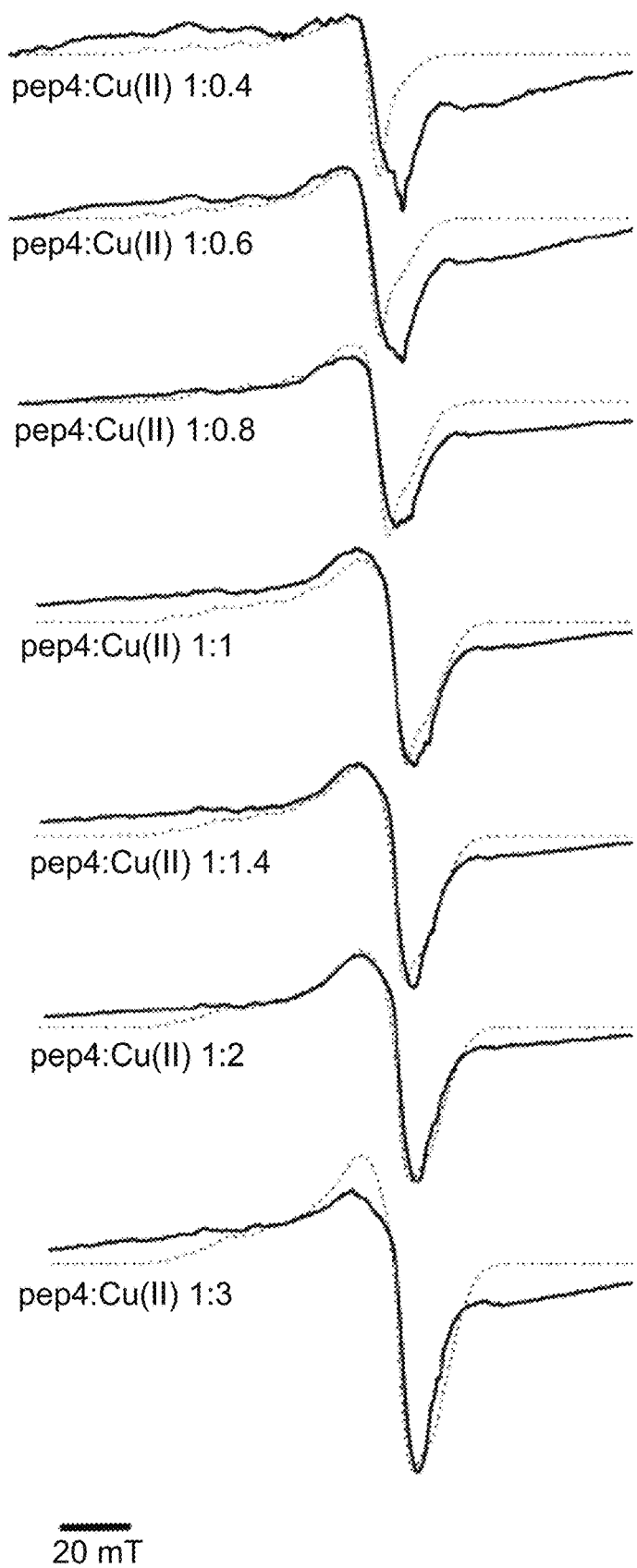

FIG. 10 presents low temperature CW-EPR spectra (solid lines) for Cu(II) in the presence of Pep4 peptide (SEQ ID NO: 4) at molar ratios of 1:0.4, 1:0.6, 1:0.8, 1:1, 1:1.4, 1:2 and 1:3 (Pep4:Cu(II)), as well as simulated data (dashed lines) using the following parameters:

for the 1:0.4 ratio—a) (70%) g=[2.07 2.32], line width [mT]=13.0, hyperfine [MHz]=[20 400], 2N2O/1N3O coordination; b) (30%) g=[2.07 2.395], line width [mT]=3.7, hyperfine [MHz]=[20 420], 4O coordination;

for the 1:0.6 ratio—a) (80%) g=[2.06 2.28], line width [mT]=13.0, hyperfine [MHz]=[20 400], 2N2O/1N3O coordination; b) (20%) g=[2.07 2.395], line width [mT]=3.7, hyperfine [MHz]=[20 420], 4O coordination;

for the 1:0.8 ratio—a) (85%) g=[2.06 2.3], line width [mT]=13.0, hyperfine [MHz]=[20 390], 2N2O/1N3O coordination; b) (15%) g=[2.07 2.395], line width [mT]=3.7, hyperfine [MHz]=[20 420], 4O coordination;

for the 1:1 ratio—a) (90%) g=[2.06 2.31], line width [mT]=14.0, hyperfine [MHz]=[20 390], 2N2O/1N3O coordination; b) (10%) g=[2.07 2.395], line width [mT]=3.7, hyperfine [MHz]=[20 420], 4O coordination;

for the 1:1.4 ratio—a) (92%) g=[2.06 2.31], line width [mT]=14.0, hyperfine [MHz]=[20 390], 2N2O/1N3O coordination; b) (8%) g=[2.07 2.395], line width [mT]=3.7, hyperfine [MHz]=[20 420], 4O coordination;

for the 1:2 ratio—a) (94%) g=[2.06 2.31], line width [mT]=14.0, hyperfine [MHz]=[20 390], 2N2O/1N3O coordination; b) (6%) g=[2.07 2.395], line width [mT]=3.7, hyperfine [MHz]=[20 420], 4O coordination;

for the 1:3 ratio—a) (97%) g=[2.06 2.31], line width [mT]=15.0, hyperfine [MHz]=[20 390], 2N2O/1N3O coordination; b) (3%) g=[2.07 2.395], line width [mT]=3.7, hyperfine [MHz]=[20 420], 4O coordination.

Figure 11:
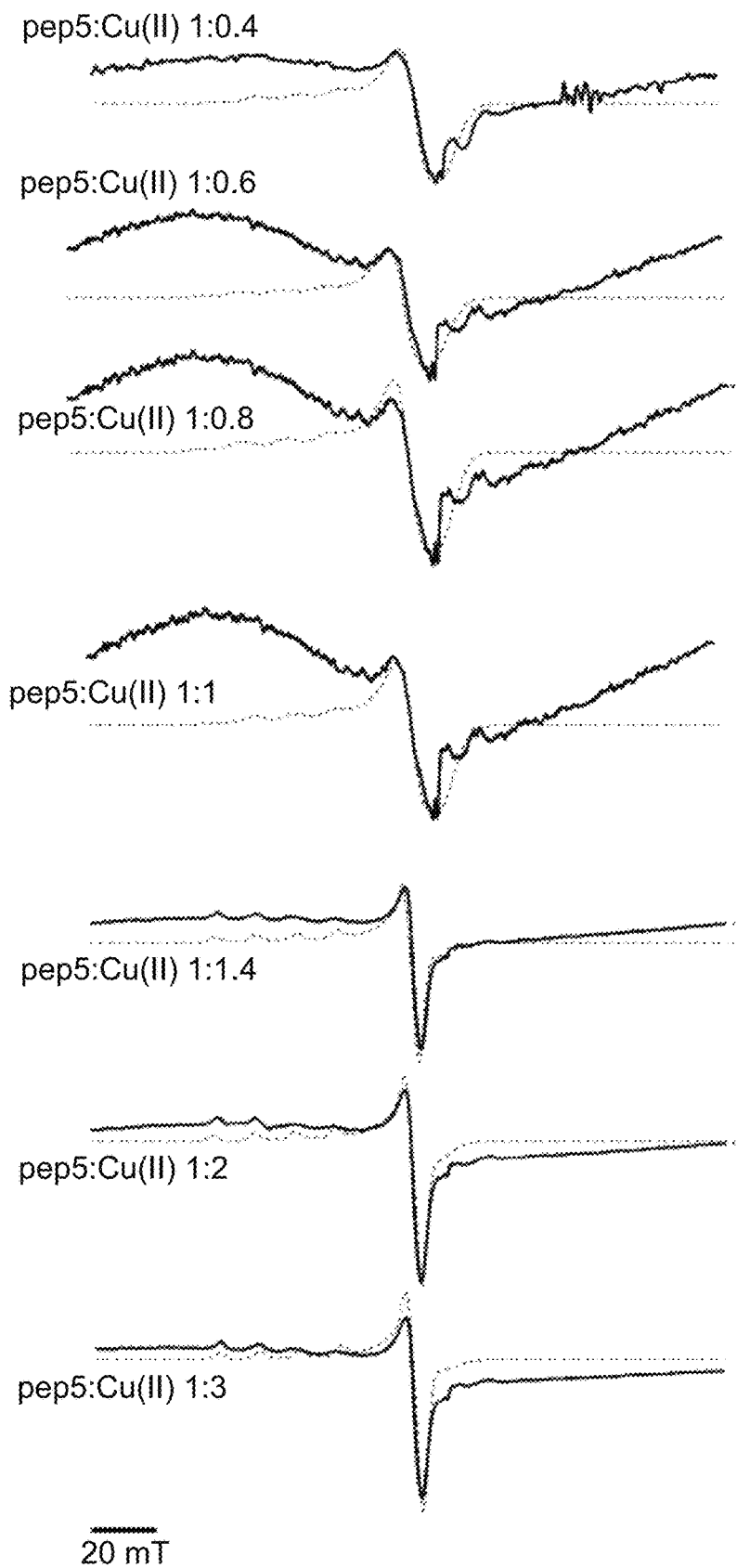

FIG. 11 presents low temperature CW-EPR spectra (solid lines) for Cu(II) in the presence of Pep5 peptide (SEQ ID NO: 5) at molar ratios of 1:0.4, 1:0.6, 1:0.8, 1:1, 1:1.4, 1:2 and 1:3 (Pep5:Cu(II)), as well as simulated data (dashed lines) using the following parameters:

for the 1:0.4 ratio—a) (75%) g=[2.04 2.28], line width [mT]=10.0, hyperfine [MHz]=[20 420], 2N2O/3N1O coordination; b) (25%) g=[2.07 2.395], line width [mT]=6.0, hyperfine [MHz]=[20 420], 4O coordination;

for the 1:0.6 ratio—a) (75%) g=[2.04 2.28], line width [mT]=10.0, hyperfine [MHz]=[20 420], 2N2O/3N1O coordination; b) (25%) g=[2.07 2.395], line width [mT]=6.0, hyperfine [MHz]=[20 420], 4O coordination;

for the 1:0.8 ratio—a) (75%) g=[2.04 2.28], line width [mT]=10.0, hyperfine [MHz]=[20 420], 2N2O/3N1O coordination; b) (25%) g=[2.07 2.395], line width [mT]=6.0, hyperfine [MHz]=[20 420], 4O coordination;

for the 1:1 ratio—a) (75%) g=[2.04 2.28], line width [mT]=10.0, hyperfine [MHz]=[20 420], 2N2O/3N1O coordination; b) (25%) g=[2.07 2.395], line width [mT]=6.0, hyperfine [MHz]=[20 420], 4O coordination;

for the 1:1.4 ratio—a) (40%) g=[2.06 2.28], line width [mT]=10.0, hyperfine [MHz]=[20 420], 2N2O/3N1O coordination; b) (60%) g=[2.08 2.395], line width [mT]=3.0, hyperfine [MHz]=[20 420], 4O coordination;

for the 1:2 ratio—a) (40%) g=[2.06 2.28], line width [mT]=10.0, hyperfine [MHz]=[20 420], 2N2O/3N1O coordination; b) (60%) g=[2.07 2.395], line width [mT]=3.0, hyperfine [MHz]=[20 420], 4O coordination;

for the 1:3 ratio—a) (30%) g=[2.06 2.28], line width [mT]=10.0, hyperfine [MHz]=[20 420], 2N2O/3N1O coordination; b) (70%) g=[2.07 2.395], line width [mT]=3.0, hyperfine [MHz]=[20 420], 4O coordination.

Figure 12:
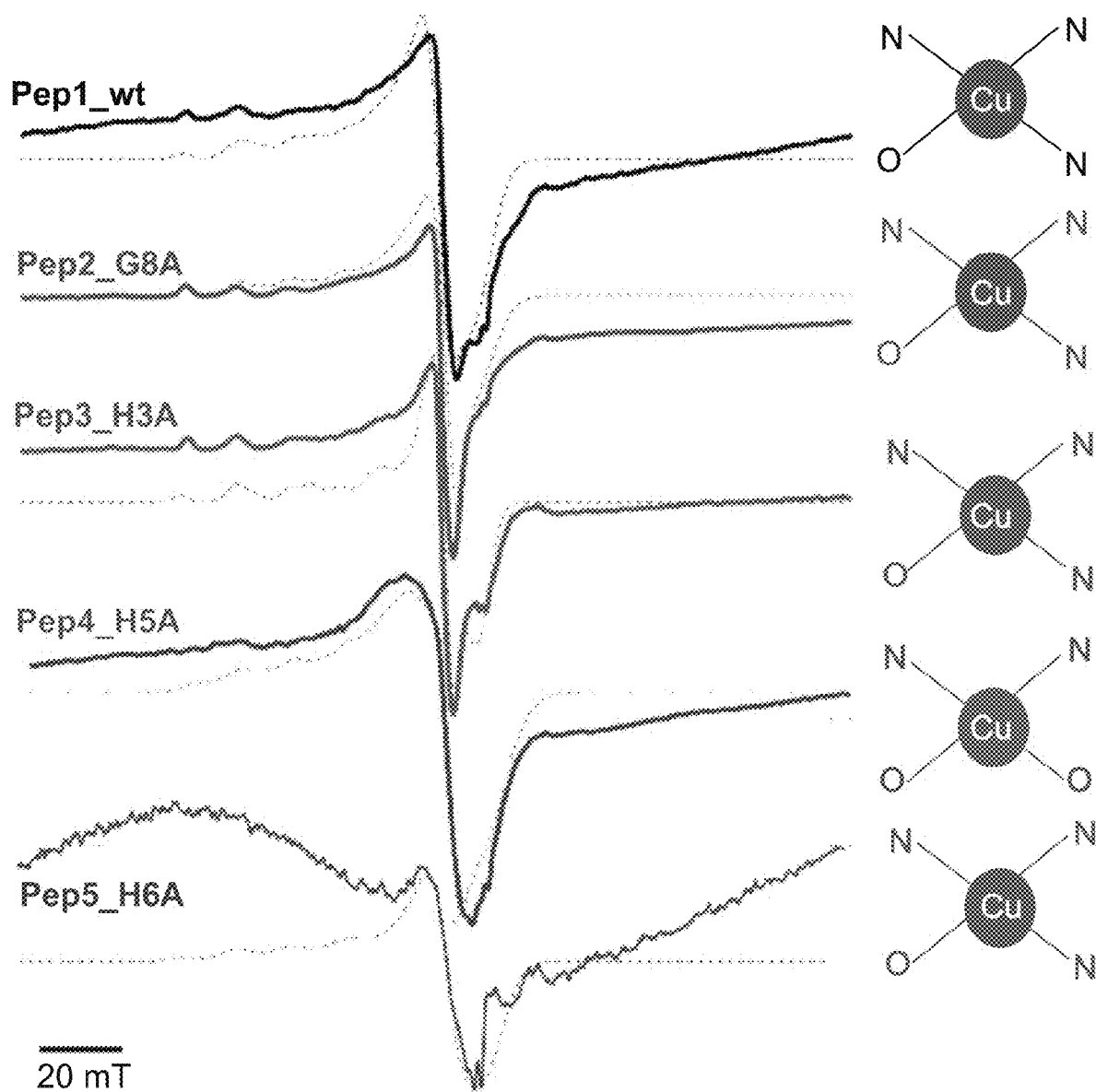

FIG. 12 presents the low temperature (130±5 K) CW-EPR spectra (solid line) and simulated data (dashed line) for Pep1 (wild-type), Pep2 (G8A mutant), Pep3 (H3A mutant), Pep4 (H5A mutant) and Pep5 (H5A mutant) peptides in the presence of Cu(II) at a molar ratio of 1:1, as presented in FIGS. 7-11, respectively, along with a schematic depiction of the predominant coordination type (on right).

Figure 13:
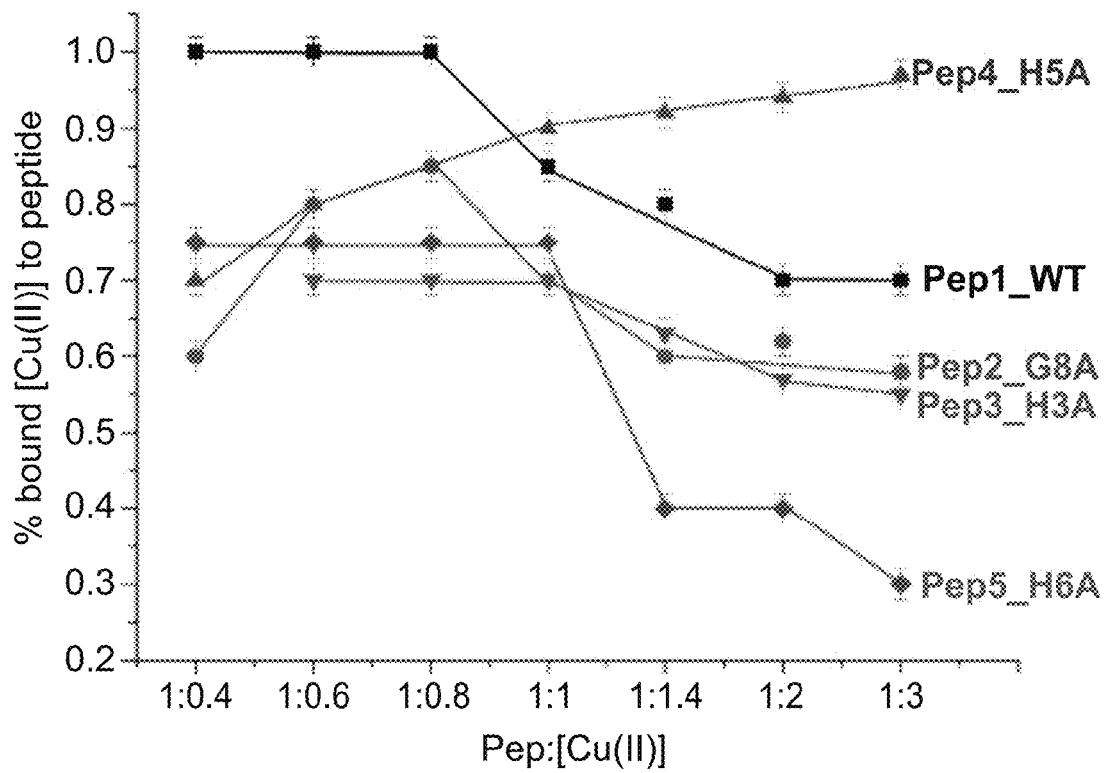

FIG. 13 presents a graph showing the percentage of Cu(II) bound to Pep1 (wild-type), Pep2 (G8A mutant), Pep3 (H3A mutant), Pep4 (H5A mutant) and Pep5 (H5A mutant) peptides as a function of peptide:Cu(II) molar ratio (based on the data presented in FIGS. 7-11, wherein 4O coordination represents unbound Cu(II)).

Figure 14:
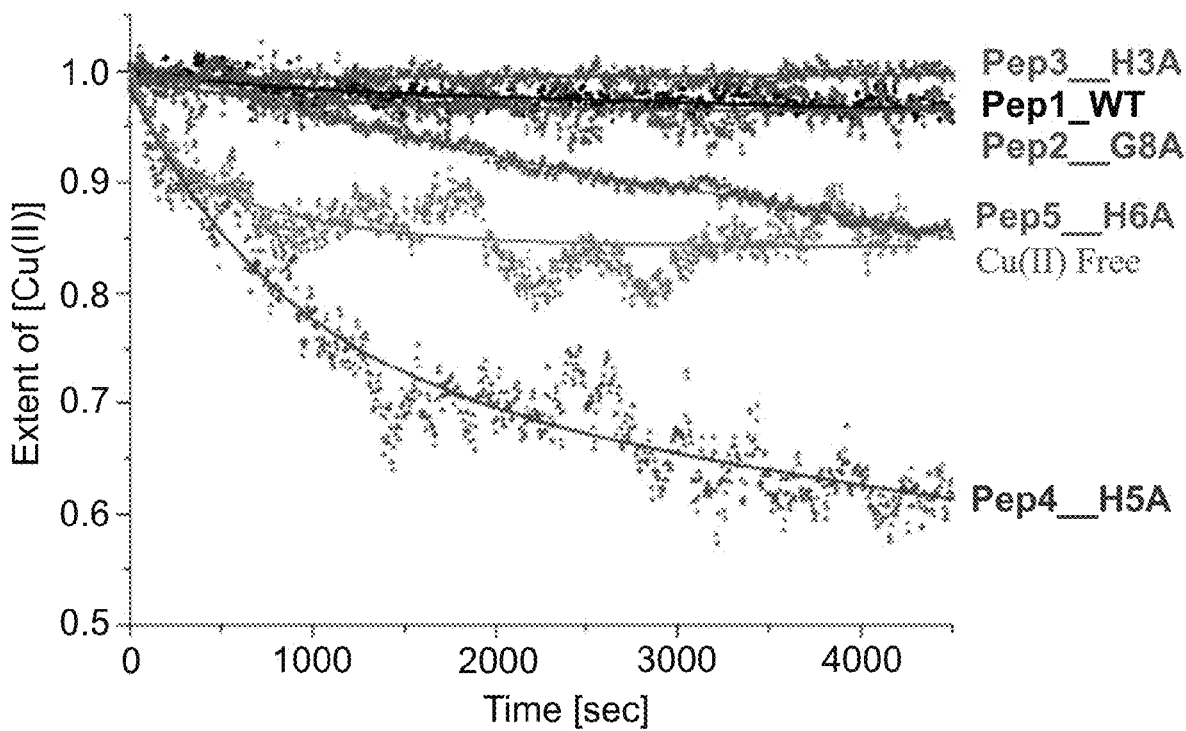

FIG. 14 presents a graph showing the fraction of copper ions in a Cu(II) state as a function of time following addition of ascorbate, for free Cu(II) and for Cu(II) in the presence of Pep1 (wild-type), Pep2 (G8A mutant), Pep3 (H3A mutant), Pep4 (H5A mutant) and Pep5 (H5A mutant) peptides.

Figure 15A:
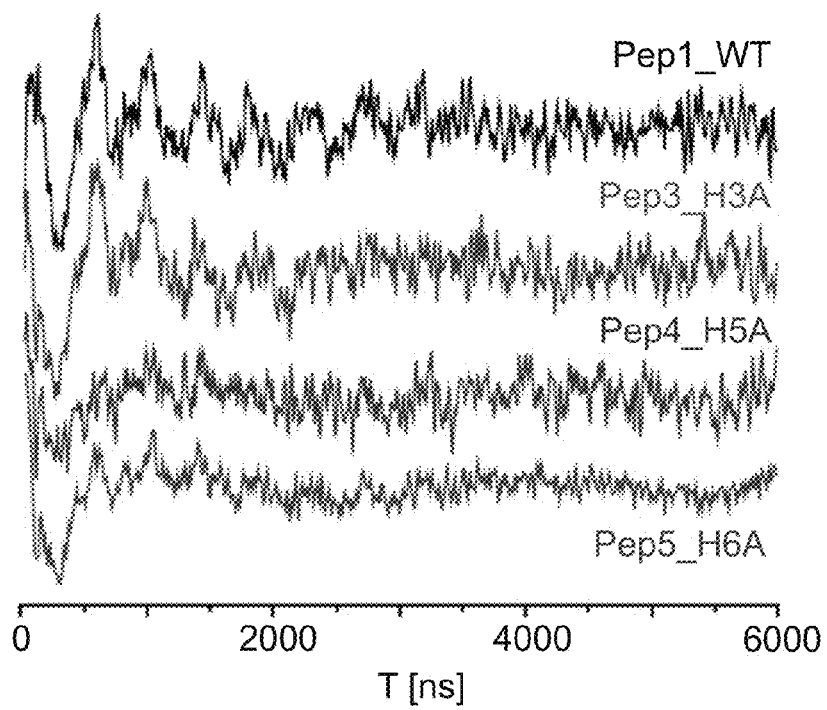
Figure 15B:
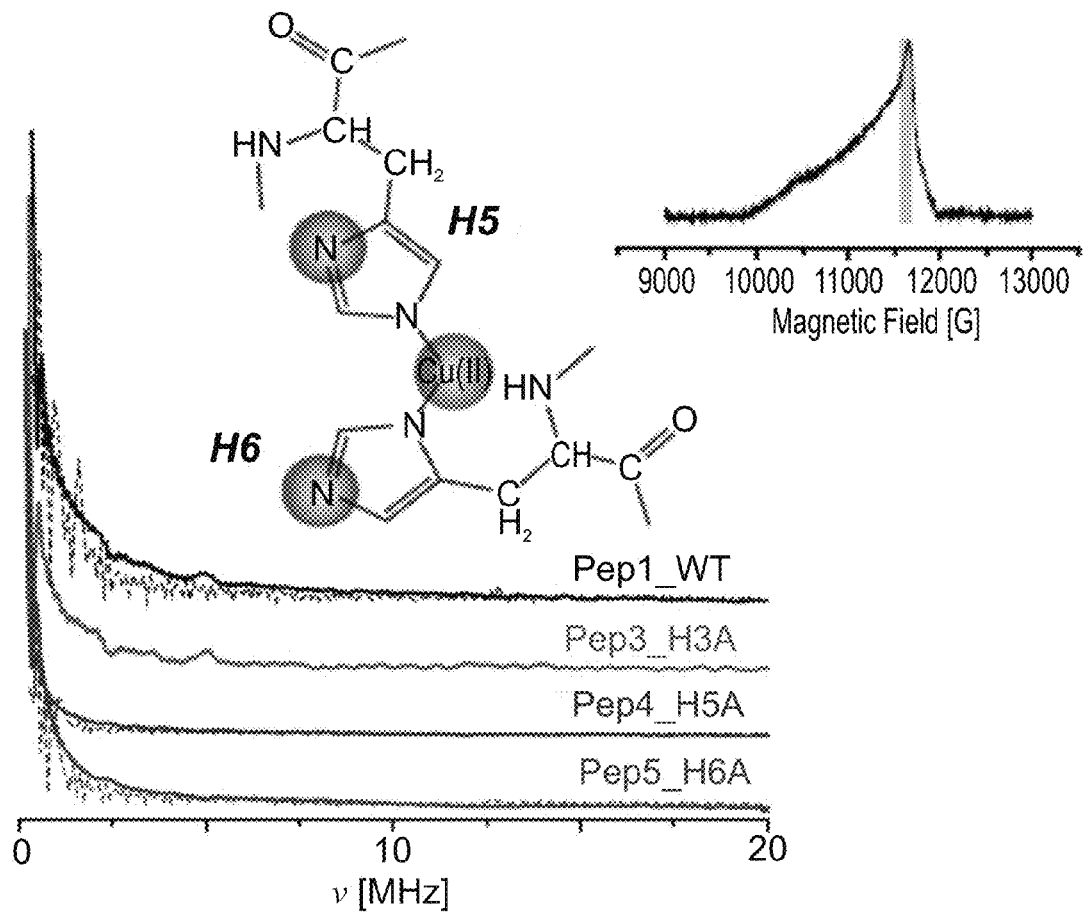

FIGS. 15A and 15B present time domain ESEEM signals (FIG. 15A) and corresponding ESEEM spectra for Pep1 (wild-type), Pep3 (H3A mutant), Pep4 (H5A mutant) and Pep5 (H5A mutant) peptides, as well as simulated spectra (dashed lines in FIG. 15B); inset of FIG. 15B shows magnetic field position where ESEEM was conducted and a schematic depiction of Cu(II) binding to His5 and His6.

FIG. 16 presents a table listing $^1$H-NMR chemical shifts upon addition of Cu(I) to Pep1 (a: $^{14}$NH$_2$→7.15→7.11, 7.59→7.53; b or c: signals with the same superscript may be interchanged; d: undetermined signal location; changes in chemical shift of at least 0.09 ppm indicated in red, changes in chemical shift in range of 0.05 to 0.08 indicated in blue).

Figure 17:
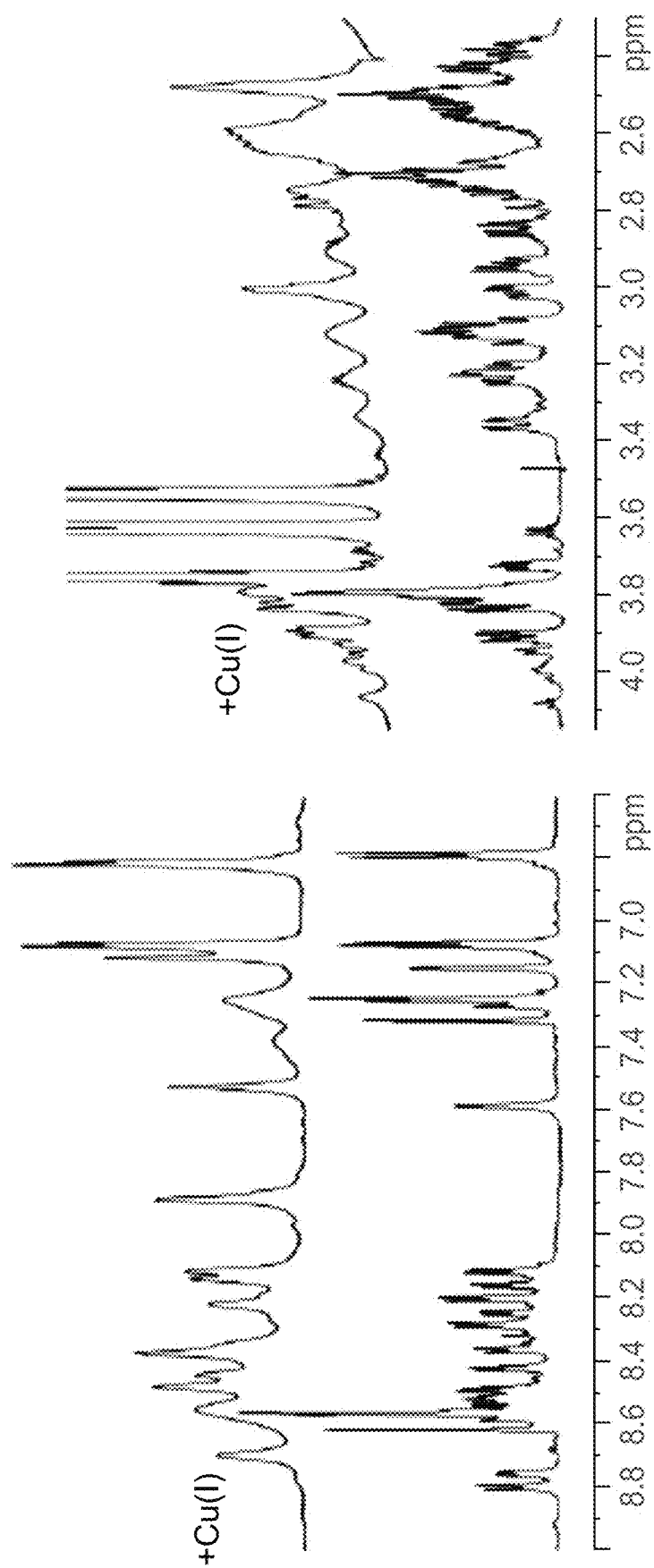

FIG. 17 presents regions in $^1$H-NMR spectra of Pep1 in the presence (top) or absence (bottom) of Cu(I).

Figure 18A:
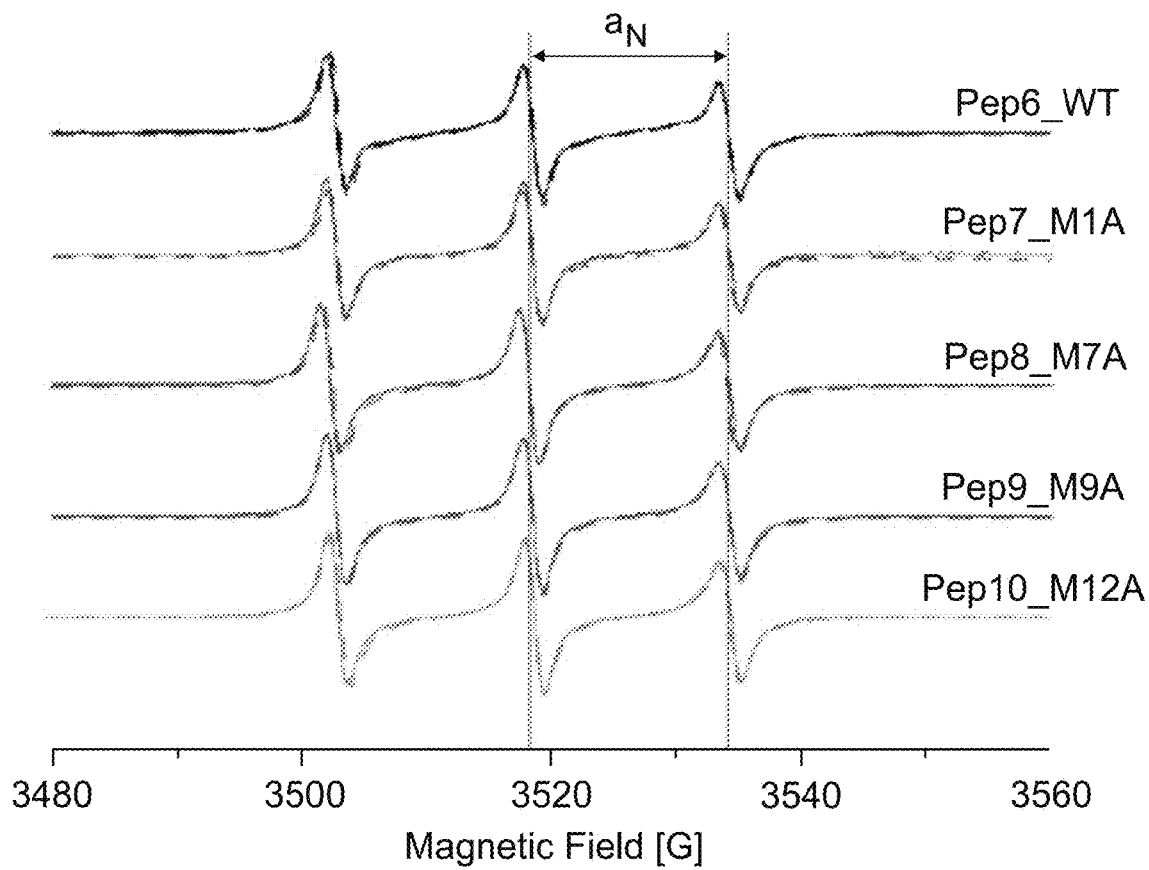
Figure 18B:
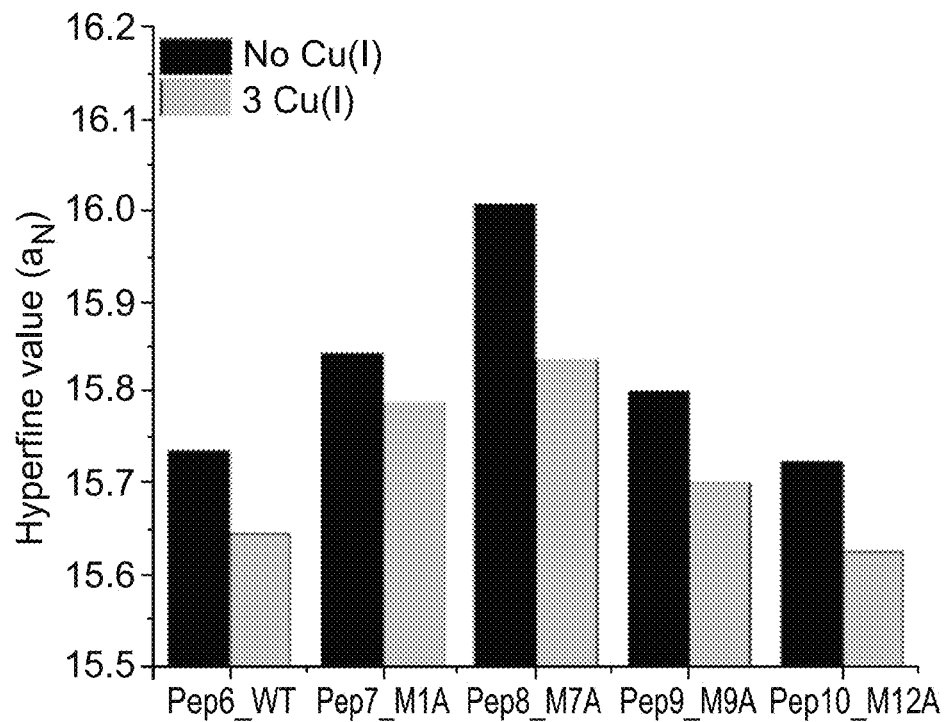

FIGS. 18A and 18B present room temperature CW-EPR spectra (FIG. 18A) of the spin-labeled peptides Pep6 (wild-type sequence), Pep7 (M1A mutant), Pep8 (M7A mutant), Pep9 (M9A mutant) and Pep10 (M12A mutant), in the presence (dashed line) or absence (solid line) of Cu(I) (at a Cu(I):peptide molar ratio of 3:1), and the hyperfine value ($\alpha_N$) derived from the spectrum for each peptide (FIG. 18B) (error in hyperfine values is ±0.05 G).

Figure 19A:
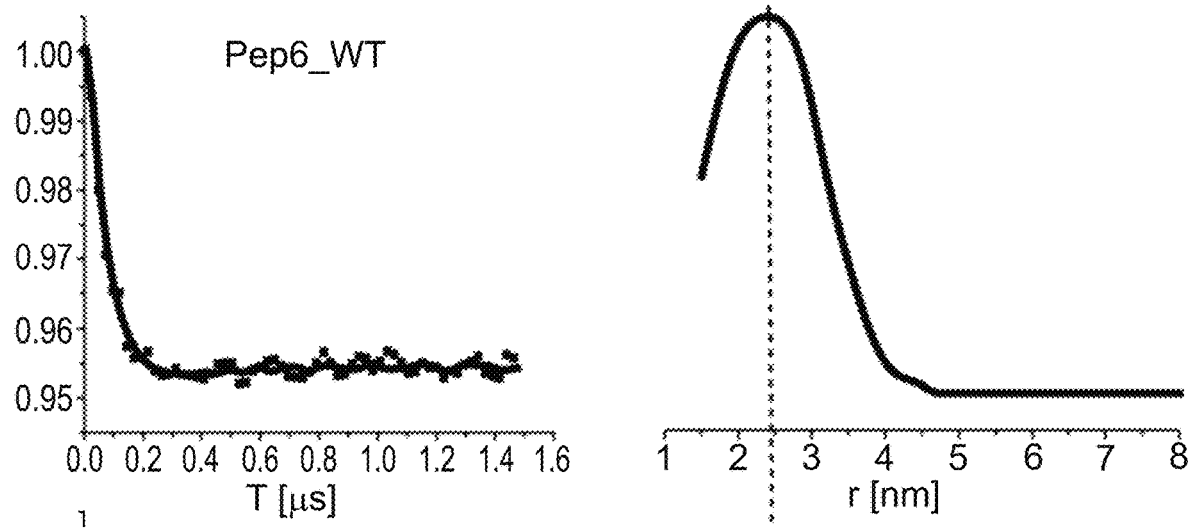
Figure 19B:
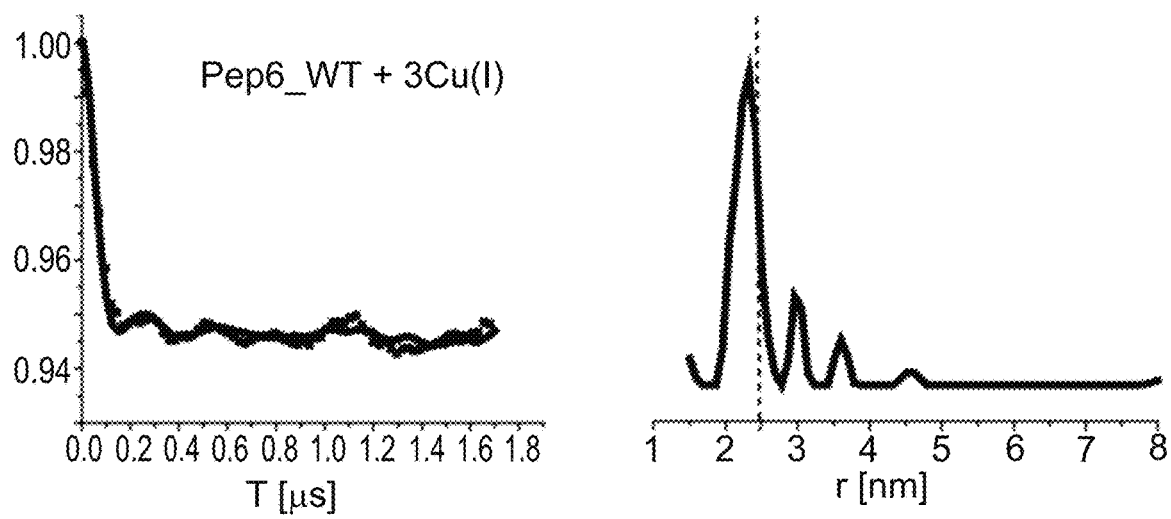

FIGS. 19A and 19B present Q-band DEER (double electron resonance) signals as a function of time (left), and the corresponding distance distribution obtained by Tikhonov regularization (right), for the spin-labeled peptide Pep6 (wild-type sequence), in the presence (FIG. 19B) or absence (FIG. 19A) of Cu(I).

Figure 20:
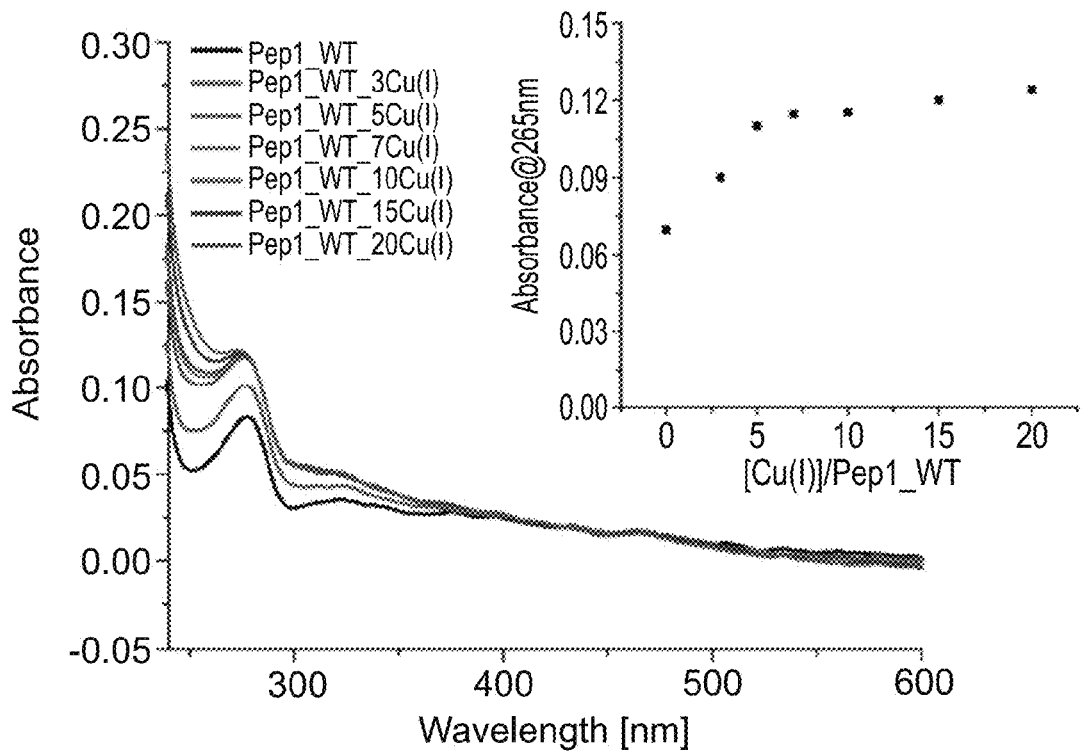

FIG. 20 presents a UV-visible absorption spectrum of Pep1 (wild-type peptide) in the absence of Cu(I) or in the presence of 3, 5, 7, 10, 15 or 20 molar equivalents of Cu(I) (relative to peptide concentration), as well as a graph (inset) showing the absorbance at 265 nm as a function of Cu(I):Pep1 molar ratio.

Figure 21:
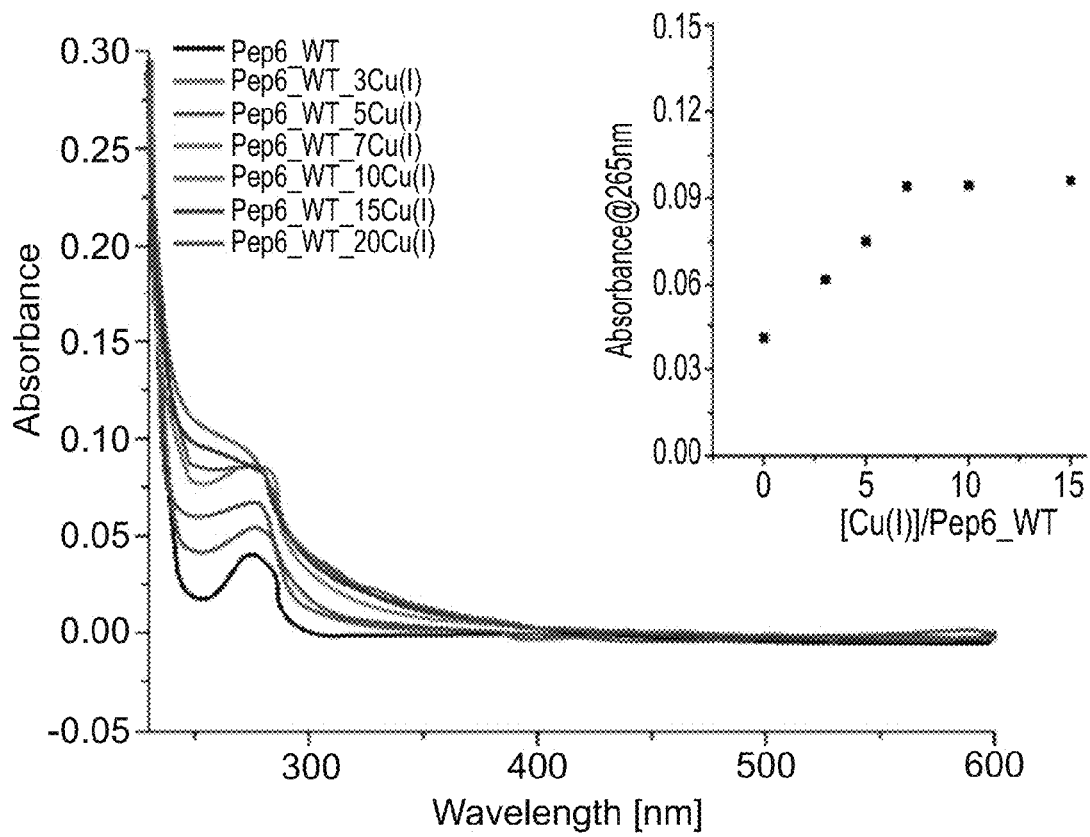

FIG. 21 presents a UV-visible absorption spectrum of Pep6 (wild-type peptide with spin-labels) in the absence of Cu(I) or in the presence of 3, 5, 7, 10, 15 or 20 molar equivalents of Cu(I) (relative to peptide concentration), as well as a graph (inset) showing the absorbance at 265 nm as a function of Cu(I):Pep6 molar ratio.

Figure 22:
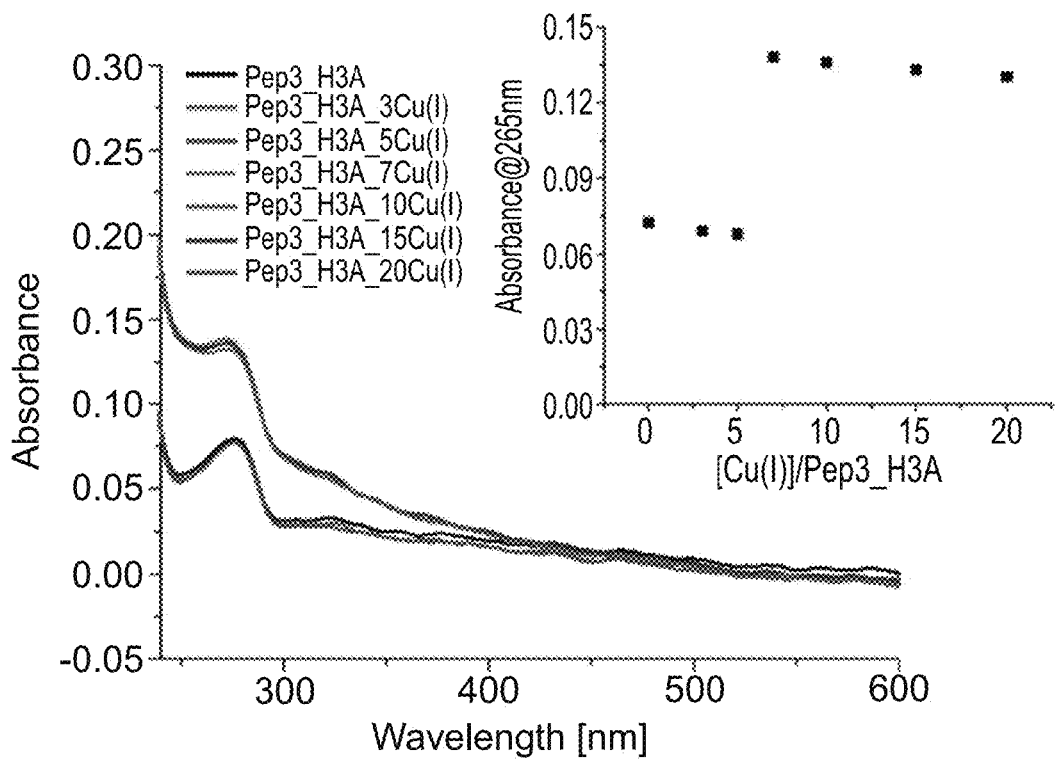

FIG. 22 presents a UV-visible absorption spectrum of Pep3 (H3A mutant peptide) in the absence of Cu(I) or in the presence of 3, 5, 7, 10, 15 or 20 molar equivalents of Cu(I) (relative to peptide concentration), as well as a graph (inset) showing the absorbance at 265 nm as a function of Cu(I):Pep3 molar ratio.

Figure 23:
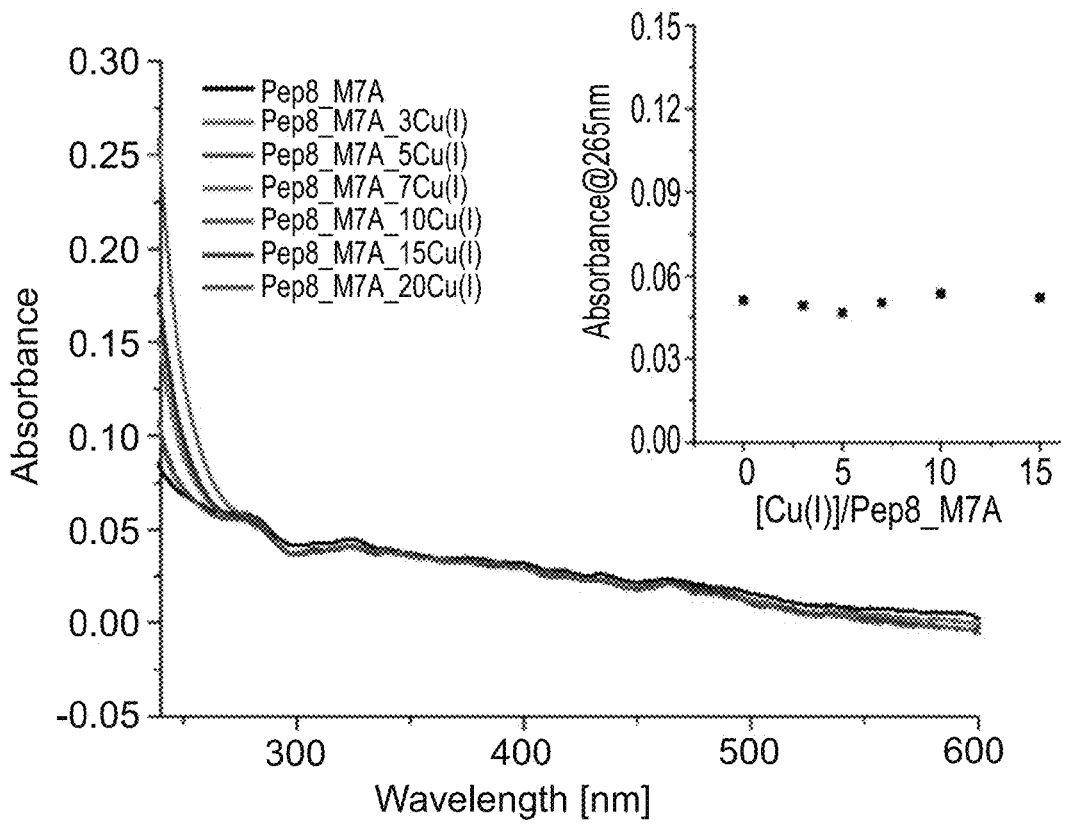

FIG. 23 presents a UV-visible absorption spectrum of Pep8 (M7A mutant peptide) in the absence of Cu(I) or in the presence of 3, 5, 7, 10, 15 or 20 molar equivalents of Cu(I) (relative to peptide concentration), as well as a graph (inset) showing the absorbance at 265 nm as a function of Cu(I):Pep8 molar ratio.

Figure 24:
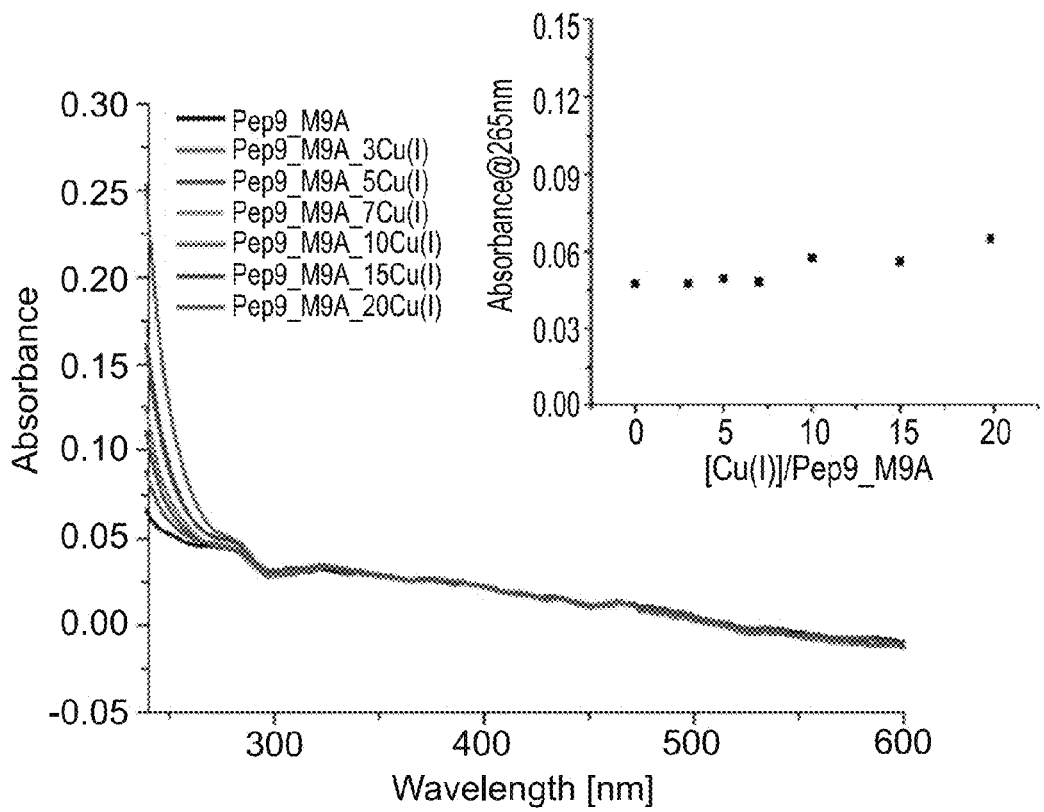

FIG. 24 presents a UV-visible absorption spectrum of Pep9 (M9A mutant peptide) in the absence of Cu(I) or in the presence of 3, 5, 7, 10, 15 or 20 molar equivalents of Cu(I) (relative to peptide concentration), as well as a graph (inset) showing the absorbance at 265 nm as a function of Cu(I):Pep9 molar ratio.

Figure 25:
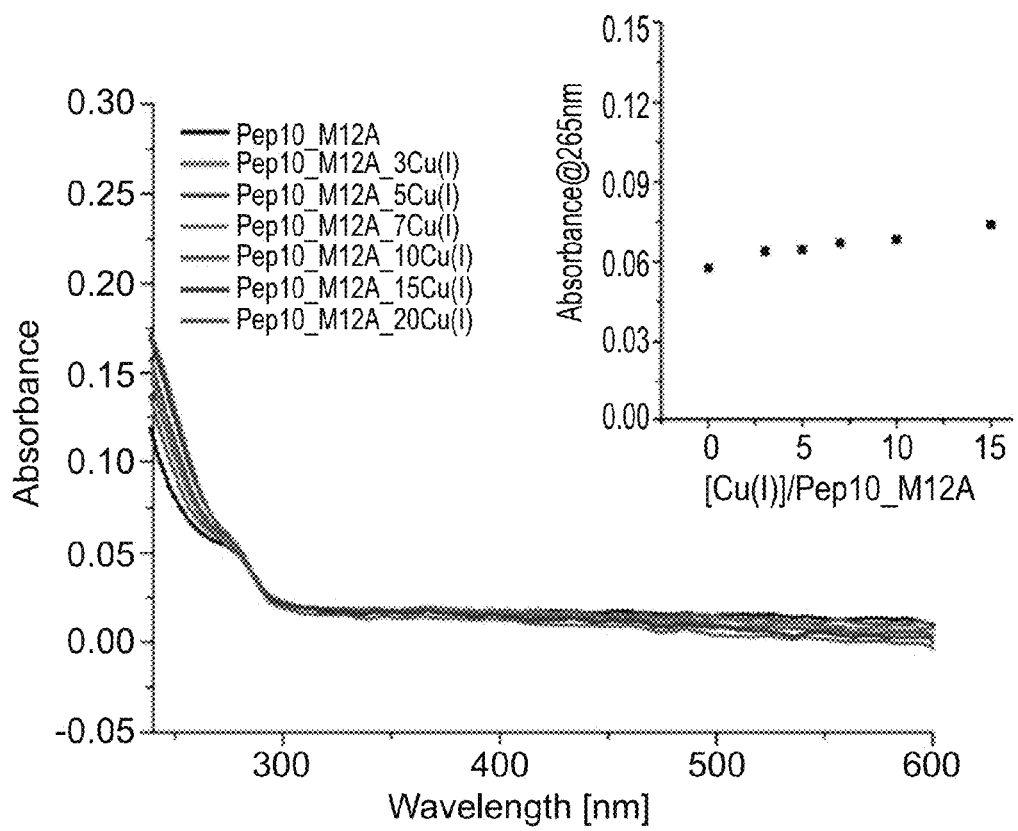

FIG. 25 presents a UV-visible absorption spectrum of Pep10 (M12A mutant peptide) in the absence of Cu(I) or in the presence of 3, 5, 7, 10, 15 or 20 molar equivalents of Cu(I) (relative to peptide concentration), as well as a graph (inset) showing the absorbance at 265 nm as a function of Cu(I):Pep10 molar ratio.

Figure 26:
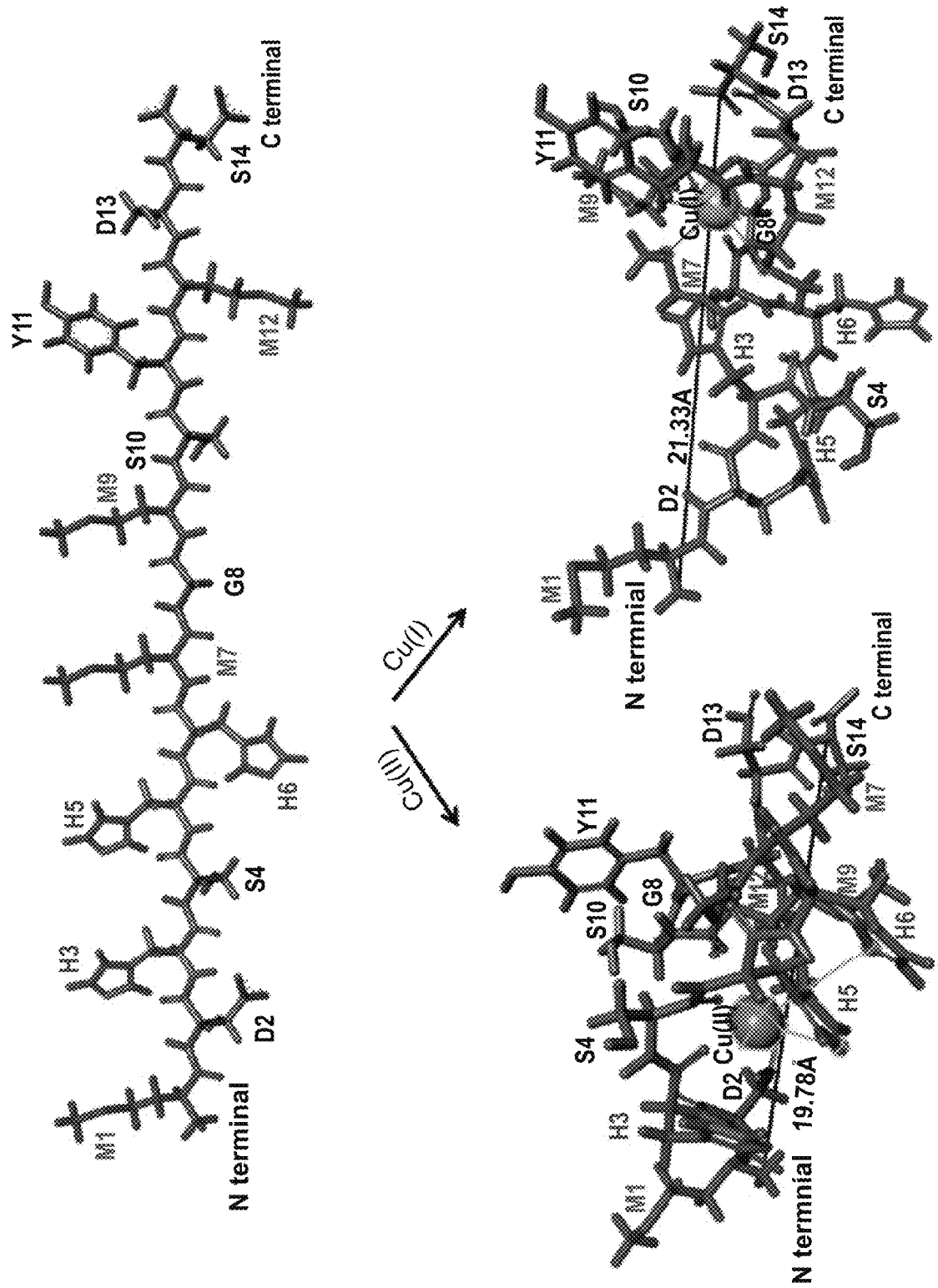

FIG. 26 presents a model of the structure of Pep1 (wild-type N-terminal portion of Ctr1) upon coordination to Cu(I) and Cu(II) (His residues depicted in blue, Met residues depicted in red, black lines indicate approximate N-terminal to C-terminal distance for Pep1).

Figure 27:
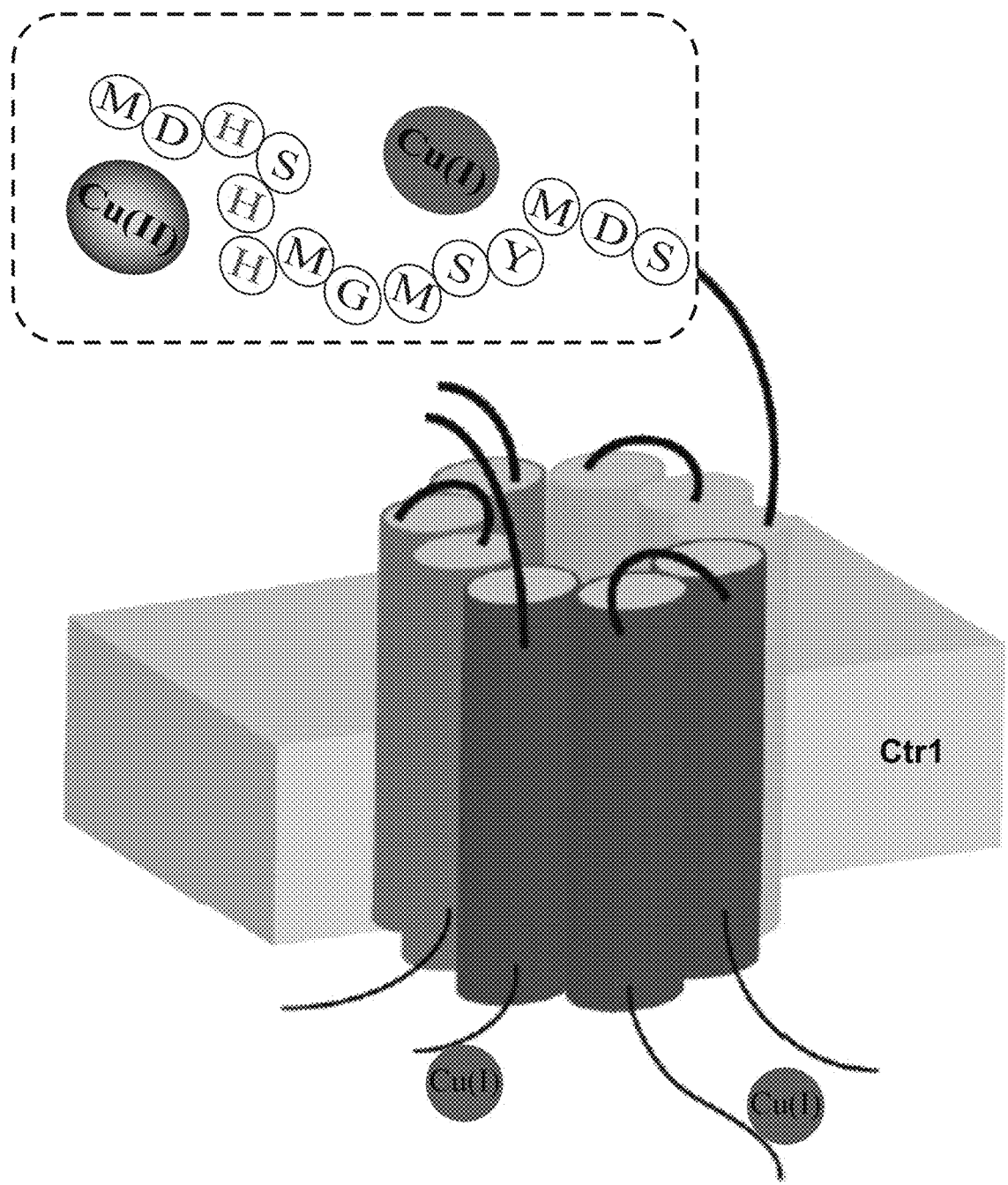

FIG. 27 presents a schematic depiction of the coordination to Cu(I) and Cu(II) to the N-terminal portion of Ctr1.

Figure 28:
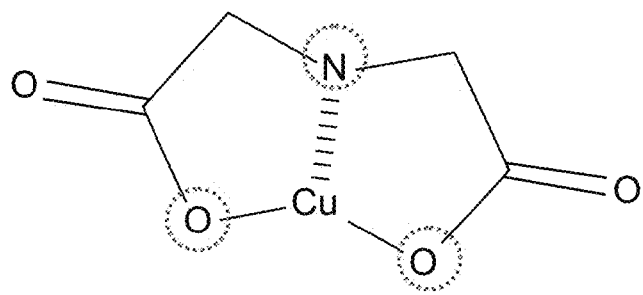
Figure 28:
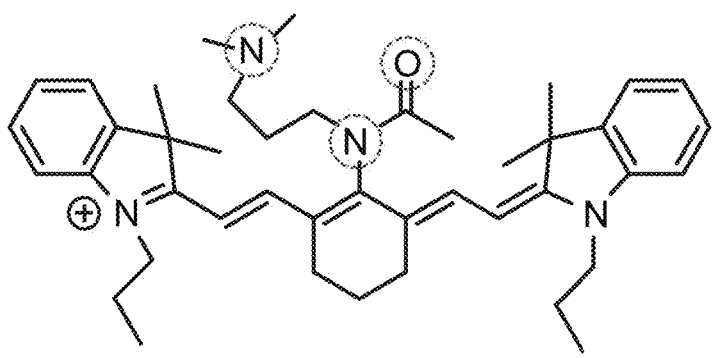
Figure 28:
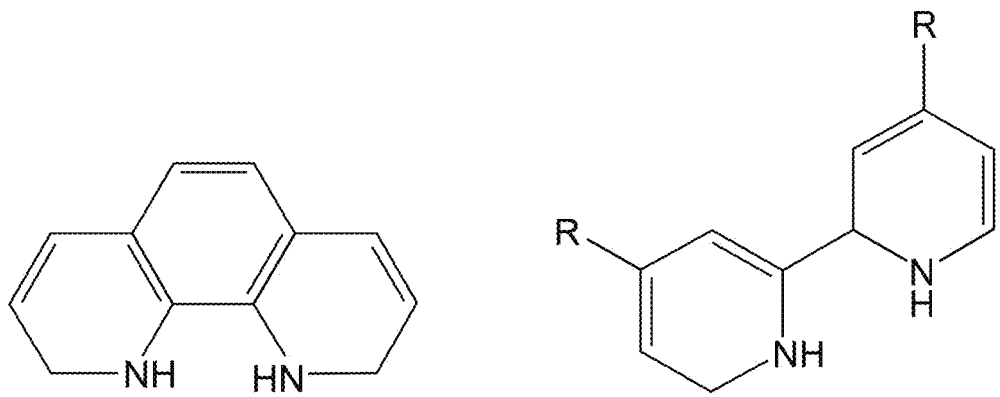

FIG. 28 depicts exemplary ligands for coordinating to copper in a Cu(II)-ligand-peptide complex according to some embodiments of the invention (the copper-coordinating atoms are encircled in the structures of the ligands IDA and CyNA-427; the structure of CyNA-427 further depicts the coordinated Cu(II)).

Figure 29:
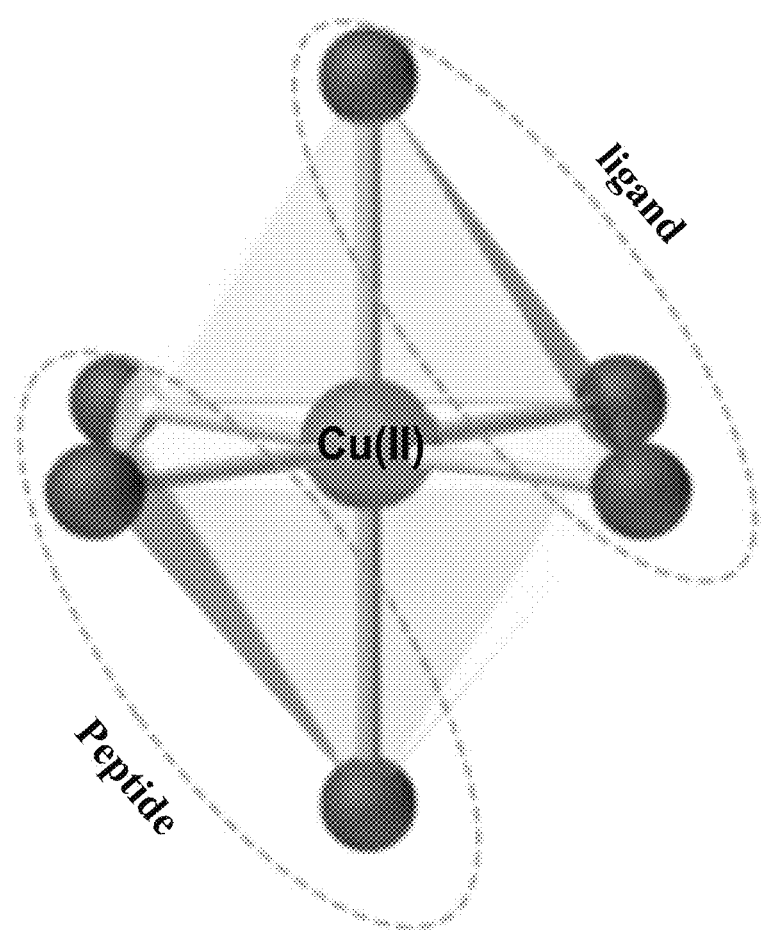

FIG. 29 presents a schematic depiction of Cu(II) and the Cu(II)-coordinating atoms of a ligand and peptide in a Cu(II)-ligand-peptide complex according to some embodiments of the invention.

Figure 30:
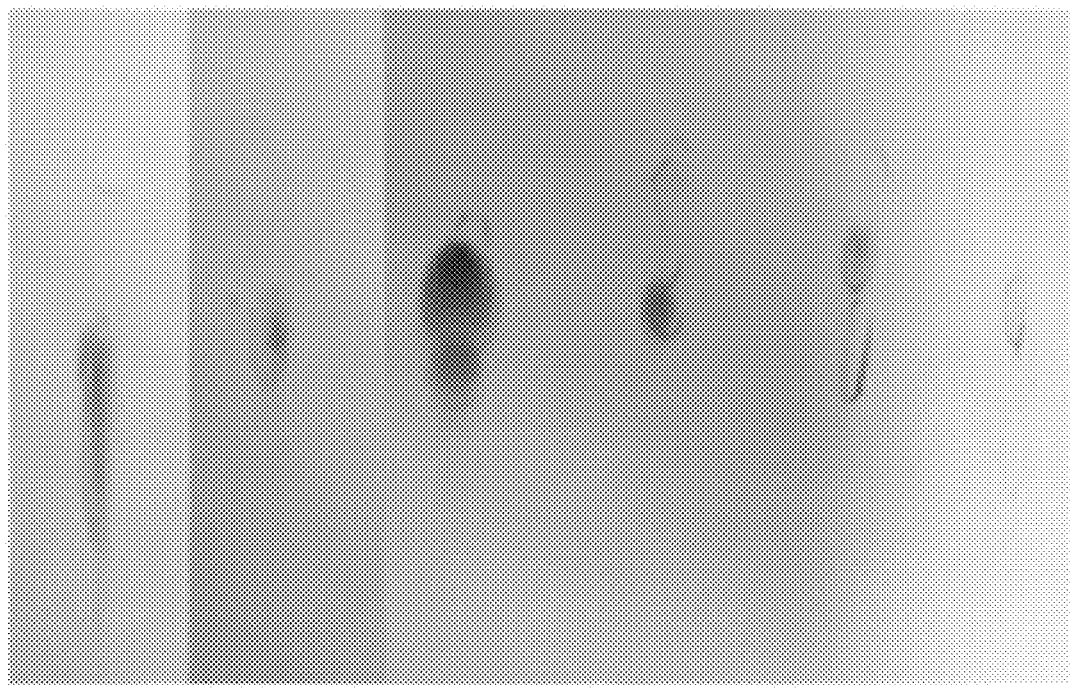

FIG. 30 presents images of a CyNA ligand alone or with Cys1 peptide or Cu(II) ions, and a Cu(II)-CyNA-Cys1 complex before purification or after 3 or 4 purification stages, as observed by thin payer chromatography.

Figure 31A:
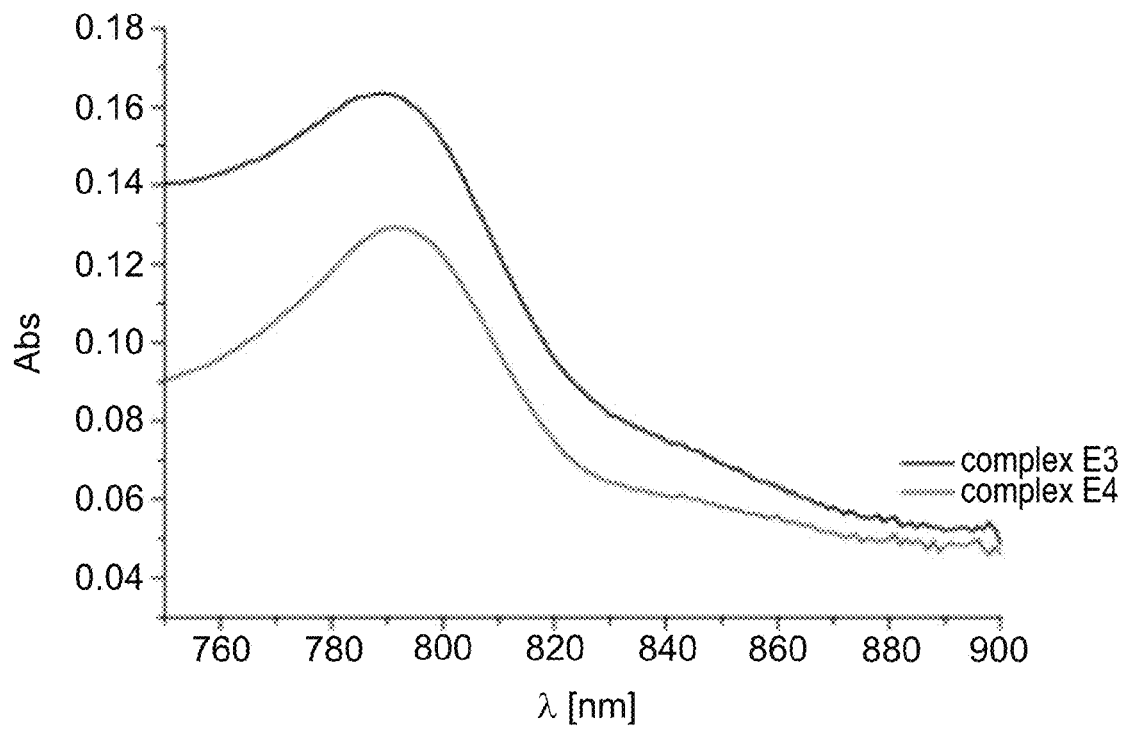
Figure 31B:
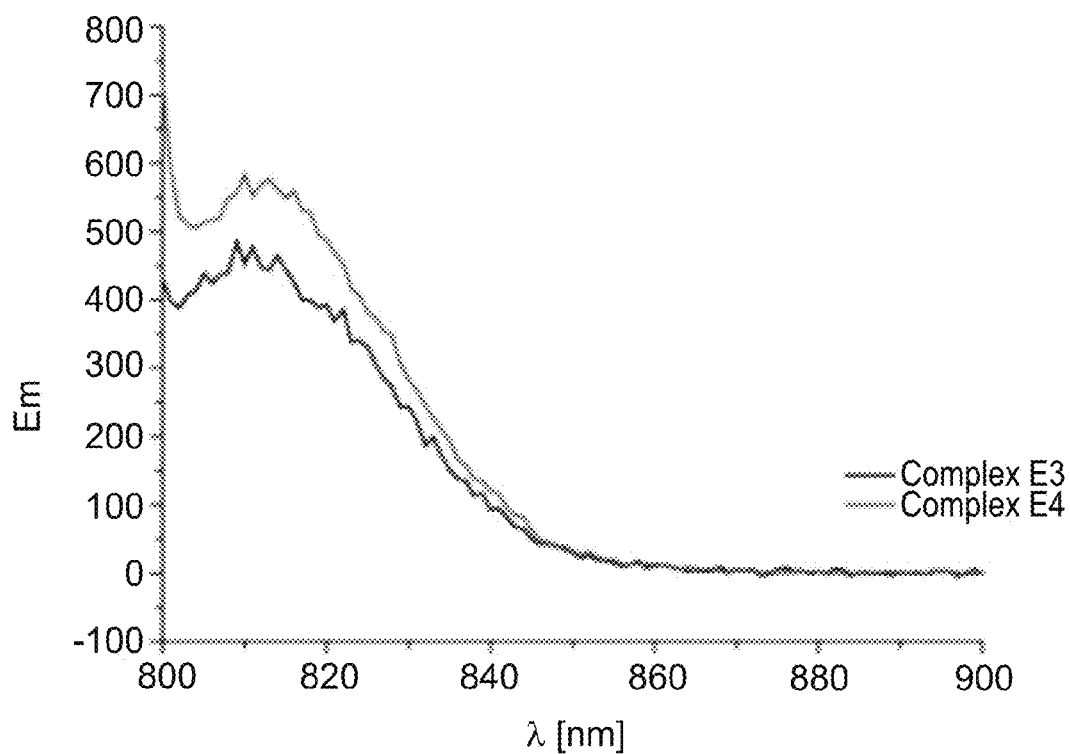

FIGS. 31A and 31B present absorption spectra (FIG. 31A) and emission spectra upon excitation at a wavelength of 794 nm (FIG. 31B) of a Cu(II)-CyNA-Cys1 complex (E3 and E4 represent two different elution fractions containing the complex).

Figure 32:
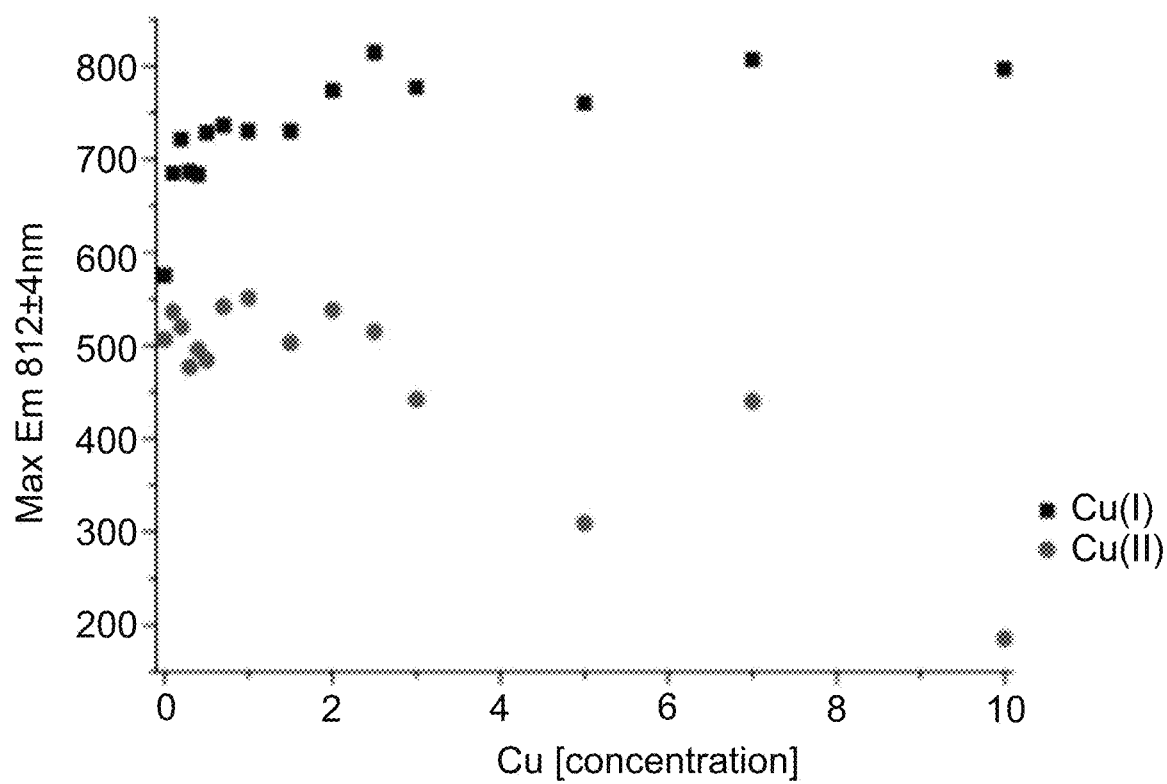

FIG. 32 is a graph showing the fluorescent emission at a wavelength of 812 nm of CyNA-427 titrated with Cu(I) or Cu(II), as a function of copper concentration, upon excitation at a wavelength of 794 nm (emission intensity in arbitrary units; copper concentration in mM).

Figure 33:
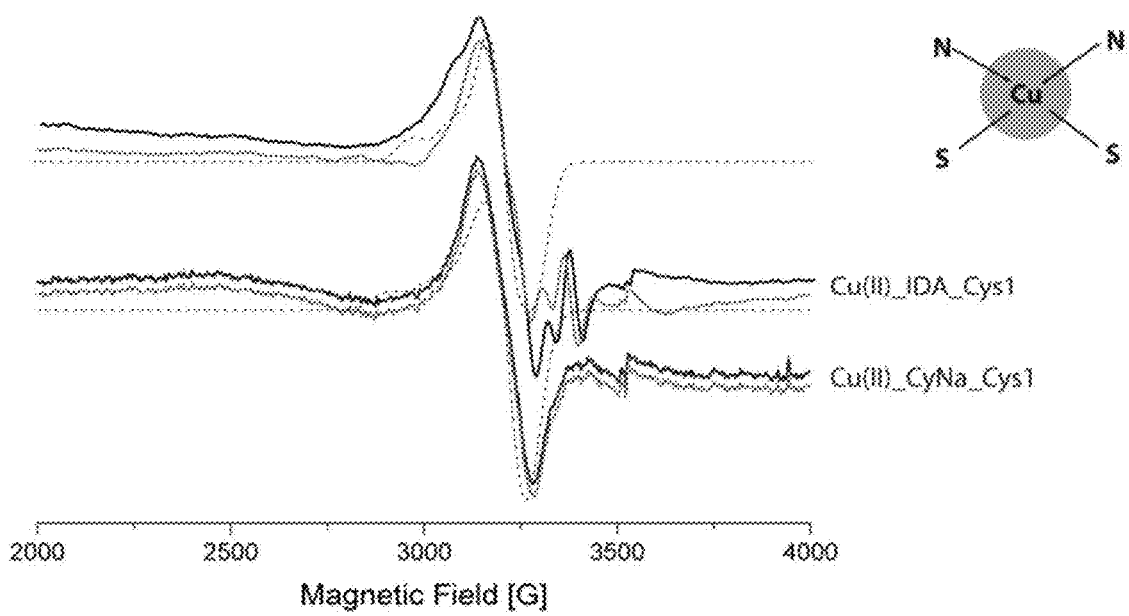

FIG. 33 presents electron paramagnetic resonance (EPR) spectra of Cu(II)-IDA-Cys1 or Cu(II)—CyNA-Cys1 complexes, 1 hour (black solid line) or 24 hours (gray line) after purification (spectra obtained at room temperature and concentration of 0.5 mM), as well as simulated spectra (dotted lines) for 2N2S coordination of Cu(II) (depicted at upper right).

Figure 34:
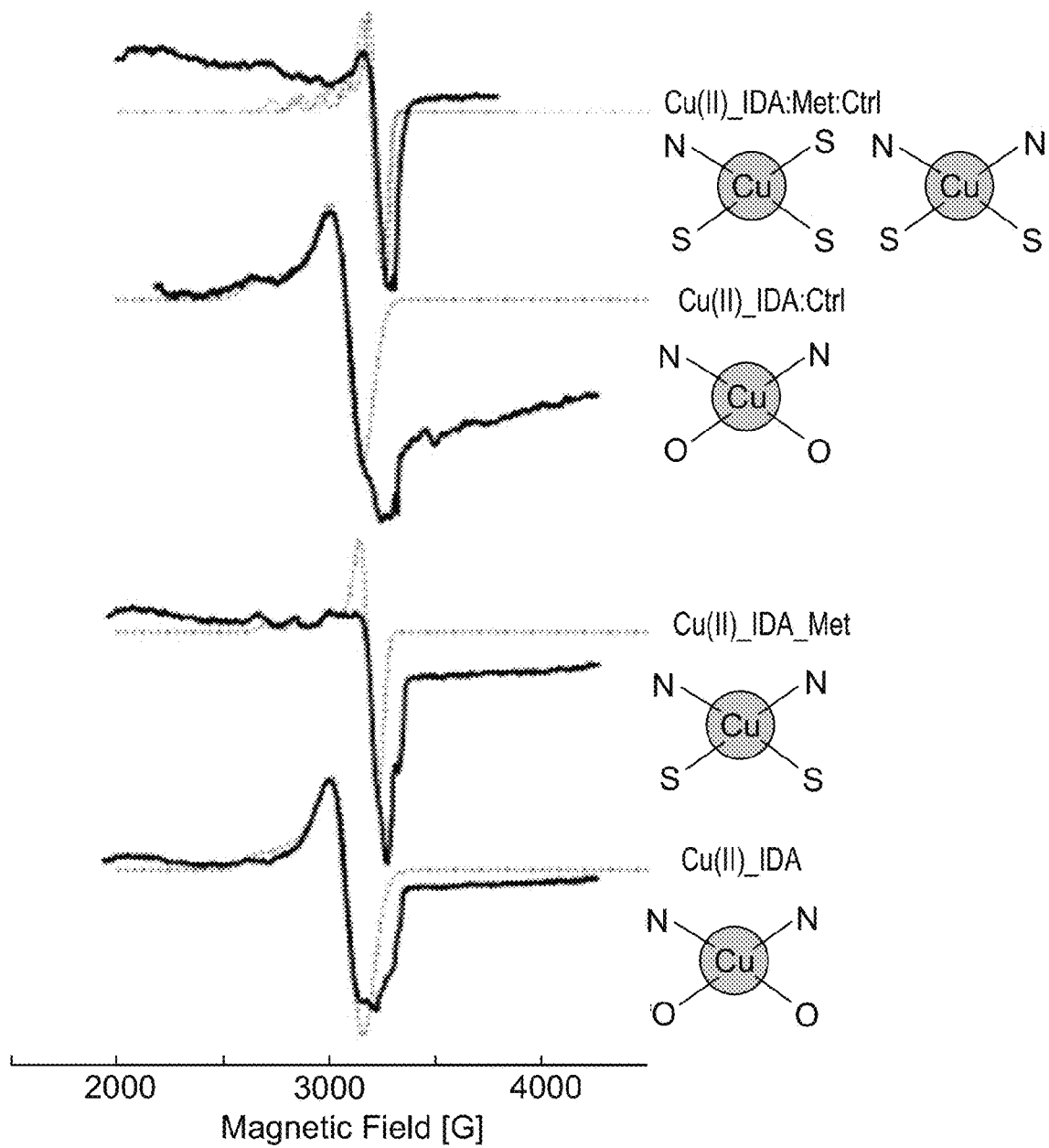

FIG. 34 presents EPR spectra of Cu(II)-IDA and Cu(II)-IDA-Met1 complexes (solid lines), in the presence or absence of Ctr1 protein (spectra obtained at 9.02 GHz and 120 K, at a concentration of 0.5 mM), as well as simulated spectra (dotted lines) for the respective coordination state (or mixture of two coordination states) of Cu(II) depicted on right (from bottom to top: 2N2O, 2N2S, 2N2O, and mixture of 2N2S and 1N3S).

Figure 35:
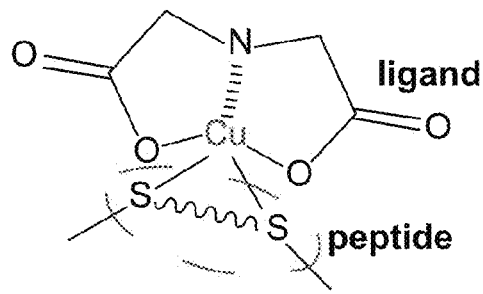

FIG. 35 presents a schematic depiction of Cu(II) coordinated to an IDA (imino-diacetic acid) ligand and to two sulfur atoms of Met residues in a peptide, in a Cu(II)-IDA-peptide complex according to some embodiments of the invention.

Figure 36:
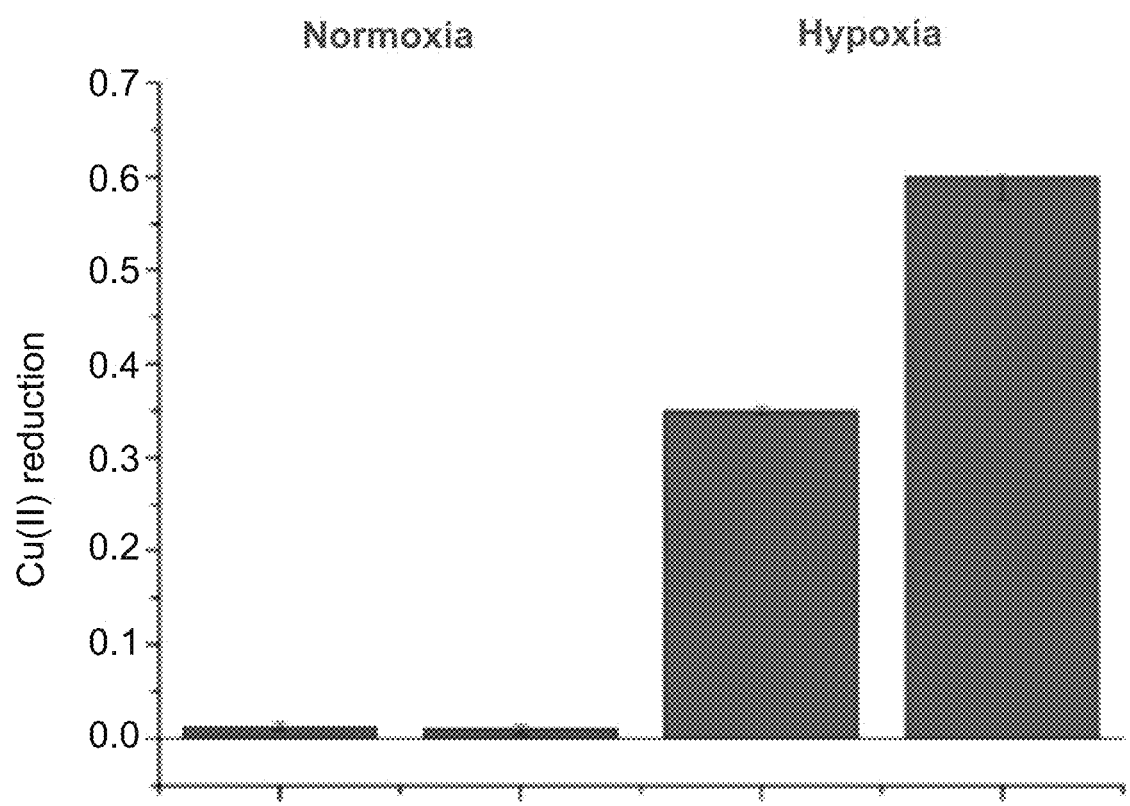

FIG. 36 presents a bar graph showing the fraction of Cu(II) in a Cu(II)-IDA-Met1 complex reduced after 4 hours under normoxia (air atmosphere) or hypoxia (N2 atmosphere), in the presence (right-hand bar) or absence (left-hand bar) of Ctr1.

Figure 37:
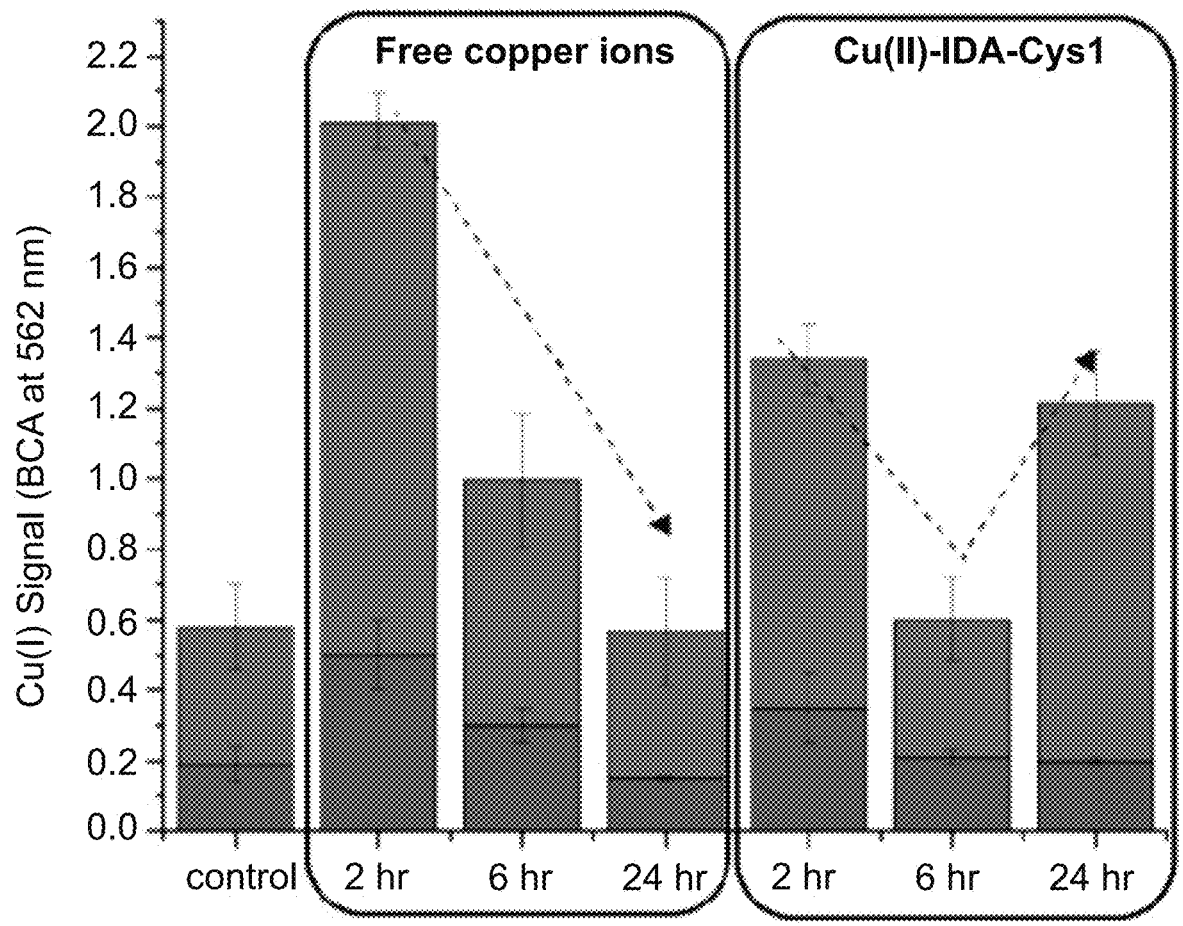

FIG. 37 presents a bar graph showing levels of Cu(I) (as determined by absorption at 562 nm in the presence of bicinchoninic acid (BCA)) in DA3 breast cancer cells 2, 6 or 24 hours after exposure to 1.5 mM $CuCl_2$ (free copper ions) or Cu(II)-IDA-Cys1 complex, under normoxic (blue) or hypoxic (red) conditions (control group without added copper).

Figure 38:
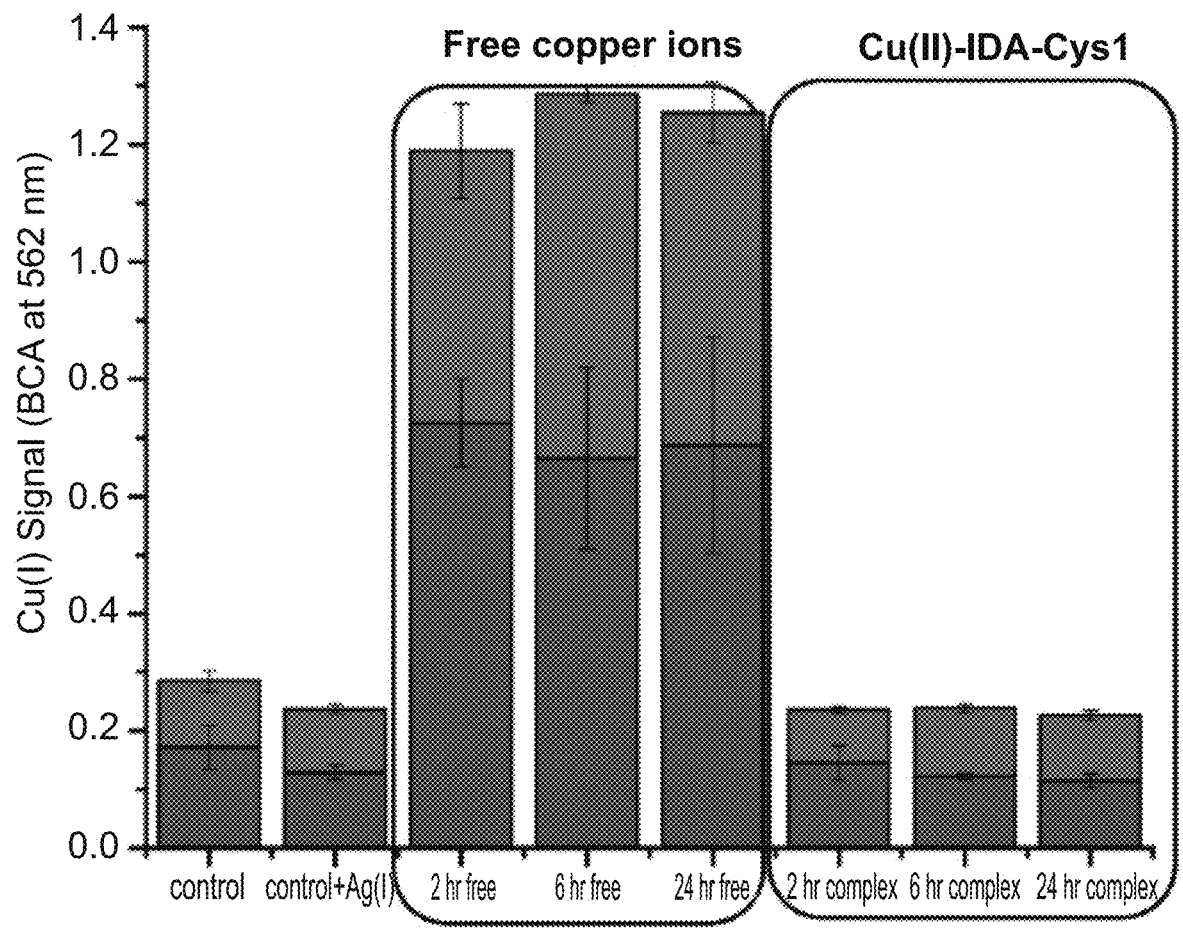

FIG. 38 presents a bar graph showing levels of Cu(I) (as determined by absorption at 562 nm in the presence of bicinchoninic acid (BCA)) in DA3 breast cancer cells 2, 6 or 24 hours after exposure to 1.5 mM $CuCl_2$ (free copper ions) or Cu(II)-IDA-Cys1 complex in the presence of 3 mM Ag(I) ions, under normoxic (blue) or hypoxic (red) conditions (control group without added Cu or Ag; control+Ag(I) group without added Cu).

Figure 39:
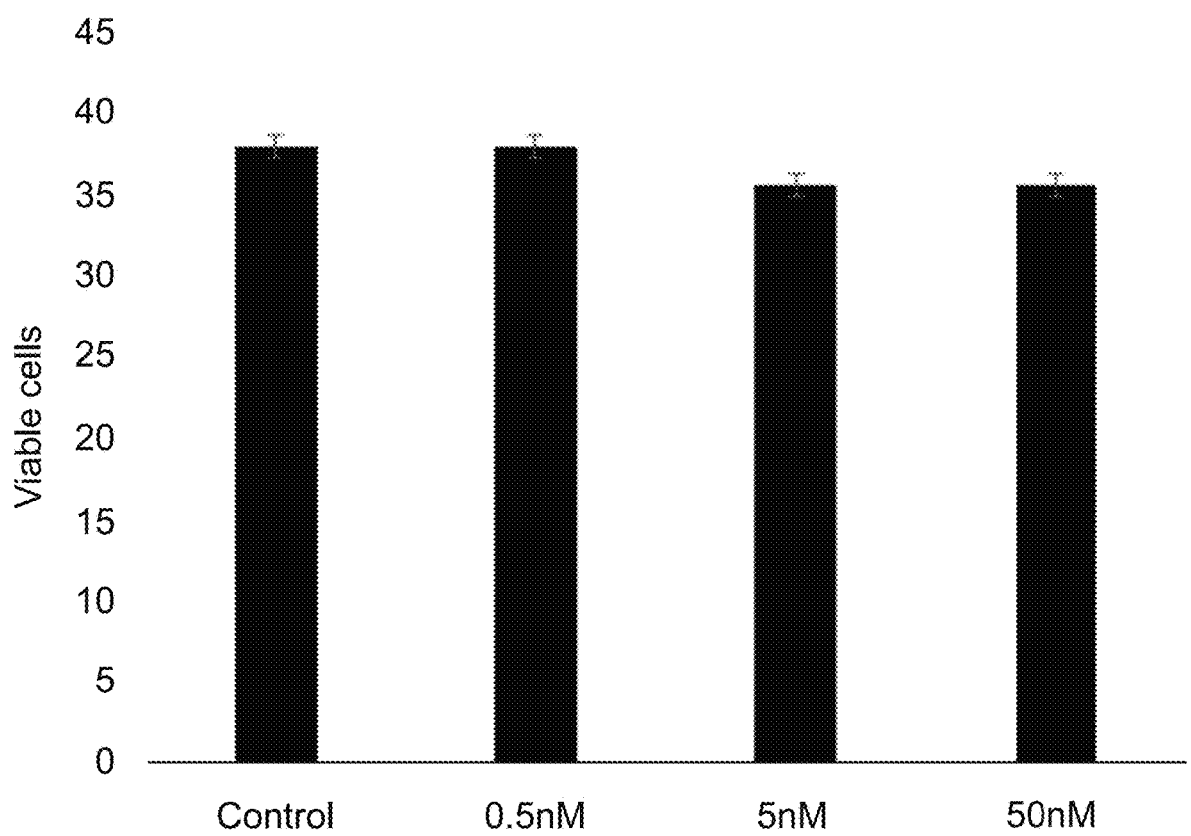

FIG. 39 is a bar graph showing viability of DA-3 cells following incubation for 12 hours with 0.5, 5 or 50 nM of Cu(II)-IDA-Cys1 complex, or with no complex (control).

Figure 40A:
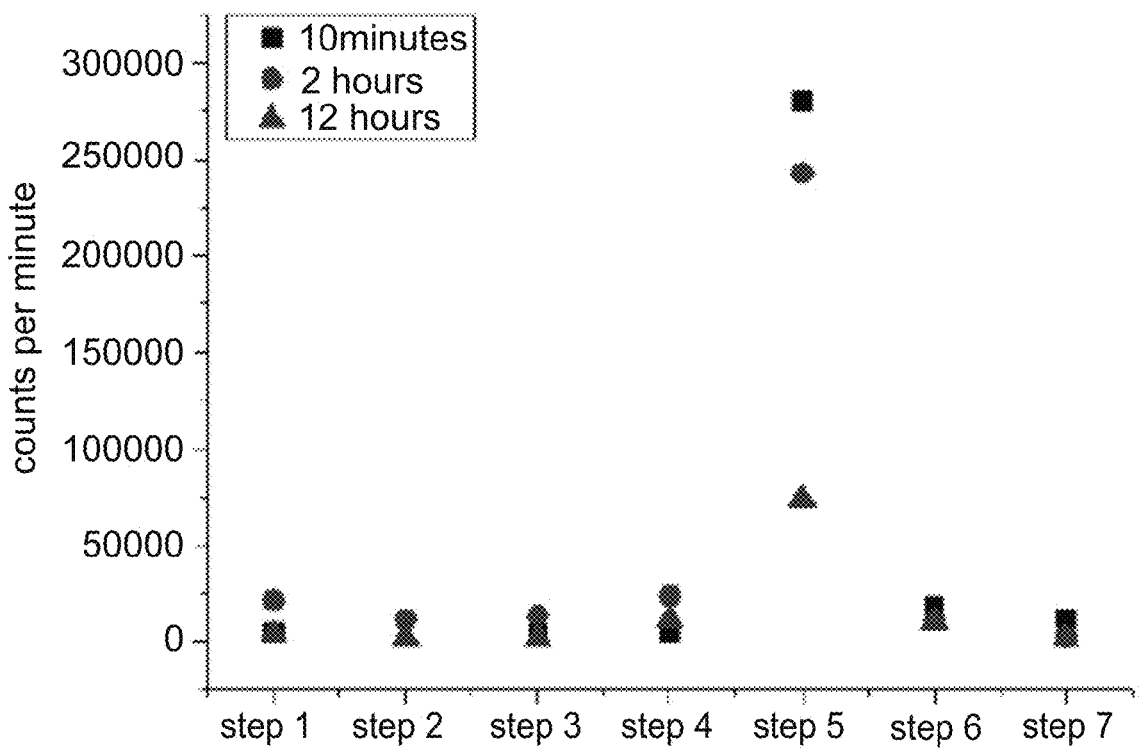
Figure 40B:
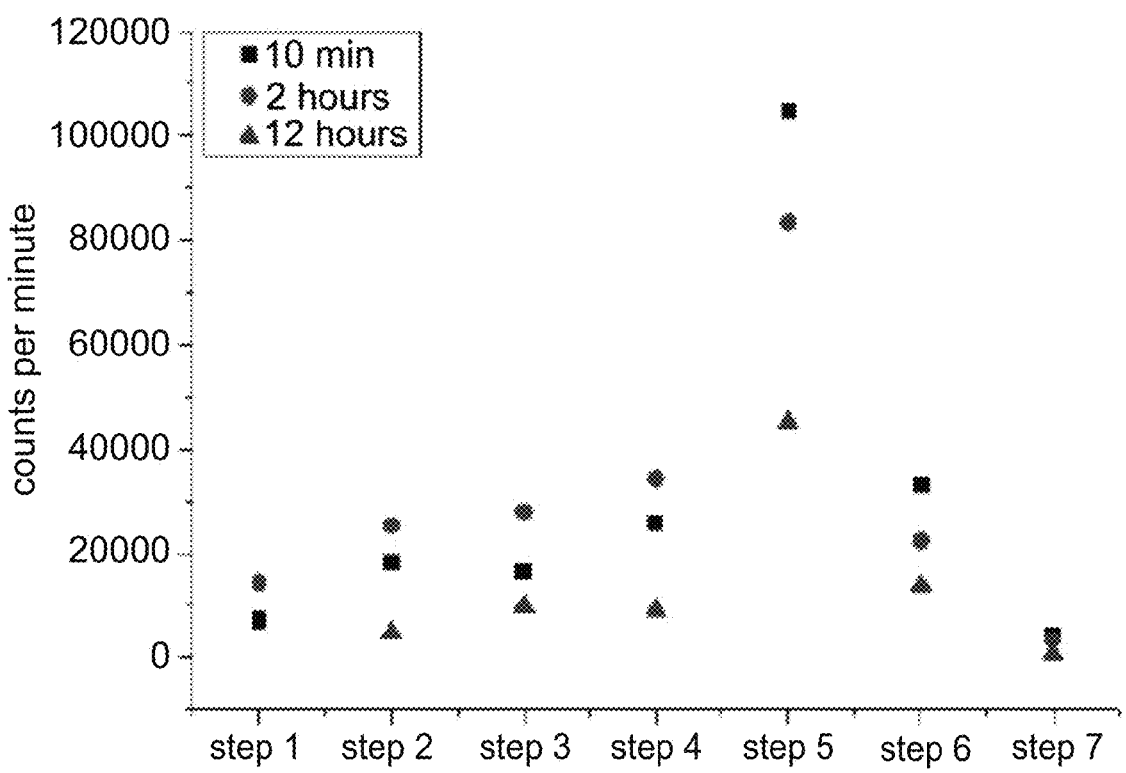

FIGS. 40A and 40B present graphs showing radioactive signal of $^{64}$Cu(II)-CyNA-Cys1 (FIG. 40A) and $^{64}$Cu(II)-IDA-Cys1 (FIG. 40B) complexes 10 minutes, 2 hours and 12 hours after preparation of the complexes, at different steps of thin layer chromatography.

Figure 41:
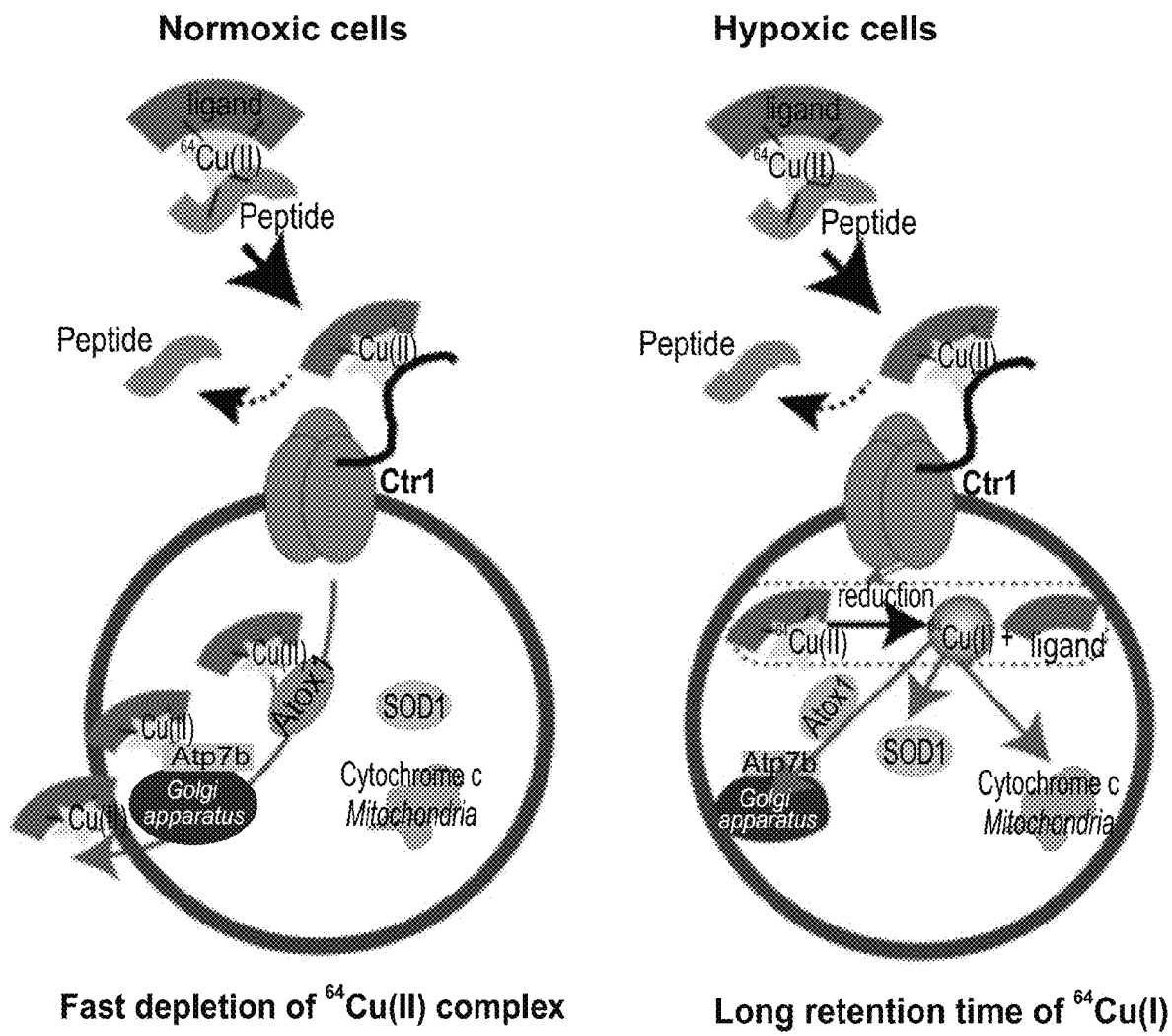

FIG. 41 presents a schematic depiction of a mechanism by which a $^{64}$Cu(II)-ligand-peptide complex preferentially radio-labels hypoxic cells, according to some embodiments of the invention.

Figure 42:
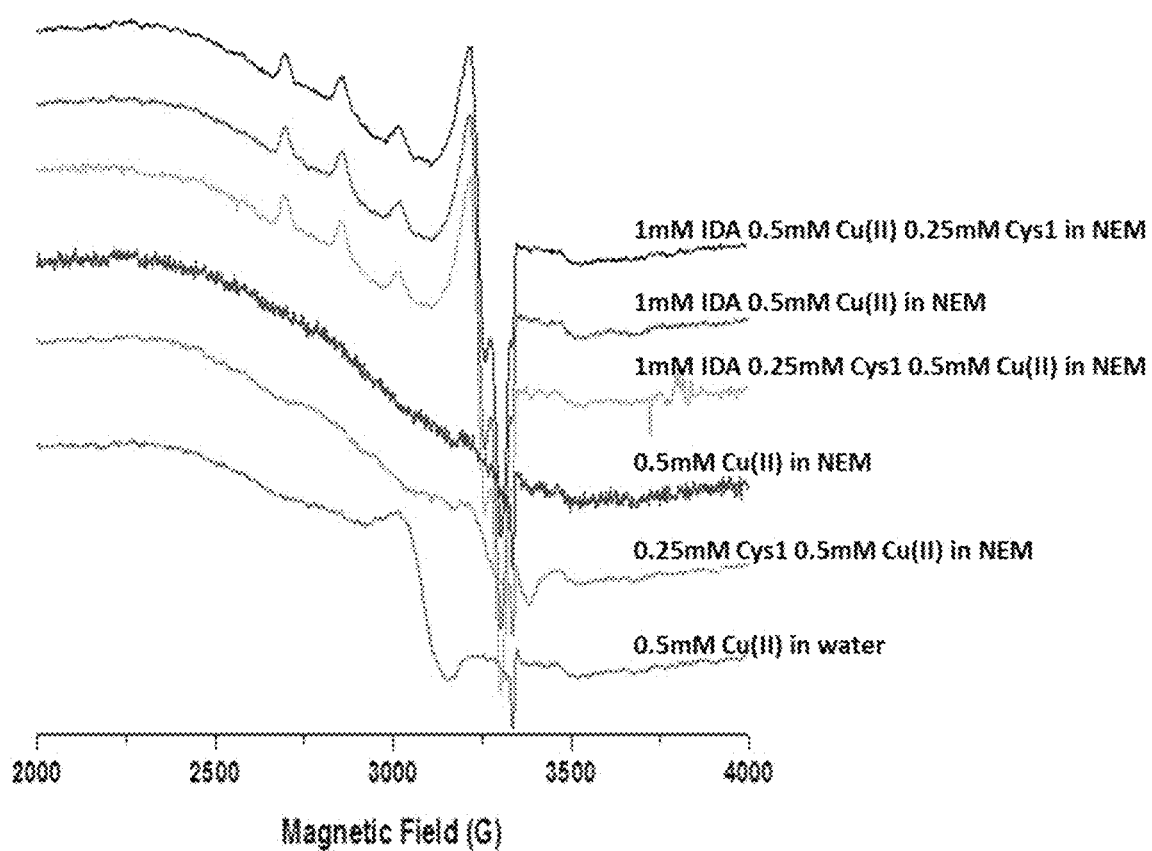

FIG. 42 presents EPR spectra of samples with 0.5 mM Cu(II) and 1 mM IDA and/or 0.25 mM Cys1 peptide, in NEM buffer or water ("0.5 mM Cu(II) 0.25 mM Cys1" at top spectrum indicates that Cu(II) was added prior to Cys1, and "0.25 mM Cys1 0.5 mM Cu(II)" at spectrum third from top indicates that Cys1 was added prior to Cu(II)).

Figure 43:
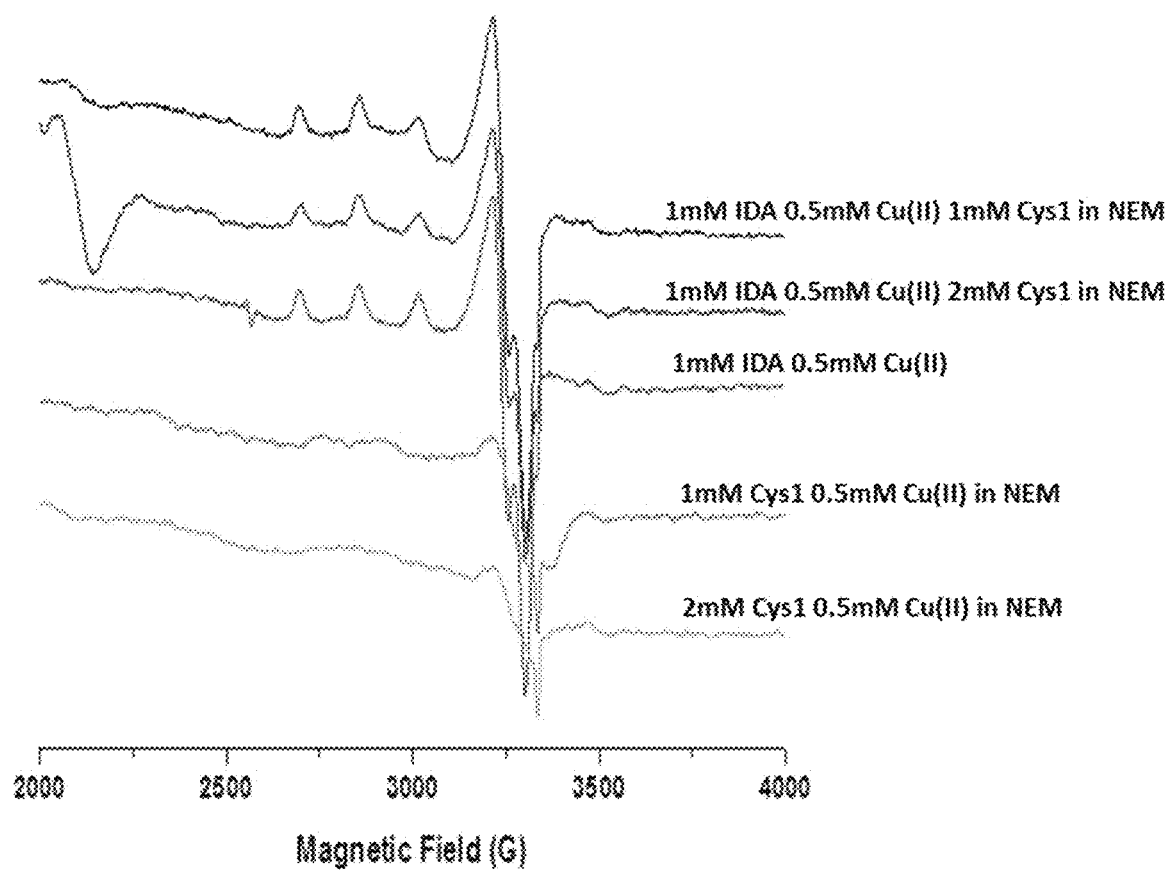

FIG. 43 presents EPR spectra of samples with 0.5 mM Cu(II), 0 or 1 mM IDA, and 1 or 2 mM Cys1 peptide in NEM buffer.

Figure 44:
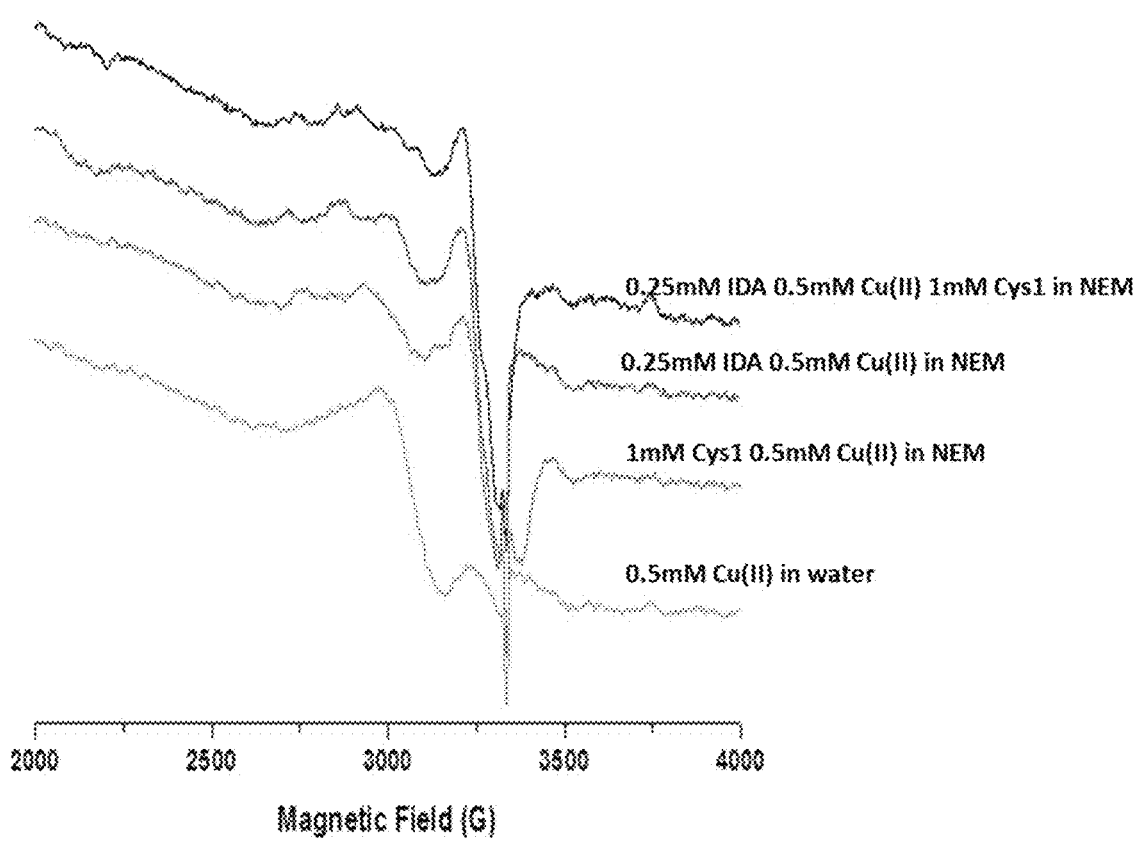

FIG. 44 presents EPR spectra of samples with 0.5 mM Cu(II), 0 or 0.25 mM IDA, and 0 or 1 mM Cys1 peptide, in NEM buffer or water.

Figure 45:
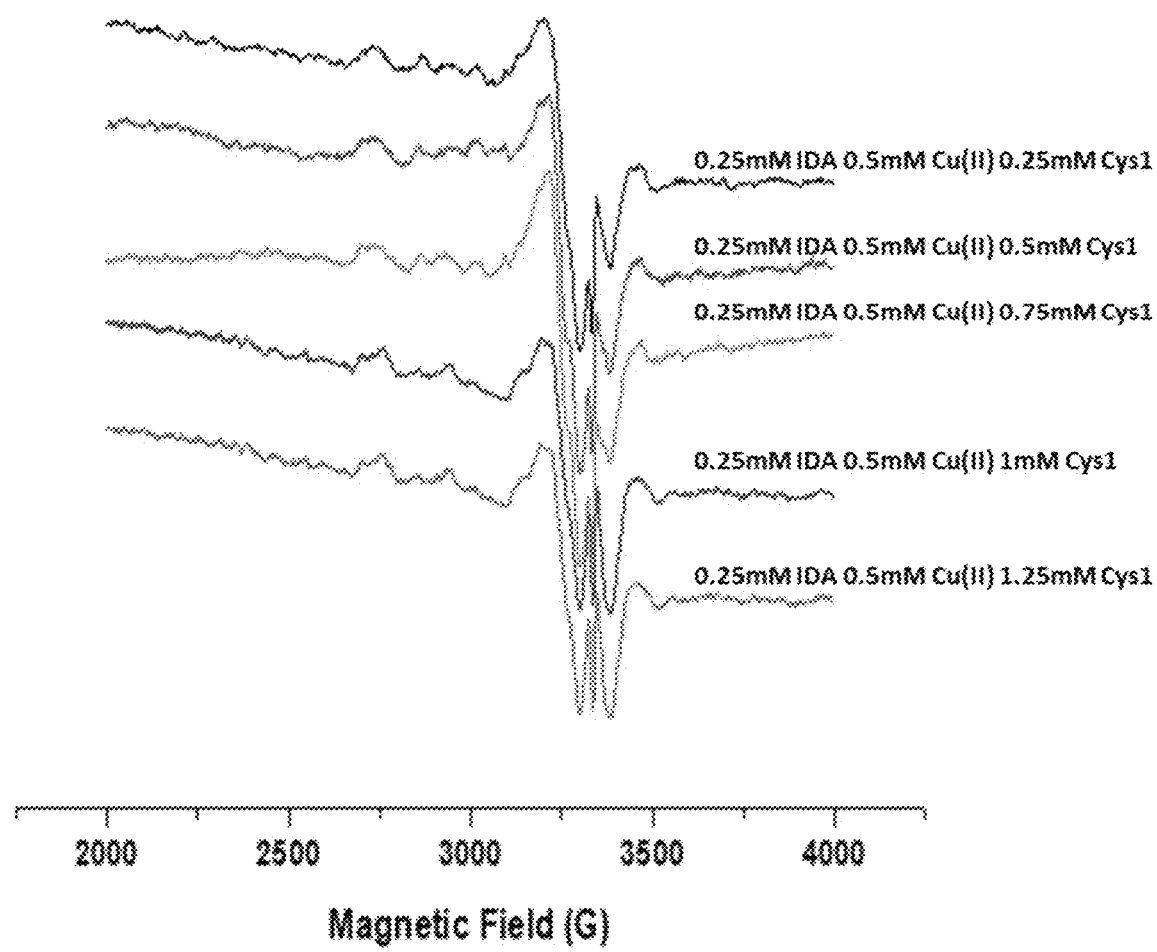

FIG. 45 presents EPR spectra of samples with 0.5 mM Cu(II) and 0.25 mM IDA titrated with 0.25, 0.5 0.75, 1 and 1.25 mM Cys1 peptide in NEM buffer (50 mM).

Figure 46:
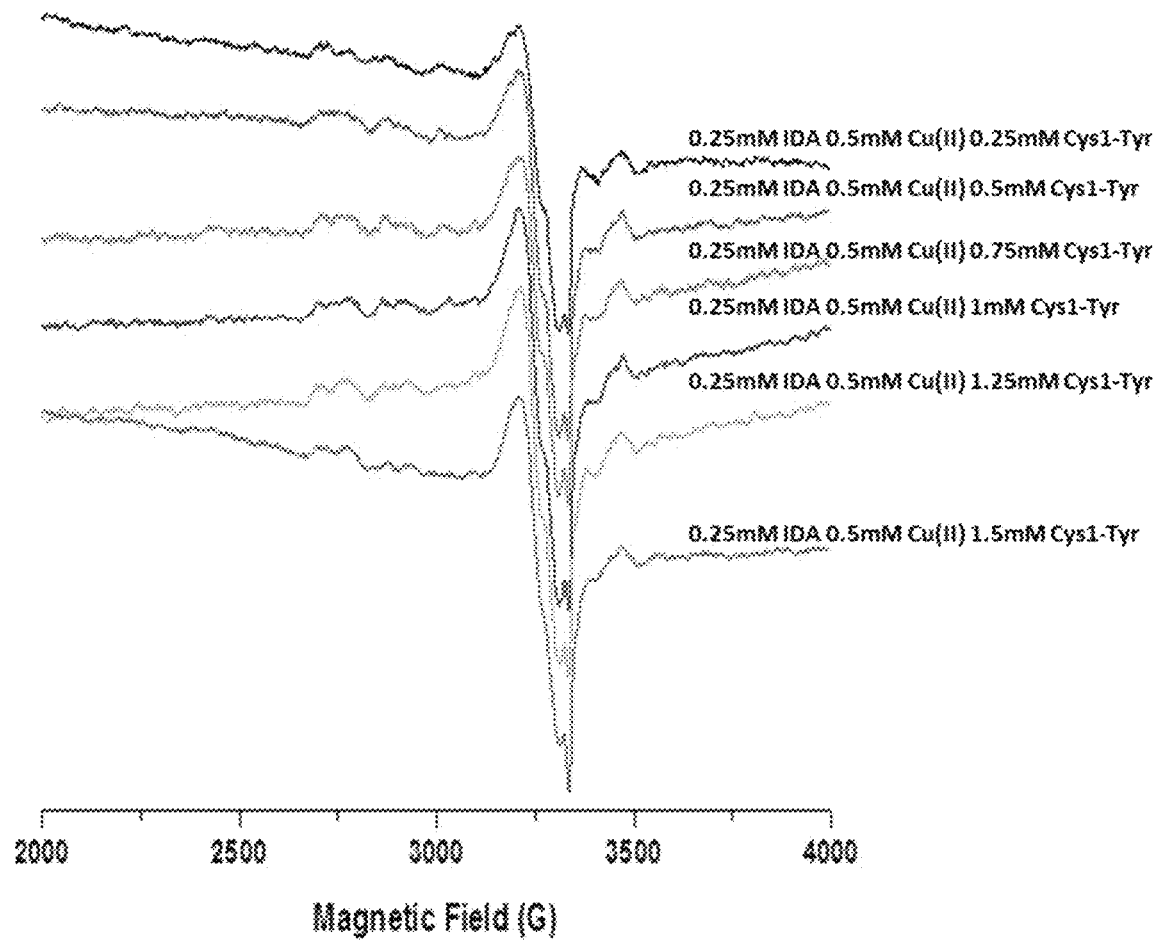

FIG. 46 presents EPR spectra of samples with 0.5 mM Cu(II) and 0.25 mM IDA titrated with 0.25, 0.5 0.75, 1, 1.25 and 1.5 mM Cys1-Tyr peptide in NEM buffer (50 mM).

Figure 47:
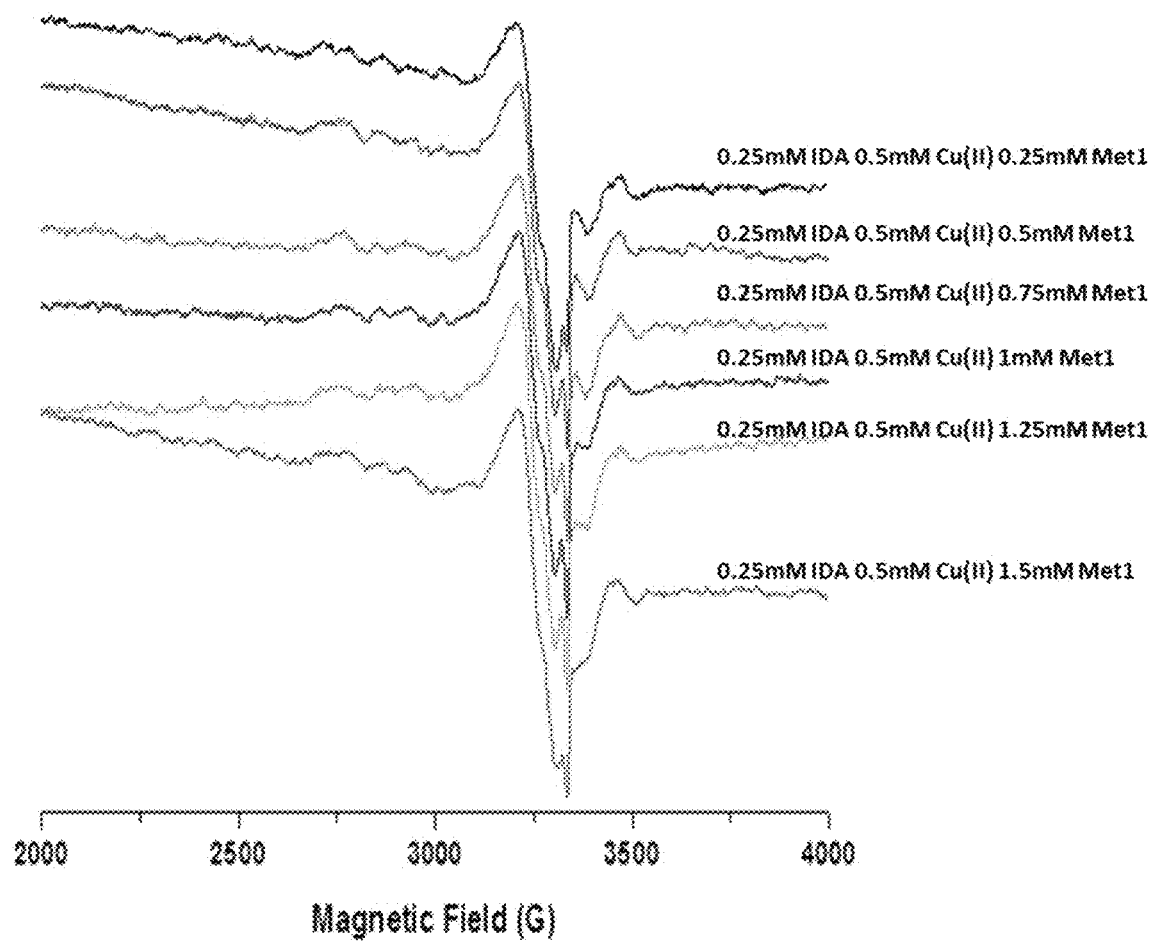

FIG. 47 presents EPR spectra of samples with 0.5 mM Cu(II) and 0.25 mM IDA titrated with 0.25, 0.5 0.75, 1, 1.25 and 1.5 mM Met1 peptide in NEM buffer (50 mM).

Figure 48:
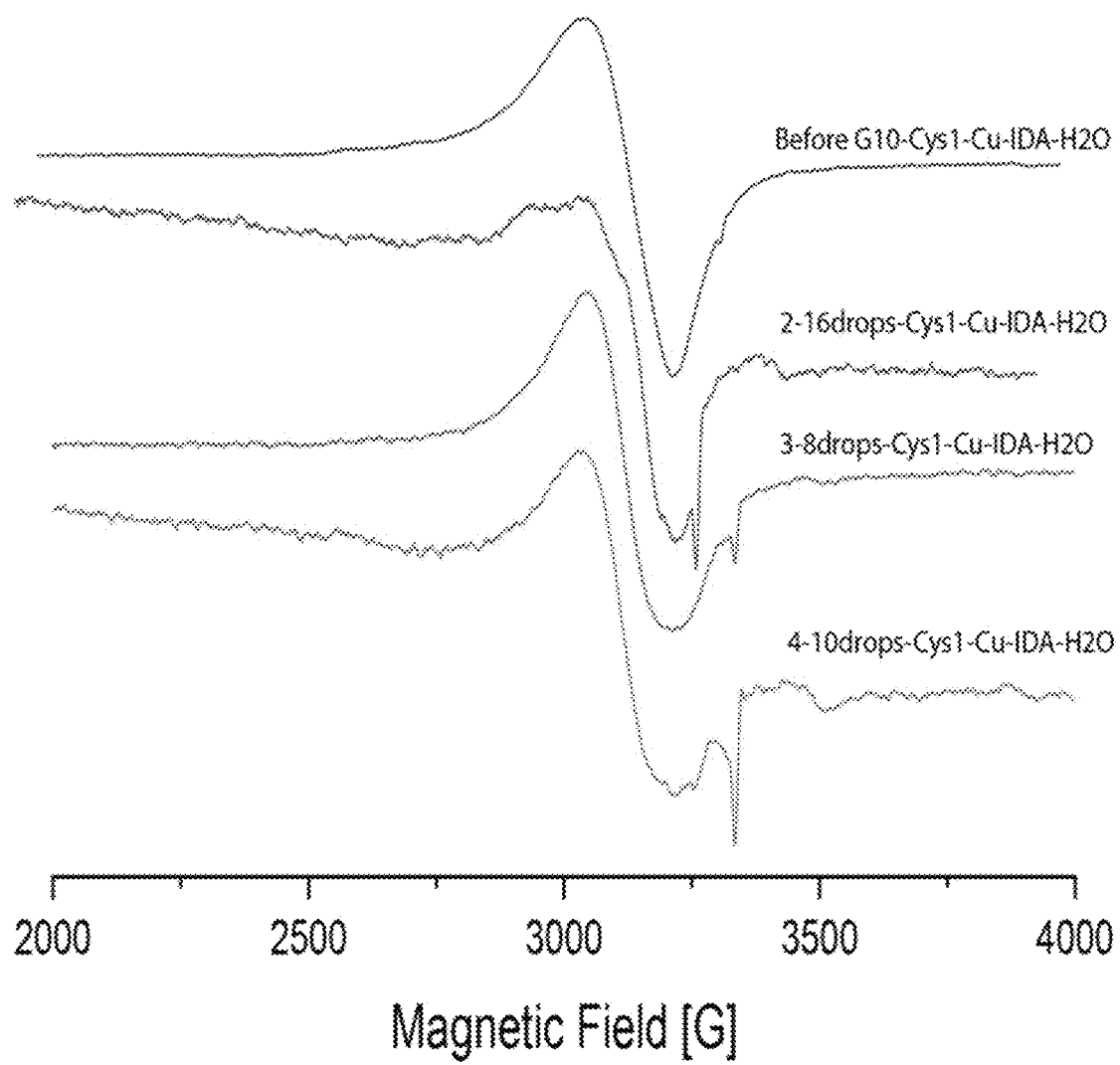

FIG. 48 presents EPR spectra of samples with IDA-Cu(II)-Cys1 complex formed in H2O, before (top spectrum) and after elution from a G10 column to obtain 3 fractions (sample 2 represents first 16 drops eluted, sample 3 represents next 8 drops, and sample 4 represents next 10 drops after sample 3).

Figure 49:
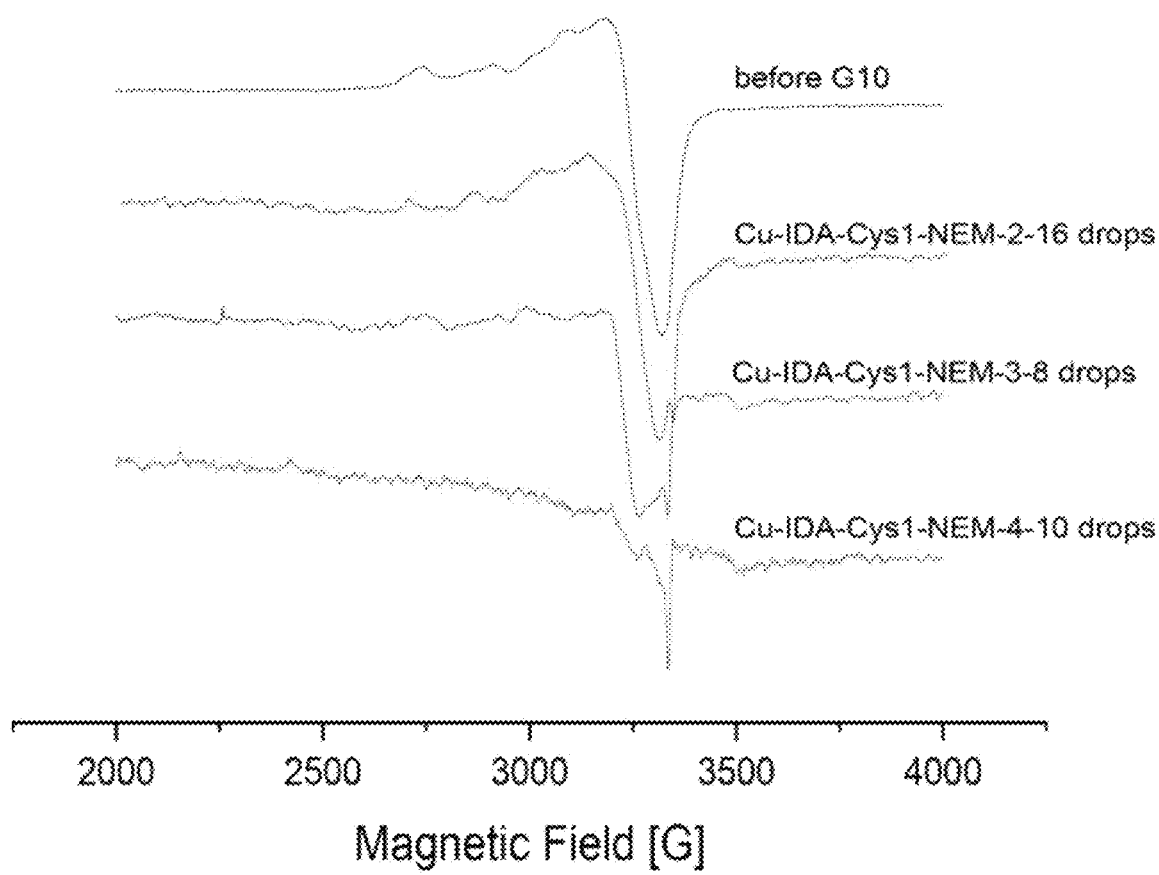

FIG. 49 presents EPR spectra of samples with IDA-Cu(II)-Cys1 complex formed in NEM buffer (pH 7.4), before (top spectrum) and after elution from a G10 column to obtain 3 fractions (sample 2 represents first 16 drops eluted, sample 3 represents next 8 drops, and sample 4 represents next 10 drops after sample 3).

Figure 50:
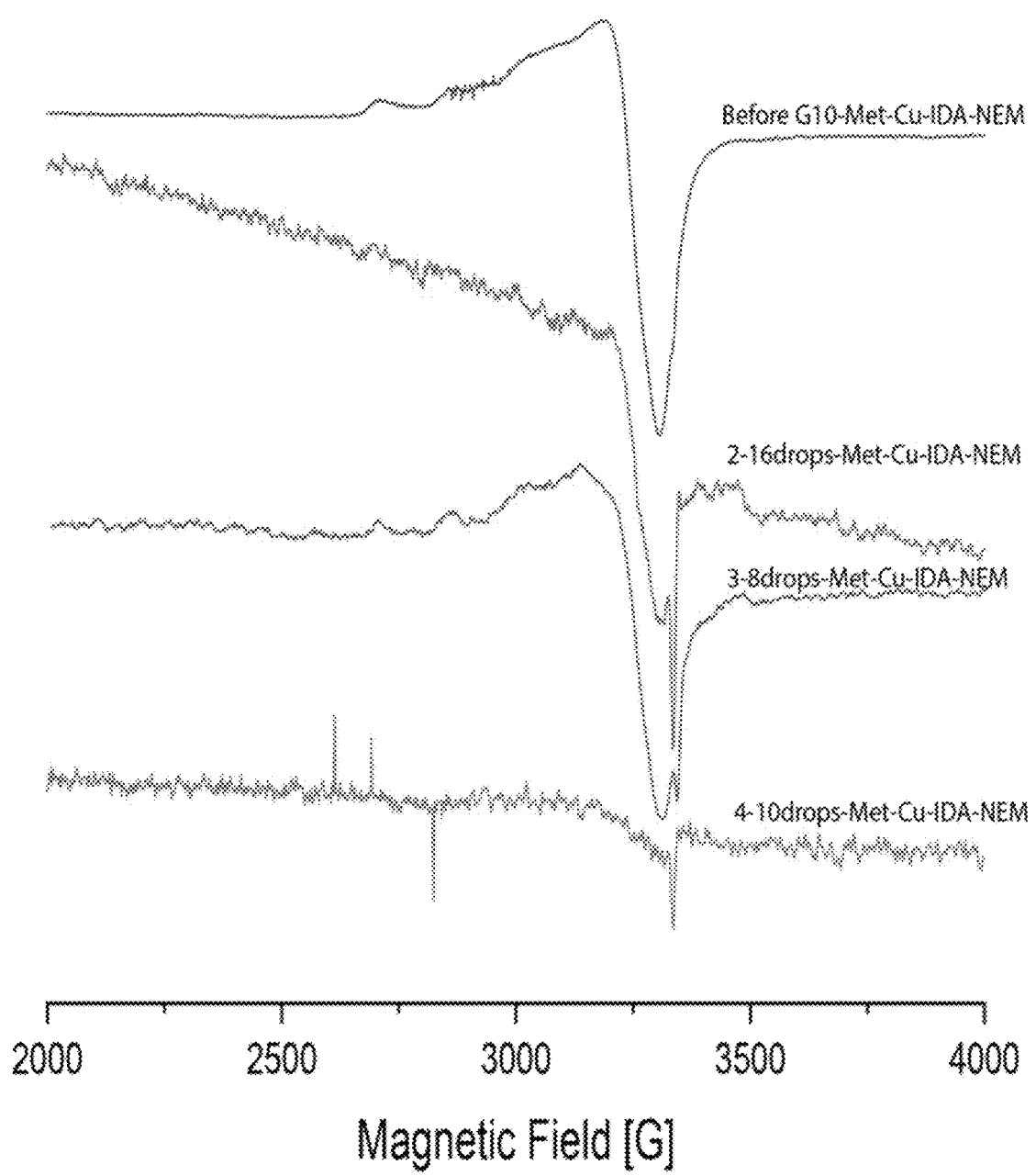

FIG. 50 presents EPR spectra of samples with IDA-Cu(II)-Met1 complex formed in NEM buffer (pH 7.4), before (top spectrum) and after elution from a G10 column to obtain 3 fractions (sample 2 represents first 16 drops eluted, sample 3 represents next 8 drops, and sample 4 represents next 10 drops after sample 3).

Figure 51:
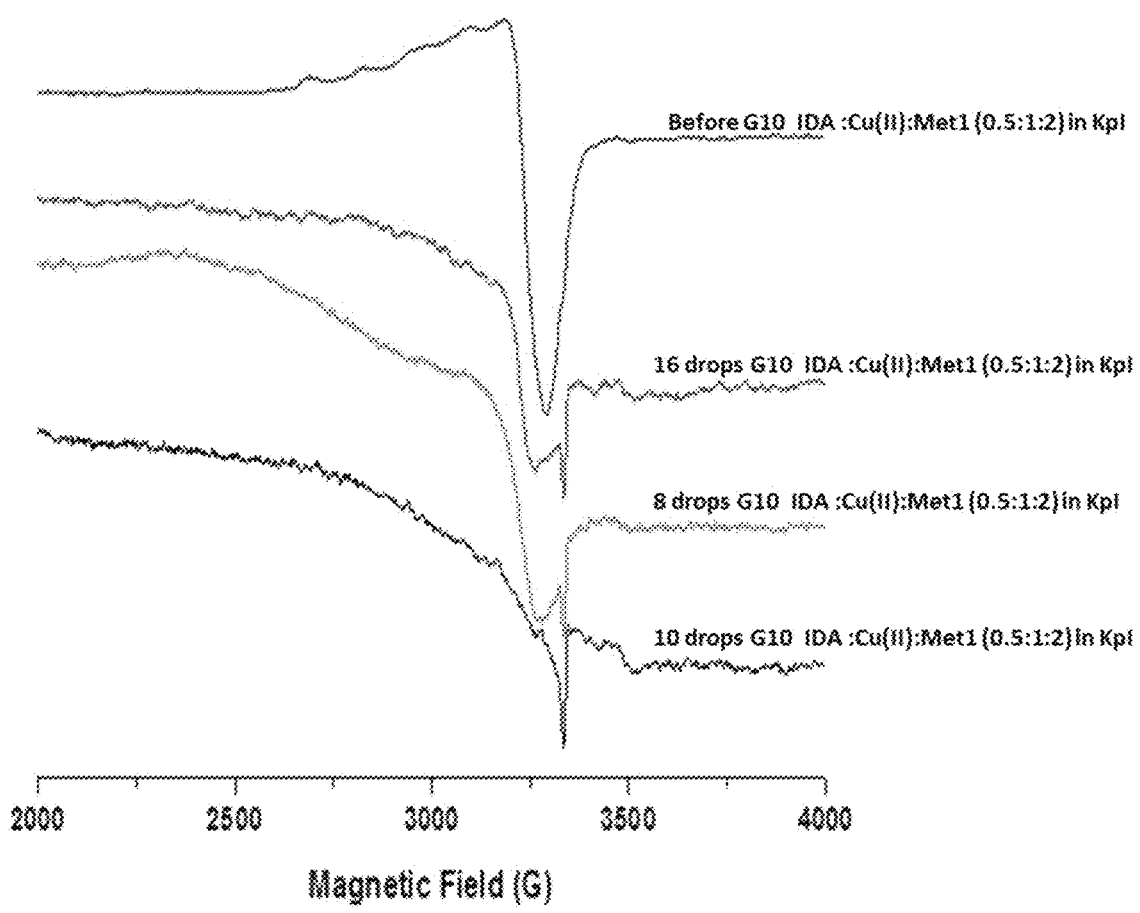

FIG. 51 presents EPR spectra of samples with IDA-Cu(II)-Met1 complex formed in KPi buffer (pH 7.4, 0.1 M phosphate) at a stoichiometric ratio of 0.5:1:2 IDA:Cu(II):Met1, before (top spectrum) and after elution from a G10 column to obtain 3 fractions (one fraction comprising the first 16 drops eluted, another fraction representing the next 8 drops, and another fraction representing the next 10 drops).

Figure 52A:
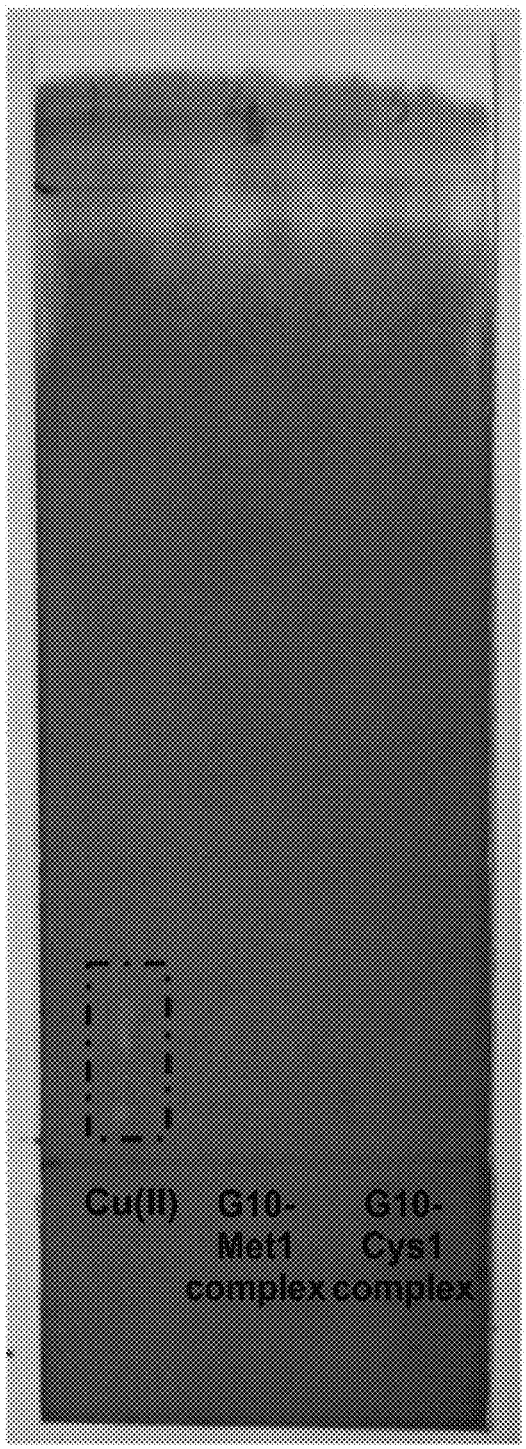
Figure 52B:
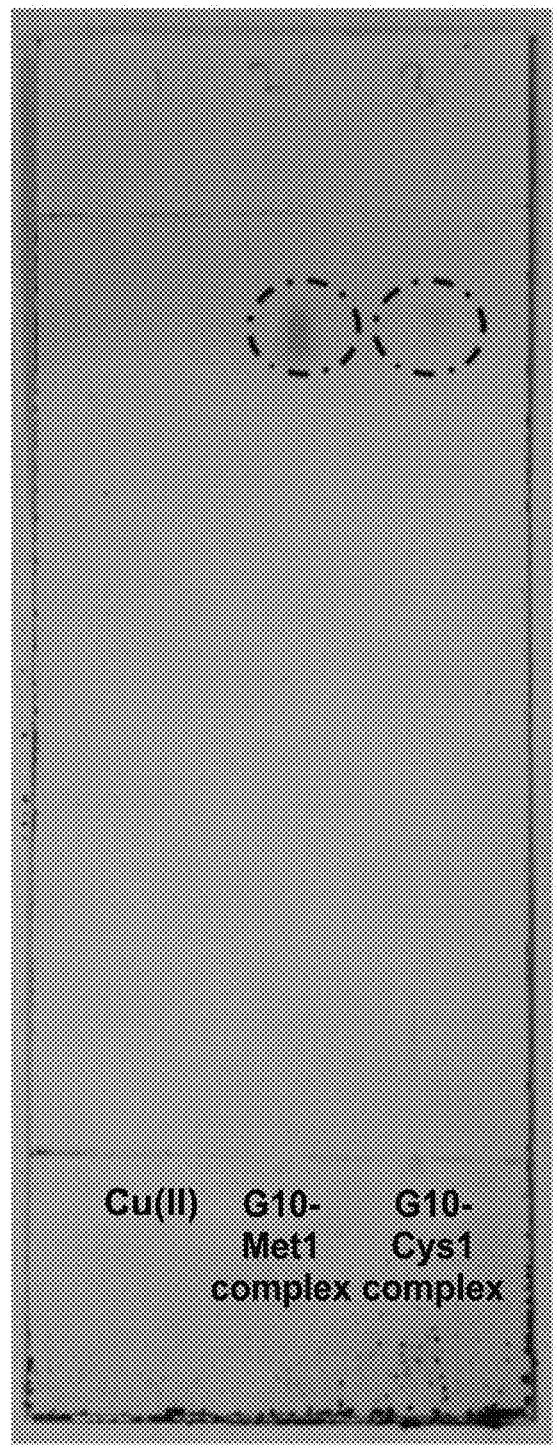

FIGS. 52A and 52B present images of thin layer chromatography plates stained with $KMnO_4$ (FIG. 52A) or iodine (FIG. 52B), with free Cu(II) and IDA-Cu(II)-Met1 and IDA-Cu(II)-Cys1 complexes separated by G10 column ("G10-Met1 complex" and "G10-Cys1 complex", respectively); portions with stained material indicated by dashed lines (plates composed of silica gel and developed with methanol/water (90:10) and a few drops of HCl).

Figure 53A:
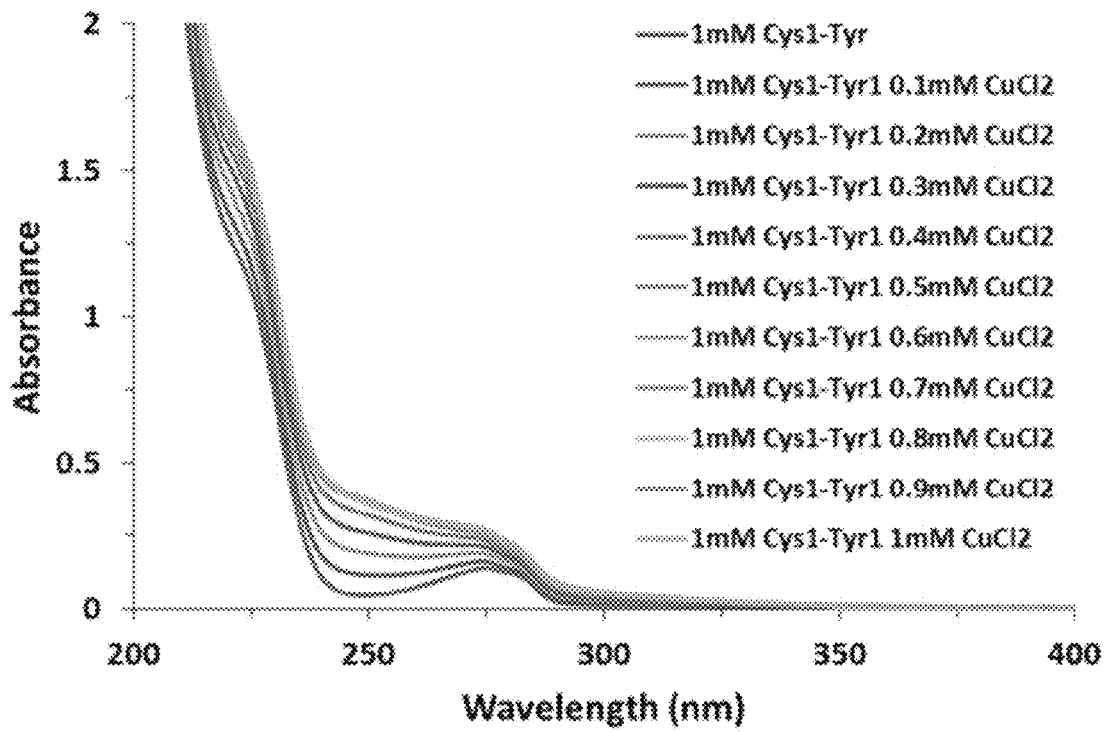
Figure 53B:
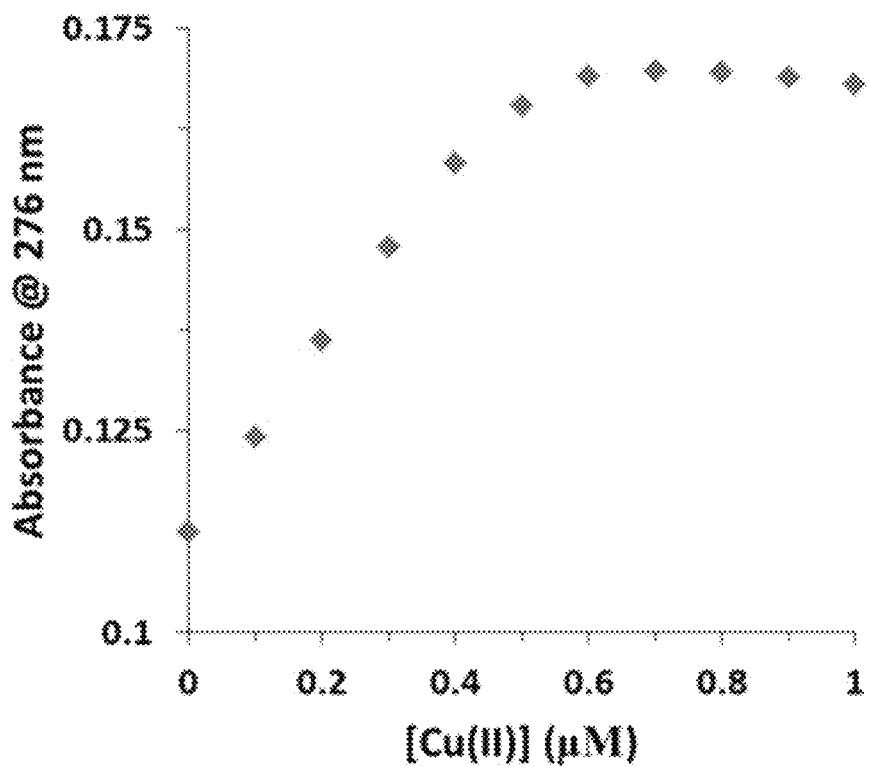

FIGS. 53A and 53B present UV-visible spectra of 1 mM Cys1-Tyr peptide titrated with various concentrations of $CuCl_2$ (FIG. 53A), as well as a graph showing absorption at 276 nm (in the aforementioned spectra) as a function of Cu(II) concentration (FIG. 53B); total volume of the sample was 300 μl, and the path length of the cuvette was 0.1 cm.

Figure 54A:
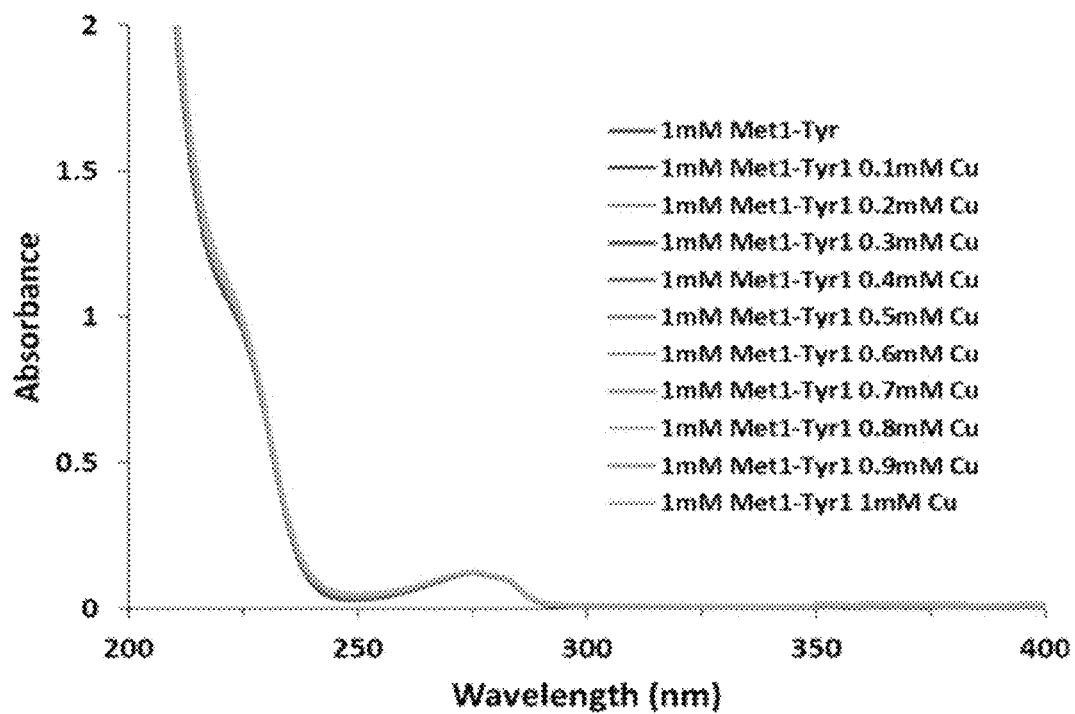
Figure 54B:
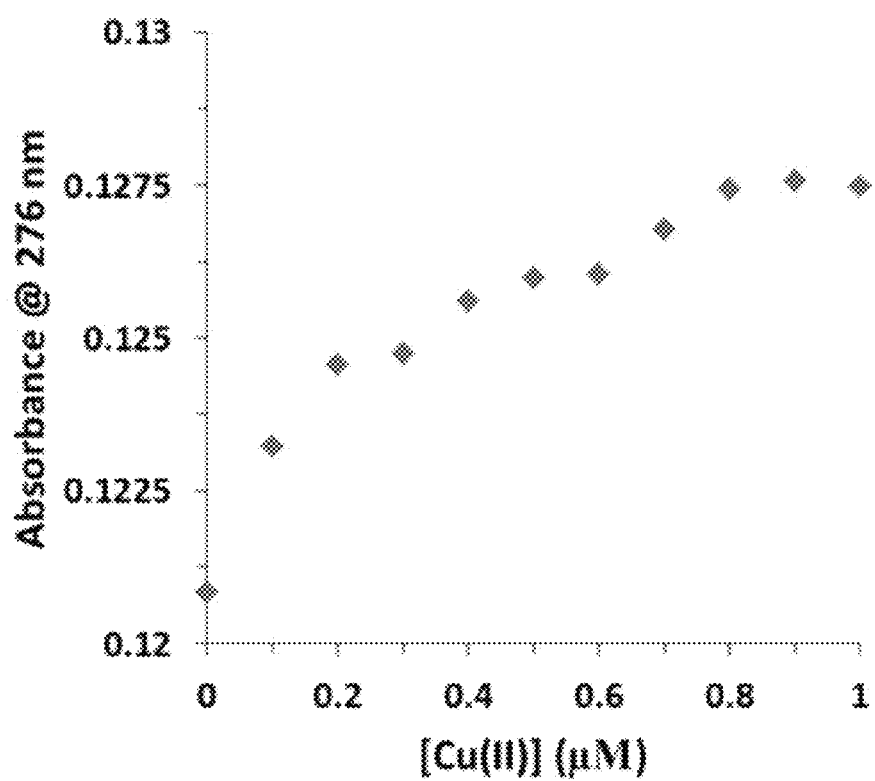

FIGS. 54A and 54B present UV-visible spectra of 1 mM Met1-Tyr peptide titrated with various concentrations of $CuCl_2$ (FIG. 54A), as well as a graph showing absorption at 276 nm (in the aforementioned spectra) as a function of Cu(II) concentration (FIG. 54B); total volume of the sample was 300 μl, and the path length of the cuvette was 0.1 cm.

Figure 55A:
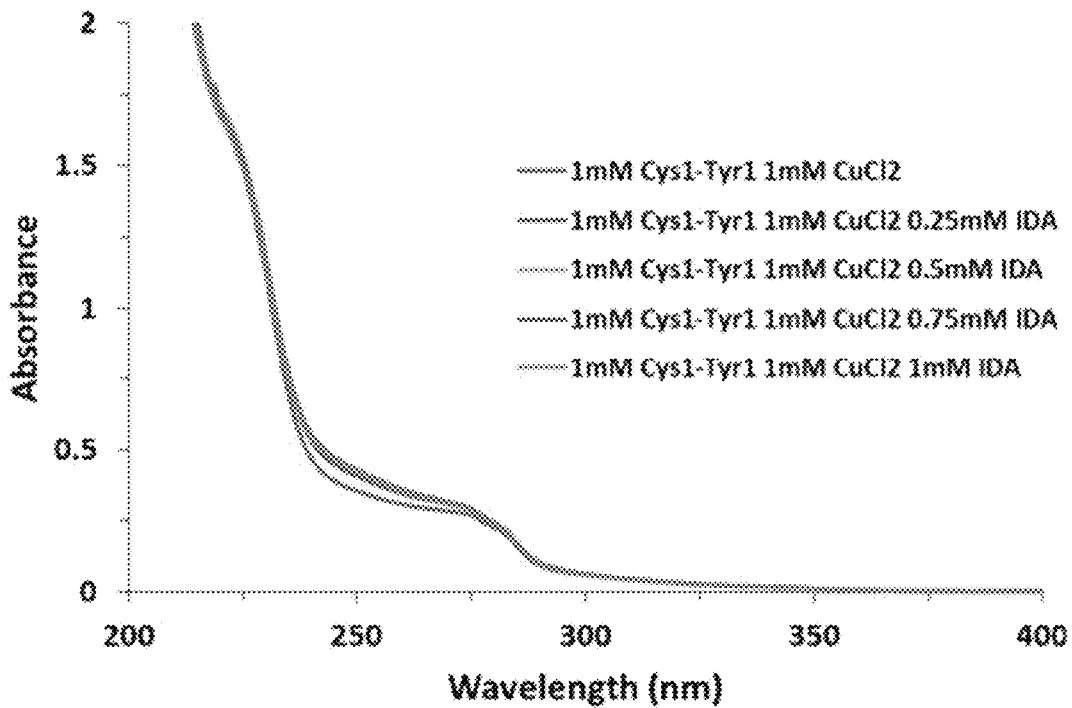
Figure 55B:
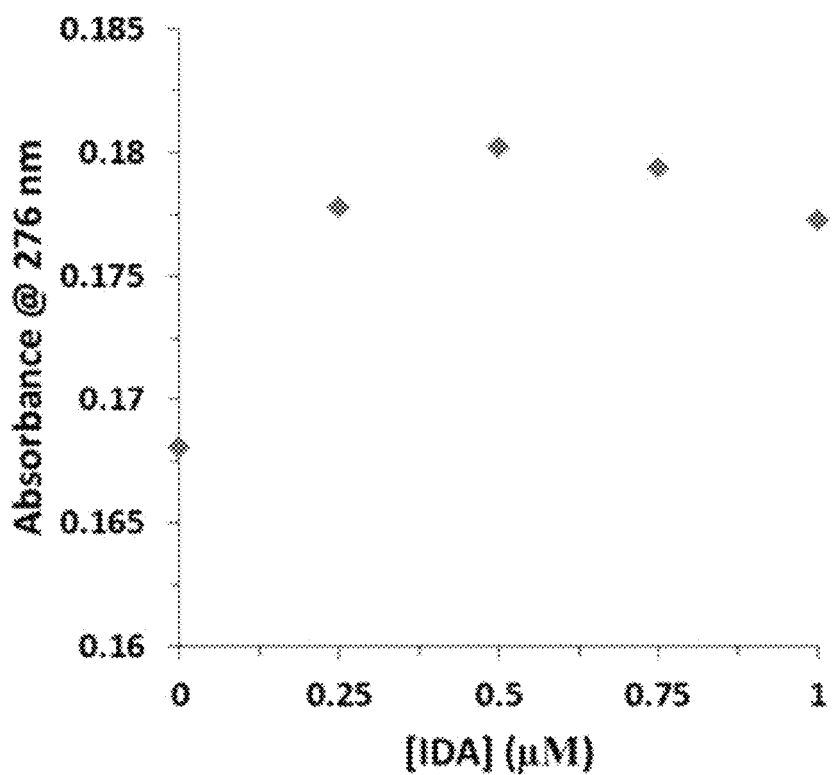

FIGS. 55A and 55B present UV-visible spectra of 1 mM Cys1-Tyr peptide and 1 mM Cu(II) titrated with various concentrations of IDA (FIG. 55A), as well as a graph showing absorption at 276 nm (in the aforementioned spectra) as a function of IDA concentration (FIG. 55B); total volume of the sample was 300 μl, and the path length of the cuvette was 0.1 cm.

Figure 56A:
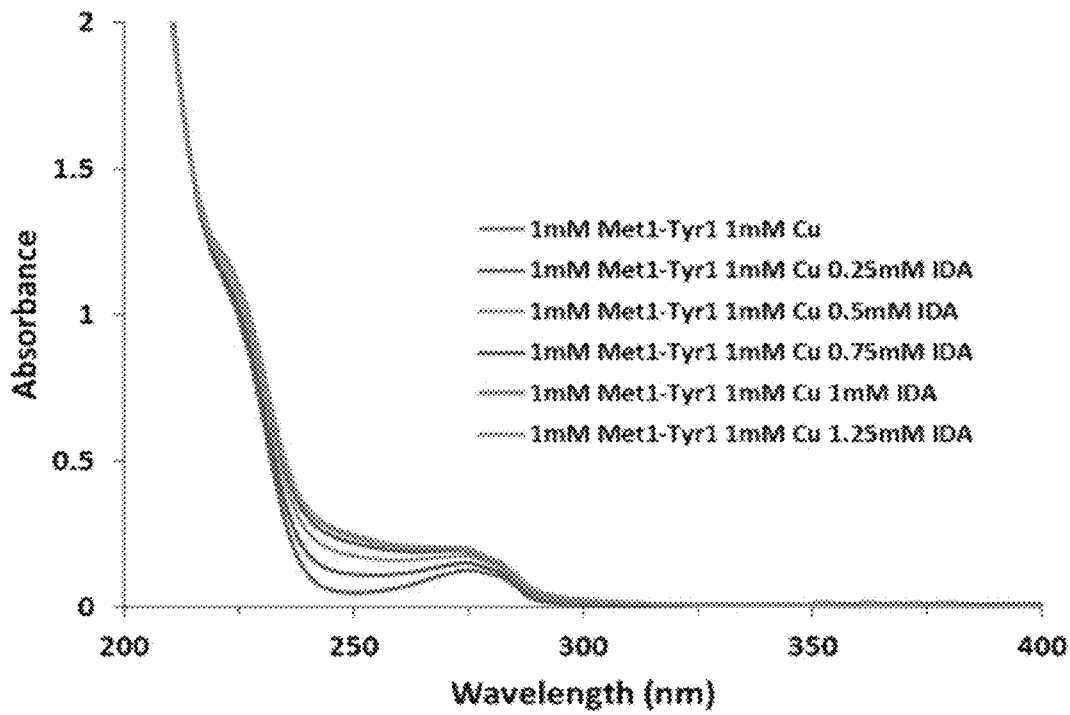
Figure 56B:
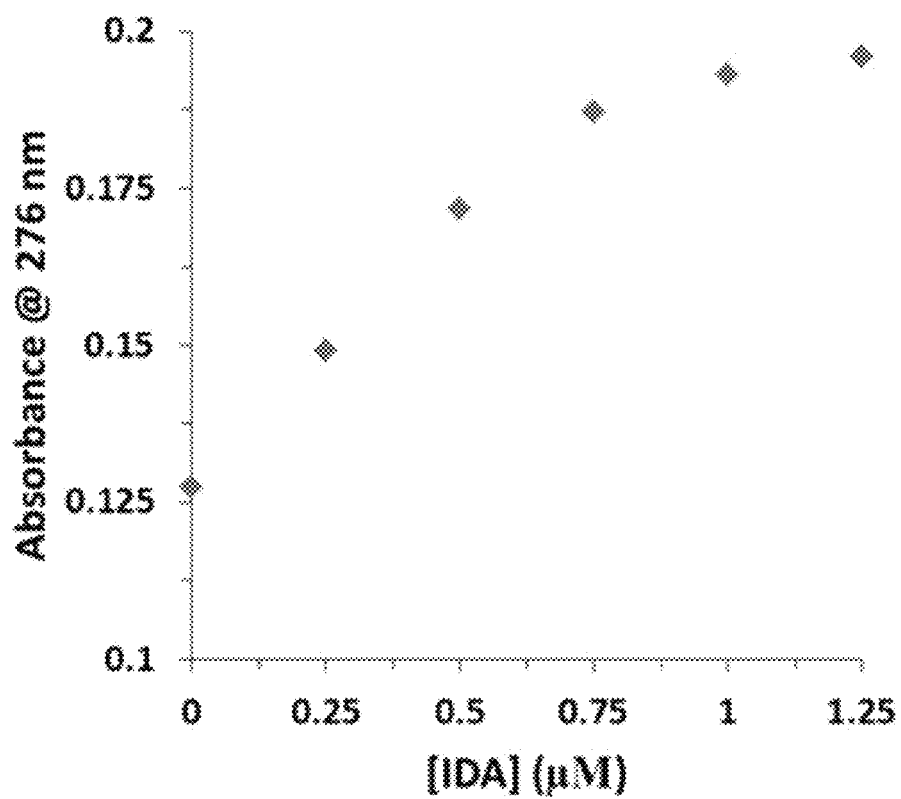

FIGS. 56A and 56B present UV-visible spectra of 1 mM Met1-Tyr peptide and 1 mM Cu(II) titrated with various concentrations of IDA (FIG. 56A), as well as a graph showing absorption at 276 nm (in the aforementioned spectra) as a function of IDA concentration (FIG. 56B); total volume of the sample was 300 μl, and the path length of the cuvette was 0.1 cm.

Figure 57:
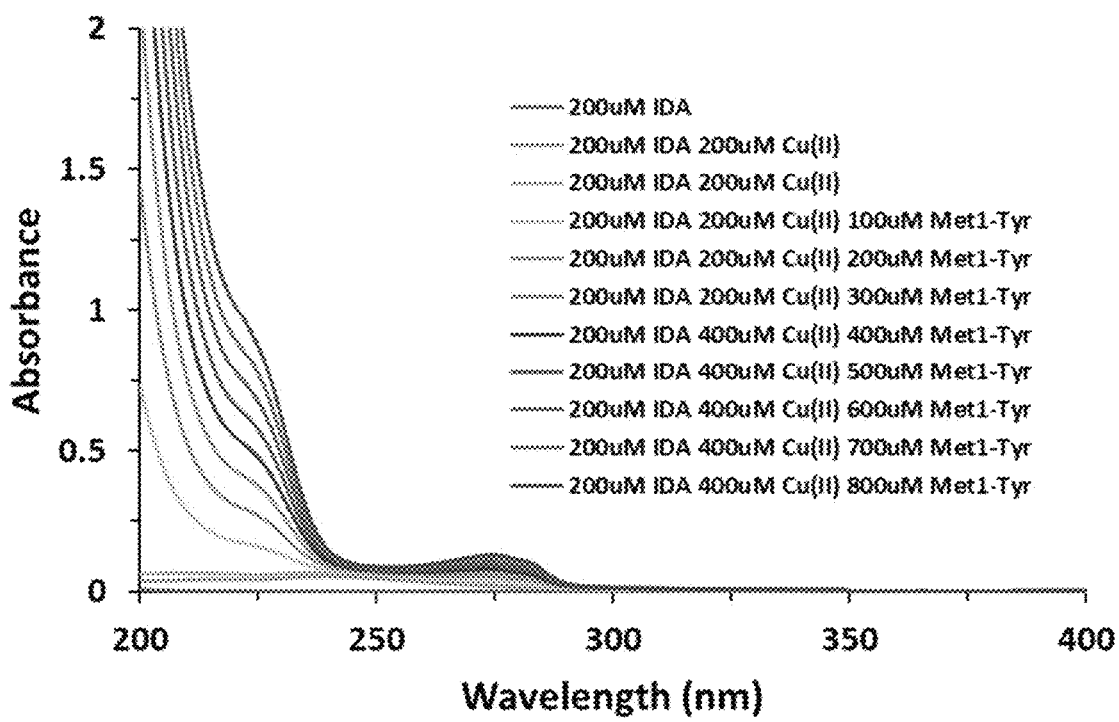

FIG. 57 presents UV-visible spectra of 0.2 mM IDA and 0.2 or 0.4 mM Cu(II) titrated with various concentrations of Cys1-Tyr peptide; total volume of the sample was 300 μl, and the path length of the cuvette was 0.1 cm.

Figure 58:
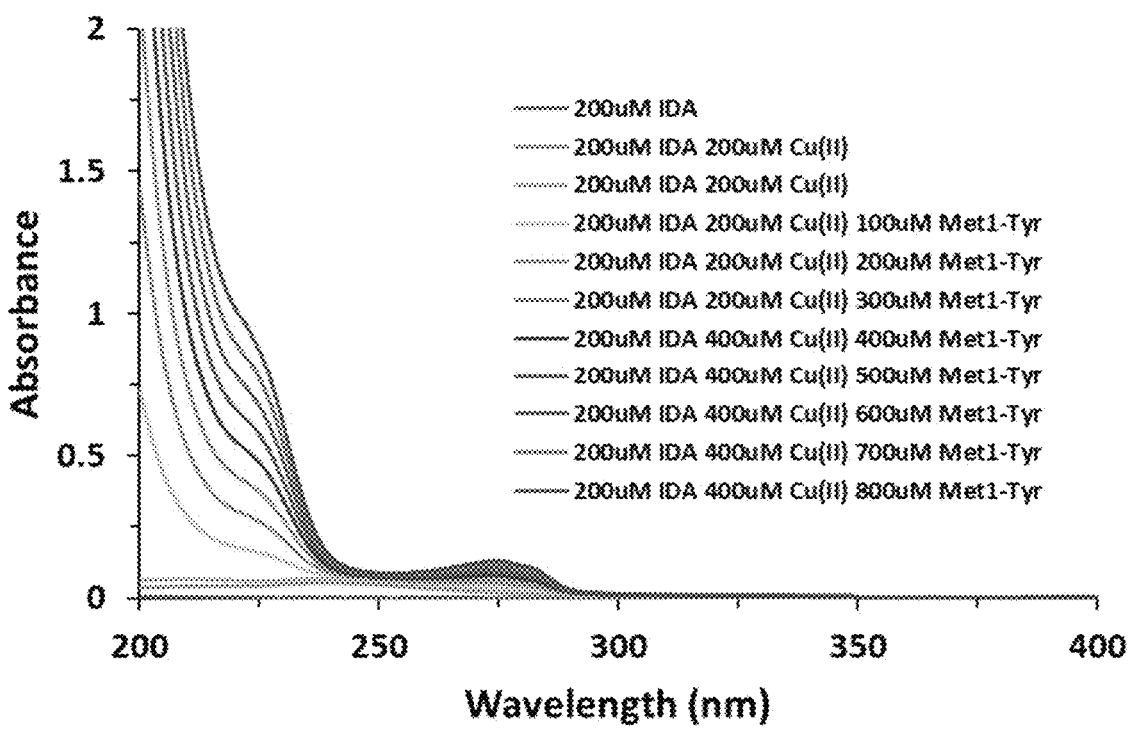

FIG. 58 presents UV-visible spectra of 0.2 mM IDA and 0.2 or 0.4 mM Cu(II) titrated with various concentrations of Met1-Tyr peptide; total volume of the sample was 300 μl, and the path length of the cuvette was 0.1 cm.

Figure 59A:
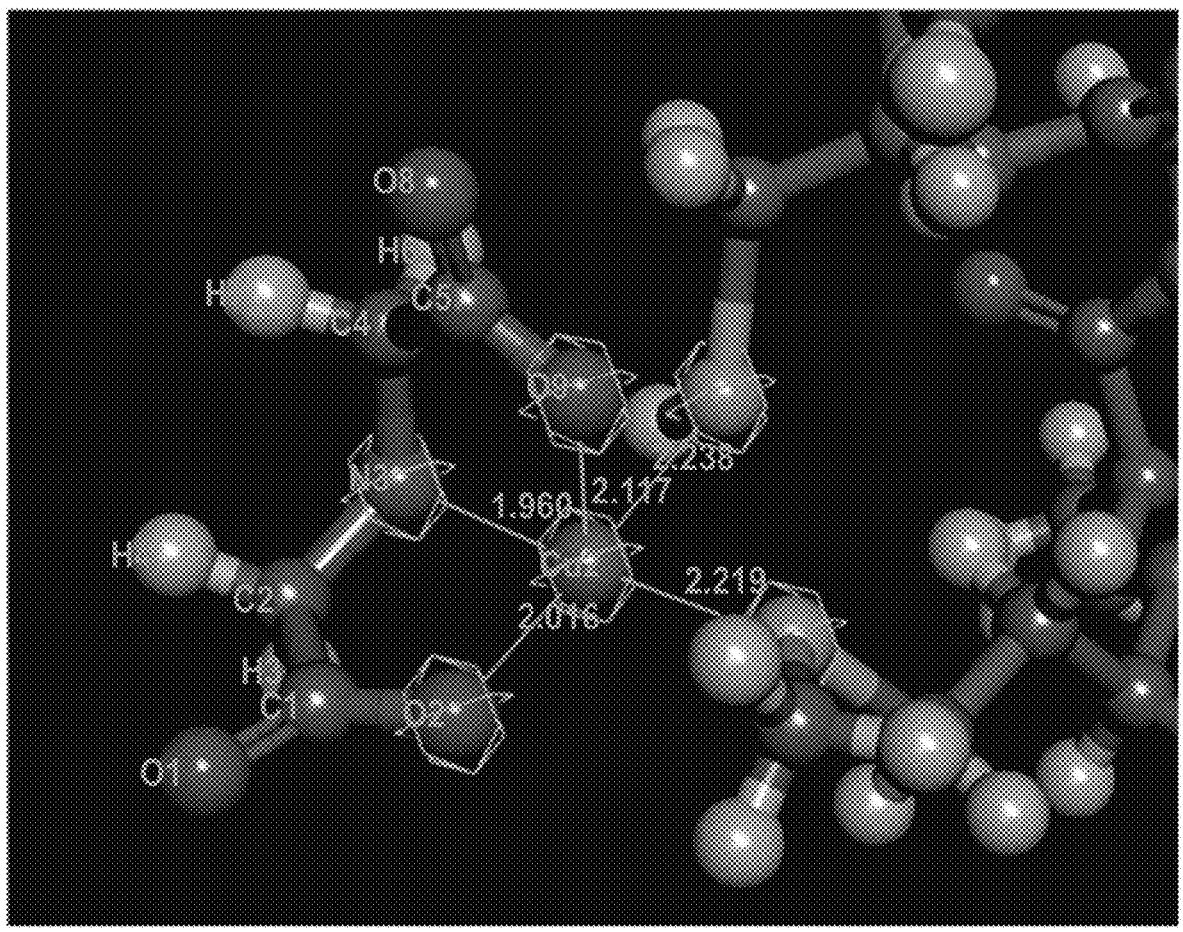
Figure 59B:
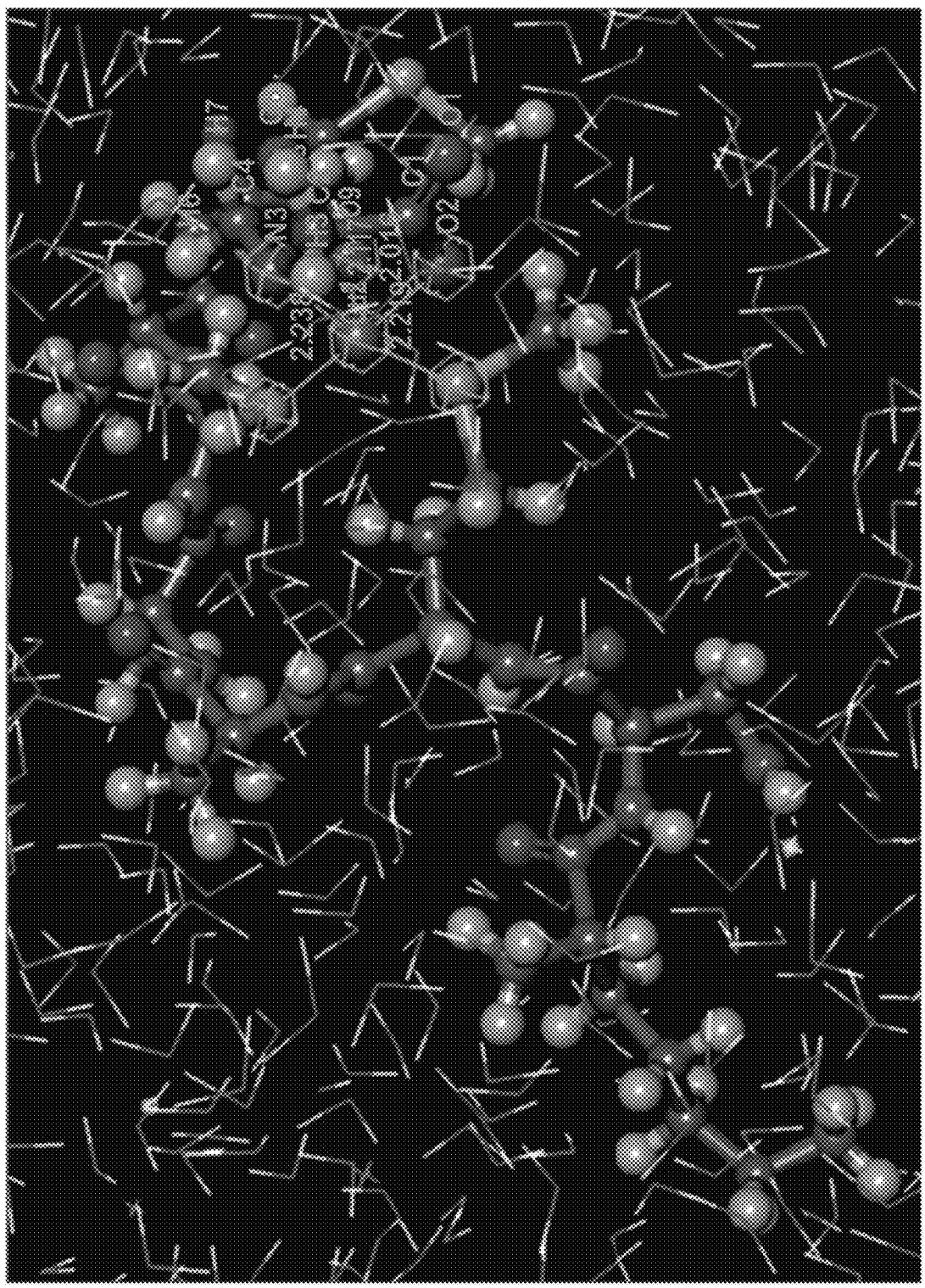

FIGS. 59A and 59B presents a model of the structure of the complex Cu(II)-IDA-Cys1, including distances (in A) between copper atom and coordinating atoms (FIG. 59A is a zoom-in of FIG. 59B, from a different angle, and FIG. 59B further shows solvent.

Figure 60:
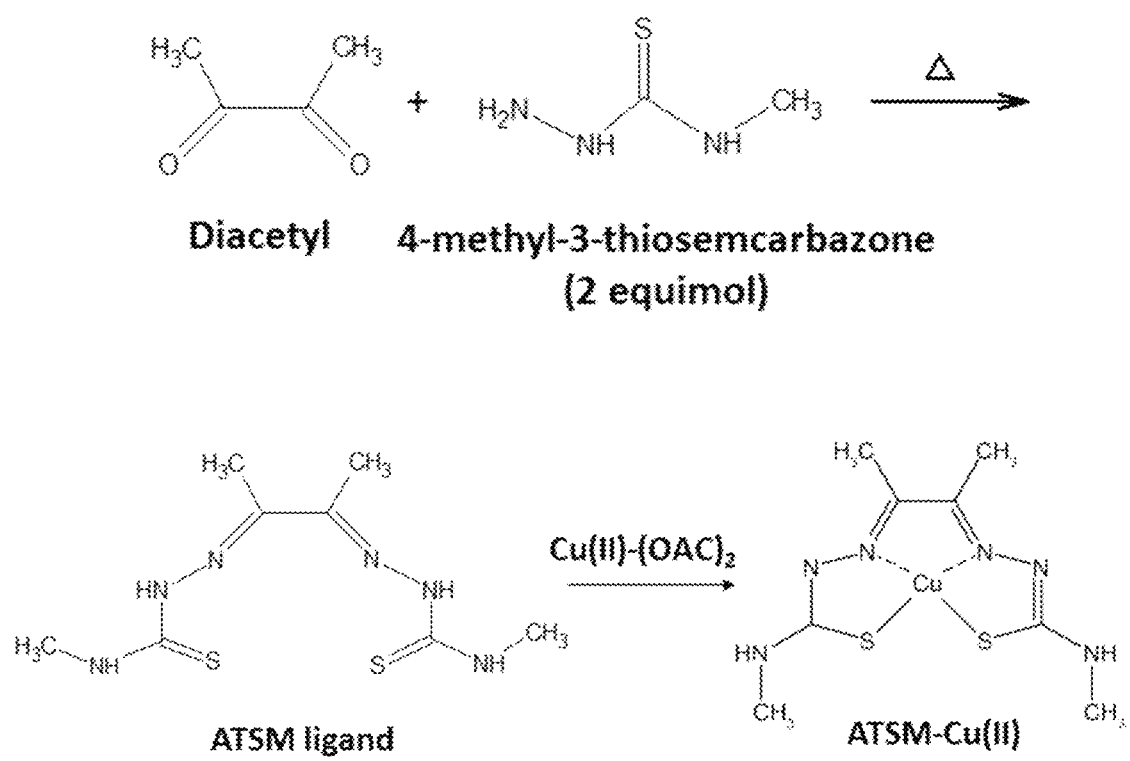

FIG. 60 presents a scheme depicting a route for preparation of ATSM-Cu(II) complex.

Figure 61:
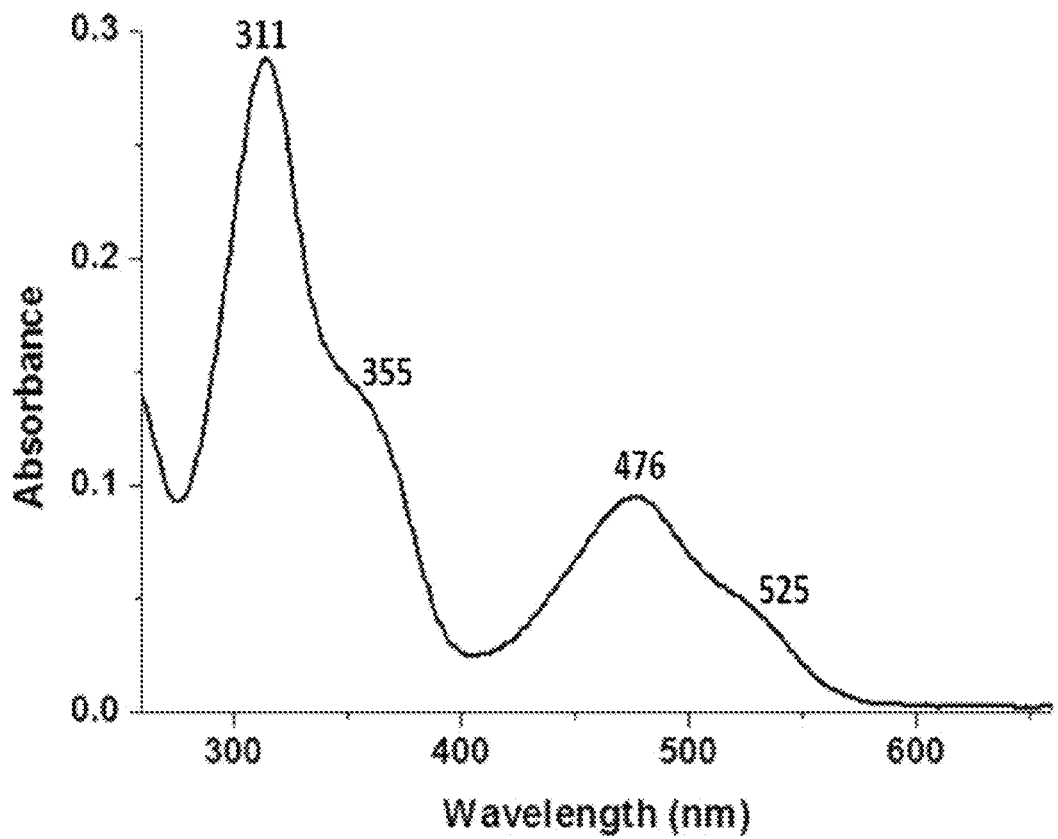

FIG. 61 presents a UV-visible absorption spectrum of an ATSM-Cu(II) complex in DMSO.

Figure 62:
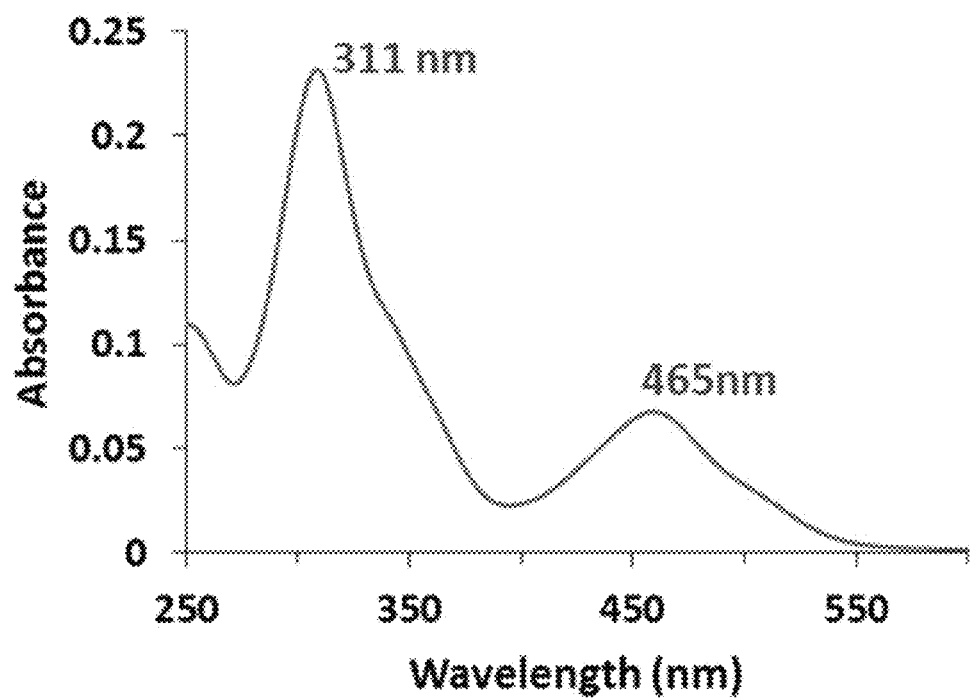

FIG. 62 presents a UV-visible absorption spectrum of 0.1 mM ATSM-Cu(II) complex in 30% DMSO with 0.1 M phosphate buffer (pH 7.4).

Figure 63:
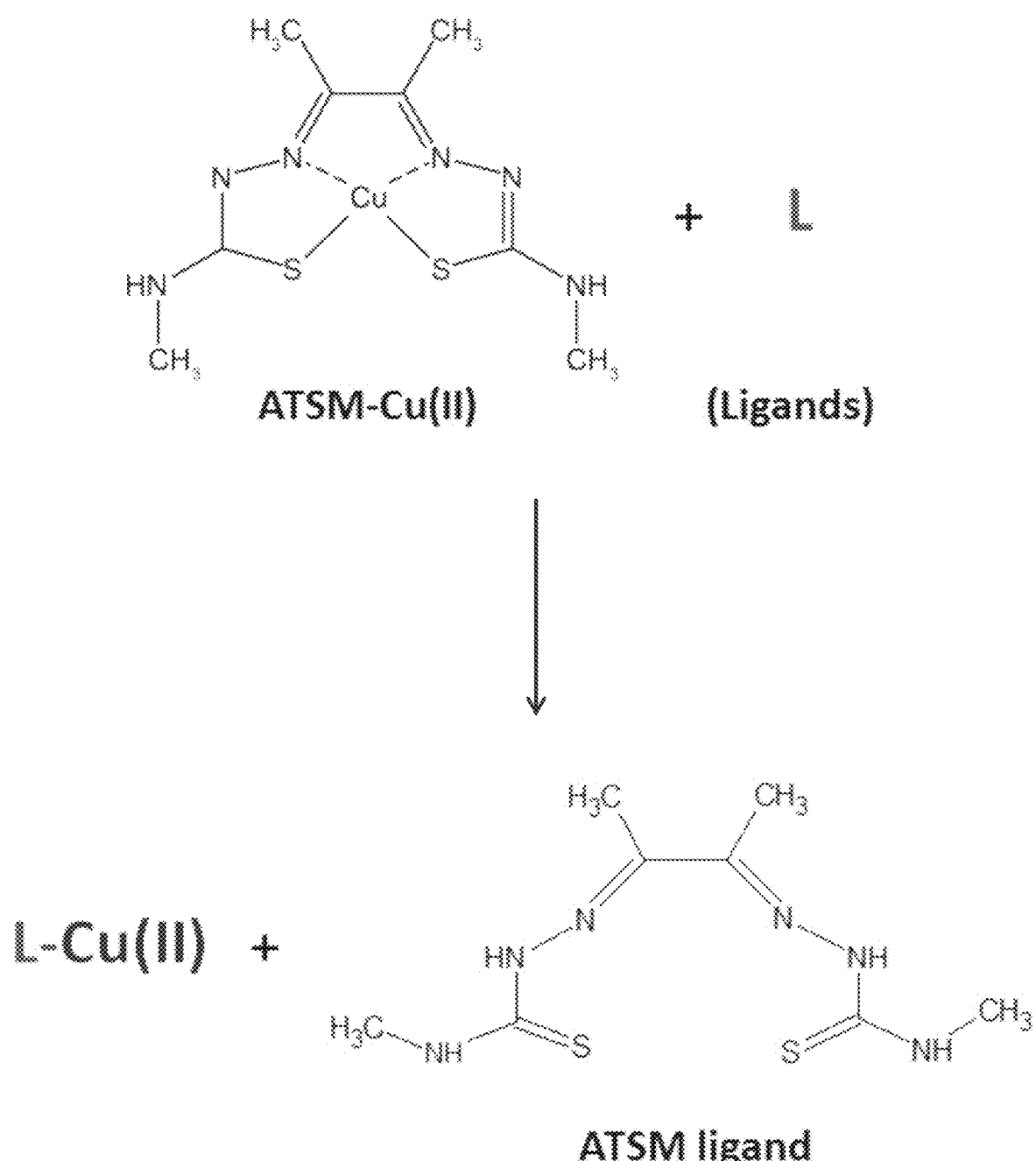
Figure 64A:
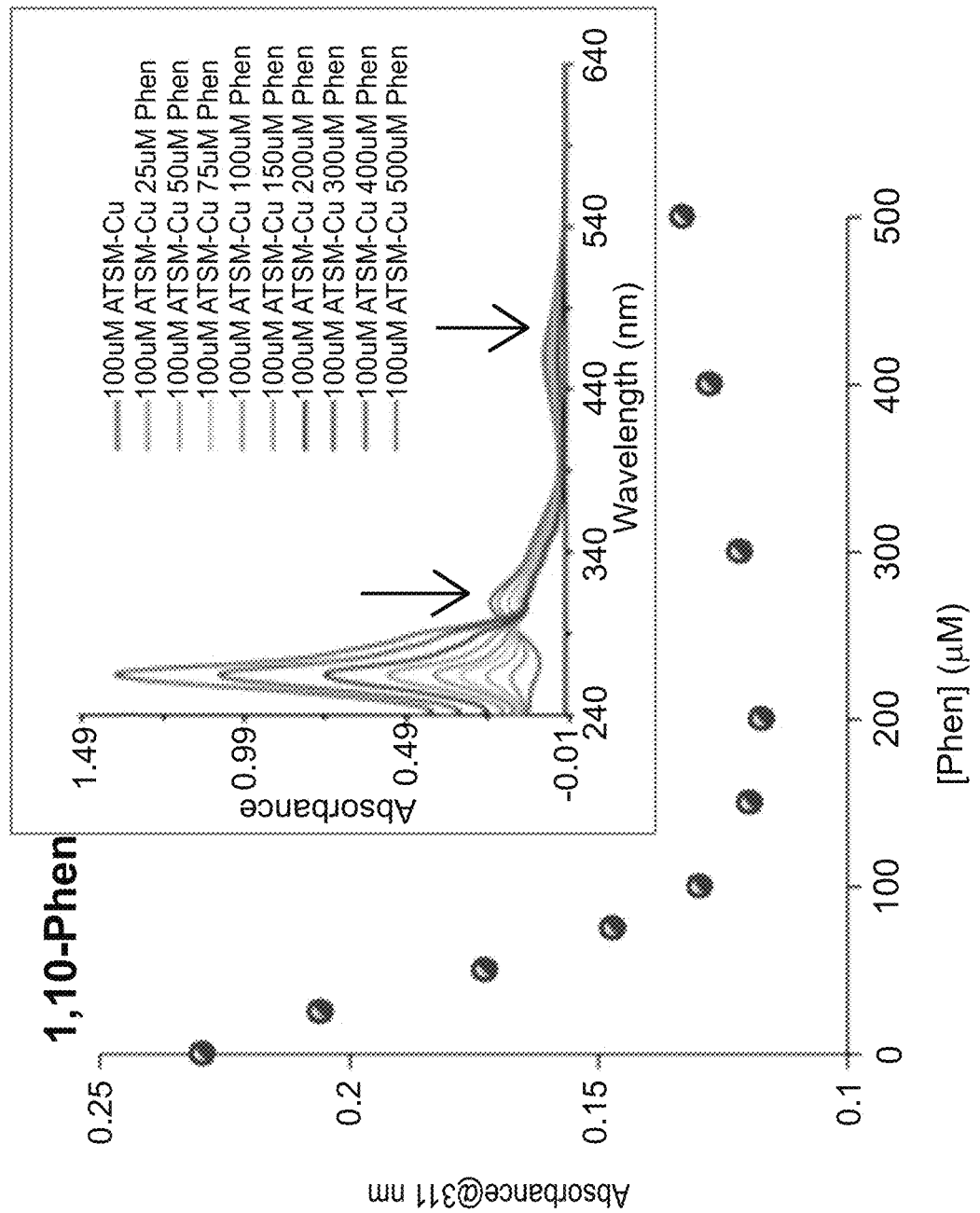
Figure 64B:
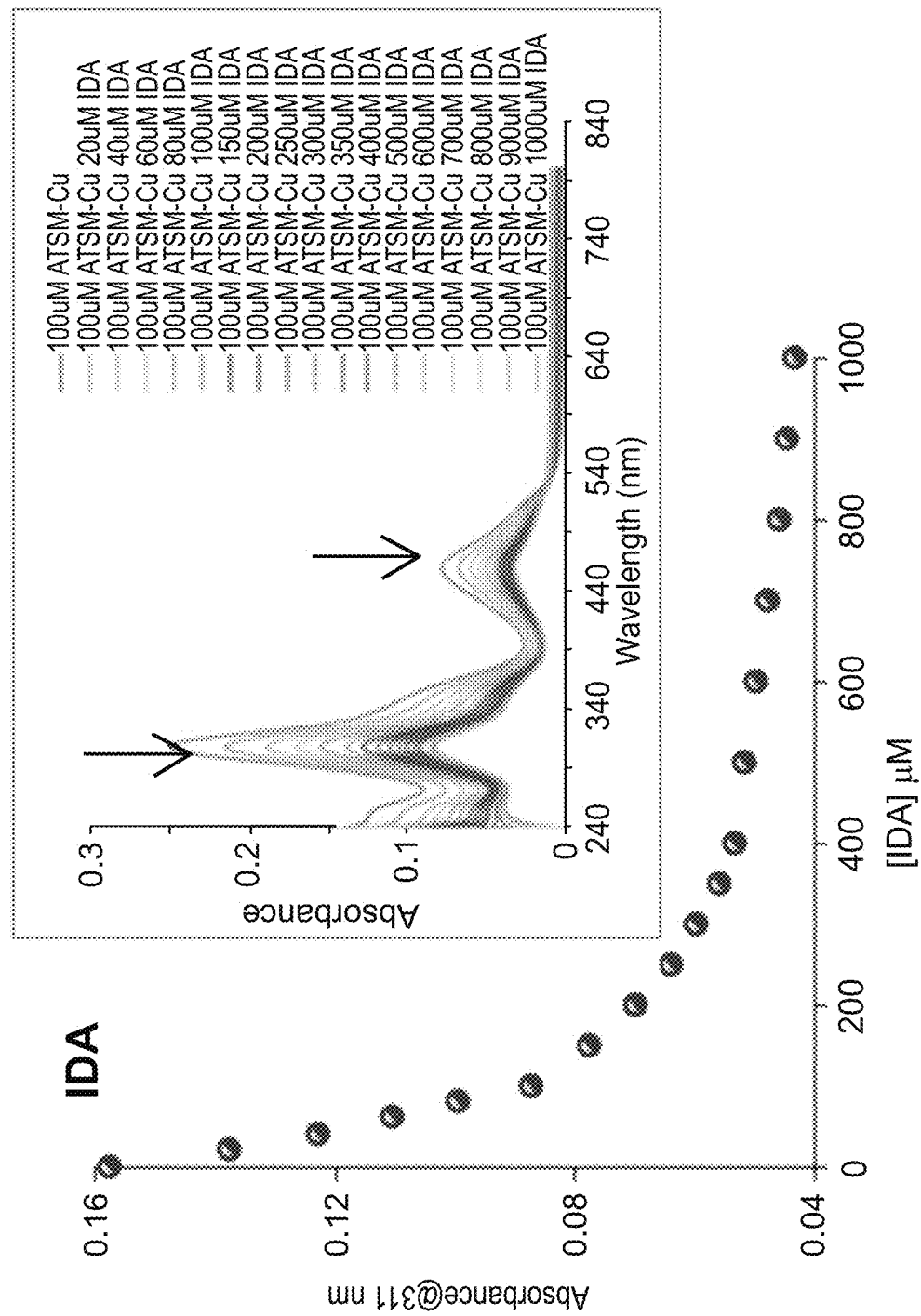
Figure 64C:
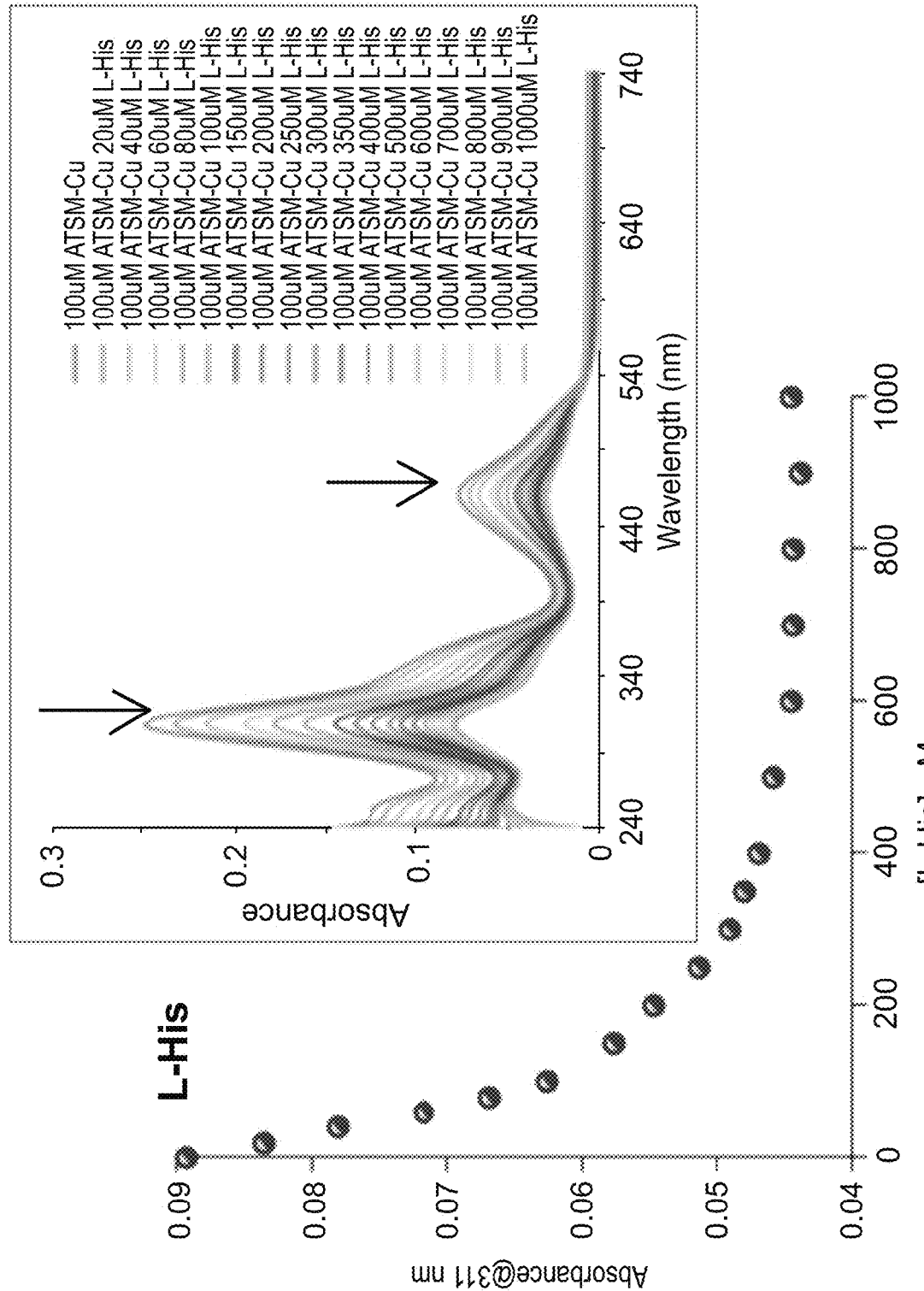
Figure 64D:
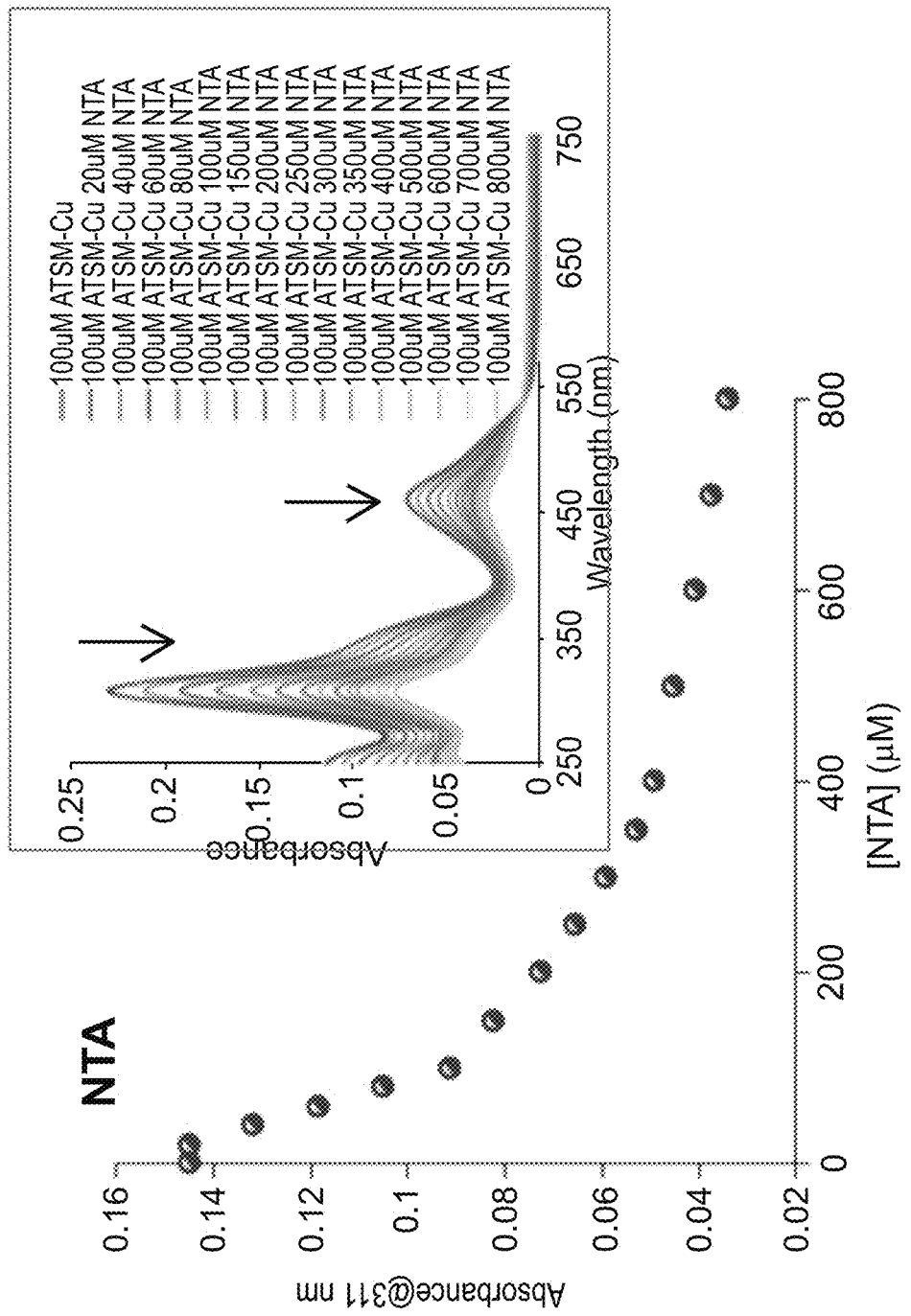

FIG. 63 presents a scheme depicting chelation of copper from ATSM-Cu(II) complex by a ligand to form a corresponding ligand-Cu(II) complex and free ATSM ligand.

FIGS. 64A-64D present absorption at 311 nm as a function of concentration of 1,10-phenanthroline ("Phen") (FIG. 64A), IDA (FIG. 64B), L-histidine (FIG. 64C) or NTA (FIG. 64D), and UV-visible absorption spectra (insets), upon titration of 100 mM ATSM-Cu(II) complex with various concentrations of the 1,10-phenanthroline, IDA, L-histidine or NTA; all measurements performed in 30% DMSO with 0.1 M phosphate buffer (pH 7.4).

FIGS. 65A-65D present absorption at 311 nm as a function of concentration of the peptides HAGAH (SEQ ID NO: 47) (FIG. 65A), HGGH (SEQ ID NO: 48) (FIG. 65B), HTGMK (SEQ ID NO: 49) (FIG. 65C) or Pep1 (SEQ ID NO: 1) (FIG. 65D), and UV-visible absorption spectra (insets), upon titration of 100 mM ATSM-Cu(II) complex with various concentrations of peptide; all measurements performed in 30% DMSO with 0.1 M phosphate buffer (pH 7.4).

Figure 66:
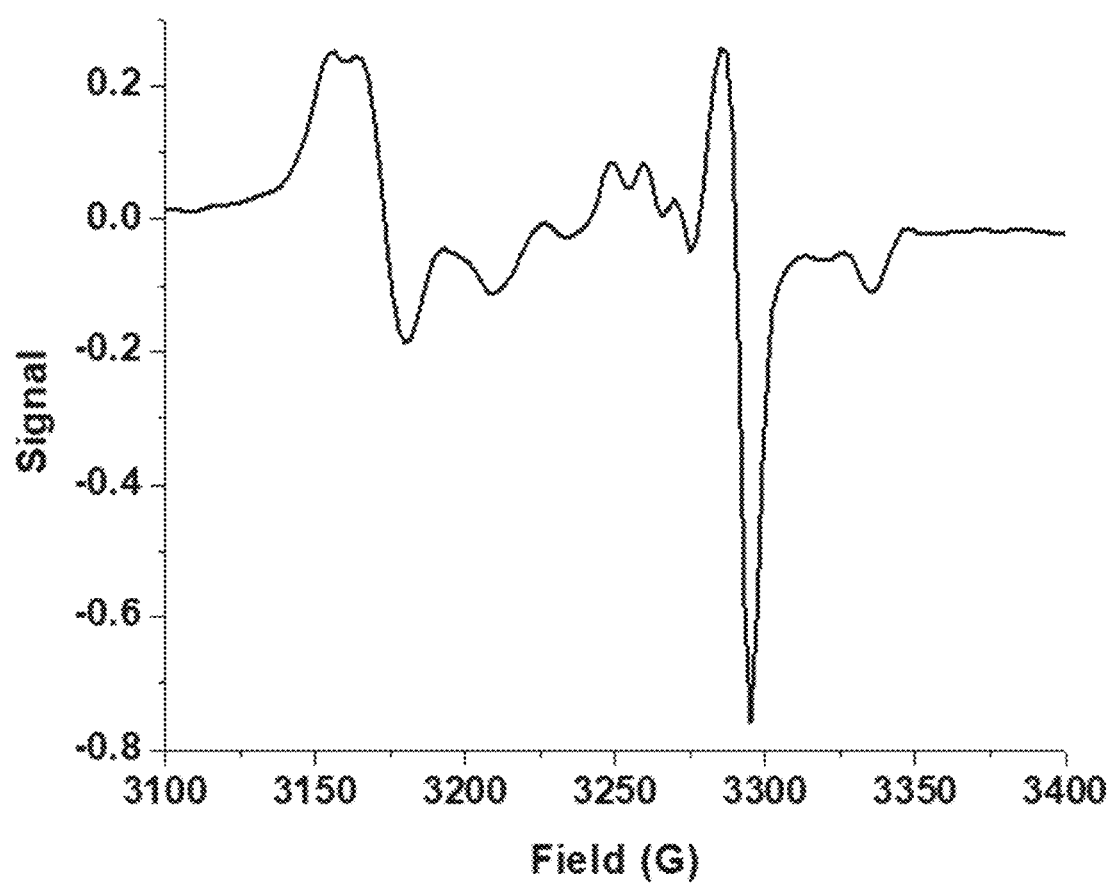

FIG. 66 presents an EPR spectrum of 0.1 mM ATSM-Cu (II) complex.

Figure 67A:
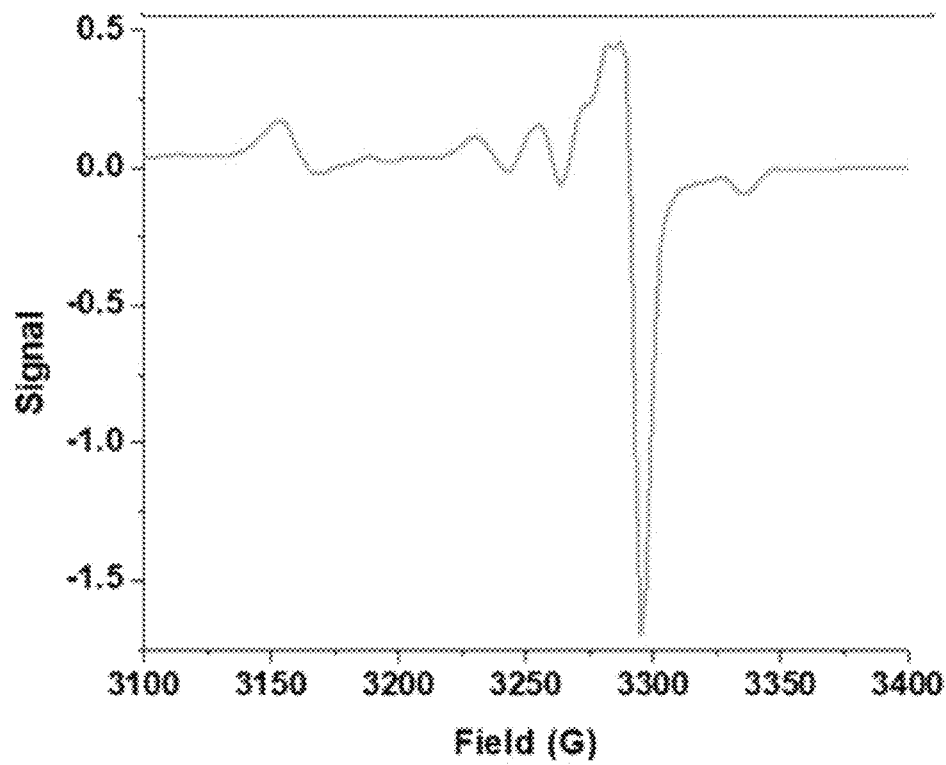
Figure 67B:
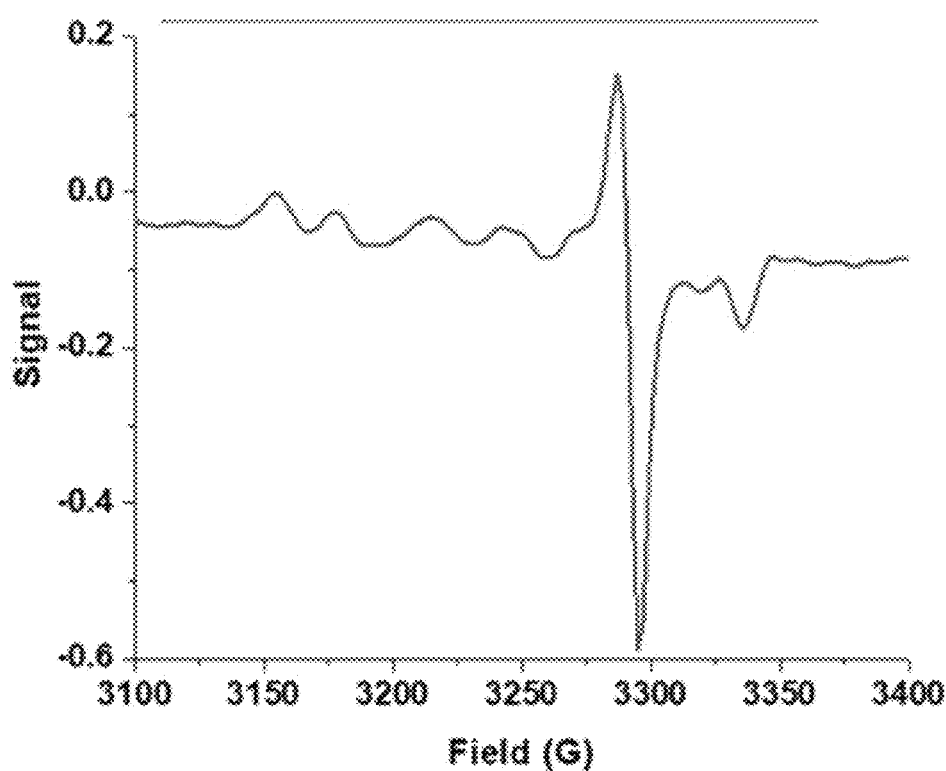
Figure 67C:
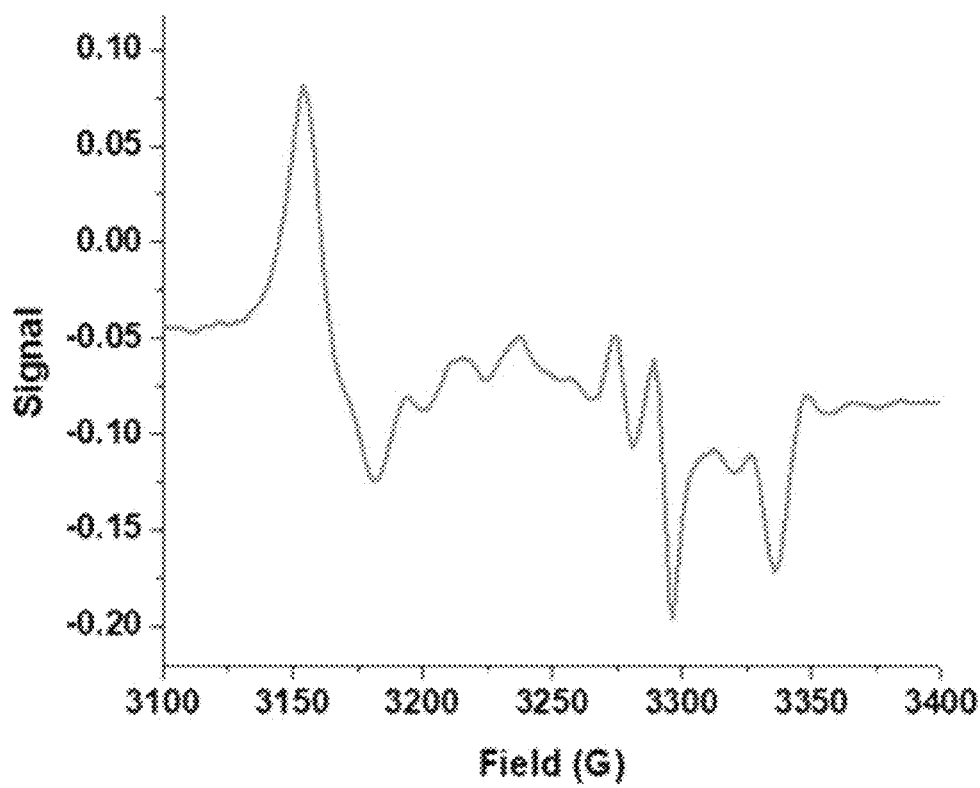
Figure 67D:
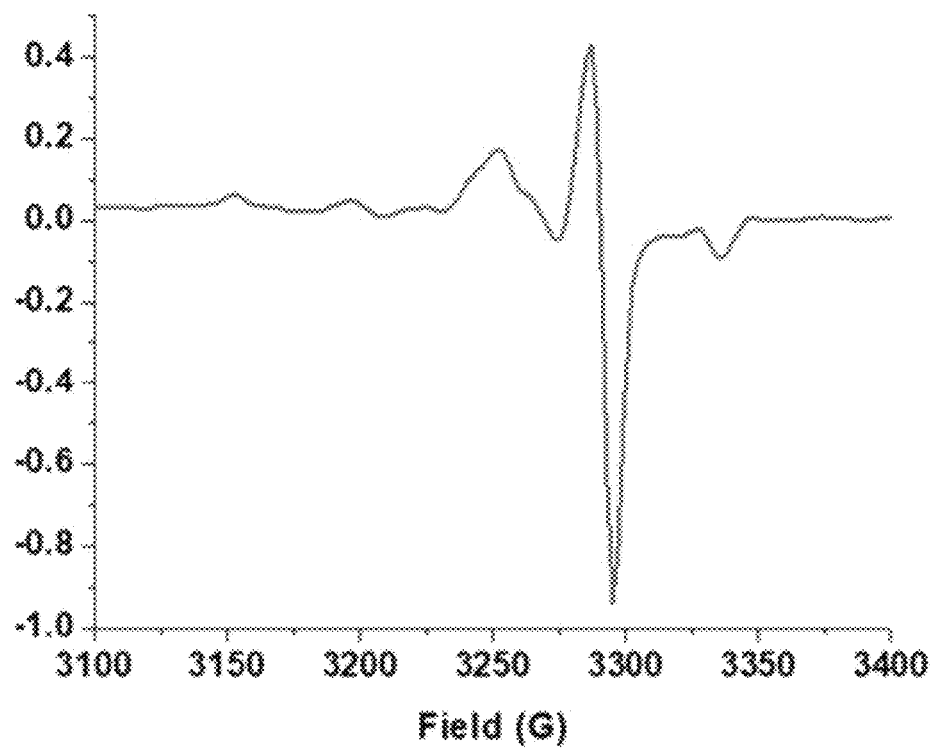
Figure 67E:
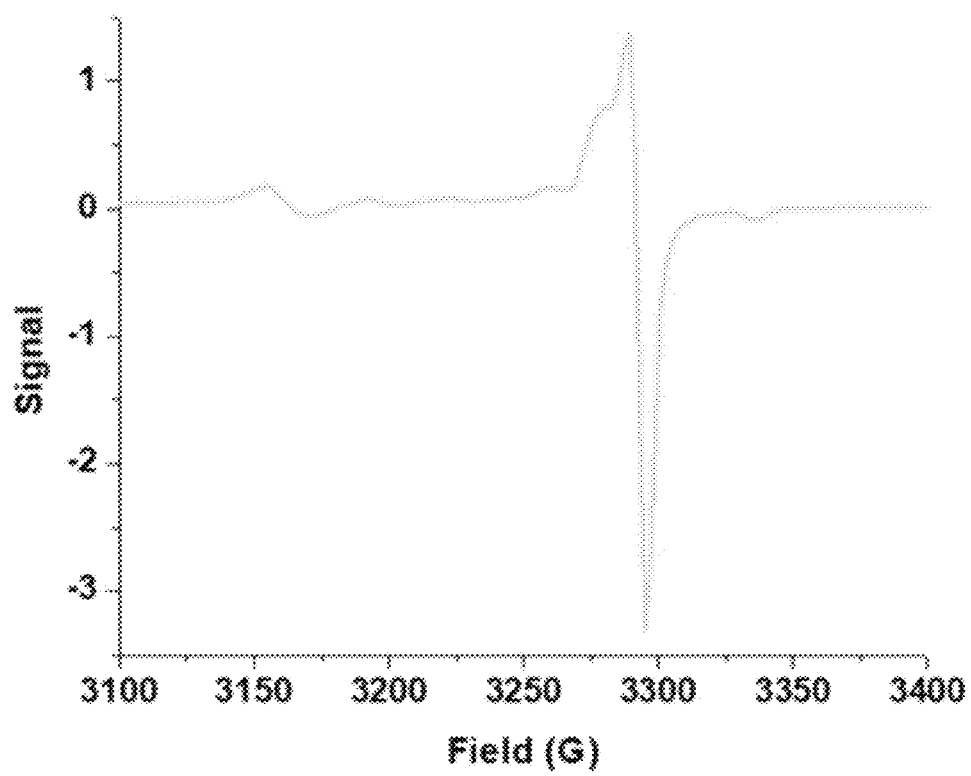
Figure 67F:
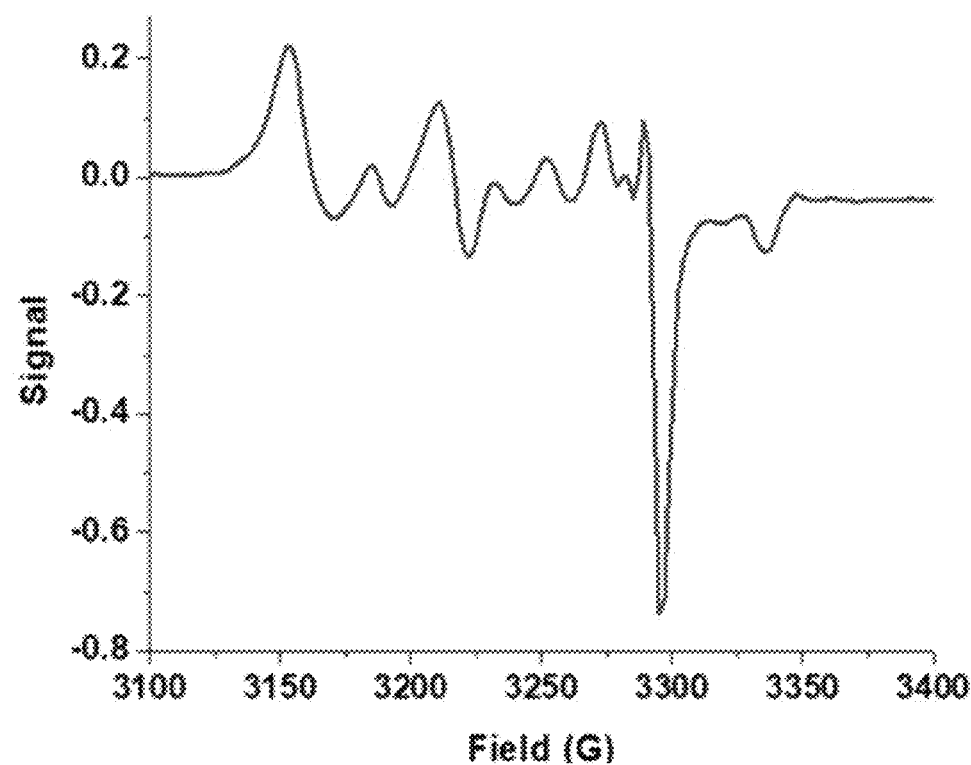

FIGS. 67A-67F present EPR spectra of samples comprising 0.1 mM ATSM-Cu(II) complex following addition of 0.4 mM of 1,10-phenanthroline (FIG. 67A), IDA (FIG. 67B), L-histidine (FIG. 67C), NTA (FIG. 67D), HTGMK (SEQ ID NO: 49) (FIG. 67E) or Pep1 (SEQ ID NO: 1) (FIG. 67F).

DESCRIPTION OF SPECIFIC EMBODIMENTS OF THE INVENTION

The present invention, in some embodiments thereof, relates to copper-containing complexes, and more particularly, but not exclusively, to novel copper-containing complexes which are usable in introducing copper into cells and to uses thereof in imaging and in radiation therapy, and for determining a redox state of cells.

Figure 1:
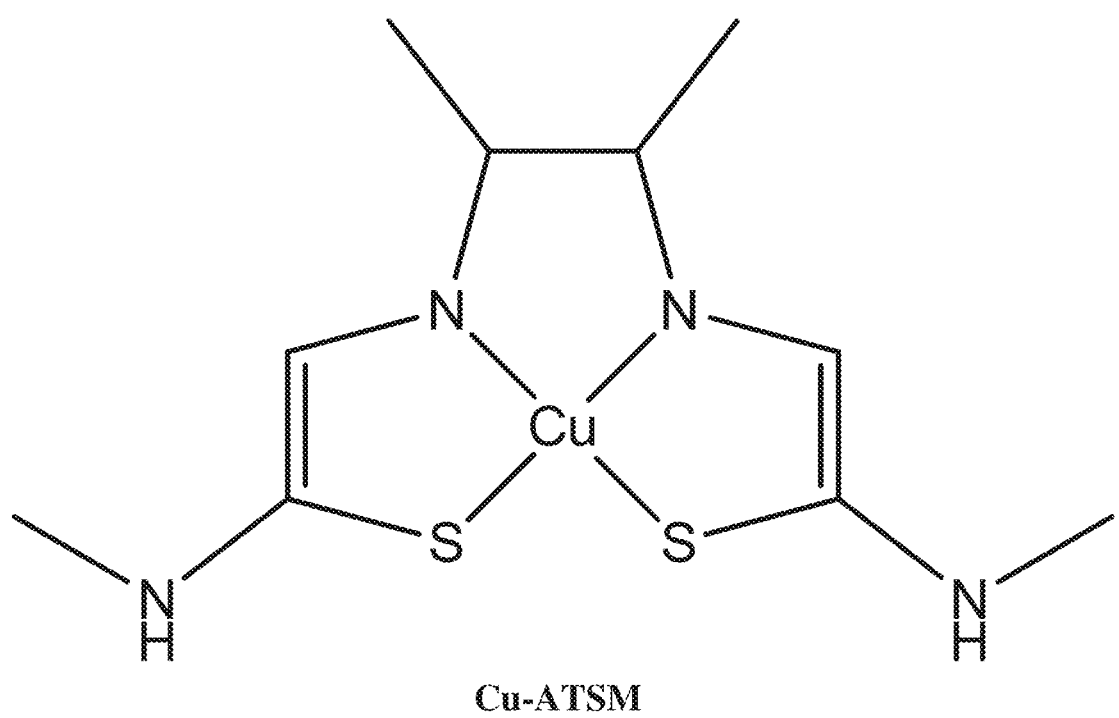

For purposes of better understanding some embodiments of the present invention, reference is first made to the structure of Cu-ATSM (Cu(II)-diacetyl-bis(N4-methylthiosemicarbazone), a state of the art copper complex, as illustrated in FIG. 1.

As exemplified herein, Cu(II)-ATSM is susceptible to dissociation of Cu(II) from the ATSM ligand, which reduces the signal to background ratio, and may cause chelation of Cu(II) by SOD, cytochrome C and other histidine-rich proteins, resulting in unwanted reactions and toxicity.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered that normal cellular uptake of copper ions (by the transporter Ctr1) involves reduction of Cu(II) to Cu(I) at the extracellular surface, independently of the chemical state inside the cell, which reduces the amount of medically useful information which can be obtained by detecting copper uptake, for example, by reducing the observable differences between hypoxic cells and normoxic cells. The present inventors have further uncovered binding sites of Ctr1 which facilitate transport of copper ions and which favor copper ions in the Cu(I) oxidation state, and have designed a Cu(II)-containing complex which can bind to such binding sites of Ctr1 (which normally transport Cu(I)) in order to enhance transport of complexed Cu(II) into the cell. Intracellular reduction of Cu(II) to Cu(I) is then dependent on intracellular conditions (e.g., hypoxia), which may provide valuable information. A ligand bound transported into the cell along with Cu(II) may also be selected to provide a useful function, for example, as a fluorescent label.

While reducing the present invention to practice, the present inventors designed complexes comprising Cu(II) coordinated to a ligand and to a peptide, wherein the peptide comprises sulfur atoms (to which the Cu(II) is coordinated), and shown that the sulfur atoms of the peptide are readily replaced by sulfur atoms of Met residues in Ctr1, thereby promoting coordination of the Cu(II) to Met residues in Ctr1 which facilitate transport copper ions into the cell. The present inventors have further shown that such complexes enhance uptake of copper via Ctr1, and that the amount of Cu(I) ions in cells following contact with the complexes is sensitive to the cellular redox state.

Thus, the complexes facilitate transport of Cu(II) into cells, whereas in the absence of such complexes, Cu(II) would remain at the extracellular surface until being reduced to Cu(I). Referring now to the drawings, FIGS. 7-15B show that Cu(II) ion is coordinated primarily to nitrogen atoms of the N-terminal portion of Ctr1, and that Gly8, His3, His5 and His6 are involved in coordination of Cu(II) to Ctr1. In comparison, FIGS. 16-25 show that His3, Met7, Met9 and Met12 are involved in coordination of Cu(I) to Ctr1, that Met7, Met9 and Met12 play a particularly important role in Cu(I) coordination, and that the N-terminal portion of Ctr1 becomes more rigid upon binding Cu(I).

FIGS. 26 and 27 present a model (based on the above-mentioned results) of the structure of the N-terminal portion of Ctr1 upon coordination to Cu(I) and Cu(II), and of transport of Cu(I) by Ctr1 into the cell.

FIG. 29 schematically depicts a Cu(II)-ligand-peptide complex according to some embodiments of the invention. FIG. 35 depicts an exemplary Cu(II)-ligand-peptide complex according to some embodiments of the invention. FIG.

28 shows exemplary ligands for coordinating to copper in a Cu(II)-ligand-peptide complex according to some embodiments of the invention.

FIG. 30 shows the preparation of an exemplary Cu(II)-ligand-peptide complex comprising a fluorescent cyanine dye (CyNA-427) as ligand. FIGS. 31A-32 show that the cyanine ligand fluorescence is affected by the oxidation state of copper ions (Cu(I) or Cu(II)) coordinated to the ligand.

FIG. 33 shows that exemplary Cu(II)-ligand-peptide complexes (comprising an IDA or cyanine ligand) comprise Cu(II) coordinated to two sulfur atoms in the peptide and to two nitrogen or oxygen atoms in the ligand. FIG. 34 shows that a methionine residue of Ctr1 coordinates to Cu(II) in the presence of exemplary Cu(II)-ligand-peptide complexes, but not in the presence of corresponding Cu(II)-ligand complexes lacking the peptide. These results indicate that the Cu(II)-ligand-peptide complex promotes coordination of Cu(II) to methionine residues of Ctr1 (which normally coordinate to Cu(I)).

FIGS. 59A and 59B show a computed structure of an exemplary Cu(II)-ligand-peptide complex.

FIG. 36 shows that the Cu(II) in an exemplary Cu(II)-ligand-peptide complex is not reduced to Cu(I) under normal conditions, but is reduced to Cu(I) under hypoxic conditions, and that Ctr1 enhances reduction under hypoxic conditions. FIGS. 37-38 shows that the Cu(II)-ligand-peptide complex enhances long-term retention of Cu(I) by cells following copper uptake mediated by Ctr1, and that retention of Cu(I) is enhanced considerably under hypoxia. These results indicate that the Cu(II)-ligand-peptide complex promotes coordination of Cu(II) by Ctr1 in a manner which facilitates copper uptake by cells. FIG. 39 shows that the complex is not toxic to cells.

FIGS. 40A-40B show the preparation of an exemplary Cu(II)-ligand-peptide complex comprising radioactive copper ($^{64}$Cu). FIG. 41 depicts preferential radio-labeling of hypoxic cells by a $^{64}$Cu(II)-ligand-peptide complex, according to some embodiments of the invention.

FIGS. 42-47 show the preparation to exemplary Cu(II)-ligand-peptide complexes under various conditions. FIGS. 48-52B show the separation of the complexes (e.g., from free copper) using a gel filtration column. FIGS. 48 and 49 show that preparation of the complex in NEM (N-ethylmorpholine) buffer reduces copper aggregation. FIGS. 50 and 51 show that separation was better when the complex was prepared in NEM buffer than when prepared in phosphate buffer.

FIGS. 53A-58 show that a cysteine-containing peptide binds to the Cu(II) in the complex more strongly than does a peptide containing only sulfur atoms in methionine residues.

FIGS. 64A-67F show that Cu(II)-ATSM is susceptible to dissociation of Cu(II) from the ATSM ligand, suggesting one reason why it is inferior to complexes according to embodiments of the invention for many applications.

According to an aspect of some embodiments of the invention, there is provided a complex comprising a coordinated Cu(II) ion, the complex being capable of binding to an extracellular portion of Ctr1 such that the complex with the Cu(II) ion is transported through the Ctr1. In some embodiments, the complex comprises a ligand selected to be capable of being transported with the Cu(II) ion. In some embodiments, the complex comprises two or more ligands coordinated to the Cu(II), wherein at least one ligand is selected capable of being transported with the Cu(II) through Ctr1, and at least one ligand is selected to be capable of being released prior to or during transport, for example, upon binding to the extracellular portion of Ctr1.

Herein and in the art, a "complex" comprising one or more metal atoms (e.g., a copper ion described herein) refers to a chemical structure wherein a central metal atom (optionally a metal ion) is surrounded by bound molecules or ions, which are referred to as "ligands". Each ligand may optionally be bound to the central metal atom via one or more atoms.

Herein, the terms "coordinate", "coordinated" and "coordination", and variants thereof, refer to a bond (also referred to as a "coordinative bond") between the central atom (e.g., copper ion) of a complex (as defined herein) and an indicated ligand or indicated atom of a ligand, wherein the central metal ion and the ligand (or atom of the ligand) are described as being coordinated to one another. Alternatively, the central metal atom (e.g., copper ion) of a complex may be described simply as being "coordinated" (e.g., without explicit reference to a ligand of the complex).

Herein, a "coordinative bond" refers to a bond between a metal atom (including a metal ion) and a ligand (typically an organic ligand), as this term is recognized by those skilled in the art of transition metal coordination in the art.

Typically, the coordinative bond is a dipolar bond, e.g., wherein the bond between the central atom and a ligand involves two electrons, which both derive from the ligand (e.g., a free electron pair of an atom in the ligand, which coordinates to the central atom). However, the nature of coordinative bonds may be highly complicated and the aforementioned description should not be considered as limiting.

According to some embodiments of any of the embodiments described herein, the complex is capable of binding to the extracellular portion of Ctr1, for example, via coordination of the copper ion to at least one Met(methionine) residue (and optionally to at least two Met residues) of the extracellular portion of Ctr1. As shown in the Examples section herein, Met residues are associated with transport of copper ions through Ctr1 (as opposed to initial binding of copper ions to Ctr1), but usually tend to coordinate to Cu(I) rather than to Cu(II).

According to some embodiments of any of the embodiments described herein, the complex comprises a Cu(II) copper ion coordinated to a ligand and to a peptide (the ligand and peptide being two distinct molecules). In some embodiments, the ligand is selected capable of being transported with the Cu(II) through Ctr1, and the peptide is selected to be capable of being released prior to or during transport, for example, upon binding to the extracellular portion of Ctr1. The ligand remains coordinated to the copper ion (which remains in the Cu(II) oxidation state) during release of the peptide and during transport through Ctr1.

It is to be understood that the "ligand" and "peptide" in a complex described herein may each be considered as ligands of the copper ion (in the sense that the copper ion is coordinated to each of them), wherein the "peptide" is a ligand which comprises a peptide structure (according to any of the respective embodiments described herein), and the "ligand" of the complex is a ligand which is not necessarily a peptide (although it may be characterized by particular features according to any of the respective embodiments described herein). It is to be understood that the "ligand" may optionally also comprise a peptide structure (i.e., be composed of amino acid residues), although preferably a different structure (e.g., amino acid sequence) than that of the "peptide".

In some embodiments of any of the respective embodiments described herein, upon contact of the complex comprising a ligand and a peptide (according to any of the respective embodiments described herein) with an extracellular portion of Ctr1, the peptide is released, thereby forming a second complex comprising the ligand, the copper ion and the extracellular portion of Ctr1. In some embodiments, the copper ion comprised by the second complex is primarily (i.e., in more than 50% of such complexes) Cu(II) ion coordinated to at least one Met(methionine) residue (and optionally to at least two Met residues) of the extracellular portion of Ctr1—for example, Met7, Met9 and/or Met12 of Ctr1—at a physiological partial pressure of oxygen.

Herein, a "physiological partial pressure of oxygen" refers to a partial pressure in a range of from 4 to 13 kPa (optionally 4 kPa), e.g., at 37° C.

In some embodiments of any of the respective embodiments described herein, upon formation of the second complex (with Ctr1) on a cell surface (in which Ctr1 is present), the Cu(II) ion is transported through the Ctr1 (e.g., into the cell) while coordinated to the ligand (e.g., a ligand selected to remain coordinated to a Cu(II) copper ion during transport, according to any of the embodiments described herein).

Herein, the term "Ctr1" refers to a trimeric protein (also known in the art as high affinity copper uptake protein 1).

According to some embodiments of any of the embodiments described herein, the Ctr1 is a human Ctr1, as set forth in SEQ ID NO: 42 (the sequence being for each monomer of the trimer).

Also contemplated are homologs (i.e., functional equivalents) and orthologs (e.g., mouse NM_780299) of the human Ctr1. An exemplary homolog of Ctr1 is set forth in SEQ ID NO: 43, which may be used according to some of any of the embodiments described herein.

Such homologs can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO: 42 or homologous (identity+homology) to SEQ ID NO: 42, as defined herein, optionally as determined using the BestFit software of the Wisconsin sequence analysis package, utilizing the Smith and Waterman algorithm, where gap weight equals 50, length weight equals 3, average match equals 10 and average mismatch equals −9.

The numbering herein of amino acid residues of Ctr1 is in respect to SEQ ID NO: 42. Thus, for example, in embodiments relating to a Ctr1 having a homologous sequence to SEQ ID NO: 42, Met7, Met9 and Met12 refer to a Met residue which is homologous to Met7, Met9 and Met12, respectively, of SEQ ID NO: 42, although such a residue may optionally not be in the 7, 9 or 12 position, respectively, of the homologous sequence.

Herein, an "extracellular portion of Ctr1" refers to any one or more of the 60 N-terminal amino acids of Ctr1 (residues 1-60 of SEQ ID NO: 42 or corresponding residues of a homolog thereof).

Binding to Ctr1 or any portion thereof (according to any of the respective embodiments described herein) may optionally be determined using purified Ctr1 (e.g., SEQ ID NO: 42 or SEQ ID NO: 43), for example, according to procedures described in the Examples section herein. Alternatively or additionally, binding to a portion (e.g., N-terminal) of Ctr1 may optionally be determined using a peptide corresponding to the portion of Ctr1, for example, according to procedures described in the Examples section herein.

Binding of a copper-containing complex described herein to Ctr1 or any portion thereof (according to any of the respective embodiments described herein) may optionally be monitored using EPR spectroscope (e.g., low temperature EPR spectroscopy of Cu(II)) and/or NMR spectroscope (e.g., NMR spectroscopy focusing on amino acids of Ctr1), for example, according to procedures described in the Examples section herein.

Transport of a complex and/or copper ion through Ctr1 (according to any of the respective embodiments described herein) may optionally be determined as transport of the complex and/or copper ion into a cell (from an extracellular space) which expresses Ctr1, wherein the transport is inhibited by the presence of Ag ions, for example, according to procedures described in the Examples section herein.

In some embodiments of any of the embodiments described herein, a total number of atoms in the ligand and the peptide coordinated to the copper ion is in a range of from 4 to 6. In some embodiments, a total number of atoms in the ligand and the peptide coordinated to the copper ion is 4 or 5. In some embodiments, a total number of atoms in the ligand and the peptide coordinated to the copper ion is 5 or 6.

In some embodiments of any of the embodiments described herein, the copper of the complex comprises a radioactive isotope of copper. That is, at least a portion of the copper ions in a plurality of complexes comprising a copper ion (according to any of the respective embodiments described herein) are a radioactive copper isotope.

Examples of radioactive copper isotopes include, without limitation, $^{60}Cu$, $^{61}Cu$, $^{62}Cu$, $^{64}Cu$ and $^{67}Cu$. $^{64}Cu$ is an exemplary radioactive copper isotope.

Radioactive copper isotopes may optionally be prepared by any suitable technique known in the art, including, without limitation, a technique such as described by Asabella et al. [*BioMed Res Int* 2014, 2014:786463], the contents of which are incorporated herein by reference, especially descriptions therein of techniques for preparing a radioactive copper isotope.

It is expected that during the life of a patent maturing from this application many relevant techniques for preparing radioactive copper isotopes will be developed and the scope of the phrase "radioactive copper isotope" is intended to include all such new technologies a priori.

Complexes (according to any of the respective embodiments described herein) comprising radioactive copper ions are optionally in admixture with corresponding complexes comprising non-radioactive copper, for example, $^{63}Cu$ and/or $^{65}Cu$.

Complexes (according to any of the respective embodiments described herein) are optionally formulated in an aqueous solution, for example, having a pH in a range of at least 6.5 (e.g., from 6.5 to 8.5), or at least 7.0 (e.g., from 7.0 to 8.0), or about 7.4.

The aqueous solution optionally further comprises a buffer compound (according to any of the respective embodiments described herein), for example, N-ethylmorpholine. The buffer compound may be at a concentration suitable for maintaining a desired pH (e.g., at least 20 mM, or at least 50 mM or at least 100 mM). Alternatively, the buffer compound may be in a residual amount (e.g., from 1 nM to 20 mM, or from 1 nM to 1 mM, or from 1 nM to 1 μM or from 1 μM to 1 mM), for example, as may be obtained by separating the complex from a buffer in which the complex is prepared, according to any of the respective embodiments described herein.

Ligand:

A ligand according to any of the embodiments described in this section may be included in a complex according to any of the respective embodiments described herein (e.g., in combination with a peptide according to any of the respective embodiments described herein), unless indicated otherwise.

In some embodiments of any of the embodiments described herein, 2, 3 or 4 atoms of the ligand are coordinated to the copper ion. In some such embodiments, 2 or 3 atoms of the ligand are coordinated to the copper ion.

In some embodiments of any of the embodiments described herein, the ligand comprises at least 2 (optionally 2, 3 or 4) nitrogen, oxygen and/or sulfur atoms coordinated to the copper atom. In some embodiments, each of the atoms of the ligand which are coordinated to the copper ion is independently nitrogen, oxygen or sulfur.

In some embodiments of any of the embodiments described herein, no more than two atoms of the ligand which are coordinated to the copper ion are sulfur atoms. In some embodiments, no more than one atom of the ligand, which is coordinated to the copper ion, is a sulfur atom. In some embodiments, the ligand is devoid of sulfur atoms coordinated to the copper ion.

In some embodiments of any of the embodiments described herein, at least one of the atoms of the ligand, which is coordinated to the copper ion, is not sulfur. In some such embodiments, the ligand comprises at least one (optionally 1, 2, 3 or 4) nitrogen and/or oxygen atom coordinated to the copper atom (e.g., wherein the ligand atoms coordinated to the copper comprise one nitrogen and/or oxygen atom, and 1 or 2 sulfur atoms). In some embodiments, the ligand comprises at least 2 (optionally 2, 3 or 4) nitrogen and/or oxygen atoms coordinated to the copper atom (e.g., wherein the ligand atoms coordinated to the copper comprise 2 nitrogen and/or oxygen atom, and 0, 1 or 2 sulfur atoms). In some embodiments, the ligand comprises at least 3 (optionally 3 or 4) nitrogen and/or oxygen atoms coordinated to the copper atom (e.g., wherein the ligand atoms coordinated to the copper comprise 3 nitrogen and/or oxygen atom, and 0 or 1 sulfur atoms). In some embodiments, each of the atoms of the ligand, which are coordinated to the copper ion, is independently nitrogen or oxygen (e.g., wherein the ligand comprises 2, 3 or 4 nitrogen and/or oxygen atoms coordinated to the copper ion).

Without being bound by any particular theory, it is believed that atoms other than sulfur, such as nitrogen or oxygen atoms (and particularly nitrogen atoms), stabilize the Cu(II) oxidation state of a copper ion coordinated thereto (as compared to the Cu(I) oxidation state), and thus reduce a likelihood of reduction of Cu(II) to Cu(I) (e.g., prior to transport of copper by Ctr1). It is further believed that atoms other than sulfur may be more resistant to replacement by atoms (e.g., sulfur atoms of Met or Cys residues) in Ctr1, and thus reduce a likelihood of release of the ligand (e.g., rather than the peptide of the complex) upon contact with Ctr1.

In some embodiments of any of the embodiments described herein, a molecular weight of the ligand is no more than 2000 Da. In some embodiments, a molecular weight of the ligand is no more than 1500 Da. In some embodiments, a molecular weight of the ligand is no more than 1000 Da. In some embodiments, a molecular weight of the ligand is no more than 750 Da. In some embodiments, a molecular weight of the ligand is no more than 500 Da. In some embodiments, a molecular weight of the ligand is no more than 250 Da. In some embodiments, a molecular weight of the ligand is no more than 150 Da.

Without being bound by any particular theory, it is believed that small (e.g., low-molecular weight) ligands are more readily capable of being transported through the pore of Ctr1, thus entering the cell while coordinated to the copper ion.

It is to be appreciated that ligands with certain features (e.g., fluorescence) according to some embodiments described herein may result in an effective lower limit to the molecular weight of the ligand.

In some embodiments of any of the embodiments described herein, the ligand has the general formula I or general formula II:

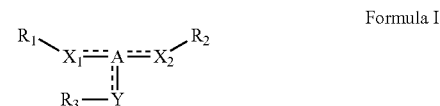

Formula I

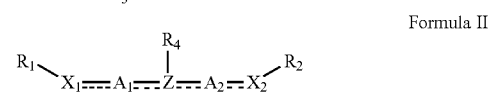

Formula II wherein:

each dashed line independently denotes a saturated or unsaturated bond;

$X_1$, $X_2$ and Z are each independently an electron-donating atom;

Y is absent or is an electron-donating atom;

A, $A_1$ and $A_2$ each independently a hydrocarbon moiety of 1 to 4 atoms in length; and $R_1$-$R_4$ are each independently absent or hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, or amino, wherein when Y is absent, $R_3$ is also absent, or, alternatively, at least one of $R_1$-$R_4$, and at least one of A, $A_1$ and $A_2$, together form a 5- or 6-membered cyclic or heterocyclic ring.

It is to be understood that $X_1$ may be connected to more than one $R_1$ (although only one $R_1$ is explicitly depicted), for example, wherein $X_1$ is a trivalent atom (e.g., nitrogen) which is attached to A or $A_1$ and to two $R_1$ groups, each by a saturated bond. Similarly, $X_2$ may be connected to more than one $R_2$, and Y may be attached to more than one $R_3$.

It is noted that Formula II corresponds to Formula I, wherein the electron-donating atom Z (in Formula II) corresponds to an electron-donating atom Y (in Formula I) which has been incorporated into the moiety A (in Formula I), such that moieties $A_1$ and $A_2$ (in Formula II) may be regarded as the two portions of a moiety A separated by the electron-donating atom Z.

Herein, a "length" of a hydrocarbon moiety refers to the length along the shortest path between two atoms attached to opposite termini of the hydrocarbon chain, e.g., between $X_1$ and Y or Z, or between $X_2$ and Y or Z.

Herein, the phrase "electron-donating atom" refers to an atom capable of donating electrons to form a coordinative bond with a copper ion (as described herein), for example, an atom having a free electron pair.

Examples of suitable electron-donating atoms include, without limitation, nitrogen, oxygen and sulfur.

In some embodiments of any of the embodiments described herein, at least one of the electron-donating atoms ($X_1$, $X_2$, and/or Y or Z) is an atom other than sulfur, for example, nitrogen and/or oxygen. In some embodiments, each of the electron-donating atoms is an atom other than sulfur, for example, nitrogen and/or oxygen.

The skilled person will appreciate how to select electron donating-atoms suitable for providing corresponding atoms coordinated to a copper ion according to any of the respective embodiments described herein.

In some embodiments of any of the embodiments described herein relating to one or more electron-donating atoms which is oxygen, at least one of the electron-donating oxygen atoms is comprised by a carboxylic acid group ($-CO_2H$ or $-CO_2^-$), e.g., wherein the $R_1$, $R_2$, $R_3$ or $R_4$ attached the oxygen atom is hydrogen or absent. In some such embodiments, $X_1$ and/or $-X_2$ is an oxygen atom of a carboxylic acid group.

In some embodiments of any of the respective embodiments described herein, $A_1$ and/or $A_2$ is one carbon atom in length (i.e., $X_1$ and/or $X_2$ is separated from Z by one carbon atom). In some such embodiments, the carbon atom of $A_1$ and/or $A_2$ which is attached to Z is also attached by an unsaturated bond to an oxygen atom (represented by $X_1$ or $X_2$, respectively, wherein $R_1$ or $R_2$ is absent), thereby forming an acyl group (also referred to herein interchangeably as "carbonyl") $-C(=O)R'$ (wherein $A_1$ and/or $A_2$ is C—R'), e.g., formyl (wherein R' is hydrogen), acetyl (wherein R' is methyl), propanoyl (wherein R' is ethyl), or butanoyl (wherein R' is propyl).

In some embodiments of any of the respective embodiments described herein, $A_1$ and/or $A_2$ is two carbon atoms in length (i.e., $X_1$ and/or $X_2$ is separated from Z by two carbon atoms). In some such embodiments, $A_1$ and/or $A_2$ is terminated by an $X_1$ or $X_2$, respectively, which is an oxygen atom. In some embodiment, $A_1$ and $X_1$, and/or $A_2$ and $X_2$, together comprise a carboxylic acid group; for example, together forming $-CH_2-C(=O)OH$ (or $CH_2-CO_2$).

In some embodiments of any of the respective embodiments described herein, $A_1$ and/or $A_2$ is three carbon atoms in length (i.e., $X_1$ and/or $X_2$ is separated from Z by three carbon atoms). In some such embodiments, $A_1$ and/or $A_2$ is terminated by an $X_1$ or $X_2$, respectively, which is a nitrogen atom. In some embodiments, $R_1$ and $X_1$, and/or $R_2$ and $X_2$, together form an amine group; for example, methylamino or dimethylamino.

In some embodiments of any of the respective embodiments described herein, Z is a nitrogen atom.

In some embodiments of any of the respective embodiments described herein wherein Z is a nitrogen atom, $R_4$ is hydrogen (or $R_4$ is absent and the nitrogen atom represented by Z is negatively charged), and each of the bonds linking Z to $A_1$ and Z to $A_2$ is saturated. In some such embodiments, $A_1$ and/or $A_2$ is two carbon atoms in length; for example, wherein $A_1$ and $X_1$, and/or $A_2$ and $X_2$, together form $-CH_2-C(=O)OH$ (or $CH_2-CO_2$).

Imino-diacetic acid (IDA) is an exemplary ligand wherein Z is nitrogen, and $A_1$ and $A_2$ are each two carbon atoms in length.

In some embodiments of any of the respective embodiments described herein wherein Z is a nitrogen atom, $X_2$ is O, $R_2$ is absent, and $A_2$ attached to $X_2$ is an acyl group, e.g., as described herein in any of the respective embodiments.

The acyl group together with the nitrogen atom represented by Z forms an amide group $N-C(=O)-R'$ (wherein $A_2$ is C—R'). Acetyl is an exemplary acyl group attached to Z.

In some embodiments of any of the respective embodiments described herein wherein Z is a nitrogen atom, $X_1$ is N, $R_1$ is alkyl (optionally methyl), and $A_1$ is three atoms in length, optionally $-CH_2CH_2CH_2-$. In some embodiment, $X_1$ is attached to two alkyl groups (represented by $R_1$), optionally two methyl groups.

3-Dimethylamino-propylacetamide (wherein the amide nitrogen is optionally substituted, e.g., as in CyNA-427 depicted in FIG. 28) is an exemplary ligand wherein Z is a nitrogen atom which forms a part of an amide group.

In some embodiments of any of the embodiments described herein, a ligand according to Formula I or Formula II comprises a fluorescent moiety (according to any of the respective embodiments described herein), for example, wherein $R_1$, $R_2$, $R_3$ and/or $R_4$ comprise a fluorescent moiety. In some embodiments, $R_1$, $R_3$ and/or $R_4$ comprise a fluorescent moiety. In some embodiments, the fluorescent moiety is a cyanine moiety (e.g., according to any of the respective embodiments described herein). In exemplary embodiments, $R_4$ is a cyanine moiety.

In some embodiments of any of the embodiments described herein, the ligand is a compound of the general formula III:

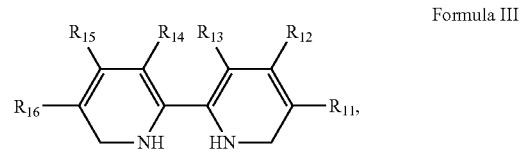

Formula III wherein $R_{11}$-$R_{16}$ are each independently hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, or amino; or alternatively, $R_{13}$ and $R_{14}$ together form a 5-membered or 6-membered cycloalkyl, heteroalicyclic, aryl or heteroaryl ring.

In some embodiments of any of the embodiments relating to Formula III, $R_{13}$ and $R_{14}$ are each hydrogen.

It is to be appreciated that compounds of Formula III may be considered also as compounds of Formula I, e.g., wherein Y and $R_3$ are absent, $X_1$ and $X_2$ are each a nitrogen atom, and A is two carbon atoms in length.

In some embodiments of any of the embodiments relating to Formula III, $R_{13}$ and $R_{14}$ together form a 6-membered aryl ring.

In some embodiments of any of the embodiments relating to Formula III, $R_{11}$ and $R_{16}$ are each hydrogen. In some such embodiments, $R_{13}$ and $R_{14}$ are each hydrogen, or $R_{13}$ and $R_{14}$ together form a 6-membered aryl ring (e.g., as in exemplary compounds depicted in FIG. 28).

In some embodiments of any of the embodiments described herein, the ligand is a peptide, for example, a tetrapeptide or pentapeptide. In some such embodiments, the ligand comprises (and optionally consists of) a peptide having the formula $W^1-X^1-X^2-X^3-W^2$ (SEQ ID NO:

44) or $W^1$—$X^1$—$X^2$—$W^2$ (SEQ ID NO: 45), wherein $W^1$ and $W^2$ are each independently a His residue, a Met residue or a Gly residue, and each of $X^1$, $X^2$ and $X^3$ is independently an Ala residue or a Gly residue. In some embodiments, at least one of $W^1$ and $W^2$ is a His residue.

Exemplary tetrapeptides for use in a ligand according to any of the respective embodiments described herein include, without limitation, HAAH (SEQ ID NO: 11), HAAM (SEQ ID NO: 12) and HAAG (SEQ ID NO: 13).

In some embodiments of any of the embodiments described herein, the ligand is fluorescent, for example, upon coordination to a copper ion. In some embodiments, the fluorescent ligand emits visible light (i.e., at a wavelength in a range of from 400 to 800 nm) upon excitation by visible or ultraviolet light.

In some embodiments of any of the respective embodiments described herein, the fluorescence of the fluorescent ligand is affected by the oxidation state of a copper ion coordinated thereto, e.g., whether the copper ion is Cu(I) or Cu(II).

Sensitivity to the oxidation state of a coordinated copper ion may be obtained, for example, by having at least one atom in the ligand which coordinates to a copper ion—for example, an electron-donating atom (e.g., $X_1$, $X_2$, Y or Z in Formula I or II) according to any of the respective embodiments described herein)—being part of a conjugated π-electron system associated with fluorescence.

Cyanines are non-limiting examples of fluorescent ligands.

Herein, the term "cyanine" refers to a molecule that has two nitrogen-containing moieties, which are joined by a polymethine chain, that is, a chain containing an odd number of carbon atoms bound together by alternating single bonds and double bonds. Each carbon atom in the polymethine chain is independently attached to a single hydrogen atom or substituent, provided that the substituent is compatible with the aforementioned structure of alternating single bonds and double bonds.

Examples of suitable cyanines include, without limitation, cyanines described in International Patent Application Publication WO 2011/119114 (e.g. amine-acetylated cyanines (CyNA)) or in Li et al. [*Chem Commun* 2011, 47:7755-7757], the contents of each of which are incorporated herein by reference, especially with respect to cyanines described therein.

One or both nitrogens can be a part of a nitrogen-containing heteroaryl or heteroalicyclic moiety (which may also comprise one or more carbon atom from the polymethine chain), or alternatively, be a secondary or tertiary amine or ammonium.

In cyanines, one nitrogen is positively charged (e.g., in a form of an ammonium ion) and one nitrogen atom is neutral (e.g., in a form of an amine) and thus has a lone pair of electrons. The positive charge in a cyanine therefore resonates between the two nitrogen atoms via the polymethine chain.

In some embodiments, the polymethine chain comprises 5 carbon atoms. In some embodiments, the polymethine chain comprises 7 carbon atoms. In some embodiments, the polymethine chain comprises 9 carbon atoms. In some embodiments, the polymethine chain comprises 11 carbon atoms.

In some embodiments of any of the respective embodiments described herein, at least one carbon atom in the polymethine chain is substituted by a group, which coordinates to a copper ion. In some such embodiments, the polymethine carbon atom is attached to an atom, which coordinates to copper, for example, an electron-donating atom (e.g., $X_1$, $X_2$, Y or Z in Formula I or II) according to any of the respective embodiments described herein. In exemplary embodiments, the polymethine carbon atom is attached to an amide nitrogen atom of a 3-dimethylaminopropylacetamide moiety.

Cyanines according to some of the respective embodiments can be represented by the general Formula IV:

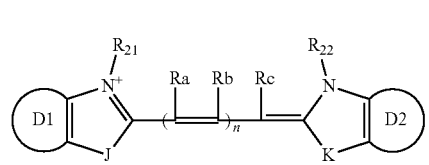

Formula IV wherein:

$D_1$ and $D_2$ are each independently an aryl, as defined herein, or is absent;

J and K are each independently $CR_{23}R_{24}$, $NR_{25}$, O or S, wherein $R_{23}$ and $R_{24}$ are each independently hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, or amino; and $R_{21}$, $R_{22}$ and $R_{25}$ are each independently hydrogen, alkyl, alkenyl, alkynyl, cycloalkyl, aryl, heteroaryl, or heteroalicyclic;

n is an integer of from 1 to 5 (optionally from 2 to 4); and

Ra, Rb and Rc are each independently hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, or amino, or alternatively, Rb along with Ra and/or Rc together form a cycloalkyl, heteroalicyclic, aryl or heteroaryl ring.

It is noted that the number of carbon atoms in the polymethine chain in Formula IV equals 2n+3; and that the number of Ra moieties and the number of Rb moieties each equals n. In embodiments wherein multiple Ra moieties and Rb moieties are present (i.e., wherein n>1), each of the Ra moieties (and/or Rb moieties) may be the same or different.

In some embodiments, $D_1$ and $D_2$ are each a substituted or unsubstituted phenyl. In some embodiments, J and K are each $CR_{23}R_{24}$ (wherein $R_{23}$ and $R_{24}$ in J may be the same as $R_{23}$ and $R_{24}$ in K, or different). In exemplary embodiments, J and K are each $C(CH_3)_2$.

In some embodiments, $R_3$ and $R_4$ (in J and/or K) are each alkyl. In some embodiments, $R_3$ and $R_4$ are each methyl (in J and/or K).

In some embodiments, $R_{21}$ and $R_{22}$ are each independently a substituted or unsubstituted alkyl, for example, a $C_{1-4}$-alkyl (optionally unsubstituted). Propyl is an exemplary alkyl for $R_{21}$ and $R_{22}$.

In exemplary embodiments, n is 3.

In embodiments wherein n>1, multiple —CRa=CRb— groups are present, which groups may have the same Ra and/or Rb, or different Ra and Rb.

In some embodiments of any of the respective embodiments described herein, the Ra groups of two adjacent —CRa=CRb— groups together form a 6-membered cyclic ring (e.g., a cyclohexene ring), and if more than two Ra groups are present (i.e., if n>2), the other Ra groups are optionally hydrogen.

In some embodiments of any of the respective embodiments described herein, at least one Ra or Rb, or Rc is a moiety which coordinates to a copper ion (according to any of the respective embodiments described herein), for example, a moiety comprising an electron-donating atom (e.g., $X_1$, $X_2$, Y or Z in Formula I or II) according to any of the respective embodiments described herein, optionally attached directly to the polymethine carbon atom. In some such embodiments, one Rb is a group which coordinates to a copper ion (according to any of the respective embodiments described herein), and if multiple Rb groups are present (i.e., if n>1), the other Rb groups are optionally hydrogen. In exemplary embodiments, the group which coordinates to a copper ion is a 3-dimethylamino-propylacetamide moiety, optionally attached to the polymethine carbon via the amide nitrogen atom (i.e., a —N(C(=O)CH$_3$)—CH$_2$CH$_2$CH$_2$—N(CH$_3$)$_2$ moiety).

In some embodiments of any of the respective embodiments described herein, a cyanine moiety corresponding to the compound of Formula IV, excluding an Ra, Rb or Rc moiety of Formula IV, is incorporated into a ligand of Formula I or II (according to any of the respective embodiments described herein), e.g., wherein $R_1$, $R_2$, $R_3$ and/or $R_4$ of Formula I or II is a cyanine moiety (according to any of the respective embodiments described herein).

It is to be noted that cyanines in which one or more of the indolenine-like rings (comprising D1 and J, or D2 and K) depicted in Formula IV is replaced by any other nitrogen-containing moiety, e.g., a pyridine/pyridinium moiety, are also contemplated.

Peptide:

A peptide according to any of the embodiments described in this section may be included in a complex according to any of the respective embodiments described herein (e.g., in combination with a ligand according to any of the respective embodiments described herein), unless indicated otherwise.

In some embodiments of any of the embodiments described herein, the peptide is a water-soluble peptide.

Herein, the phrase "water-soluble peptide" refers to a peptide which (when not coordinated to copper) exhibits a solubility of at least 1 gram/liter in aqueous solution (e.g., pure water) at pH 7 (e.g., at a temperature of 20, 25 or 37° C.).

Without being bound by any particular theory, it is believed that a water-soluble peptide may be more readily released from the complex under physiological conditions, e.g., upon contact with Ctr1.

Water-soluble peptides preferably include one or more (non-natural or natural) polar amino acids, including but not limited to serine and threonine which are capable of increasing peptide water-solubility due to their hydroxyl-containing side chain.

In some embodiments of any of the embodiments described herein, the peptide is at least 4 amino acids in length. In some embodiments, the peptide is at least 5 amino acids in length. In some embodiments, the peptide is at least 6 amino acids in length. In some embodiments, the peptide is at least 7 amino acids in length. In some embodiments, the peptide is at least 8 amino acids in length.

In some embodiments of any of the embodiments described herein, the peptide is no more than 20 amino acids in length. In some embodiments, the peptide is no more than 15 amino acids in length. In some embodiments, the peptide is no more than 10 amino acids in length. In some embodiments, the peptide is no more than 8 amino acids in length. In some embodiments, the peptide is no more than 6 amino acids in length.

In some embodiments of any of the embodiments described herein, the peptide comprises 2 or 3 atoms coordinated to the copper ion. In some such embodiments, at least one of the 2 or 3 atoms is a sulfur atom. In some such embodiments, the peptide comprises 2 or 3 sulfur atoms coordinated to the copper ion. In some embodiments, the peptide comprises 3 sulfur atoms coordinated to the copper ion.

In some embodiments of any of the embodiments described herein wherein the peptide comprises 2 or 3 atoms coordinated to the copper ion, the ligand comprises 2, 3 or 4 atoms (optionally 2 or 3 atoms) atoms coordinated to the copper ion. For example, each of the peptide and ligand may comprise 2 atoms coordinated to the copper ion, for a total of 4 atoms coordinated to the copper ion; or each of the peptide and ligand may comprise 3 atoms coordinated to the copper ion, for a total of 6 atoms coordinated to the copper ion; or the peptide (or ligand) comprises two atoms coordinated to the copper ion and the ligand (or peptide) comprises 3 atoms coordinated to the copper ion, for a total of 5 atoms coordinated to the copper ion; or the peptide (or ligand) comprises two atoms coordinated to the copper ion and the ligand (or peptide) comprises 4 atoms coordinated to the copper ion, for a total of 6 atoms coordinated to the copper ion.

In some embodiments of any of the embodiments described herein, the peptide comprises at least 2 sulfur atoms (e.g., 2 or 3 sulfur atoms) coordinated to the copper ion. The sulfur atoms are optionally comprised by sulfur-containing amino acid residues, such as Met and/or Cys residues.

In some embodiments of any of the embodiments described herein, the peptide comprises a first residue and a second residue, which are coordinated to the copper ion, wherein the first residue is Met (M) or Cys (C), and the second residue is Met (M), Cys (C) or His (H). In some embodiments, the first and second residues are separated by 2 or 3 other amino acid residues (i.e., other than the first and second residues), each of which independently which may be any amino acid residue. For example, the first and second residues, and the residues between them, may form a MXXXM (SEQ ID NO: 23), MXXXC (SEQ ID NO: 24), MXXXH (SEQ ID NO: 25), CXXXM (SEQ ID NO: 26), CXXXC (SEQ ID NO: 27), CXXXH (SEQ ID NO: 28), HXXXM (SEQ ID NO: 29), HXXXC (SEQ ID NO: 30), MXXM (SEQ ID NO: 31), MXXC (SEQ ID NO: 32), MXXH (SEQ ID NO: 33), CXXM (SEQ ID NO: 34), CXXC (SEQ ID NO: 35), CXXH (SEQ ID NO: 36), HXXM (SEQ ID NO: 37) or HXXC (SEQ ID NO: 38) sequence (wherein X is any amino acid residue). In some embodiments, the first and second residues are separated by 2 other amino acid residues.

In some embodiments of any of the embodiments described herein, the first residue and second residue are each independently Met (M) or Cys (C). In some embodiments, the first and second residues are separated by 2 or 3 other amino acid residues (i.e., other than the first and second residues), each of which independently which may be any amino acid residue. For example, the first and second residues, and the residues between them, may form a MXXXM (SEQ ID NO: 23), MXXXC (SEQ ID NO: 24), CXXXM (SEQ ID NO: 26), CXXXC (SEQ ID NO: 27), MXXM (SEQ ID NO: 31), MXXC (SEQ ID NO: 32), CXXM (SEQ ID NO: 34) or CXXC (SEQ ID NO: 35) sequence (wherein X is any amino acid residue). In some embodiments, the first and second residues are separated by 3 amino acid residues.

The peptide is optionally terminated by the first and second residues (e.g., wherein the peptide is a tetrapeptide or pentapeptide), or alternatively, the peptide comprises additional amino acid residues attached to the first residue and/or second residue (e.g., wherein the peptide is longer than a tetrapeptide or pentapeptide).

Met2 (MYGMK (SEQ ID NO: 15)) is an exemplary peptide which comprises a MXXM (SEQ ID NO: 31) region.

Cys1 (KSMAACAM (SEQ ID NO: 16)) is an exemplary peptide which comprises a MXXC (SEQ ID NO: 32) region.

Cys2 (ASCGGCAM (SEQ ID NO: 17)) is an exemplary peptide which comprises a CXXC (SEQ ID NO: 35) region.

Cys3 (HTGCK (SEQ ID NO: 18)) is an exemplary peptide which comprises a HXXC (SEQ ID NO: 38) region.

In embodiments wherein the peptide comprises additional amino acid residues, the peptide may comprise additional Met, Cys or His residues, which may optionally be coordinated to copper. Such additional Met, Cys or His residues may optionally be separated from each other or from a first residue or second residue by 2 or 3 other amino acid residues, such that the peptide optionally comprises a plurality of regions having a MXXXM (SEQ ID NO: 23), MXXXC (SEQ ID NO: 24), MXXXH (SEQ ID NO: 25), CXXXM (SEQ ID NO: 26), CXXXC (SEQ ID NO: 27), CXXXH (SEQ ID NO: 28), HXXXH (SEQ ID NO: 39), HXXXM (SEQ ID NO: 29), HXXXC (SEQ ID NO: 30), MXXM (SEQ ID NO: 31), MXXC (SEQ ID NO: 32), MXXH (SEQ ID NO: 33), CXXM (SEQ ID NO: 34), CXXC (SEQ ID NO: 35), CXXH (SEQ ID NO: 36), HXXH (SEQ ID NO: 40), HXXM (SEQ ID NO: 37) and/or HXXC (SEQ ID NO: 38) sequence (e.g., as described hereinabove). Two of a plurality of such regions may share a Met, Cys or His residue; for example, forming a MXXMXXM (SEQ ID NO: 41), CXXMXXM (SEQ ID NO: 19), CXXHXXH (SEQ ID NO: 20) or MXXHXXH (SEQ ID NO: 21) sequence.

Met1 (MYGMKGMS (SEQ ID NO: 14)) is an exemplary peptide which comprises a MXXMXXM (SEQ ID NO: 41) sequence.

In some embodiments of any of the embodiments described herein, the first residue and second residue are each a Met residue, and the peptide optionally comprises at least one additional Met residue (e.g., three Met residues in all). Such Met residues may optionally form, for example, a MXXM (SEQ ID NO: 31), MXXXM (SEQ ID NO: 23) or MXXMXXM (SEQ ID NO: 41) sequence (wherein X is any amino acid residue) comprised by the peptide.

In some embodiments of any of the embodiments described herein, the peptide comprises at least one Cys residue, for example, 1 or 2 Cys residues, optionally in combination with at least one Met residue (e.g., 1 or 2 Met residues).

Without being bound by any particular theory, it is believed that Cys residues provide greater affinity to Cu(II) than do Met residues, thereby enhancing stability and/or yield of the complex.

Examples of peptides comprising a Cys residue include, without limitation, peptides comprising MXXXC (SEQ ID NO: 24), CXXXM (SEQ ID NO: 26), CXXXC (SEQ ID NO: 27), CXXXH (SEQ ID NO: 28), HXXXC (SEQ ID NO: 30), MXXC (SEQ ID NO: 32), CXXM (SEQ ID NO: 34), CXXC (SEQ ID NO: 35), CXXH (SEQ ID NO: 36), HXXC (SEQ ID NO: 38), CXXMXXM (SEQ ID NO: 19), and/or CXXHXXH (SEQ ID NO: 20) sequence (wherein X is any amino acid residue). Cys1 (SEQ ID NO: 16) is an exemplary peptide which comprises a Cys residue.

In some embodiments of any of the embodiments described herein, the peptide comprises at least one Ala, Arg, Asp, Glu, Gly, Lys, Ser, Thr and/or Tyr residue (e.g., in addition to Met, Cys and/or His residues, according to any of the respective embodiments described herein). In some such embodiments, the peptide comprises at least two Ala, Arg, Asp, Glu, Gly, Lys, Ser, Thr and/or Tyr residues, and optionally at least 3, at least 4, or at least 5 Ala, Arg, Asp, Glu, Gly, Lys, Ser, Thr and/or Tyr residues.

In some embodiments of any of the embodiments described herein, at least 50% of the amino acid residues of the peptide are Ala, Arg, Asp, Glu, Gly, Lys, Ser, Thr and/or Tyr residues. In some embodiments, at least 60% of the amino acid residues of the peptide are Ala, Arg, Asp, Glu, Gly, Lys, Ser, Thr and/or Tyr residues.

In some embodiments of any of the embodiments described herein, at least 60% of the amino acid residues of the peptide are Met, Cys, His, Ala, Arg, Asp, Glu, Gly, Lys, Ser, Thr and/or Tyr residues. In some embodiments, at least 70% of the amino acid residues of the peptide are Met, Cys, His, Ala, Arg, Asp, Glu, Gly, Lys, Ser, Thr and/or Tyr residues. In some embodiments, at least 80% of the amino acid residues of the peptide are Met, Cys, His, Ala, Arg, Asp, Glu, Gly, Lys, Ser, Thr and/or Tyr residues. In some embodiments, at least 90% of the amino acid residues of the peptide are Met, Cys, His, Ala, Arg, Asp, Glu, Gly, Lys, Ser, Thr and/or Tyr residues. In some embodiments, the peptide consists essentially of Met, Cys, His, Ala, Arg, Asp, Glu, Gly, Lys, Ser, Thr and/or Tyr residues.

In some embodiments of any of the respective embodiments described herein, amino acid residues represented by X in a MXXXM (SEQ ID NO: 23), MXXXC (SEQ ID NO: 24), MXXXH (SEQ ID NO: 25), CXXXM (SEQ ID NO: 26), CXXXC (SEQ ID NO: 27), CXXXH (SEQ ID NO: 28), HXXXH (SEQ ID NO: 39), HXXXM (SEQ ID NO: 29), HXXXC (SEQ ID NO: 30), MXXM (SEQ ID NO: 31), MXXC (SEQ ID NO: 32), MXXH (SEQ ID NO: 33), CXXM (SEQ ID NO: 34), CXXC (SEQ ID NO: 35), CXXH (SEQ ID NO: 36), HXXH (SEQ ID NO: 40), HXXM (SEQ ID NO: 37) or HXXC (SEQ ID NO: 38) sequence (according to any of the respective embodiments described herein) are Ala, Arg, Asp, Glu, Gly, Lys, Ser, Thr and/or Tyr residues. Such peptides may optionally be characterizing as comprising at least one peptide region having the formula $W^3$—$X^4$—$X^5$—$W^4$ (SEQ ID NO: 46), wherein $W^3$ and $W^4$ are each independently a His, Met or Cys residue (optionally wherein at least one is Met or Cys), and each of $X^4$ and $X^5$ is independently Ala, Arg, Asp, Glu, Gly, Lys, Ser, Thr or Tyr residue.

Preparation of Complex:

The complex according to any of the embodiments described herein may optionally be prepared by contacting the respective ligand (according to any of the embodiments described herein) with a Cu(II) ion and respective peptide (according to any of the embodiments described herein) in solution (e.g., aqueous solution). The aforementioned components may optionally be combined in any order, for example, adding the peptide to a mixture of ligand and copper ion, or adding copper ion to a mixture of ligand and peptide.

According to an aspect of some embodiments of the invention, there is provided a process of preparing the complex according to any of the embodiments described herein, the process comprising contacting the copper ion with the respective ligand (according to any of the embodiments described herein) and respective peptide (according to any of the embodiments described herein) in solution. In some such embodiments, a concentration of copper ion in the solution is greater than a concentration of said ligand, for example, at least 20% greater than (i.e., 120% of) the concentration of the ligand, and optionally at least 50% greater than (i.e., 150% of) the concentration of the ligand. In some exemplary embodiments, a concentration of copper ion in the solution is about twice the concentration of the ligand.

The copper ion is optionally in a form of a Cu(II) salt, which dissolves in the solution, for example, a water-soluble Cu(II) salt such as $CuCl_2$.

In some of any of the respective embodiments described herein, the solution in which the complex is formed is an aqueous solution. In some embodiments, a pH of the aqueous solution is at least 6.5, for example, from 6.5 to 8.5. In some embodiments, a pH of the aqueous solution is at least 7.0, for example, from 7.0 to 8.0. In exemplary embodiments, a pH of the aqueous solution is about 7.4.

The pH of the solution may optionally be controlled using a suitable buffer compound.

In some of any of the respective embodiments described herein, the buffer compound is not HEPES (4-(2-hydroxyethyl)-1-piperazineethanesulfonic acid). In some such embodiments, the buffer compound does not comprise a sulfonic acid/sulfonate group. Alternatively or additionally, the buffer compound is not Tris(tris(hydroxymethyl)aminomethane).

In some of any of the respective embodiments described herein, the buffer compound comprises a tertiary amine group and/or a phosphate ion.

Potassium phosphate (KPi) buffer is an exemplary buffer comprising a phosphate group, which may optionally have a pH such as described herein.

NEM (N-ethylmorpholine) is an exemplary buffer compound comprising a tertiary amine group, which may optionally have a pH such as described herein.

As exemplified herein, NEM buffer provided excellent results when preparing exemplary complexes.

Following preparation of a complex, according to any of the respective embodiments described herein, the complex is optionally separated (e.g., from free copper ions, free ligand and/or free peptide).

In some of any of the respective embodiments, separation is effected by contacting a solution comprising the complex with a gel filtration resin, for example, via elution from a column. Elution is optionally effected using water or a medium suitable for administration (e.g., when the complex is intended to be administered to a subject, according to any of the respective embodiments described herein), such as saline and/or phosphate buffer.

As exemplified herein, for a given column and complex, one or more fractions (optionally defined by volume of elution medium and/or by number of drops of elution medium) with well separated complex may be readily identified by a test run, in which different fractions are analyzed for content of complex and other components, such as free copper (which may be distinguished from the complex, for example, by EPR spectroscopy).

Uses and Methods:

In some embodiments of any of the embodiments described herein, the complex (according to any of the respective embodiments described herein) is for use as a medicament, and/or for use in the manufacture of a medicament. In some embodiments, the complex comprises a radioactive copper isotope (according to any of the respective embodiments described herein).

According to an aspect of some embodiments of the invention, there is provided a use of a complex (according to any of the respective embodiments described herein) in the manufacture of a medicament. In some embodiments, the complex comprises a radioactive copper isotope (according to any of the respective embodiments described herein), which may be used, for example, in a medicament for radiation therapy (according to any of the respective embodiments described herein).

In some embodiments of any of the embodiments described herein, the complex (according to any of the respective embodiments described herein) is for use in diagnostics, for example, in in vivo diagnostics. In some embodiments, the complex comprises a radioactive copper isotope (according to any of the respective embodiments described herein). In some embodiments, the diagnostics comprises of in vivo imaging of a body or a portion thereof (e.g., according to any of the respective embodiments described herein).

In some embodiments of any of the embodiments described herein, the complex (according to any of the respective embodiments described herein) is for use as an imaging agent, and/or for use in the manufacture of an imaging agent. In some embodiments, the complex comprises a radioactive copper isotope (according to any of the respective embodiments described herein).

According to an aspect of some embodiments of the invention, there is provided a use of a complex (according to any of the respective embodiments described herein) in the manufacture of an imaging agent. In some embodiments, the complex comprises a radioactive copper isotope (according to any of the respective embodiments described herein).

In some embodiments of any of the embodiments described herein, the complex (according to any of the respective embodiments described herein) is for use in a method of in vivo imaging of a body or a portion thereof, in a subject in need thereof. In some embodiments, the complex comprises a radioactive copper isotope (according to any of the respective embodiments described herein).

According to an aspect of some embodiments of the invention, there is provided a method of imaging of a body or a portion thereof, in a subject in need thereof, the method comprising administering to the subject an imaging agent comprising a complex (according to any of the respective embodiments described herein), and imaging the body or a portion thereof by a suitable imaging technique.

In some embodiments of any of the embodiments described herein relating to a method or use comprising in vivo imaging, the method or use comprises administering a complex comprising a radioactive copper isotope (according to any of the respective embodiments described herein) to a subject, and employing an imaging technique to thereby determine a level and/or distribution of radioactive copper in the subject's body or a portion thereof.

An imaging technique employed by some embodiments of the invention may be any suitable imaging technique known in the art based on detection of a radioactive isotope. Examples of suitable imaging techniques include positron emission tomography (PET) (e.g., wherein the radioactive isotope emits positrons) and single photon emission computed tomography (SPECT) (e.g., wherein the radioactive isotope emits γ radiation).

It is expected that during the life of a patent maturing from this application many relevant imaging techniques and/or variations of imaging techniques (e.g., new PET and/or SPECT techniques) will be developed and the scope of the terms "imaging" and "imaging technique" is intended to include all such new technologies a priori.

Examples of copper isotopes suitable for use in SPECT include, without limitation, $^{61}$Cu, $^{64}$Cu and $^{67}$Cu, which emit (in part) γ radiation.

Examples of copper isotopes suitable for use in positron emission tomography include, without limitation, $^{60}$Cu, $^{61}$Cu, $^{62}$Cu and $^{64}$Cu, which emit positrons ($\beta^+$ decay).

$^{62}$Cu is an example of a copper isotope which emits positrons almost exclusively (~98% of $^{62}$Cu emission is $\beta^+$ decay), which may be advantageous in positron emission tomography.

$^{61}$Cu and $^{64}$Cu are examples of copper isotopes with a relatively long half-life (~3.3 hours for $^{61}$Cu, and ~12.7 hours for $^{64}$Cu), which may be advantageous for many applications.

$^{61}$Cu and $^{64}$Cu are non-limiting examples of copper isotopes, which may be prepared at relatively low cost.

In some embodiments of any of the embodiments described herein relating to in vivo imaging, the imaging is for monitoring or determining a level of hypoxic tissue (e.g., a volume of hypoxic tissue and/or a degree of hypoxia in the tissue) and/or a distribution of hypoxic tissue (e.g., location(s) in the body) within the body of the subject. In some embodiments, the imaging is for determining if the subject has a disease or disorder associated with hypoxic tissue, for example, wherein the hypoxic tissue is associated with a tumor (benign or malignant) and/or with a blood supply deficiency.

Cancer is a non-limiting example of a disease or disorder associated with a tumor.

Examples of a disease or disorder associated with a blood supply deficiency include, without limitation, ischemic heart disease (e.g., stable angina, unstable angina, myocardial infarction), atherosclerosis, heart failure, irregular heartbeat, ischemic colitis, mesenteric ischemia, stroke, acute limb ischemia, cyanosis and gangrene.

In some embodiments of any of the embodiments described herein, imaging utilizing the complex (in any of the respective embodiments according to any of the aspects described herein) is for determining aggressiveness of a tumor, for example, wherein tumor aggressiveness is associated with increased copper concentration (e.g., a tumor characterized by a moderately high copper concentration is determined to be less aggressive than a tumor with an even higher copper concentration, or vice versa).

Without being bound by any particular theory, it is believed that tumor aggressiveness is associated with a degree of hypoxia in the tumor, and can be determined according to any technique described herein suitable for measuring hypoxia.

In some embodiments of any of the embodiments described herein, imaging utilizing the complex (in any of the respective embodiments according to any of the aspects described herein) is for determining if a tissue is sensitive to cisplatin. For example, a tumor characterized by a relatively low copper concentration (compared to other tumors) is optionally determined to be relatively resistant to cisplatin; and/or a tumor characterized by a relatively high copper concentration (compared to other tumors) is optionally determined to be relatively susceptible to cisplatin.

Without being bound by any particular theory, it is believed that cisplatin resistance is associated with reduced Ctr1 expression, which results in low cellular uptake of copper.

According to an aspect of some embodiments of the invention, there is provided a method of detecting uptake of copper by cells, the method comprising contacting the cells with a complex (according to any of the respective embodiments described herein) and determining a level of copper in the cells. The method may optionally be effected in vitro (e.g., as part of research of cell behavior) and/or in vivo, e.g., by administering the complex to a subject in need thereof and/or by employing an imaging technique (according to any of the respective embodiments described herein) to determine a level of copper in cells.

In some embodiments, determining a level of copper in the cells is for determining if the cells are sensitive to cisplatin (e.g., as described herein).

Determining an amount of copper in cells (according to any of the respective embodiments according to any of the respective aspects described herein) may optionally be effected contacting the cells with a complex comprising radioactive copper (according to any of the respective embodiments described herein) and determining a level of radioactivity of emitted from the cells, and/or with a complex comprising a fluorescent ligand (according to any of the respective embodiments described herein) whose fluorescence is sensitive to the presence of copper and determining a level of fluorescence emitted from the cells (e.g., during open surgery or in tissue near a skin surface).

According to an aspect of some embodiments of the invention, there is provided a method of determining a redox state of cells, the method comprising contacting the cells with the complex (according to any of the respective embodiments described herein), and determining a level of at least one oxidation state of copper ion in the cells. The method may optionally be effected in vitro (e.g., as part of research of cell behavior) and/or in vivo, e.g., by administering the complex to a subject in need thereof and/or by employing an imaging technique (according to any of the respective embodiments described herein) to determine a redox state of cells in vivo.

Herein, the phrase "redox state of cells" refers to an overall degree to which molecules in a cell are oxidized or reduced. Whether a redox state of cells is relatively oxidized or reduced (e.g., in comparison with "normal" or "average" cells) has been associated with many differences in cell behavior and/or function, including regulation of many signaling pathways.

In some embodiments, determining a redox state of cells comprises distinguishing between hypoxic cells (e.g., hypoxic tissue), characterized by a relatively reduced redox state, and other cells (e.g., characterized by a common baseline redox state). Optionally, a plurality of degrees of hypoxia in cells are distinguished from one another (and from other cells), for example, by distinguishing between mildly hypoxic and severely hypoxic states. In some embodiments, distinguishing between hypoxic cells (e.g., hypoxic tissue) and other cells is effected in vivo for monitoring or determining a level and/or distribution of hypoxic tissue within the body of a subject.

In some embodiments of any of the embodiments described herein relating to determining a redox state of cells and/or a level and/or distribution of hypoxic tissue, the ligand exhibits fluorescence sensitive to an oxidation state of a copper ion coordinated thereto (e.g., according to any of the respective embodiments described herein). In some embodiments, the ligand is a cyanine, according to any of the respective embodiments described herein.

It is to be appreciated that any method or use described herein utilizing fluorescence may optionally utilize a complex (e.g., a complex comprising a fluorescent ligand) without radioactive copper.

In some embodiments, an increase in fluorescence is associated with Cu(I) (as opposed to Cu(II)), which may be indicative of hypoxia and/or reduced state of a cell.

As exemplified in the Examples section herein, a cyanine ligand (CyNA-427) exhibited increased fluorescence in the presence of Cu(I), in comparison to Cu(II).

Alternatively or additionally, determining a redox state of cells and/or a level and/or distribution of hypoxic tissue (according to any of the respective embodiments described herein) may optionally comprise determining an amount of copper in cells, wherein an increased level of copper is indicative of a relatively high proportion of Cu(I) in the cells, which may be indicative of hypoxia and/or reduced state of a cell.

Without being bound by any particular theory, it is believed that Cu(I) is removed from cells more slowly than is Cu(II), such that when a relatively high proportion of the copper in a cell is (Cu(I)), a relatively high amount of copper may accumulate in a cell.

In some embodiments of any of the embodiments described herein, the complex comprises radioactive copper (according to any of the respective embodiments described herein) and is for use in radiation therapy.

Herein and in the art, the term "radiation therapy" refers to the use of ionizing radiation delivered to a tissue in order to obtain a therapeutic effect, for example, to kill harmful cells (e.g., benign or malignant tumor cells).

In some embodiments of any of the embodiments described herein, the radiation therapy comprises killing tumor cells, for example, tumor cells which exhibit enhanced uptake of copper (e.g., upon administration of a complex according to any of the respective embodiments described herein).

Examples of copper isotopes suitable for use in radiation therapy include, without limitation, $^{64}$Cu and $^{67}$Cu.

Without being bound by any particular theory, it is believed that ($\beta^-$ decay, which is emitted by $^{64}$Cu (in part) and by $^{67}$Cu, is advantageous in radiation therapy by causing considerable cellular damage in the vicinity of the decaying isotope, in comparison with other radioactive decay mechanisms (e.g., ($\beta^+$ decay).

Compositions:

In any of the embodiments described herein relating to in vivo use, the complex (according to any of the respective embodiments described herein) may optionally be administered to an organism per se, or in a form of a pharmaceutical composition which may optionally further comprise suitable carriers or excipients.

As used herein a "pharmaceutical composition" refers to a preparation of one or more of the active ingredients described herein (including diagnostic and/or imaging agents) with other chemical components such as physiologically suitable carriers and excipients. The purpose of a pharmaceutical composition is to facilitate administration of a compound to an organism (e.g., for a therapeutic and/or diagnostic application).

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of active agents (according to any of the aspects of embodiments of the invention described herein) may be found in "Remington's Pharmaceutical Sciences," Mack Publishing Co., Easton, PA, latest edition, which is incorporated herein by reference.

Suitable routes of administration may, for example, local or systemic routes, and include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Local administration may optionally be effected, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations, which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinylpyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethylcellulose, sorbitol or dextran. Optionally, the suspension may also contain suitable stabilizers or agents, which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

In some of any of the embodiments described herein, the carrier is or comprises a cyclodextrin.

Pharmaceutical compositions suitable for use in context of some embodiments of the invention include compositions wherein the active ingredients are contained in an amount effective to achieve the intended purpose (e.g., a therapeutic and/or diagnostic purpose). More specifically, an effective amount means an amount of a complex described herein sufficient to effect a method and/or imaging technique described herein, or (e.g., in radiation therapy) to prevent, alleviate or ameliorate symptoms of a treated disorder (e.g., a benign or malignant tumor) or prolong the survival of the subject being treated.

Determination of an effective amount is well within the capability of those skilled in the art (e.g., based on the expected background signal of a given imaging technique, which will be known to one skilled in the art pertaining to the imaging technique), especially in light of the detailed disclosure provided herein.

For any preparation used in the methods of the invention, the effective amount or dose can be estimated initially from in vitro and cell culture assays. For example, a dose can be formulated in animal models to achieve a desired concentration or titer. Such information can be used to more accurately determine useful doses in humans.

Toxicity and effective amounts of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cells (e.g., tumor cells) levels of the active ingredient that are sufficient (e.g., in radiation therapy) to induce or suppress the biological effect (minimal effective concentration, MEC), or to distinguish the cells (e.g., in hypoxic tissue) from surrounding cells. The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated (according to any of the respective embodiments described herein), dosing can be of a single or a plurality of administrations, with course of treatment lasting from several days to several weeks or until cure is effected or diminution of the disease state is achieved.

The amount of a composition to be administered will, of course, be dependent on the subject being treated or imaged, the type of imaging technique, the severity of the affliction, the manner of administration, the judgment of the prescribing physician, etc.

Compositions of some embodiments of the invention (according to any of the aspects described herein) may, if desired, be presented in a pack or dispenser device, such as an FDA approved kit, which may contain one or more unit dosage forms containing complex described herein. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceutical and diagnostic agents, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated use or method (according to any of the respective embodiments described herein).

Additional Definitions and Information:

As used herein throughout, the term "alkyl" refers to any saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or non-substituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and/or amino, as these terms are defined herein.

Herein, the term "alkenyl" describes an unsaturated aliphatic hydrocarbon comprise at least one carbon-carbon double bond, including straight chain and branched chain groups. Preferably, the alkenyl group has 2 to 20 carbon atoms. More preferably, the alkenyl is a medium size alkenyl having 2 to 10 carbon atoms. Most preferably, unless otherwise indicated, the alkenyl is a lower alkenyl having 2 to 4 carbon atoms. The alkenyl group may be substituted or non-substituted. Substituted alkenyl may have one or more substituents, whereby each substituent group can independently be, for example, cycloalkyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and/or amino.

Herein, the term "alkynyl" describes an unsaturated aliphatic hydrocarbon comprise at least one carbon-carbon triple bond, including straight chain and branched chain groups. Preferably, the alkynyl group has 2 to 20 carbon atoms. More preferably, the alkynyl is a medium size alkynyl having 2 to 10 carbon atoms. Most preferably, unless otherwise indicated, the alkynyl is a lower alkynyl having 2 to 4 carbon atoms. The alkynyl group may be substituted or non-substituted. Substituted alkynyl may have one or more substituents, whereby each substituent group can independently be, for example, cycloalkyl, alkenyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and/or amino.

A "cycloalkyl" group refers to a saturated on unsaturated all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and/or amino, as these terms are defined herein. When a cycloalkyl group is unsaturated, it may comprise at least one carbon-carbon double bond and/or at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and/or amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and/or amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or non-substituted. When substituted, the substituted group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and/or amino, as these terms are defined herein. Representative examples are piperidine, piperazine, tetrahydrofuran, tetrahydropyran, morpholine and the like.

Herein, the terms "amine" and "amino" each refer to either a —NR'R" group or a —N⁺R'R"R'" group, wherein R', R" and R'" are each independently hydrogen or (substituted or non-substituted) alkyl, alkenyl, alkynyl, cycloalkyl, aryl, heteroalicyclic (bound to the nitrogen via a ring carbon) or heteroaryl (bound to the nitrogen via a ring carbon), as these groups are defined herein. Optionally, R' and R" (and R'", if present) are hydrogen or alkyl comprising 1 to 4 carbon atoms. Optionally, R' and R" (and R'", if present) are hydrogen. When substituted, the carbon atom of an R', R" or R'" hydrocarbon moiety which is bound to the nitrogen atom of the amine is preferably not substituted by oxo, such that R', R" and R'" are not (for example) carbonyl, C-carboxy or amide, as these groups are defined herein, unless indicated otherwise.

An "azide" group refers to a —N=N⁺=N⁻ group.

An "alkoxy" group refers to both an —O-alkyl and an —O-cycloalkyl group, as defined herein.

An "aryloxy" group refers to both an —O-aryl and an —O-heteroaryl group, as defined herein.

A "hydroxy" group refers to a —OH group.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" or "acyl" group refers to a —C(=O)—R' group, where R' is defined as hereinabove.

A "thiocarbonyl" group refers to a —C(=S)—R' group, where R' is as defined herein. A "carboxy" refers to both "C-carboxy" and O-carboxy".

A "C-carboxy" group refers to a —C(=O)—O—R' groups, where R' is as defined herein.

An "O-carboxy" group refers to an R'C(=O)—O— group, where R' is as defined herein.

A "carboxylic acid" refers to a —C(=O)OH group, including the deprotonated ionic form and salts thereof.

An "oxo" group refers to a =O group.

A "thiocarboxy" or "thiocarboxylate" group refers to both —C(=S)—O—R' and —O—C(=S)R' groups.

A "halo" group refers to fluorine, chlorine, bromine or iodine.

A "sulfinyl" group refers to an —S(=O)—R' group, where R' is as defined herein.

A "sulfonyl" group refers to an —S(=O)₂—R' group, where R' is as defined herein.

A "sulfonate" group refers to an —S(=O)₂—O—R' group, where R' is as defined herein.

A "sulfate" group refers to an —O—S(=O)₂—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)₂—NR'R" group, with each of R' and R" as defined herein.

An "N-sulfonamido" group refers to an R'S(=O)₂—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses O-thiocarbamyl and N-thiocarbamyl groups.

A "C-amido" group refers to a —C(=O)—NR'R" group, where each of R' and R" is as defined herein.

An "N-amido" group refers to an R'C(=O)—NR"— group, where each of R' and R" is as defined herein.

A "urea" group refers to an —N(R')—C(=O)—NR"R'" group, where each of R', R" and R'" is as defined herein.

A "thiourea" group refers to a —N(R')—C(=S)—NR"R'" group, where each of R', R" and R'" is as defined herein.

A "nitro" group refers to an —NO₂ group.

A "cyano" group refers to a —C≡N group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

The term "phosphinyl" describes a —PR'R" group, with each of R' and R" as defined hereinabove.

The term "hydrazine" describes a —NR'—NR"R'" group, with R', R", and R'" as defined herein.

As used herein, the term "hydrazide" describes a —C(=O)—NR'—NR"R'" group, where R', R" and R' are as defined herein.

As used herein, the term "thiohydrazide" describes a —C(=S)—NR'—NR"R'" group, where R', R" and R'" are as defined herein.

A "guanidinyl" group refers to an —RaNC(=NRd)-NRbRc group, where each of Ra, Rb, Rc and Rd can be as defined herein for R' and R".

A "guanyl" or "guanine" group refers to an RaRbNC(=NRd)— group, where Ra, Rb and Rd are as defined herein.

Herein, the term "peptide" refers to a polymer comprising at least 2 amino acid residues (optionally at least 4 amino acid residues) linked by peptide bonds or analogs thereof (as described herein below), and optionally only by peptide bonds per se. In some embodiments, the peptide comprises at least 10 amino acid residues or analogs thereof, and may also be referred to as a "polypeptide". The term "peptide" encompasses native peptides (e.g., degradation products, synthetically synthesized peptides and/or recombinant peptides), including, without limitation, native proteins, fragments of native proteins and homologs of native proteins and/or fragments thereof; as well as peptidomimetics (typically, synthetically synthesized peptides) and peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein below.

Peptide bonds (—CO—NH—) within the peptide may be substituted, for example, by N-methylated amide bonds (—N(CH$_3$)—CO—), ester bonds (—C(=O)—O—), ketomethylene bonds (—CO—CH$_2$—), sulfinylmethylene bonds (—S(=O)—CH$_2$—), α-aza bonds (—NH—N(R)—CO—), wherein R is any alkyl (e.g., methyl), amine bonds (—CH$_2$—NH—), sulfide bonds (—CH$_2$—S—), ethylene bonds (—CH$_2$—CH$_2$—), hydroxyethylene bonds (—CH(OH)—CH$_2$—), thioamide bonds (—CS—NH—), olefinic double bonds (—CH=CH—), fluorinated olefinic double bonds (—CF=CH—), retro amide bonds (—NH—CO—), peptide derivatives (—N(R)—CH$_2$—CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |

TABLE 2-continued

| Non-conventional amino acid | Code | Non-conventional amino acid | Code |
|---|---|---|---|
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The peptides of some embodiments of the invention are preferably utilized in a linear form, although it will be appreciated that in cases where cyclization does not severely interfere with peptide characteristics, cyclic forms of the peptide can also be utilized.

The peptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptides of some embodiments of the invention (e.g., a therapeutically active agent and/or a protease inhibitor described herein) involves solid phase peptide synthesis.

Large scale peptide synthesis is described by Andersson et al. [*Biopolymers* 2000; 55:227-250].

Herein, a "homolog" of a given polypeptide refers to a polypeptide that exhibits at least 80% homology, preferably at least 90% homology, and more preferably at least 95% homology, and more preferably at least 98% homology to the given polypeptide. In some embodiments, a homolog of a given polypeptide further shares a therapeutic activity with the given polypeptide. The percentage of homology refers to the percentage of amino acid residues in a first polypeptide sequence, which match a corresponding residue of a second polypeptide sequence to which the first polypeptide is being compared. Generally, the polypeptides are aligned to give maximum homology. A variety of strategies are known in the art for performing comparisons of amino acid or nucleotide sequences in order to assess degrees of identity, including, for example, manual alignment, computer assisted sequence alignment and combinations thereof. A number of algorithms (which are generally computer implemented) for performing sequence alignment are widely available, or can be produced by one of skill in the art. Representative algorithms include, e.g., the local homology algorithm of Smith and Waterman (Adv. Appl. Math., 1981, 2:482); the homology alignment algorithm of Needleman and Wunsch (J. Mol. Biol., 1970, 48: 443); the search for similarity method of Pearson and Lipman (Proc. Natl. Acad. Sci. (USA), 1988, 85: 2444); and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.). Readily available computer programs incorporating such algorithms include, for example, BLASTN, BLASTP, Gapped BLAST, PILEUP, CLUSTALW etc. When utilizing BLAST and Gapped BLAST programs, default parameters of the respective programs may be used. Alternatively, the practitioner may use non-default parameters depending on his or her experimental and/or other requirements (see for example, the Web site having URL www(dot)ncbi(dot)nlm(dot)nih(dot)gov).

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, preferably human beings at any age.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Materials:
Acetyl chloride was obtained from Sigma-Aldrich.
(O-benzotriazol-1-yl)-N,N,N',N'-tetramethyluronium (HBTU) salt was obtained from D-Chem, Ltd.
Bromotrimethylsilane (TMSBr) was obtained from Alfa Aesar.
$^{64}CuCl_2$ was obtained from Akom S.p.A. Italy.
Diisopropylethylamine (DIPEA) was obtained from Bio-Lab (Israel).
3-(Dimethylamino)propylamine was obtained from Sigma-Aldrich.
Dimethylformamide (DMF) was obtained from Bio-Lab.
Dimethylsulfoxide (DMSO) was obtained from Bio-Lab.
Dithiothreitol (DTT) was obtained from Sigma.
Ethane dithiol (EDT) was obtained from Alfa Aesar.
Imino-diacetic acid (IDA) was obtained from Sigma-Aldrich.
IR-780 was obtained from Sigma-Aldrich.
MTS SL (S-(1-oxyl-2,2,5,5-tetramethyl-2,5-dihydro-1H-pyrrol-3-yl)methyl methanesulfonothioate) was obtained from TRC (Toronto Research Chemicals).
NEM (N-ethylmorpholine) was obtained from Sigma-Aldrich.
Piperidine was obtained from Bio-Lab.
Tetrakis(acetonitrile)copper(I) hexafluorophosphate was obtained from Sigma-Aldrich.
Thioanisole was obtained from Alfa Aesar.
Trifluoroacetic acid (TFA) was obtained from Bio-Lab.
Triisopropylsilane (TIS) was obtained from Alfa Aesar.
Human Ctr1 (hCtr1) was obtained by expression and purification of a protein (SEQ ID NO: 43), using a pYTB12-hCTR1 plasmid, in which the full length hCTR1 sequence was cloned into the pYTB12 plasmid. This construct encodes for a fusion protein composed of hCTR1, intein, and a chitin-binding domain. The plasmid was transformed into the *Escherichia coli* strain BL21 (DE3).

*E. coli* cultured cells (in 200 ml LB medium+0.2% glucose) reached 0.6-0.8 OD at 600 nm. The culture was then induced with 10 mM of IPTG (isopropyl β-D-1-thiogalactopyranoside) for 3.5 hours at 37° C. The cells were then centrifuged and the pellet was frozen and thawed in liquid nitrogen and cold water three times (10 minutes for each step). Afterwards, the pellet was re-suspended in chitin buffer containing 20 μM of PMSF (phenylmethylsulfonyl fluoride). A 20 ml volume was sonicated with 6 pulses of 1 minute each and a 1 minute pause between each pulse. The pulse amplitude was 65%. The sonicated lysate was centrifuged and the Intein-hCTR1 fusion protein was observed over a SDS-Page gel (Glycine 6%) in the pellet. The amino acid sequence of the obtained Ctr1 (SEQ ID NO: 43) corresponds to the native sequence (SEQ ID NO: 42) with 3 additional amino acids (Gly-Thr-Thr) at the N-terminus.

Peptide Synthesis:
Peptides were synthesized on a Rink amide resin (Applied Biosystems). Couplings of standard Fmoc (9-fluorenyl-methoxy-carbonyl)-protected amino acids were achieved with (O-benzotriazol-1-yl)-N,N,N',N'-tetramethyluronium (HBTU) in N,N-dimethylformamide in combination with N,N-diisopropylethylamine for a one hour cycle. Fmoc deprotection was achieved with piperidine. Side-chain deprotection and peptide cleavage from the resin were achieved by treating the resin-bound peptides with a 5 ml cocktail of 90% trifluoroacetic acid, 5% ethane dithiol, 2.5% triisopropylsilane and 2.5% thioanisole, for 2.5-3.5 hours under N2. An additional 65 µl of bromotrimethylsilane was added during the final 30 minutes to minimize methionine oxidation. The peptides were washed four times with cold diethyl ether, vortexed and then centrifuged for 5 minutes at 3500 or 4000 rotations per minute. After evaporation of TFA under N2, 10 mM dithiothreitol (DTT) was added to the peptide and it was then dissolved in HPLC (high-performance liquid chromatography) water. The peptide was then purified by preparative reverse-phase HPLC, using a Vydac® C18 column (5 cm). The mass of the peptides was confirmed by either MALDI-TOF or electron spray ionization (ESI) mass spectrometry. Peptide samples were typically mixed with two volumes of premade dihydrobenzoic acid (DHB) matrix solution, deposited onto stainless steel target surfaces, and allowed to dry at room temperature.

For site-directed spin labeling (SDSL) of peptides, 1 mg of lyophilized peptide was dissolved in 0.8 ml phosphate buffer (25 mM KPi) (pH=7.3-7.4). 0.25 mg of MTSSL (S-(1-oxyl-2,2,5,5-tetramethyl-2,5-dihydro-1H-pyrrol-3-yl) methyl methanesulfonothioate) dissolved in 15 µl dimethylsulfoxide was added to the solution (at a 50-fold molar excess of MTSSL). The spin-label and peptide solution were then vortexed overnight at 4° C. The free spin-label was removed by semi-preparative HPLC, using a Vydac® C18 column (5 cm). The mass of the spin-labeled peptide was confirmed by mass spectrometry.

Buffers:

KPi buffer was prepared by dissolving $KH_2PO_4$ and $K_2HPO_4$ in deuterium-depleted water (e.g., 13.6 grams $KH_2PO_4$ and 17.2 grams $K_2HPO_4$ in 4 liters of deuterium-depleted water to obtain 25 mM KPi buffer), and titrated with NaOH until a pH of 7.35 was obtained. For low temperature EPR measurements, 10% glycerol was added to the solution to create a glass solution, and was then freeze-quenched to liquid N2 temperature. No indication of a temperature-dependent change to pH was detected in the presence of potassium.

HEPES buffer (25 mM) was prepared by dissolving 5.95 grams HEPES in 1 liter deuterium-depleted water, and titrated with NaOH until a pH of 7.35 was obtained. For low temperature EPR measurements, 10% glycerol was added to the solution.

Thin Layer Chromatography (TLC):

Purified complexes were observed by thin layer chromatography analysis, using 60 RP-18 silica gel, and a solution of 90% methanol, 10% $H_2O$ and 3 drops of HCl.

Mass Spectrometry:

MALDI-TOF mass spectrometry was performed using an Autoflex™ III MALDI-TOF & TOF/TOF mass spectrometry system (Bruker) equipped with a 337 nm nitrogen laser.

Electron spray ionization (ESI) mass spectrometry was performed using a Micromass® Waters® Q-ToF (quadruple time of flight) low-resolution spectrometer.

UV-Visible-IR Spectrometry:

UV-Visible-IR absorption spectra were obtained using a Cary® Bio 100 spectrophotometer, or using a Chirascan™ spectrometer (Applied Photophysics), at room temperature with a 1 mm optical path-length cell. Acetone was used as a reference. Typically, peptides were measured at a concentration of 0.3 mg/ml. Difference absorption spectra were obtained for peptides titrated with Cu(I) from 200 to 600 nm with a step size and a bandwidth of 0.5 nm.

Fluorescence emission spectra were obtained using a Cary® fluorescence spectrophotometer.

Electron Paramagnetic Resonance (EPR) Spectroscopy:

Continuous wave electron magnetic resonance (CW-EPR) spectra were recorded using an Elexsys™ E500 spectrometer (Bruker) operating at 9.0-9.5 GHz, equipped with a super-high-sensitivity CW resonator. The spectra were recorded at room temperature (RT; 295±2 K) or at low temperature (130±5 K) at a microwave power of 20.0 mW, modulation amplitude of 1.0 G, time constant of 60 or 80 milliseconds, and receiver gain of 60.0 dB. The samples were measured in 0.8 mm or 1.0 mm capillary quartz tubes (VitroCom) at RT. Solutions that were measured at low temperature were mixed with 20% glycerol, and measured in a 3.0 mm or 4.0 mm Wilmad® quartz tube.

Simulation of CW-EPR spectra was performed using MATLAB, with the EasySpin™ toolbox, according to procedures described by Stoll & Schweiger [*J Magn Reson* 2006, 178:42-55]. In fitting a spectrum to a simulation, emphasis is placed on small peaks of in the region of under 3000G.

For measuring Cu(II) reduction by EPR spectroscopy, 20 µl of aqueous $CuCl_2$ solution (2 mM) was added to 20 µl of a solution of a tested peptide (1 mM). At time zero, 20 µl of ascorbic acid solution (2 mM) was added, and the solution was mixed under anaerobic conditions. Cu(II) EPR signal intensity (at the maximum EPR signal intensity ($g_\perp$ position)) was measured as a function of time.

Electron Spin Echo Envelope Modulation (ESEEM) Experiments:

2P-ESEEM experiments and 3P-ESEEM experiments were carried out at 10±0.1 K on a Q-band Elexsys E580 spectrometer (equipped with a 2-mm probe head). The parameters for echo detected two-pulse experiment were $\tau$=200 ns with $t(\pi/2)$=20 ns, dt=10 ns, and repetition time of 5 milliseconds.

The three-pulse ESEEM experiments were performed as follows: A $\pi/2-\tau-\pi/2-T+dt-\pi/2-\tau$–echo sequence was used with a four-step phase-cycle. The $\pi/2$ pulse length was 20 ns, and the $\tau$ value was set to 220 ns to amplify $^{14}N$ modulations at $g_\perp$ position. The initial T was 100 ns and dt was 10 ns. The data were processed by subtracting the baseline using a polynomial fit. The resulting time domain was convoluted with Hamming window function and the spectrum obtained by cross-term averaging Fourier transform, according to procedures such as described in Ruthstein et al. [*Biophys J* 2010, 99:2497-2506], Jiang et al. [*J Am Chem Soc* 1990, 112:9035-9044], Burns et al. [*Biochemistry* 2002, 41:3991-4001], and/or Yeagle et al. *Philos Trans R Soc Lond B Biol Sci* 2008, 363:1157-1166].

ESEEM measurements were performed with 1 mM peptide dissolved in 100 mM KPi buffer.

Constant-Time Four-Pulse Double Electron Electron Resonance (DEER) Experiments:

The DEER experiment $(\pi/2(vobs)-\tau_1-\pi(\sigma_{obs})-t'-\pi(\nu_{pump})-(\tau_1+\tau_2-t')-\pi(\nu_{obs})-\tau_2$–echo) was carried out at a temperature of 80±1.0 K on a Q-band Elexsys E580 spectrometer (equipped with a 2-mm probe head). A two-step phase cycle was employed on the first pulse. The echo was measured as a function of t', whereas $\tau_2$ was kept constant to eliminate relaxation effects. The observer pulse was set at 60 MHz higher than the pump pulse. The observer $\pi/2$ and $\pi$ pulses had a length of 40 ns, the $\pi$ pump pulse had a length of 40 ns as well, and the dwell time was 20 ns. The observer frequency was 33.77 GHz. The power of the 40-ns it pulse was 20.0 mW. $\tau_1$ was set to 200 ns and $\tau_2$ to 1200 ns. Each set of DEER data was collected for 24 hours. The spin concentration was between 0.1 and 0.2 mM. The samples were measured in 1.6-mm capillary quartz tubes (Wilmand).

The data were analyzed using the DeerAnalysis 2015 program, with Tikhonov regularization, according to procedures described by Jeschke [*Chem Phys Chem* 2002, 3:927-932]. The regularization parameter in the L curve was optimized by examining the fit of the time domain signal.

Nuclear Magnetic Resonance (NMR) Spectroscopy:

NMR experiments were performed on an Avance™ III 700 spectrometer (Bruker) equipped with a cryoprobe (700.5 and 176.1 MHz for $^1$H-NMR and $^{13}$C-NMR, respectively), in D20 solutions at a temperature of 300 K. The concentration of the peptide was 7 mM.

Cyna-427 Preparation:

A copper-chelating fluorescent dye was prepared according to the procedure depicted in Scheme 1:

$^1$H-NMR (600 MHz, Acetone): 7.731 (d, J=14.5 HZ, 2H), 7.609 (d, J=7.6 HZ, 2H), 7.441 (m, 4H), 7.299 (m, 2H), 6.462 (d, J=14.5 HZ, 2H), 4.295 (t, J=8.54 HZ, 4H), 3.847 (t, J=8.5 HZ, 2H), 3.198 (t, J=8.5 HZ, 2H), 2.91 (m, 2H), 2.768 (s, 6H), 2.627 (m, 2H), 2.335 (m, 2H), 1.972 (s, 3H), 1.928 (m, 4H), 1.792 (s, 6H), 1.681 (s, 6H), 1.066 (t, J=8.54 HZ, 6H), 0.881 (m, 2H). (chloroform s, 8.044).

$^{13}$C-NMR (150 MHz, Acetone): 174.149, 144.039, 142.966, 142.802, 130.071, 129.321, 126.708, 123.946, 112.805, 103.380, 55.163, 50.285, 48.776, 46.547, 42.732, 29.331, 29.269, 26.215, 25.541, 22.168, 22.069, 21.702, 12.212.

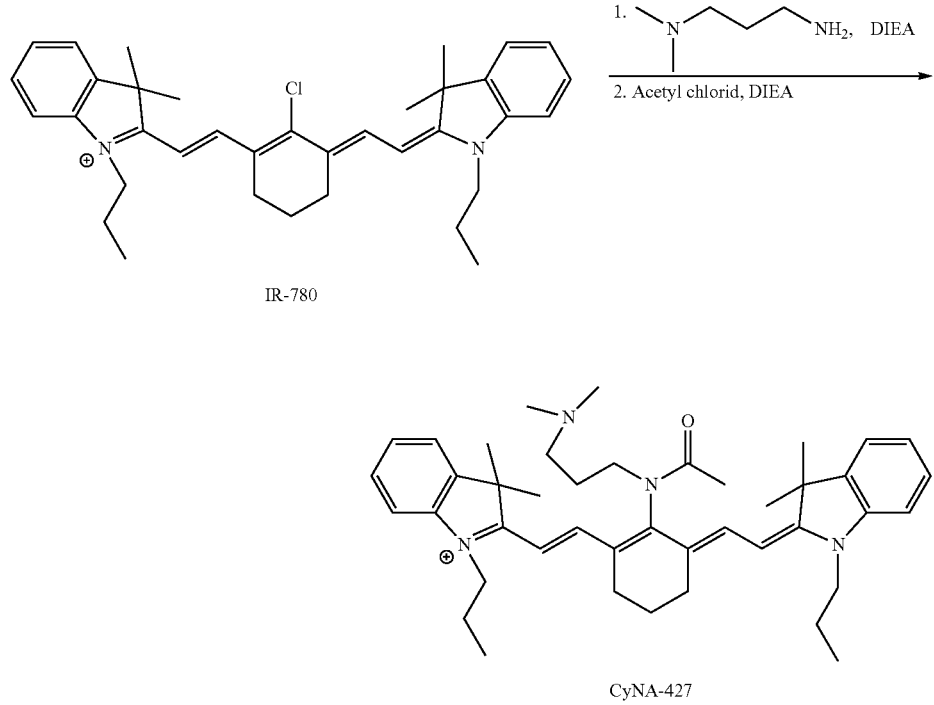

Scheme 1

IR-780

CyNA-427

100 mg (1 equivalent) of IR-780 and 0.075 ml (4 equivalents) of 3-(dimethylamino)propylamine were dissolved in dry acetonitrile under a N2 atmosphere, and 0.052 ml (2 equivalents) of N,N-diisopropylethylamine (DIEA) was added. The reaction mixture was heated at 80° C. for 60 minutes. The resulting blue-colored crude mixture (CyN, i.e., lacking the acetyl group of CyNA-427) was concentrated under vacuum.

The obtained CyN crude mixture was dissolved in dry dichloromethane (DCM) under a N2 atmosphere, and treated with excess DIEA (0.652 ml, 25 equivalents) and acetyl chloride (0.106 ml, 10 equivalents) at 0° C. for 30 minutes. The obtained green product was absorbed in silica gel, which was washed with ethyl acetate and then with methanol. The methanol was concentrated under vacuum and the remaining crude was washed with 0.1 N HCl/DCM, brine solution and dried with magnesium sulfate. The organic layer was then concentrated under vacuum, and the identity of the obtained CyNA-427 was confirmed by $^1$H-NMR, $^{13}$C-NMR and thin-layer chromatography (TLC).

Example 1

Coordination of Cu(II) and Cu(I) to N-Terminal Portion of Ctr1

Cu(II) Coordination to N-Terminal Portion of Ctr1:

In order to investigate Cu(II) binding to the extracellular (N-terminal) domain of Ctr1, the following peptides were prepared:

```
Pep1 (wild-type)-
                                    (SEQ ID NO: 1)
MDHSHHMGMSYMDS Pep2 (G8A mutant)-
                                    (SEQ ID NO: 2)
MDHSHHMAMSYMDS Pep3 (H3A mutant)-
                                    (SEQ ID NO: 3)
MDASHHMGMSYMDS
```

```
Pep4 (H5A mutant)-
                                            (SEQ ID NO: 4)
MDHSAHMGMSYMDS Pep5 (H6A mutant)-
                                            (SEQ ID NO: 5)
MDHSHAMGMSYMDS
```

The mutations of Pep2-Pep5 (converting a His or Gly residue to Ala) were based on reports that Cu(II) preferentially binds His and Gly [Migliorini et al., *J Biol Inorg* 2014, 19:635-645].

The choice of the buffer is important since it can affect the Cu(II) coordination. HEPES, KPi, NEM, and Tris buffers have been reported in studies of Cu(II) coordination. It has been reported that in Tris buffer the pH is dependent on the temperature, and therefore is not suitable for EPR measurements, with KPi buffer and HEPES buffer being suggested to retain the coordination environment of Cu(II) at low temperature [Faller et al., *Coord Chem Rev* 2012, 256:2381-2396; Drew et al., *PLoS One* 2010, 5:e15875].

Initial CW-EPR measurements were performed using HEPES buffer. However, the Cu(II) was not well dissolved in HEPES, as manifested by a blue/purple color at the bottom of the vial.

In addition, as shown in FIG. 2, when increasing Cu(II) concentration (at 130 K), the EPR spectrum of Pep1 peptide became broad and not resolved, suggesting that the peptide was aggregating in the presence of Cu(II).

In contrast, as shown in FIG. 3, in KPi (potassium phosphate) buffer, Cu(II) coordination of Pep1 was stable at various Cu(II) concentrations (130 K), and the spectrum was well resolved, suggesting that no peptide aggregation occurred in the tested concentration range.

As shown in FIG. 4, at room temperature, the EPR spectrum of Pep1 was also considerably better resolved in KPi buffer than in HEPES buffer, suggesting that Cu(II)-Pep1 aggregates can even form at room temperature in HEPES buffer.

In order to confirm such aggregate formation in HEPES buffer, pulsed EPR experiments were performed at Q-band (33.8 GHz).

As shown in FIG. 5, the field sweep spectra of Pep1 in KPi and HEPES buffer at 10 K show a less resolved spectrum in HEPES than in KPi.

In addition, as shown in FIG. 6, the relaxation time of Cu(II) in HEPES was much faster than in KPi.

Taken together, the above results indicate that aggregates are indeed formed in HEPES buffer. Further EPR measurements were therefore performed using KPi buffer rather than HEPES buffer.

In addition KPi buffers at concentrations of 25 mM, 50 mM and 100 mM were compared. When the ratio between the peptide and the salt was larger than 25, the spectra were identical. CW-EPR experiments with 1 mM peptide were thus performed with 25 mM KPi buffer.

The abovementioned peptides Pep1-Pep5 were investigated by CW-EPR measurements at low temperature (130 K), in the presence of different concentrations of Cu(II). The data were subsequently incorporated into simulations using the EasySpin™ tool box, and the first coordination sphere of Cu(II) was determined for each peptide, according to procedures described in Peisach & Blumberg [*Arch Biochem Biophys* 1974, 165:691-708]. The experimental data and comparisons with simulated data (including parameters derived from the simulations) for peptides Pep1-Pep5, at a variety of peptide:Cu(II) molar ratios, are presented in FIGS. 7-11. FIG. 12 presents the experimental data and comparisons with simulated data for peptides Pep1-Pep5 at a peptide:Cu(II) molar ratio of 1:1.

The simulation for each peptide took into account two Cu(II) species. The first species corresponds to free Cu(II) ions in water, where Cu(II) is coordinated to four oxygen atoms (4O coordination), with $g_\parallel = 2.39 \pm 0.005$, $A_\parallel = 154 \pm 2.0$ G. The second species corresponds to Cu(II) that is bound to the peptide with coordination of 3N1O or 2N2O.

As shown in FIG. 12, the EPR spectra of the tested peptides differed, indicating that each mutation had an effect on Cu(II) coordination. In particular, the EPR spectra of Cu(II) coordinated to either Pep4 or Pep5 were much broader than the other EPR spectra, indicating that the mutations H5A and H6A each led to peptide aggregation in the presence of Cu(II).

As further shown in FIG. 12, the spectra for Pep1, Pep2, Pep3 and Pep5 in the presence of Cu(II) are consistent with a simulated EPR spectrum for a 3N1O coordination of Cu(II). This result indicates that Cu(II) binds to Pep1 (the wild-type sequence) with 3N1O coordination, and that this coordination is preserved in the presence of G8A (Pep2), H3A (Pep3), and H6A (Pep5) mutations.

However, as further shown in FIG. 12, the spectrum for Pep4 (H5A mutant) in the presence of Cu(II) is consistent with a 2N2O coordination. This result suggests that His5 (which is replaced by Ala in Pep4) is an essential residue for Cu(II) coordination.

As shown in FIG. 13, substantially all Cu(II) is bound to Pep1 at low Cu(II) concentrations, with addition of Cu(II) resulting in an increased percentage of free Cu(II). This result indicates a high affinity of Cu(II) to the wild-type sequence Pep1, which is consistent with the reports of high affinity between Cu(II) and wild-type Ctr1 [Pushie et al., *Inorg Chem* 2015, 54:8544-8551].

As further shown in FIG. 13, Pep2, Pep3 and Pep5 each exhibited a lower affinity to Cu(II) than did Pep1; with the maximum percentage of bound Cu(II) in the presence of Pep2 being 80%, obtained at a Pep2:Cu(II) molar ratio of 1:0.8, and with only about 70% of the Cu(II) being bound to Pep3 or Pep5 at a peptide:Cu(II) molar ratio of 1:1. This result indicates that the G8A mutation of Pep2, the H3A mutation of Pep3 and the H6A mutation of Pep5 each decreased the peptide's affinity to Cu(II).

Similarly, as further shown in FIG. 13, Pep4 achieved 100% bound Cu(II) only at a high Cu(II) concentration (a Pep4:Cu(II) molar ratio of 1:3), which suggests that the H5A mutation of Pep4 also reduced affinity to Cu(II). In addition, at this concentration, more than one Cu(II) ion is bound to the peptide, which eventually leads to aggregation of the peptide.

The effects of the mutations of the Pep2-Pep5 peptides on the reduction of Cu(II) to Cu(I) was then investigated, by evaluating the room temperature (RT) change in EPR intensity over time, as Cu(I) is EPR-silent. Reduction of Cu(II) was effected in the presence of 2 mM ascorbate (a peptide:ascorbate:Cu(II) molar ratio of 1:2:2). For comparison, the reduction of free Cu(II) in buffer was also measured.

As shown in FIG. 14, Cu(II) was quite stable in the presence of Pep1, Pep2 and Pep3, with only about 5% of the Cu(II) being reduced within 4000 seconds. These results suggest tight binding of Cu(II) to the peptides, which hinders the capability of the ascorbate to reach Cu(II), thereby controlling reduction.

As further shown in FIG. 14, in the presence of Pep4 (H5A mutant peptide) or Pep5 (H6A mutant peptide), the reduction of Cu(II) was more rapid than in the presence of Pep1 (wild-type peptide). Moreover, in the presence of Pep4, the reduction of Cu(II) was more rapid than reduction of free Cu(II) ions.

These results provide further indication that His5 and His6 are directly involved in the coordination of Cu(II).

Without being bound by any particular theory, it is believed that Pep4 forms aggregates in the presence of Cu(II) (as discussed hereinabove) which may create a cluster of Cu(II) ions that facilitates Cu(II) reduction, resulting in the abovementioned result of more rapid reduction than for free Cu(II) ions.

In order to evaluate interactions between electron spin with nearby (~2-6 Å) nuclei, 3P-ESEEM experiments were performed (according to procedures described in the Materials and Methods section hereinabove). Such nuclei are typically not directly coordinated to the metal ion but rather lie within a residue that is directly bound to the metal ion. ESEEM experiments are therefore suitable for targeting the remote nitrogen atom in an imidazole ring (of His) that is directly coordinated to Cu(II).

As shown in FIGS. 15A and 15B, the ESEEM signals and FT (Fourier transform) of Pep1 and Pep3 are essentially identical, thereby confirming that His3 (which is replaced in Pep3) is not directly coordinated to Cu(II).

In contrast, further shown therein, the ESEEM signals of Pep4 and Pep5 are different than that of Pep1, with less intense $^{14}N$ modulations.

As further shown in FIG. 15B, the Pep1 signal was simulated (using the saffron function of the EasySpin™ toolbox) using two $^{14}N$ nuclei with the following quadrupole parameters: $e^2qQ/h=1.44$ MHz, $\eta=0.5$ for one nucleus and $e^2qQ/h=1.44$ MHz, $\eta=0.35$ for the other nucleus; the Pep4 signal was simulated with one $^{14}N$ nucleus ($e^2qQ/h=1.44$ MHz, $\eta=0.5$), and the Pep5 signal was also simulated with one $^{14}N$ nucleus ($e^2qQ/h=1.44$ MHz, $\eta=0.35$).

Taken together, the above results indicate that the His5 and His6 residues play an important role in both providing high affinity of Cu(II) to the extracellular domain of Ctr1 and for ensuring proper coordination to Ctr1.

The above results further indicate that the Gly8 and His3 residues play a role in Cu(II) affinity to Ctr1 (a role for the His3 residue in Cu(II) affinity to Ctr1 was already reported by Haas et al. [*J Am Chem Soc* 2011, 133:4427-4437]).

Without being bound by any particular theory, it is believed that Gly8 does not participate directly in binding to Cu(II), but may help provide an appropriate degree of flexibility of the peptide chain.

Cu(I) Coordination to N-Terminal Portion of Ctr1:

The Pep1 (wild-type) peptide was investigated by $^1H$-NMR measurements in D20, as well as by 2D experiments (COSY, NOESY) in a 700 MHz NMR spectrometer. In order to observe the amide NH signals, $^1H$-NMR spectra (1D, TOCSY and NOESY) were also obtained in 90% $H_2O$ with water suppression. The amino-acid sequence was confirmed by observation in the HMBC spectrum (long-range $^1H \times {}^{13}C$ correlation) of interactions between the carbonyl carbons not only with intra-residue α and β protons, but also with the α protons of the adjacent residue in the chain. This process enabled assignation of signals to most of the amino acids in the peptide, as presented in FIG. 16.

Cu(I) was added to peptide solutions in the form of tetrakis(acetonitrile)copper(I) hexafluorophosphate under nitrogen gas in order to preserve anaerobic conditions. No Cu(II) signal was observed by EPR, thereby confirming the purity of the Cu(I).

As shown in FIGS. 16 and 17, addition of Cu(I) to the wild-type peptide induced shifts in the $^1H$-NMR spectrum.

As further shown in FIG. 16, the most significant changes occurred near His and Met residues, with His3, Met7, Met9 and Met12 exhibiting the largest shifts upon exposure to Cu(I). These results indicate that His and Met residues are the most relevant residues for Cu(I) binding in the peptide, which is consistent with the reports of Pushie et al. [*Inorg Chem* 2015, 54:8544-8551] and Schwab et al. [*J Inorg Biochem* 2016, 158:70-76].

In order to utilize EPR measurements in order to investigate binding of Cu(I) (which is diamagnetic and therefore EPR-silent) to the extracellular (N-terminal) domain of Ctr1, the following peptides were prepared with an MTSSL (S-(1-oxyl-2,2,5,5-tetramethyl-2,5-dihydro-1H-pyrrol-3-yl) methyl methanesulfonothioate) spin label, conjugated to a terminal Cys residue (note that the terminal Cys residues conjugated to MTSSL are not considered when numbering the other 14 amino acid residues of the peptides):

```
Pep6 (wild-type)-
                                    (SEQ ID NO: 6)
MTSSL-CMDHSHHMGMSYMDSC-MTSSL Pep7 (M1A mutant)-
                                    (SEQ ID NO: 7)
MTSSL-CADHSHHMGMSYMDSC-MTSSL Pep8 (M7A mutant)-
                                    (SEQ ID NO: 8)
MTSSL-CMDHSHHAGMSYMDSC-MTSSL Pep9 (M9A mutant)-
                                    (SEQ ID NO: 9)
MTSSL-CMDHSHHMGASYMDSC-MTSSL Pep10 (M12A mutant)-
                                    (SEQ ID NO: 10)
MTSSL-CMDHSHHMGMSYADSC-MTSSL
```

As shown in FIG. 18A, the presence of Cu(I) did not considerably alter the signals of the MTSSL-labeled peptides.

However, as shown in FIGS. 18A and 18B, Cu(I) introduction resulted in a slight broadening of the signal and a decrease in the hyperfine value ($a_N$), for each of the MTSSL-labeled peptides (at a peptide:Cu(I) molar ratio of 1:3).

The broadening of the signal suggests that the two termini of each peptide get closer to each other upon Cu(I) binding. The decrease in the hyperfine value following Cu(I) introduction, a phenomenon observed previously for other segments containing Met [Shenberger et al., *J Biol Inorg Chem* 2015, 20:719-727], suggests that, upon Cu(I) coordination, the spin-labels shift towards a somewhat more hydrophobic environment.

As further shown in FIG. 18B, the hyperfine ($a_N$) value varies slightly among the different peptides, with Pep8 (the M7A mutant) exhibiting the largest change in hyperfine value relative to the wild-type sequence (Pep6).

These results suggest that each mutation in Pep7-Pep10 has a slight effect on the folding of the peptide (relative to the wild-type Pep6), and that Met7 is involved in Cu(I) coordination. In order to trace the structural changes in Pep6 upon addition of Cu(I), DEER measurements were performed according to procedures described in the Materials and Methods section hereinabove, in the presence or absence of Cu(I) (at a Pep6:Cu(I) molar ratio of 1:3). DEER is a pulsed EPR technique that can measure the dipolar interaction between two paramagnetic centers, thereby providing a distance distribution function in the range of 2.0-8.0 nm

[Jeschke & Polyhach, *Phys Chem Chem Phys* 2007, 9:1895-1910; Milov et al., *App Magn Res* 1998, 15:107-143; Pannier et al., *J Magn Res* 2000, 142:331-340].

As shown in FIGS. 19A and 19B, the DEER measurements of Pep6 indicate that the distance between the two termini of the Pep6 peptide was 2.5±0.7 nm (FIG. 19A), and that addition of Cu(I) to the solution resulted in a much narrower distance distribution of 2.3±0.2 nm, along with clear time domain modulations in the DEER signal (FIG. 19B).

The decrease in the average distance upon addition of Cu(I) is in agreement with the slight broadening of the CW-EPR spectra discussed hereinabove.

The above results indicate that upon Cu(I) coordination, the peptide becomes considerably more rigid and confined in space.

Taken together, the above NMR and EPR data indicate that His3, Met7, Met9, and Met12 play a role in Cu(I) coordination, and that upon Cu(I) coordination, the Ctr1 N-terminal peptide becomes less flexible.

In order to gain further insight into Cu(I) coordination, UV-VIS measurements were performed on the various peptides (as described n the Materials and Methods section hereinabove).

As shown in FIGS. 20-25, titration of Cu(I) into the peptides Pep1, Pep3, Pep6 and Pep8-Pep10, resulted in the appearance of an absorption peak at a wavelength of 265 nm.

The absorption peak at 265 nm is apparently due to S→Cu charge transfer transitions [Du et al., *Chem Comm* 2013, 49:9134-9136; Xiao et al., *J Am Chem Soc* 2004, 126:3081-3090].

As shown in FIG. 20, the absorption at 265 nm by Pep1 (wild-type peptide) increased as Cu(I) concentration increased, until a plateau was reached at a Pep1:Cu(I) molar ratio of 1:3. This result indicates that Cu(I) binds to the Pep1 peptide in a dose-dependent manner.

As shown in FIG. 21, the absorption at 265 nm by Pep6_(wild-type peptide with conjugated spin labels) exhibited a similar dependence on Cu(I) concentration as did that of Pep1, indicating that the addition of spin labels to the peptide did not affect its copper binding properties.

As shown in FIG. 22, Pep3 (an H3A mutant) exhibited a different pattern of absorption than did Pep1 and Pep6, namely, binding to Pep3 occurred only at a Cu(I):peptide molar ratio exceeding 5.0. This result indicates that Cu(I) affinity of Pep3 is considerably lower than in the wild-type peptide, suggesting that His3 plays a role in Cu(I) binding.

As shown in FIGS. 23-25, absorption of Pep8 (FIG. 23), Pep9 (FIG. 24) and Pep10 (FIG. 25) did not change upon addition of Cu(I). These results indicate that these peptides (M7A, M9A and M12A mutants) did not bind Cu(I) to an appreciable degree, and that Met7, Met9 and Met12 play an important role in binding Cu(I).

Discussion

Taken together, the above results indicate that His3, His5, His6, and Gly8 residues of Ctr1 participate in Cu(II) binding, and, in particular, His5 and His6 are involved in direct coordination of Cu(II). The above results further indicate that His3, Met7, Met9 and Met12 are involved in Cu(I) binding, with Met7 being involved in Cu(I) coordination, and that Cu(I) coordination is associated with increased peptide rigidity.

Pushie et al. [*Inorg Chem* 2015, 54:8544-8551] have suggested, based on XAS data, that Cu(I) binds to the Ctr1 N-terminal segment in an N2OS coordination, and that His5 and His6 and one of the methionine residues are involved in this coordination. The measurements presented herein do not detect such a coordination state. As the results presented herein show that Cu(II) is directly coordinated to His5 and His6, a copper-coordinating site that involves His5, His6 and one of the methionine residues (as described by Pushie et al.) might reflect an intermediate site that is formed during the reduction process from Cu(II) (which coordinates to His5 and His6) to Cu(I) (which coordinates to Met residues).

Without being bound by any particular theory, it is believed that the three methionine residues Met7, Met9, and Met12 are involved in a Cu(I)-binding site that is the first stable binding site in the Ctr1 N-terminal domain. It is further believed that Cu(II) binding is closer to the N-terminal region of Ctr1, whereas Cu(I) binding is concentrated in the C-terminal region.

FIG. 26 presents a model of copper binding to Pep1, whereby Cu(II) binding is closer to the N-terminal region of Pep1, and Cu(I) is closer to the C-terminal region of Pep1, as is believed to occur in Ctr1 (as discussed hereinabove).

FIG. 27 schematically depicts such Cu(II) binding being closer than Cu(I) to the N-terminus of the extracellular region of Ctr1.

The models of peptide with Cu(II) or Cu(I) were obtained by computational simulation using a Discovery Studio™ program, while restraining the distances between Cu(I)/Cu (II) and the relevant amino acids that bind it using bond length parameters described in the literature [Rubino et al., *J Biol Inorg Chem* 2010, 150:1033-1049; Tullius et al., *Proc Natl Acad Sci USA* 1978, 75:4069-4073; Op't Holt & Merz, *Biochemistry* 2007, 46:8816-8826; Pitts & Hall, *Inorg Chem* 2013, 52:10387-10393], followed by optimization of the structure.

In view of the above, the present inventors have conceived that in order to facilitate Cu(II) entry into the cell, a Cu(II) complex may be utilized wherein Cu(II) is coordinated to a peptide which directs Cu(II) to copper-binding Met residues in Ctr1 (by being readily replaced by such residues in a Cu(II) complex), and also coordinated to a ligand which stabilizes the Cu(II) oxidation state upon binding to Ctr1 (as opposed to the Cu(I) oxidation state favored by Ctr1 copper-binding Met residues).

Example 2

Preparation of Cu(II)-Ligand-Peptide Complexes

Cu(II) complexes are prepared by contacting Cu(II) ions (optionally comprising a radioactive isotope such as $^{64}$Cu) with a copper ligand having 2, 3 or 4 atoms (preferably nitrogen and/or oxygen atoms) which can be coordinated to Cu(II) upon complexation and with a water-soluble peptide having 2 or 3 (preferably 3) Cys, Met and/or His residues, at least one of which is Met or Cys.

The ligand is optionally a ligand depicted in FIG. 28, or a peptide having the formula $W^1$—$X^1$—$X^2$—$X^3$—$W^2$ (SEQ ID NO: 44) or $W^1$—$X^1$—$X^2$—$W^2$ (SEQ ID NO: 45), wherein $W^1$ and $W^2$ are each independently a His, Met or Gly residue, and each of $X^1$, $X^2$ and $X^3$ is independently an Ala or Gly residue (e.g., the ligand being a HAAH (SEQ ID NO: 11), HAAM (SEQ ID NO: 12) or HAAG (SEQ ID NO: 13) peptide).

The water-soluble peptide optionally comprises at least one $W^3$—$X^4$—$X^5$—$W^4$ (SEQ ID NO: 46) region, wherein $W^3$ and $W^4$ are each independently a His, Met or Cys residue (preferably wherein at least one is Met or Cys), and each of $X^4$ and $X^5$ is independently an Ala, Arg, Asp, Glu, Gly, Lys, Ser, Thr or Tyr residue (e.g., the peptide comprising a CXXMXXM (SEQ ID NO: 19), CXXHXXH (SEQ ID NO: 20) or MXXHXXH sequence (SEQ ID NO: 21), wherein each X is independently Ala, Arg, Asp, Glu, Gly, Lys, Ser, Thr or Tyr).

Using the above-described general procedure, complexes were prepared with CyNA-427 (prepared according to procedures described in the Materials and Methods section hereinabove) or IDA as ligand, and with peptides (prepared according to procedures described in the Materials and Methods section hereinabove) having the following sequences:

```
Met1:
                                        (SEQ ID NO: 14)
MYGMKGMS-3 Met residues Met2:
                                        (SEQ ID NO: 15)
MYGMK-2 Met residues Cys1:
                                        (SEQ ID NO: 16)
KSMAACAM-1 Cys residue + 2 Met residues Cys2:
                                        (SEQ ID NO: 17)
ASCGGCAM-2 Cys residues + 1 Met residue Cys3:
                                        (SEQ ID NO: 18)
HTGCK-1 Cys residue + 1 His residue
```

$CuCl_2$ was mixed with the ligand and peptide in a molar ratio of 5:1:4 Cu(II):ligand:peptide. The complex was then purified in a 700 Da MiniTrap™ G-10 column, based on 2.1 ml of Sephadex™ G-10 dextran gel for separating substances according to molecular size by gel filtration. The purity of the complex was then verified by mass spectrometry, EPR spectrometry and TLC, as described in the Materials and Methods section hereinabove.

Without being bound by any particular theory, it is believed that ligands with 2 or 3 coordinating atoms, such as IDA and CyNA-427 (also referred to herein for brevity as "CyNA"), cannot form a full equatorial plane for Cu(II) complexation (which would involve 4 to 6 coordinating atoms, e.g., as in Cu-ATSM as depicted in FIG. 1), and thus require at least two additional atoms (e.g., nitrogen or sulfur) to complete a Cu(II) coordination environment; and therefore advantageously promote binding to copper-binding proteins of the cell. It is further believed that IDA is a promising ligand for Cu(II) radiolabeled agents, as it is the smallest ligand that can coordinate to Cu(II), which may facilitate entry into the cell via the pore of transport proteins such as Ctr1 (which has a pore of about 3.0 nm in diameter).

FIG. 29 depicts a Cu(II)-ligand-peptide complex according to optional embodiments, wherein Cu(II) is coordinated to 3 atoms of a ligand and 3 atoms of a peptide.

The Cu(II)-CyNA-Cys1 complex (prepared according to the procedures described hereinabove) was obtained at a high purity, as determined by mass spectrometry (data not shown).

Similarly, as shown in FIG. 30, the Cu(II)-CyNA-Cys1 complex (prepared according to the procedures described hereinabove) was obtained at a high purity, as determined by thin layer chromatography.

As shown in FIGS. 31A and 31B, the Cu(II)-CyNA-Cys1 complex exhibited an absorption peak at a wavelength of about 794 nm (FIG. 31A), and a fluorescence emission peak at a wavelength of about 810 nm (FIG. 31B) upon excitation at a wavelength of 794 nm.

As shown in FIG. 32, the fluorescence of Cu(II)-CyNA was weaker than that of Cu(I)-CyNA at each tested copper concentration, indicating that reduction of Cu(II) to Cu(I) when complexed with CyNA results in an increase in CyNA fluorescence.

These results indicate that the CyNA in a Cu-CyNA-peptide complex can serve as a fluorescent probe sensitive to copper ions (and to the oxidation state of the Cu), based on changes in intensity of absorption and/or fluorescence (e.g., wherein fluorescence intensity increases upon reduction of Cu(II) to Cu(I)), and/or in peak wavelengths (e.g., wherein fluorescence of CyNA is characterized by absorption at 794 nm and peak emission at 816 nm (without copper), 810 nm (complexed with Cu(I)) or 815 nm (complexed with Cu(II))). Thus, such complexes may facilitate detection of copper in cells (e.g., without the use of radioactive material), for example, in biochemical research and/or in open surgery as a probe for hypoxia, blood vessel blockage and/or stroke.

The stability of the Cu(II)-CyNA-Cys1 complex and the Cu(II)-IDA-Cys1 complex were assessed by determining the EPR spectra over time.

As shown in FIG. 33, the EPR spectra of the Cu(II)-CyNA-Cys1 and Cu(II)-IDA-Cys1 complexes were similar 1 hour and 24 hours after purification.

These results indicate that the complexes exhibit considerable stability over time scales comparable to the half-life of $^{64}Cu$ (about 12 hours).

Example 3

Cu(II)-Ligand-Peptide Complexes in Physiological Environment

In order to assess the behavior of a Cu(II)-ligand-peptide complex under physiological conditions, the coordination of Cu(II) was investigated by EPR spectroscopy following exposure of a Cu(II)-IDA-Met1 complex (prepared as described in Example 2) to the copper transporter Ctr1 (in a purified state), which plays a central role in the cellular copper cycle. For comparison, the behavior of Cu(II)-IDA (without a peptide) was also investigated under such conditions. EPR spectra were interpreted by comparison to simulated spectra prepared using the EasySpin™ computational package.

As shown in FIG. 34, the EPR spectrum of a Cu(II)-IDA complex (without a peptide) is consistent with a simulated EPR spectrum of a 2N2O coordination of Cu(II), suggesting that the Cu(II) is coordinated to two IDA molecules (each having a single nitrogen atom). Furthermore, in the presence of Ctr1, the coordination remains 2N2O, but with a narrower line width (2.0 mT vs. 6.0 mT), indicating that the Cu(II) is more fixed in space. These results suggest that in the presence of Ctr1, the Cu(II) becomes coordinated to the Ctr1.

As further shown in FIG. 34, the EPR spectrum of a Cu(II)-IDA-Met1 complex) is consistent with a simulated EPR spectrum of a 2N2S or 1N1O2S coordination of Cu(II) (as these coordination states cannot be distinguished by EPR according to Peisach & Blumberg [Arch Biochem Biophys 1974, 165:691-708]), suggesting that the Cu(II) is coordinated to two Met residues (each providing a single sulfur atom). Furthermore, in the presence of Ctr1, the coordination becomes a mixture of a 2N2S (or 1N1O2S) coordination state (indicating the coordination to two Met residues) and a 1N3S coordination state (indicating the coordination to three Met residues).

FIG. 35 depicts a possible coordination structure of Cu(II) to IDA and two sulfur atoms (e.g., in Met residues) of a peptide.

These results indicate that upon exposure of Cu(II)-IDA-Met1 to Ctr1, the Cu(II)-IDA becomes coordinated to Ctr1 as a result of a transfer mechanism from the methionine segment of Met1 to Ctr1, involving release of the Met1 from the Cu(II) complex.

Furthermore, these results indicate that the Cu(II)-IDA-Met1 complex does not coordinate to His residues (contrary to typical Cu(II)-coordination to Ctr1, as described in Example 1), but rather prefers Met or Cys residues, such as in proteins involved in the cellular copper cycle.

Without being bound by any particular theory, it is believed that the abovementioned preference for Met or Cys residues is associated with sulfur atoms of the peptide which coordinate to copper being more readily replaced in the coordination complex by other sulfur atoms, as opposed, e.g., to nitrogen atoms of His residues.

Taken together, these results provide confirmation that radioactive Cu(II) in a Cu(II)-ligand-peptide complex such as described herein will be incorporated in the cellular copper cycle, and thereby act as a specific radioactive tracer.

The effect of hypoxic and normoxic environments on copper redox status in the complexes was then assessed, using EPR spectroscopy to distinguish between paramagnetic Cu(II) and diamagnetic Cu(I).

As shown in FIG. 36, the Cu(II) in Cu(II)-IDA-Met1 did not undergo any reduction upon exposure to air for 4 hours, either in the presence or absence of Ctr1; whereas upon exposure to a nitrogen atmosphere for 4 hours, 35% of the Cu(II) was reduced in the absence of Ctr1 and 60% of the Cu(II) was reduced in the presence of Ctr1. The 60% reduction in the presence of Ctr1 indicates a high uptake ratio of the Cu(II)-IDA complex by Ctr1.

These results provide further confirmation that in the presence of Ctr1, the Cu(II)-IDA complexes are in transit, and thus are more sensitive to atmospheric conditions.

Example 4

Cu(II)-Ligand-Peptide Complexes in the Presence of Cells

The interaction between cells and Cu(II)-ligand-peptide complexes under various conditions was investigated by contacting DA3 breast cancer cells with a Cu(II)-IDA-Cys1 complex (prepared as described in Example 2) or with $CuCl_2$ as a control. The concentration of reduced copper (Cu(I)) was then determined by complexation with bicinchoninic acid (BCA) and evaluating the concentration of BCA-Cu(I) by measuring absorption at a wavelength of 562 nm.

As shown in FIG. 37, more Cu(I) ions are observed in cells under hypoxic conditions than under normoxic conditions, following exposure to either free Cu(II) ions or the Cu(II)-IDA-Cys1 complex.

As further shown in FIG. 37, upon exposure to free Cu(II) ions, the reduced Cu(I) ions which appear in the cell are depleted from the cell within several hours; whereas upon exposure to the Cu(II)-IDA-Cys1 complex, the Cu(I) concentration is maintained for at least 24 hours.

These results indicate that formation of Cu(I) by reduction is a more gradual process when Cu(II) is incorporated in the complex, and that this gradual reduction balances the removal of copper ions from the cell.

As further shown in FIG. 37, the highest ratio of Cu(I) under hypoxic conditions to Cu(I) under normoxic conditions was 5.0±0.5, at 24 hours after exposure to the Cu(II)-IDA-Cys1 complex.

These results indicate that the longer lasting Cu(I) signal associated with the Cu(II)-ligand-peptide complexes provides a higher signal/baseline ratio for detecting hypoxic conditions in cells.

As shown in FIG. 38, Ag(I) ions, a Ctr1 inhibitor, block entry into cells of copper from the Cu(II)-IDA-Cys1 complex, whereas entry of free Cu(II) ions was not blocked.

This result indicates that the Cu(II)-ligand-peptide complex has a high affinity to the Ctr1 transporter, in contrast to free Cu(II) ions, which can penetrate into cells via a different transporter (possibly the divalent metal ion transporter DMT1).

The potential toxicity of the Cu(II)-IDA-Cys1 complex was also assessed, by determining viability of DA-3 (mouse lymphoma) cells following incubation for 12 hours with the complex, at concentrations of 0.5 nM, 5 nM and 50 nM.

As shown in FIG. 39, the Cu(II)-IDA-Cys1 complex did not induce any significant reduction in cell viability in the tested concentration range, indicating that the complex is substantially non-toxic.

Example 5

Preparation of Radiolabeled $^{64}$Cu(II)-Ligand-Peptide Complexes

Radioactive $^{64}$Cu(II)-IDA-Cys1 and $^{64}$Cu(II)-CyNA-Cys1 complexes were prepared according to procedures described in Example 2, while using $^{64}$Cu-containing Cu(II). All radioactive complexes were at an Isotopia Molecular Imaging Ltd. facility in Israel 30 µCi $^{64}$Cu(II) at a concentration of 1 µCi/µl was added to 200 µl solution containing 15 mM of peptide and 4 mM ligand. The radio-synthesis included purification to dispose of impurities, such as free $^{64}$Cu or byproducts. The yield was about 25-40% and depended on the ligand. The stability of the complex was evaluated during test runs up to 12 hours after radio-synthesis by thin layer chromatography (TLC), to ensure that no changes in the chemical composition of the radio-ligand have occurred.

As shown in FIGS. 40A and 40B, the $^{64}$Cu(II)-CyNA-Cys1 (FIG. 40A) and $^{64}$Cu(II)-IDA-Cys1 (FIG. 40B) complexes exhibited a considerable degree of stability over the course of 12 hours (i.e., about the half-life of $^{64}$Cu), as determined by consistent results over time in thin layer chromatography.

These results indicate that such Cu(II)-ligand-peptide complexes are suitable for delivering copper (e.g., $^{64}$Cu) radiolabeled tracer, for example, for in vivo PET imaging.

Without being bound by any particular theory, the results presented hereinabove support a use of $^{64}$Cu radiolabeled tracer to identify (e.g., image by PET) hypoxic regions in vivo based on a model such as depicted in FIG. 41, wherein the $^{64}$Cu(II)-ligand peptide binds to an extracellular domain of Ctr1, the peptide dissociates and $^{64}$Cu(II)-ligand complex enters the cell via Ctr1 (and is also removed from the cell by Atox1 and Atp7b), and reduction of $^{64}$Cu in intracellular $^{64}$Cu(II)-ligand complex to $^{64}$Cu(I) (which has a longer retention time than $^{64}$Cu(II)-complex) is promoted by hypoxic conditions, thereby correlating a radioactive signal with local hypoxia.

Example 6

Improved Preparation and Separation of Cu(II)-Ligand-Peptide Complexes

Stock solutions of $CuCl_2$ (24 mM), IDA (24 mM), and the following peptides (18 mM) were prepared in ultrapure water (Milli-Q®).

Met1:
(SEQ ID NO: 14)
MYGMKGMS

Met1-Tyr:
(SEQ ID NO: 50)
MYGMKGMSY

Cys1:
(SEQ ID NO: 16)
KSMAACAM;

Cys1-Tyr:
(SEQ ID NO: 51)
KSMAACAMY

NEM (N-ethylmorpholine) buffer (100 mM, pH 7.4) was used to decrease the EPR signal of free copper [Aronoff-Spencer et al., *Biochemistry* 2000, 39:13760-13771].

In all EPR measurements, copper concentration was 0.5 mM.

Various reaction mixtures (250 µl) were prepared with compositions as shown in Table 3 below, including controls without IDA or without peptide (Cys1). The final concentration of Cu(II), IDA and Cys1, when present, was 1 mM, 2 mM and 0.5 mM respectively, in ultrapure water. All the samples were incubated at 37° C. with shaking for overnight.

Initially, 2 molar equivalents of IDA were combined with Cu(II) to form a mono-IDA-Cu(II) complex, and then Cys1 peptide was added to the solution in order to form an IDA-Cu(II)-Cys1 complex.

As there is a possibility for formation of a $(IDA)_2$-Cu(II) complex, the effect of sequence of addition of peptide was evaluated by also combining IDA and Cys1, and then adding Cu(II). Thus, Mixture (1) and Mixture (3) (shown in Table 3 below) differed only in that for Mixture (1), Cu(II) was first mixed with IDA in water (213 µl) and then Cys1 peptide was added in the reaction mixture, whereas in case of Mixture (3), IDA was mixed with the Cys1 peptide in water (213 µL) and then Cu(II) was added to the mixture.

To prepare samples for EPR measurements, 25 µl of each of the reaction mixtures described in Table 3 was diluted with 25 µl of 0.1 M NEM buffer (pH 7.4) (or with water in the case of sample (6)). Thus, in the final composition of each of the six samples, the concentrations of IDA, Cu(II) and peptide were 50% of the concentrations indicated in Table 3.

TABLE 3

Concentrations (in mM) of exemplary reaction mixtures and volumes (in µl) of solutions combined to form the mixtures

| | Mixture (1) | Mixture (2) | Mixture (3) | Mixture (4) | Mixture (5) | Mixture (6) |
|---|---|---|---|---|---|---|
| IDA (mM) | 2 | 2 | 2 | 0 | 0 | 0 |
| Cys1 (mM) | 0.5 | 0 | 0.5 | 0 | 0.5 | 0 |
| Cu(II) (mM) | 1 | 1 | 1 | 1 | 1 | 1 |
| $H_2O$ (µl) | 213 | 220 | 213 | 240 | 233 | 240 |
| IDA (µl) | 20 | 20 | 20 | 0 | 0 | 0 |
| Cys1 (µl) | 7 | 0 | 7 | 0 | 7 | 0 |
| Cu(II) (µl) | 10 | 10 | 10 | 10 | 10 | 10 |

As shown in FIG. 42, 50 mM NEM effectively eliminated the signal associated with free Cu(II) in water, confirming that it eliminates free Cu(II), as well as that the EPR signals obtained in the presence of IDA and/or Cys1 peptide are associated with the corresponding complexes with copper, and are not due to free copper.

As further shown in FIG. 42, at a stoichiometric ratio of 2:1 IDA:Cu(II), the Cu(II) predominantly binds IDA to form IDA-Cu(II) complex, and the Cys1 peptide, when present, also binds to Cys1 to Cu(II).

As further shown therein, the sequence of addition of IDA, Cys1 and Cu(II) did not affect the EPR spectrum, indicating that the sequence does not significantly affect the obtained complex.

In order to ascertain whether an excess of peptide with excess IDA and copper can form a IDA-Cu(II)-Cys1 complex, EPR experiments for performed with a constant 2:1 stoichiometric ratio of IDA:Cu(II), and increasing concentrations of Cys1 peptide (as shown in Table 4 below).

To prepare samples for EPR measurements, 25 µl of each of the reaction mixtures described in Table 4 was diluted with 25 µl of 0.1 M NEM buffer (pH 7.4). Thus, in the final composition of each of the five samples, the concentrations of IDA, Cu(II) and peptide were 50% of the concentrations indicated in Table 4.

TABLE 4

Concentrations (in mM) of exemplary reaction mixtures and volumes (in µl) of solutions combined to form the mixtures

| | Mixture (1) | Mixture (2) | Mixture (3) | Mixture (4) | Mixture (5) |
|---|---|---|---|---|---|
| IDA (mM) | 2 | 2 | 2 | 0 | 0 |
| Cys1 (mM) | 2 | 4 | 0 | 2 | 4 |
| Cu(II) (mM) | 1 | 1 | 1 | 1 | 1 |
| $H_2O$ (µl) | 192 | 164 | 220 | 212 | 184 |
| IDA (µl) | 20 | 20 | 20 | 0 | 0 |
| Cys1 (µl) | 28 | 56 | 0 | 28 | 56 |
| Cu(II) (µl) | 10 | 10 | 10 | 10 | 10 |

As shown in FIG. 43, excess Cys1 peptide (one or two molar equivalents) did not alter the EPR signal of the IDA-Cu(II) complex.

This result indicates that excess peptide (at least up to a 2:1 molar ratio of peptide to IDA) does not substantially affect formation of the IDA-Cu(II) complex.

In order to facilitate the binding of peptide to copper in the presence of IDA, samples were prepared with 0.5 molar equivalent of IDA with copper, and 2 equivalents of Cys1 peptide was further added to the reaction mixture (as shown in Table 5). After overnight incubation at 37° C. with constant stirring, the samples were prepared in NEM buffer (pH 7.4) for EPR measurements.

TABLE 5

Concentrations (in mM) of exemplary reaction mixtures and
volumes (in µl) of solutions combined to form the mixtures

|  | Mixture (1) | Mixture (2) | Mixture (3) | Mixture (4) |
|---|---|---|---|---|
| IDA (mM) | 0.5 | 0.5 | 0 | 0 |
| Cys1 (mM) | 2 | 0 | 2 | 0 |
| Cu(II) (mM) | 1 | 1 | 1 | 1 |
| H₂O (µl) | 41.4 | 47 | 40.4 | 58 |
| IDA (µl) | 1 | 1 | 0 | 0 |
| Cys1 (µl) | 5.6 | 0 | 5.6 | 0 |
| Cu(II) (µl) | 2 | 2 | 2 | 2 |

To prepare samples for EPR measurements, 25 µl of each of the reaction mixtures described in Table 5 was diluted with 25 µl of 0.1 M NEM buffer (pH 7.4) (or with water in the case of sample (4)). Thus, in the final composition of each of the four samples, the concentrations of IDA, Cu(II) and peptide were 50% of the concentrations indicated in Table 5.

As shown in FIG. 44, two different species in the solution were observed in the EPR spectrum under these experimental conditions.

This result suggests that one of the observed species is the IDA-Cu(II)-Cys1 complex, which could be confirmed by increasing the yield of the desired complex and separating it from residual complexes such as IDA-Cu(II).

In an additional experiment, the stoichiometric ratio of Cu(II):IDA was kept constant at 1:0.5, while a peptide (Met1, Cys1 or Cys1-Tyr) was added in amounts of 0.5, 1, 1.5, 2, 2.5 and 3 molar equivalents (relative to Cu(II)). Initially, the reaction mixtures were prepared in ultrapure water, at a total volume of 50 µl (as shown in Table 6).

TABLE 6

Concentrations (in mM) of exemplary reaction mixtures and
volumes (in µl) of solutions combined to form the mixtures

|  | Mixture (1) | Mixture (2) | Mixture (3) | Mixture (4) | Mixture (5) | Mixture (6) |
|---|---|---|---|---|---|---|
| IDA (mM) | 0.5 | 0.5 | 0.5 | 0.5 | 0.5 | 0.5 |
| Peptide (mM) | 0.5 | 1 | 1.5 | 2 | 2.5 | 3 |
| Cu(II) (mM) | 1 | 1 | 1 | 1 | 1 | 1 |
| H₂O (µl) | 45.6 | 44.2 | 42.8 | 41.4 | 40 | 38.6 |
| IDA (µl) | 1 | 1 | 1 | 1 | 1 | 1 |
| Peptide (µl) | 1.4 | 2.8 | 4.2 | 5.6 | 7 | 8.4 |
| Cu(II) (µl) | 2 | 2 | 2 | 2 | 2 | 2 |

To prepare samples for EPR measurements, 25 µl of each of the reaction mixtures described in Table 6 was diluted with 25 µl of 0.1 M NEM buffer (pH 7.4) (or with water in the case of sample (4)). Thus, in the final composition of each of the four samples, the concentrations of IDA, Cu(II) and peptide were 50% of the concentrations indicated in Table 6.

The EPR spectra of exemplary complexes formed from peptides in the presence of IDA and copper are shown in FIGS. 45-47.

As shown in FIGS. 45 and 46, addition of a Tyr residue to the Cys1 sequence (FIG. 46) did not substantially affect the EPR spectrum thereof, as compared with the EPR spectrum of Cys1 sequence per se (FIG. 45).

This result indicates that the additional Tyr residue did not affect binding of the peptide to copper, and did not alter the formation of IDA-Cu(II)-peptide as a product.

Furthermore, the separation of IDA-Cu(II)-peptide complexes using a PD MiniTrap™ G-10 column was assessed. Initially, the buffer was removed from the column and the column was washed 3 times using 2 ml ultrapure water. In a separate tube, a complex was prepared from 2.5 mM IDA, 7.5 mM peptide and 5 mM Cu(II) (i.e., a stoichiometric ratio of 0.5:1.5:1). In order to assess the effect of pH, the reaction was performed in either ultrapure water or in NEM buffer (pH 7.4).

The volume of reaction mixture was raised to 300 µl with the addition of water or NEM buffer. Elution was performed using ultrapure water, and three elution fractions were collected: fraction 1 was 16 drops, fraction 2 was the next 8 drops (drops #17-24), and fraction 3 was the next 10 drops (drops #25-34). The EPR spectra of the samples were then determined.

As shown in FIGS. 48 and 49, the second elution fraction (8 drops) obtained from the G-10 column exhibited an EPR signal, which corresponds to the product, IDA-Cu(II)-Cys1 complex. The reaction was carried out in water (FIG. 48) and in NEM buffer, pH 7.4 (FIG. 49).

As shown in FIG. 48, upon reaction in water, an EPR signal similar to that of aggregated copper was observed.

As shown in FIG. 50, the IDA-Cu(II)-Met1 complex was separated using a G-10 column and NEM buffer, similarly to the corresponding IDA-Cu(II)-Cys1 complex (as shown in FIG. 49).

These results suggest that yield of the product is reduced when the reaction is carried out in water, as the pH of the reaction goes to about 5-6, which is a less preferred condition for copper binding; whereas in NEM buffer, the pH of the reaction mixture solution was 7.4, which facilitates the binding of copper to IDA and peptide.

As shown in FIG. 51, the IDA-Cu(II)-Met1 complex was also separated using a G-10 column and KPi buffer (pH 7.4), although the separation was not as good as that obtained in NEM buffer (as shown in FIG. 50).

In addition, as shown in FIGS. 52A and 52B, free copper and the copper complexes could clearly be distinguished by their difference in retardation factor (Rf) values, upon thin layer chromatography.

Taken together, the above results indicate that Cu(II)-ligand-peptide complexes can be effectively separated by elution.

Example 7

Comparison of Binding of Exemplary Peptides to Cu(II) in Complexes

In order to compare affinity of peptides to Cu(II)-ligand-peptide complexes, UV-visible spectrophotometry was used to assess the degree of incorporation of Cys1-Tyr (SEQ ID NO: 51) and Met1-Tyr (SEQ ID NO: 50) peptides into Cu(II)-containing complexes, at various concentrations of Cu(II), IDA and peptide. The spectrophotometry focused on changes in Tyr residue absorption at about 276 nm.

In one experiment, 1 mM of peptide (16.6 µl) in ultrapure water (270 µl) was titrated with various concentrations (ranging from 0.1 to 1 mM) of CuCl₂ (1.25 µl).

As shown in FIGS. 53A-54B, Cys1-Tyr exhibited a large change in absorption, which was dependent on Cu(II) concentration and reached saturation at about 0.5 µM Cu(II), whereas Met1-Tyr exhibited a smaller large change in absorption, with no clear saturation (at up to 1 µM Cu(II)).

These results indicate that Cys1 has a considerably stronger affinity to Cu(II) than does Met1.

In addition, 1 mM of peptide (16.6 µl) with 1 mM CuCl$_2$ (12.5 µl) in ultrapure water (258.4 µl) was titrated with various concentrations (ranging from 0.25 to 1 mM or 0.25 to 1.25 mM) of IDA.

As shown in FIGS. 55A-56B, Met1-Tyr exhibited a larger IDA-dependent change in absorption than did Cys1-Tyr.

These results indicate that the presence of IDA facilitates binding of Cu(II) to Met1, whereas IDA has little effect on binding of Cu(II) to Cys1 because Cys1 has high affinity to Cu(II) even in the absence of IDA (as shown, e.g., in FIG. 53B).

In addition, 0.2 or 0.4 mM of CuCl$_2$ (5 µl) with 0.2 mM IDA (2.5 µl) in ultrapure water (278.9 µl) was titrated with various concentrations (ranging from 0.1 to 0.8 mM) of peptide (Cys1-Tyr or Met1-Tyr). The obtained absorption spectra are presented in FIGS. 57 and 58.

Taken together, the above results indicate that cysteine-containing peptides such as Cys1 exhibit greater affinity to Cu(II)-ligand-peptide complexes than do peptides containing only methionine sulfur atoms.

Without being bound by any particular theory, it is believed that the higher affinity enhances stability and yield of complexes comprising a cysteine-containing peptide.

Example 8

Computational Simulation of Structure of Exemplary Cu(II)-Ligand-Peptide Complex The structure of the exemplary complex Cu(II)-IDA-Cys1 was computed by molecular dynamics simulation.

Minimized samples were gradually heated from 50 K to 300 K within 4 picoseconds, equilibrated for 10 picoseconds, followed by a 100 picosecond production procedure with the NVT canonical ensemble. The simulations were performed at 300 K for 1 nanosecond with a CHARM force field, using a Discovery Studio™ program.

The computed structure of the complex is shown in FIGS. 59A and 59B.

Example 9

Comparative Example

Cu-ATSM Complex in Physiological Environment

In order to investigate the stability of Cu-ASTM complex, the complex was prepared by a general route depicted in FIG. 60.

Specifically, in order to prepare the ATSM ligand, 1.2 gram (11.4 mmol) of 4-methyl-3-thiosemicarbazide was dissolved in ethanol (50 ml) with constant heating and stirring. An ethanolic solution of 0.5 ml (5.7 mmol) diacetyl (2,3-butanedione) was then added dropwise to the thiosemicarbazide solution. In addition, 5-6 drops of glacial acetic acid were added to the reaction mixture. The reaction mixture was refluxed at 60-70° C. for 3-4 hours, and a white colored precipitate was formed. The flask was kept at 4° C. overnight for complete precipitation. On the next day, a pale yellow precipitate was obtained, which was then washed with ethanol and diethyl ether 3-4 times each.

The identity of the product was confirmed by $^1$H-NMR spectroscopy and ESI mass spectroscopy (ESI-MS).

$^1$H-NMR (DMSO-d6): 10.22 (s, 2H) NH, 8.38 (m, 2H) NHCH$_3$, 3.02 (d, 6H) NHCH$_3$, 2.20 (s, 6H) 2xCH$_3$

ESI-MS (+): m/z 260.4

In order to prepare the ATSM-Cu(II) complex, 0.1 gram (0.38 mmol) of the ATSM ligand was dissolved in ethanol. To this solution, an ethanolic solution of 0.0768 gram (0.38 mmol) copper acetate was added dropwise. The color of the solution changed from turbid white to brown-red. The reaction mixture was refluxed at 60-70° C. for 3-4 hours and then refluxed again overnight at room temperature.

The identity of the product was confirmed by UV-visible spectroscopy and ESI mass spectroscopy (ESI-MS).

UV-visible spectroscopy-$\lambda_{max}$ (DMSO) at 311 nm and 355 sh, 476 nm and 525 sh ESI-MS (+): m/z 322.

As shown in FIG. 61, the obtained complex exhibited the characteristic absorption spectrum of ATSM-Cu(II) in DMSO solvent.

In order to investigate the effect of ligands on the stability of the ATSM-Cu(II) complex in a physiological environment, experiments were performed with 30% DMSO in 0.1 M phosphate buffer (pH 7.4).

As shown in FIG. 62, ATSM-Cu(II) complex in a solvent of 30% DMSO in 0.1 M phosphate buffer (pH 7.4) exhibited a blue shift in absorption of ATSM-Cu(II), with a shift in wavelength from 476 nm to 465 nm.

The above result may be due to a solvent effect.

It was hypothesized that a major drawback of ATSM-Cu(II) in detecting hypoxic cells is its instability in the presence of biological Cu(II) chelators present in cellular environment. To test this hypothesis, 8 Cu(II) binding ligands were selected for tests of ATSM-Cu(II) stability. These ligands can be categorized in three types, as follows:

i) classical Cu(II) chelators (ligands 1 (1.10-phenanthroline), 2 (IDA), 3 (L-histidine) and 4 (nitrilotriacetic acid) depicted in Scheme 2);

ii) peptides containing histidine residues (HAGAH (SEQ ID NO: 47) and HGGH (SEQ ID NO: 48)); and iii) peptides containing histidine and methionine residues (HTGMK (SEQ ID NO: 49) and Pep1 (SEQ ID NO: 1).

Scheme 2

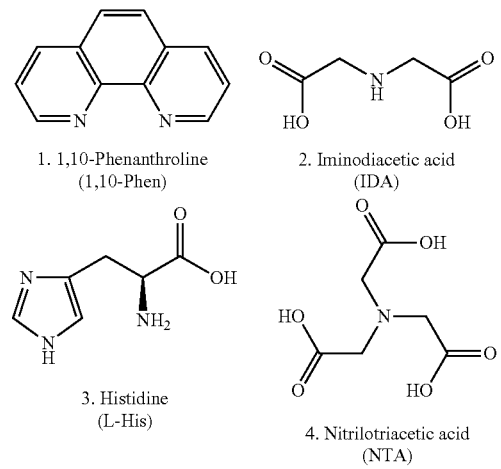

1. 1,10-Phenanthroline (1,10-Phen)
2. Iminodiacetic acid (IDA)
3. Histidine (L-His)
4. Nitrilotriacetic acid (NTA)

The abovementioned ligands may chelate the copper from ATSM coordination to form a corresponding ligand-Cu(II) complex and free ATSM ligand, as depicted in FIG. 63.

The stability of the ATSM-Cu(II) complex was tested by using UV-visible spectrophotometry. The change in the characteristic absorption of ATSM-Cu(II) at 311 nm and/or 465 nm suggests the dissociation of ATSM-Cu(II) upon titration with the tested ligands. In order to confirm the dissociation of ATSM-Cu(II) complex or the formation of copper complex with ligands or copper chelation by ligands, the effect of ligands on ATSM-Cu(II) was also tested using electron paramagnetic resonance (EPR) spectroscopy.

Stock solutions of $CuCl_2$ (10 mM), 1,10-phenanthroline (10 mM), IDA (10 mM), and L-histidine (10 mM), NTA (5 mM) and Pep1 (5 mM) were prepared in ultrapure water (Milli-Q®). Stock solutions (1 mM) of HAGAH, HGGH and HTGMK peptides were prepared by dissolution in 0.1 M phosphate buffer (pH 7.4).

100 µM of ATSM-Cu(II) complex was titrated with the abovementioned copper chelators at concentrations of 20, 40, 60, 80, 100, 150, 200, 250, 300, 350, 400, 500, 600, 700, 800, 900 and 1000 µM. For HAGAH and HGGH peptides, 40 µM of ATSM-Cu(II) complex was titrated with 5, 10, 20, 40, 50, 60, 70, 80, 90 and 100 µM of peptide. For HTGMK peptide, 40 µM of ATSM-Cu(II) complex was titrated with 5, 10, 20, 40, 60, 80 and 100 µM peptide.

In order to facilitate the solubility of ATSM-Cu(II) complex, all the measurements were carried out in 30% DMSO in 0.1 M phosphate buffer (pH 7.4), at physiological conditions.

As shown in FIGS. 64A-64D, upon titration of ATSM-Cu(II) with Cu(II) chelators, a change in the characteristic UV-visible absorption at 311 nm and 465 nm was observed, indicating that the Cu(II) which was originally complexed by ASTM was chelated by the Cu(II) chelators.

As further shown therein, 1,10-phenanthroline (FIG. 64A) exhibited a particularly strong ability to chelate copper from an ATSM coordination sphere, with two molar equivalents of 1,10-phenanthroline being sufficient to remove the copper from the ATSM-Cu(II) complex, whereas for the other tested chelators (IDA, L-His and NTA, FIGS. 64B-64D), at least four molar equivalents were needed.

Figure 65A:
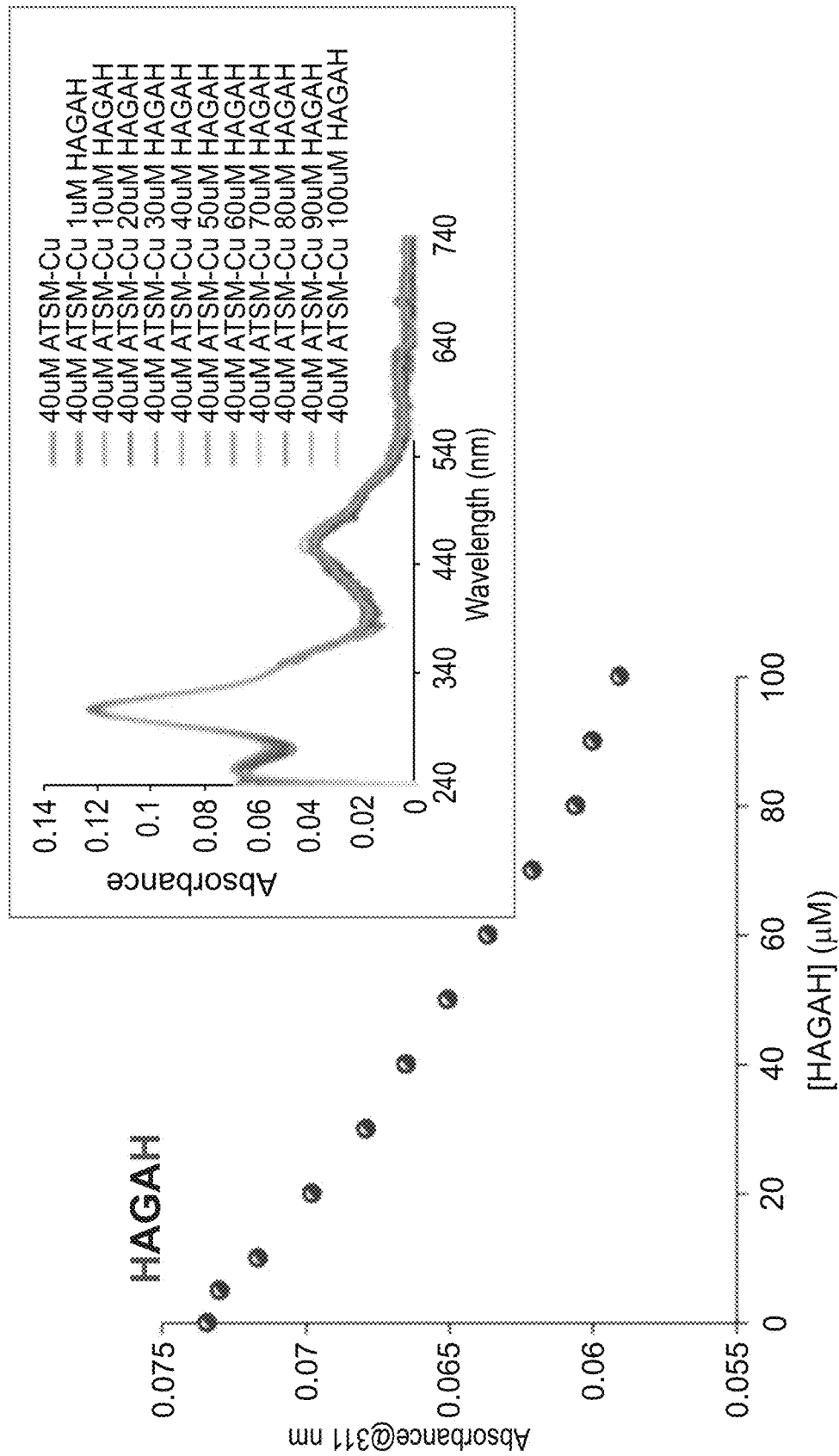
Figure 65B:
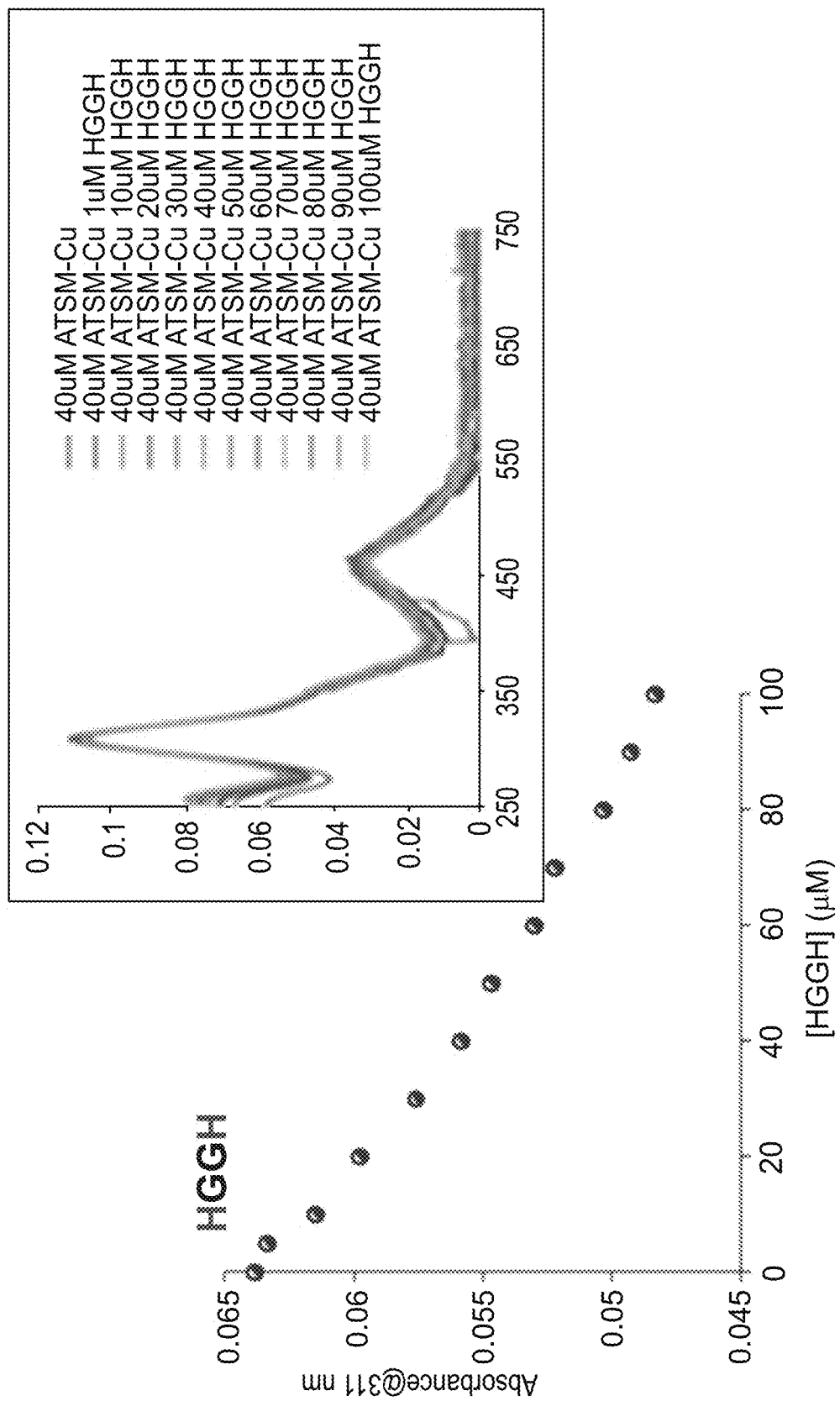

As shown in FIGS. 65A and 65B, the tested histidine-containing peptides did not induce a significant change in the absorption spectrum of ATSM-Cu(II). The observed decrease in absorption can be attributed to dilution upon addition of peptides.

These results indicate that histidine-containing peptides are not generally effective at removing copper from an ATSM-Cu(II) complex, even though such peptides can bind copper with a high affinity.

Figure 65C:
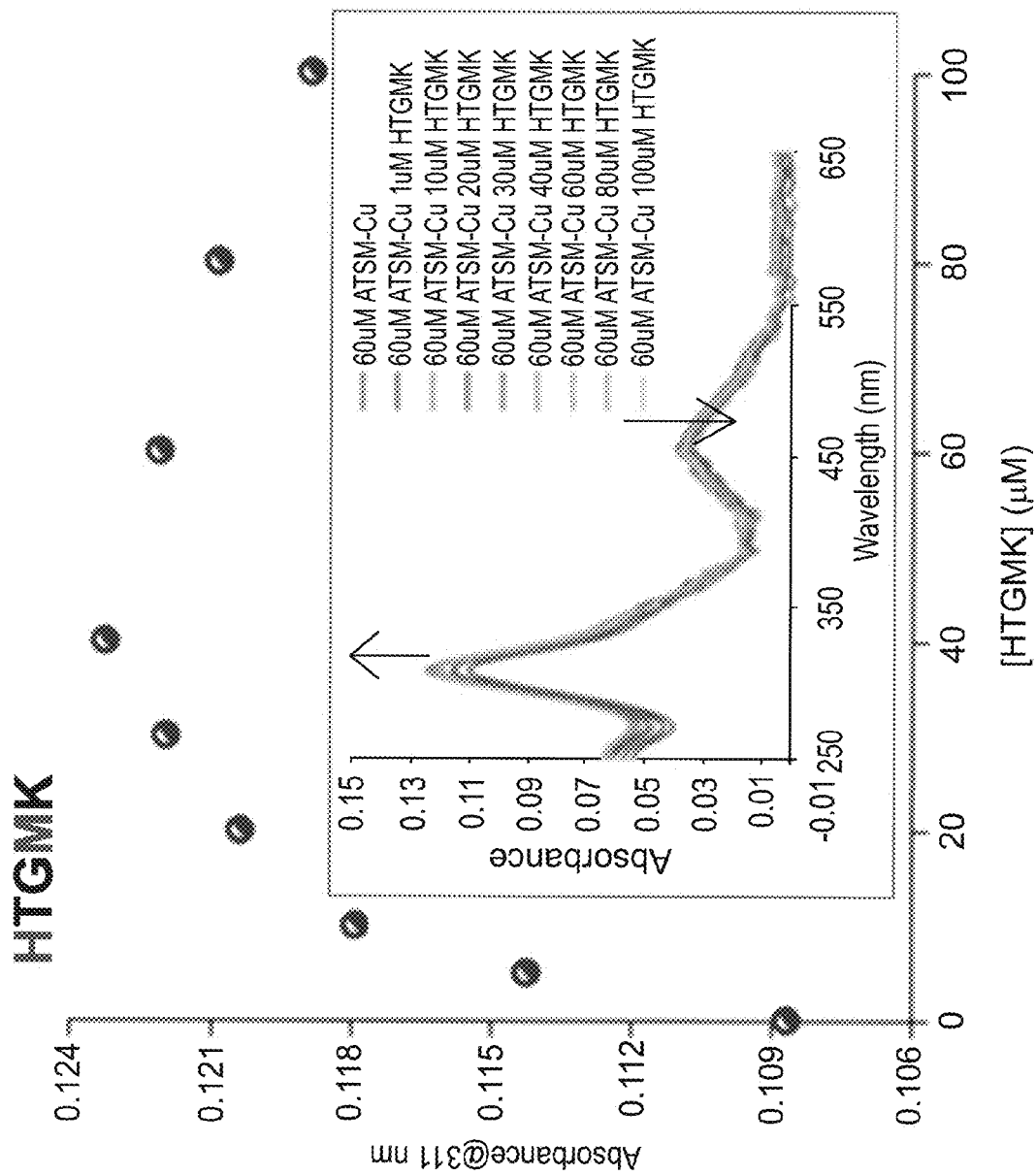
Figure 65D:
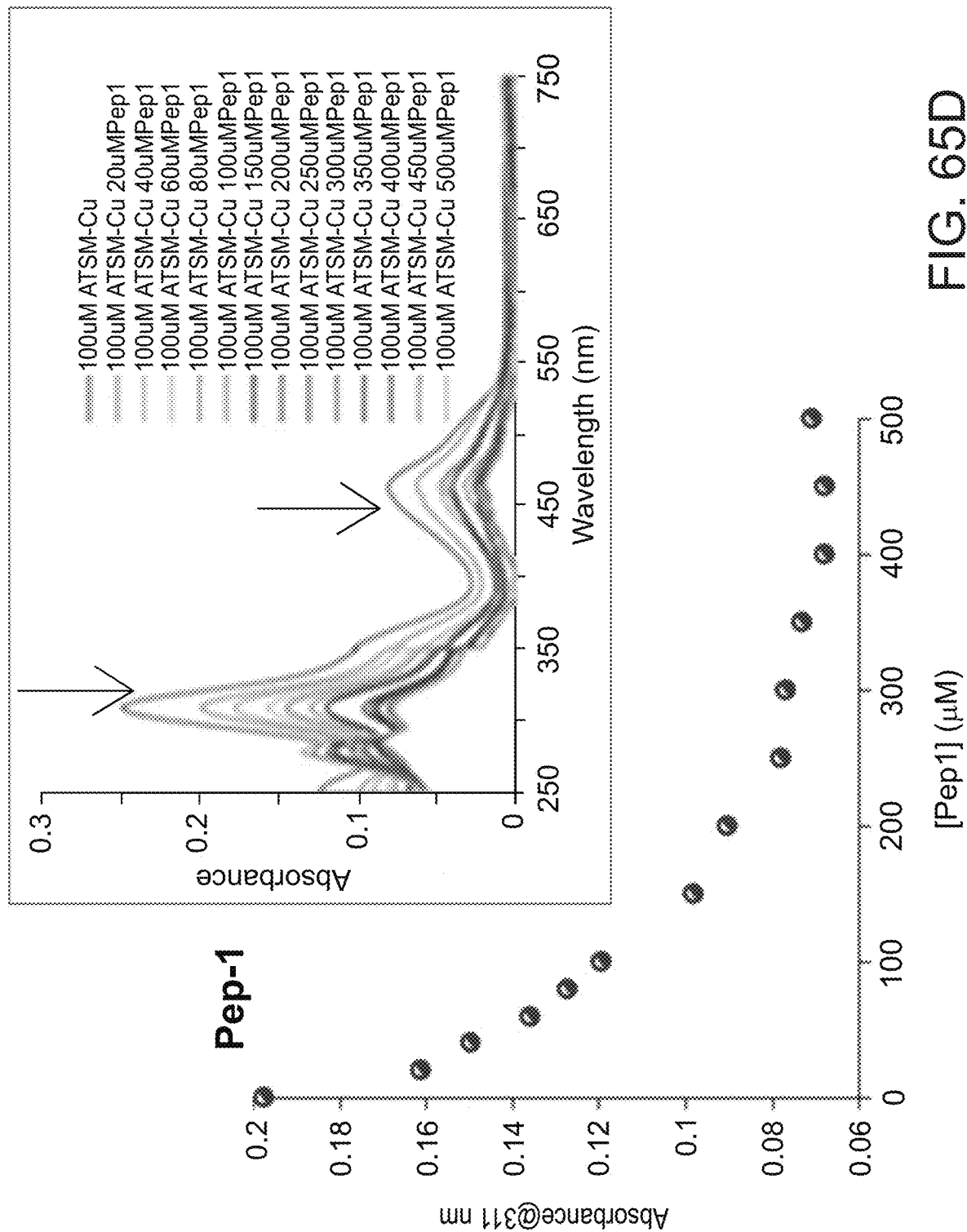

In contrast, as shown in FIGS. 65C and 65D, upon titration of ATSM-Cu(II) with peptides containing both histidine and methionine residues, an increase in absorption at 311 nm and a decrease in absorption at 465 nm were observed, indicating that such peptides removed Cu(II) from the ATSM-Cu(II) complex.

As further shown therein, even one molar equivalent of HTGMK (SEQ ID NO: 49) (FIG. 65C) was sufficient to remove Cu(II) from an ATSM coordination sphere.

The stability of ASTM-Cu(II) complex was further studied by EPR spectroscopy. 0.1 mM of ATSM-Cu(II) complex was prepared in 30% DMSO and 0.1 M phosphate buffer (pH 7.4). As the spectrophotometric studies showed that an excess of Cu(II) ligand is necessary to chelate Cu(II) from ATSM ligand, 4 molar equivalents of ligands were added.

As shown in FIGS. 67A-67F, titration of ATSM-Cu(II) complex with 1,10-phenanthroline, IDA, histidine, NTA or the exemplary peptides containing histidine and methionine residues induced significant changes in the electron paramagnetic spectrum of ATSM-Cu(II) complex (shown in FIG. 66), thereby confirming the above results obtained using spectrophotometry.

Taken together, the above results indicate that various small molecule ligands and peptides containing histidine and methionine residues can dissociate the ATSM-Cu(II) complex, suggesting that the ATSM-Cu(II) complex may be unstable in a cellular environment and unsuitable for clinical use.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A complex comprising a copper ion coordinated to a ligand and to a peptide, wherein said copper ion is a Cu(II) ion, and wherein:

said ligand has a general formula III:

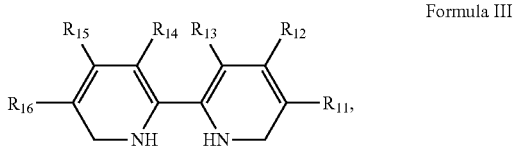

Formula III wherein:

$R_{11}$-$R_{16}$ are each independently absent or selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, a urea group, a thiourea group, O-carbamyl, N-carbamyl, O-thiocarbamyl, N-thiocarbamyl, C-amido, N-amido, C-carboxy, O-carboxy, sulfonamido, guanyl, guanidinyl, hydrazine, hydrazide, thiohydrazide, and amino, and wherein:

said peptide is at least 4 and up to 20 amino acids in length and comprises a first residue and a second residue which are coordinated to said copper ion, wherein said first residue is Met or Cys, and said second residue is selected from the group consisting of Met, Cys and His; and wherein said ligand and said peptide are not directly bound to each other.

2. The complex of claim 1, wherein said peptide comprises 2 or 3 atoms coordinated to said copper ion, at least one of said atoms being a sulfur atom, and wherein a total number of atoms in said ligand and said peptide coordinated to said copper ion is in a range of from 4 to 6.

3. The complex of claim 1, wherein said peptide is a water-soluble peptide, which has a solubility of at least 1 gram/liter in aqueous solution at pH 7.

4. The complex of claim 1, wherein said peptide comprises at least two sulfur atoms coordinated to said copper ion.

5. The complex of claim 1, wherein at least 50% of the amino acid residues of said peptide are selected from the group consisting of Ala, Arg, Asp, Glu, Gly, Lys, Ser, Thr and Tyr residues.

6. An aqueous solution comprising the complex of claim 1 and N-ethylmorpholine, wherein the solution has a pH in a range of from 6.5 to 8.5.

7. The complex of claim 1, wherein said copper is a radioactive copper isotope.

8. A process of preparing the complex of claim 1, the process comprising contacting said copper ion with said ligand and said peptide in solution, wherein a concentration of said copper ion in said solution is greater than a concentration of said ligand by at least 20%.

* * * * *